United States Patent
Poltorak

(10) Patent No.: US 11,413,425 B2
(45) Date of Patent: Aug. 16, 2022

(54) DEVICE, SYSTEM, AND METHOD FOR REDUCING CORONASOMNIA TO ENHANCE IMMUNITY AND IMMUNE RESPONSE

(71) Applicant: Neuroenhancement Lab, LLC, Suffern, NY (US)

(72) Inventor: Alexander Poltorak, Monsey, NY (US)

(73) Assignee: Neuroenhancement Lab, LLC, Suffern, NY (US)

( * ) Notice: Subject to any disclaimer, the term of this patent is extended or adjusted under 35 U.S.C. 154(b) by 0 days.

(21) Appl. No.: 17/375,599

(22) Filed: Jul. 14, 2021

(65) Prior Publication Data
US 2021/0338973 A1 Nov. 4, 2021

Related U.S. Application Data

(63) Continuation-in-part of application No. 16/883,541, filed on May 26, 2020.
(Continued)

(51) Int. Cl.
*A61M 21/02* (2006.01)
*A61M 21/00* (2006.01)

(52) U.S. Cl.
CPC ..... *A61M 21/02* (2013.01); *A61M 2021/0033* (2013.01); *A61M 2021/0044* (2013.01);
(Continued)

(58) Field of Classification Search
CPC .......... A61M 21/02; A61M 2021/0033; A61M 2021/0044; A61M 2205/502;
(Continued)

(56) References Cited

U.S. PATENT DOCUMENTS

| 5,213,562 A | 5/1993 | Monroe |
| 5,356,368 A | 10/1994 | Monroe |

(Continued)

OTHER PUBLICATIONS

Altena E, Baglioni C, Espie CA, et al. Dealing with sleep problems during home confinement due to the COVID-19 outbreak: Practical recommendations from a task force of the European CBT-I Academy. J Sleep Res. Apr. 4, 2020 ;29:e13052; pp. 1-7 (Year: 2020).*

(Continued)

*Primary Examiner* — Sunita Reddy
(74) *Attorney, Agent, or Firm* — Hoffberg & Associates; Steven M. Hoffberg

(57) ABSTRACT

A device, system, and method for facilitating a sleep cycle in a subject during a pandemic or peri COVID vaccination period, comprising determining a current awake or sleep stage of a person; automatically defining a desired sleep cycle pattern, dependent on the current awake or sleep stage of the person; generating an audio or optical stimulation pattern by an automated processor; and entraining brainwaves of the brain of the person with the stimulation pattern corresponding to the desired sleep cycle pattern, to thereby induce a sleep cycle in the person according to the sleep cycle pattern. When sleep patterns are normalized, a SARS-Cov-2 vaccination may be administered to the person.

21 Claims, 8 Drawing Sheets

Related U.S. Application Data

(60) Provisional application No. 62/862,656, filed on Jun. 17, 2019, provisional application No. 62/852,877, filed on May 24, 2019.

(52) U.S. Cl.
CPC ... *A61M 2205/502* (2013.01); *A61M 2230/06* (2013.01); *A61M 2230/10* (2013.01); *A61M 2230/50* (2013.01); *A61M 2230/63* (2013.01)

(58) Field of Classification Search
CPC .......... A61M 2230/06; A61M 2230/10; A61M 2230/50; A61M 2230/63; A61M 2021/0022; A61M 2021/0027; A61M 2021/0016; A61M 2021/0055; A61M 2021/0072; A61M 2202/30; A61M 2205/3303; A61M 2205/332; A61M 2205/3375; A61M 2205/3553; A61M 2205/3592; A61M 2205/505; A61M 2205/52; A61M 2205/587; A61M 2205/609; A61M 2205/8206; A61M 2209/088; A61M 2210/0687; A61M 2210/0693; A61M 2230/04; A61M 2230/14; A61M 2230/42; A61M 2230/60; A61M 2230/65; A61N 2005/0626; A61N 2005/0648; A61N 2005/0651; A61N 1/0456; A61N 1/36078; A61N 2/02; A61N 5/0622; A61N 1/36025; A61N 2/006; A61N 5/0618; G06F 2203/011; A61B 2505/09; A61B 5/374; A61B 5/4812; A61B 5/7267; A61B 5/7278; A61B 5/7282; A61B 5/245; A61B 5/165; A61B 5/02055; G16H 20/13; G16H 20/30; G16H 20/70; G16H 40/63; G16H 50/20; G16H 50/70; G06N 3/0445; G06N 3/084; G06N 3/088; G06V 40/16; G10H 2220/376; H04R 2225/81; Y02A 90/10
USPC ...................................................... 600/26–28
See application file for complete search history.

(56) References Cited

U.S. PATENT DOCUMENTS

| | | | |
|---|---|---|---|
| 7,674,224 B2 | 3/2010 | Hewett | |
| 9,037,224 B1 | 5/2015 | Fu | |
| 2005/0153268 A1 | 7/2005 | Junkin | |
| 2006/0217781 A1 | 9/2006 | John | |
| 2007/0084473 A1 | 4/2007 | Hewett | |
| 2008/0125620 A1* | 5/2008 | McNew | A61M 21/02 600/27 |
| 2008/0244003 A1 | 10/2008 | Springer | |
| 2008/0269652 A1 | 10/2008 | Reiner | |
| 2010/0028841 A1 | 2/2010 | Eatough | |
| 2010/0056854 A1 | 3/2010 | Chang | |
| 2010/0286747 A1 | 11/2010 | Sabesan | |
| 2011/0298706 A1 | 12/2011 | Mann | |
| 2013/0131537 A1 | 5/2013 | Tam | |
| 2013/0281798 A1 | 10/2013 | Rau | |
| 2014/0223462 A1* | 8/2014 | Aimone | H04N 21/4307 725/10 |
| 2014/0280189 A1 | 9/2014 | Tang | |
| 2015/0088024 A1 | 3/2015 | Sackarelles | |
| 2015/0105837 A1* | 4/2015 | Aguilar Domingo | A61N 1/0408 607/45 |
| 2015/0313496 A1 | 11/2015 | Connor | |
| 2015/0328467 A1 | 11/2015 | Demers | |
| 2015/0351655 A1 | 12/2015 | Coleman | |
| 2016/0066838 A1 | 3/2016 | deCharms | |
| 2016/0346545 A1 | 12/2016 | Pal | |
| 2017/0061034 A1 | 3/2017 | Ritchey | |
| 2017/0065792 A1* | 3/2017 | Bonvallet | G16H 50/50 |
| 2017/0319817 A1 | 11/2017 | Morishima | |
| 2017/0368342 A1 | 12/2017 | Tass | |
| 2018/0078164 A1 | 3/2018 | Menon | |
| 2018/0169430 A1* | 6/2018 | Kamei | A61B 5/375 |
| 2018/0318544 A1 | 11/2018 | Dogan | |
| 2019/0070386 A1 | 3/2019 | Raut | |
| 2020/0364779 A1* | 11/2020 | Wright-Freeman | G06Q 40/06 |
| 2020/0390650 A1* | 12/2020 | Zhang | A61H 39/04 |

OTHER PUBLICATIONS

Lowet E, Roberts MJ, Bonizzi P, Karel J, De Weerd P (2016) Quantifying Neural Oscillatory Synchronization: A Comparison between Spectral Coherence and Phase-Locking Value Approaches. PLOS ONE 11(1): e0146443. (Year: 2016).*

* cited by examiner

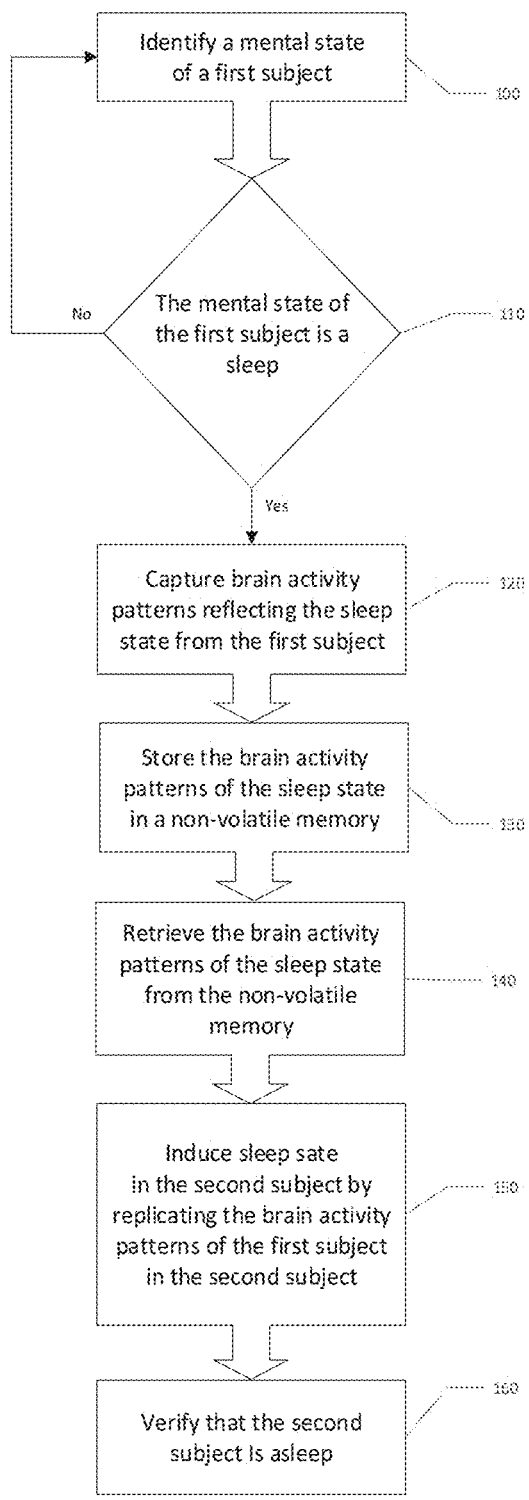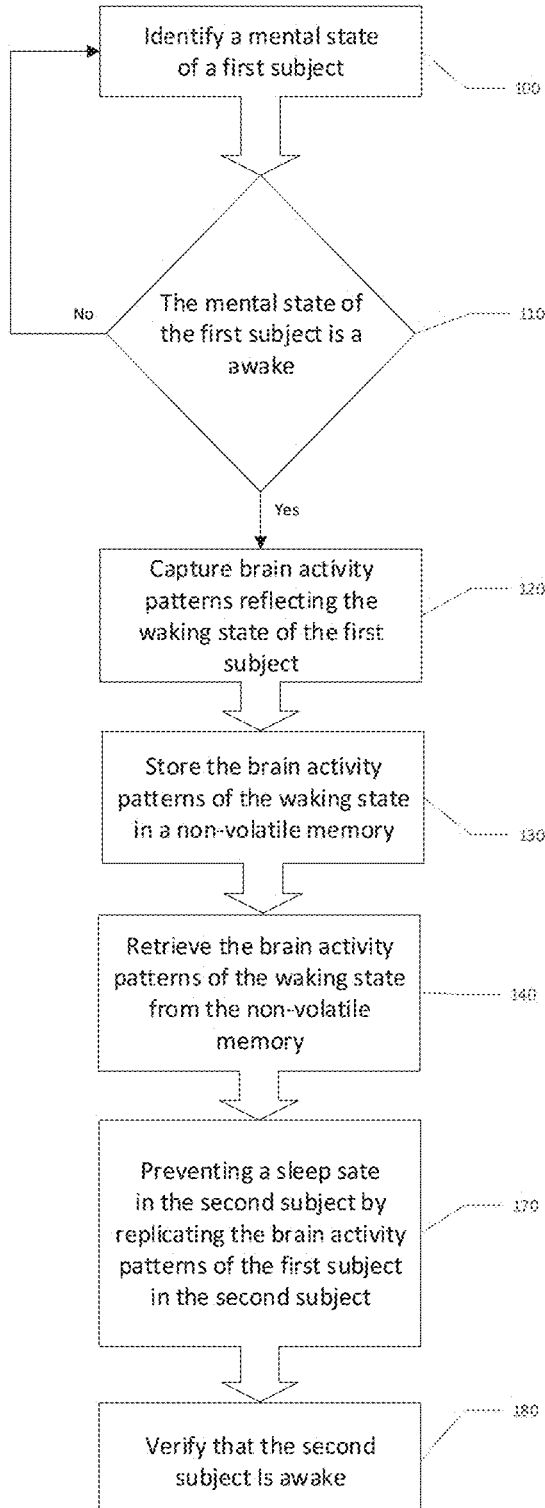
Fig. 1
Fig. 2

DEVICE, SYSTEM, AND METHOD FOR REDUCING CORONASOMNIA TO ENHANCE IMMUNITY AND IMMUNE RESPONSE

CROSS REFERENCE TO RELATED APPLICATIONS

The present application is a Continuation-in-Part of U.S. patent application Ser. No. 16/883,541, filed May 26, 2020, which is a non-provisional of, and claims benefit of priority under 35 U.S.C. § 119(e) from U.S. Provisional Patent Application No. 62/862,656, filed Jun. 17, 2019, and from U.S. Provisional Patent Application No. 62/852,877, filed May 24, 2019, each of which is expressly incorporated herein by reference in its entirety.

FIELD OF THE INVENTION

The present invention generally relates to the fields of immune modulation and sleep, and more specifically to systems, methods and applications for improving immune response to antigen challenge by inducing sleep. More particularly, the invention addresses COVID-induced insomnia that may impair vaccine response and lead to impaired outcome in cases of infection.

BACKGROUND OF THE INVENTION

Each reference and document cited herein is expressly incorporated herein by reference in its entirety, for all purposes.

Sleep-immune interaction is a well-known phenomena. In the time of a global pandemic the bidirectional interplay of sleep and immune system becomes even more consequential. In fact, science backs the relationship between sleep and effective immune response to vaccination.

2020 and 2021 have been the unprecedented years due to the rapid spread of the modified severe acute respiratory syndrome coronavirus around the world. The coronavirus disease 2019 (COVID-19) causes atypical infiltrated pneumonia with many neurological symptoms and the major sleep changes expose people to stress, such as social confinement and changes in daily routines, is accompanied by various sleep disturbances, known as "coronasomnia" phenomenon. The sleep disorders induces neuroinflammation, which promotes the blood-brain barrier (BBB) disruption and entry of antigens and inflammatory factors into the brain. Semyachkina-Glushkovskaya, Oxana, Aysel Mamedova, Valeria Vinnik, Maria Klimova, Tingting Yu, Dan Zhu, Thomas Penzel, and Jurgen Kurths. "Brain mechanisms of COVID-19-sleep disorders." (2021).

The first studies of COVID-19-associated sleep disorders were published in China. Huang and Zhao collected information from a survey of 7236 volunteers and reported 18% of poor sleep quality. Later, the sleep disorders in patients with COVID-19 have also been highlighted in several other publications from different countries. These studies examined the effect on sleep of SARS-CoV-2 infection and confounders related to isolation, quarantine, anxiety, stress, or financial losses. In Europe, symptoms of insomnia could be related to psychosocial factor, such as the confinements due to quarantine. In Italy, COVID-19-related anxiety was highly associated with sleep disorders. In a survey of 2291 Italians, 57.1% reported poor sleep quality. In the International COVID-19 Sleep Study have shown COVID-19-mediated insomnia, nightmares, sleep apnea, fatigue, exhaustion, and rapid eye moved (REM) sleep behavior disorder. There is the hypothesis that sleepiness and REM sleep behavior disorder might be related COVID-19 per se, whereas insomnia might be related mainly to confinement, anxiety, and other psychosocial factors.

The COVID-19-related sleep disorders are a major problem of rehabilitation of patients after infection. However, the exploration of mechanisms underlying the 'coronasomnia' phenomenon is still in its infancy. Sleep disorders can open the blood-brain barrier (BBB) for inflammatory factors, which might contribute to the 'coronasomnia' phenomenon.

Sleep deprivation in duration and/or quality is a common type of COVID-19-related sleep disorders. There is emerging evidence that the major complications of sleep loss is neuroinflammation, which induce the BBB disruption. Indeed, sleep loss per se, including sleep deprivation, sleep restriction, sleep fragmentation or sleep apnea in human and rodents induces a systemic low-grade inflammation characterized by the release of several molecules, such as cytokines, chemokines, and acute-phase proteins; all of them can promote changes in cellular components of the BBB, particularly on brain endothelial cells.

The low-grade systemic inflammation induced by sleep loss is characterized by a subtle but sustained increase in peripheral levels of proinflammatory mediators. Further experimental studies have demonstrated that acute and chronic sleep loss is associated with an increased levels of proinflammatory mediators, such as tumor necrosis factor-α (TFN-α), interleukin-1β (IL-1β), IL-6, IL-17A, and C-reactive protein (CRP) as well as with an increased level of immune-derived inflammatory mediators, such as cyclooxygenase-2 (COX-2), nitric oxide synthase (NOS), endothelin-1 (ET-1), vascular endothelial growth factor (VEGF), and insulin-like growth factor-1 (IGF-1). Sleep deprivation increases the BBB permeability to inflammatory mediators, immune cells, and exogenous tracers in humans and rodents.

Sleep disturbances increases the BBB permeability also in humans. Indeed, acute sleep deprivation induces an increase in the serum levels of neuron-specific enolase and S100 calcium binding protein B (S-100B) in healthy young men.

Circadian rhythms is biological clock that endogenously oscillates with a period of roughly 24 h. There is recognition of the importance that the central circadian pacemakers in mammals are both the suprachiasmatic nucleus and the BBB cells, which have autonomous circadian rhythms driven by molecular clocks. Moreover, the large cerebral blood vessels themselves exhibit the circadian clock. In the following, we highlight recent evidence demonstrating that the BBB permeability to cytokines depends on the time of day that can be important for a better understanding of the mechanisms underlying COVID-19-associated sleep disorder.

Upon invasion of bacteria and viruses, the immune system is immediately activated producing inflammatory mediators, including pro-inflammatory cytokines, such as tumor necrosis factor (TNF-α), interleukins, IL-1β/IL-6, and inflammatory mediators, prostaglandins (PGs) and leukotrienes. This immune response evokes an acute inflammatory process (hours to days) to clear the pathogens from the infected tissues.

The accumulating evidence suggests that the severity of COVID-19 is associated with an increased level of inflammatory mediators including cytokines and chemokines such as interleukins, TNF, granulocyte colony-stimulating factor (G-CSF), monocyte chemoattractant protein-1, macrophage inflammatory protein I alpha, C-reactive protein, ferritin, and D-dimers in blood upon SARS-CoV-2 infection. Note, among the elevated inflammatory mediators, the blood IL-6 level is highly correlated with the disease mortality when COVID-19 survivors and non-survivors are compared, suggesting that fatal COVID-19 is characterized as a cytokine release syndrome that is induced by a cytokine storm with high mortality. The entry of some cytokines, such as tumor necrosis factor (TNF-α), interleukins 6 (IL 6) and IL-1α into the brain undergo significant circadian oscillations. The TNF-α is a cytokine used by the immune system for cell signaling. When macrophages detect an infection, they release TNF to alert other immune system cells as part of an inflammatory response. Pan et al. showed that the spinal cord, but not the brain, demonstrates a circadian rhythm in the uptake of TNFα. The greatest TNFα uptake occurs between Zeitgeber time (LT) 20-ZT23. This pattern is similar to that of leptin but different from that of interleukin-1. The circadian rhythm of the influx of TNFα into this region of the CNS suggests a functional role for the spinal cord in the physiological actions of TNFα. TNFα transport across the BBB is abolished in receptor knockout mice. Interleukin-9 is a cytokine with pleiotropic actions in both the periphery of the body and the CNS. Altered IL-6 secretion has been associated with inflammatory dysregulation and several adverse health consequences. Evidence indicates that noradrenaline (NA) elicits anti-inflammatory actions in the CNS and consequently may play a neuroprotective role where inflammatory events contribute to the CNS pathology.

Due to the loss of BBB integrity, the endothelial cells, pericytes, and astrocytes compromise the ability to prevent immune cells from infiltrating the brain. Rather, immune cells are able to permeate the barrier and infiltrate the CNS, possibly attacking the brain cells including the neurons. The resulting neuroinflammatory process may result in a severe damage to brain function.

It is widely accepted that the main function of the BBB is the protection of the CNS from the penetration of microorganisms and toxins from the blood. However, the latest findings changed our understanding of the role of BBB in the keeping of the CNS health. The BBB opening by music or light stimulates the lymphatic clearance of macromolecules from the brain. There is strong evidence that both sleep and the BBB are interlinked with activation of clearance of macromolecules and toxins from the brain that can be accompanied by similar changes on the neurological activity of the brain.

The BBB opening can directly affect the EEG dynamics. The signals generated by the BBB originate from a transendothelial resistance between blood and brain tissue. This voltage is a membrane potential of endothelial cells forming the BBB. The BBB opening changes the voltage of endothelial cells causing depolarization of their membranes. These changes of cell potential cause up to mV-level shifts in human scalp EEG. The BBB opening can influence on the EEG behavior indirectly via astrocytes, which are essential for the BBB integrity and the EEG behavior. The astrocytic mechanism of EEG changes may be related to the astrocytic-regulation of synaptic conductance, which are crucial for the electrical activity of cortical neurons.

The COVID-19 pandemic is accompanied by the development of a growing number of COVID-19-related sleep disorders, known as the 'coronasomnia' phenomenon. The most dangerous consequence of sleep disturbances is the BBB disruption when the viruses, bacteria and toxins can entry into the brain and causes neuroinflammation.

Hui, D. S.; I Azhar, E.; Madani, T. A.; Ntoumi, F.; Kock, R.; Dar, O.; Ippolito, G.; Mchugh, T. D.; Memish, Z. A.; Drosten, C.; Zumla, A.; Petersen, E. The continuing 2019-nCoV epidemic threat of novel coronaviruses to global health The latest 2019 novel coronavirus outbreak in Wuhan, China. *Int J of Infec* Dis 2020, 91, 264-266.

Drosten, C.; Gunther, S.; Preiser, W.; Van der Werf, S.; Brodt, H. R.; Becker, S.; Rabenau, H.; Panning, M.; Kolesnikova, L.; Fouchier, R. A.; Berger, A.; Burguiere, A. M.; Cinatl, J.; Eickmann, M.; Escriou, N.; Grywna, K.; Kramme, S.; Manuguerra, J. C.; Muller, S.; Rickerts, V.; Sturmer, M.; Vieth, S.; Klenk, H. D.; Osterhaus, A. D.; Schmitz, H.; Doerr, H. W. Identification of a novel coronavirus in patients with severe acute respiratory syndrome. *N. Engl. J. Med* 2003, 348, 1967-1976.

Ksiazek, T. G.; Erdman, D.; Goldsmith, C. S.; Zaki, S. R.; Peret, T.; Emery, S.; Tong, S.; Urbani, C.; Comer, J. A.; Lim, W.; Rollin, P. E.; Dowell, S. F.; Ling, A. E.; Humphrey, C. D.; Shieh, W J; Guarner, J.; Paddock, C. D.; Rota, P.; Fields, B.; DeRisi, J.; Yang, J. Y.; Cox, N.; Hughes, J. M.; LeDuc, J. W.; Bellini, W. J.; Anderson, L. J. A novel coronavirus associated with severe acute respiratory syndrome. *N. Engl. J. Med* 2003, 348, 1953-1966.

Peiris, J. S.; Lai, S. T.; Poon, L. L.; Guan, Y.; Yam, L. Y.; Lim, W.; Nicholls, J.; Yee, W. K.; Yan, W. W.; Cheung, M. T.; Cheng, V. C.; Chan, K. H.; Tsang, D. N.; Yung, R. W.; Ng, T. K.; Yuen. K. Y. Coronavirus as a possible cause of severe acute respiratory syndrome. *Lancet* 2003, 361, 1319-1325.

Webster, R. G. Wet markets—a continuing source of severe acute respiratory syndrome and influenza? *Lancet* 2004, 363, 234-236G.

Woo, P. C.; Lau, S. K.; Yuen, K. Infectious diseases emerging from Chinese wet-markets: zoonotic origins of severe respiratory viral infections. *Curr. Opin. Infect. Dis* 2006, 19, 401-407.

Sharifian-Dorche, M.; Huot, P.; Osherov, M. et al. Neurological complications of coronavirus infection; a comparative review and lessons learned during the COVID-19 pandemic. *J Neural Sci* 2020, 417, 117085.

Varatharaj, A.; Thomas, N.; Ellul, M. A.; Davies, N. W. S.; Pollak, T. A.; Tenorio, E. L.; Sultan, M.; Easton, A.; Breen, G.; Zandi, M.; Coles, J. P.; Manji, H.; Al-Shahi Salman, R.; Menon, D. K.; Nicholson, T. R.; Benjamin, L. A.; Carson, A.; Smith, C.; Turner, M. R.; Solomon, T.; Kneen, R.; Pett, S. L.; Galea, I.; Thomas, R. H.; Michael, B. D.; CoroNerve Study Group. Neurological and neuropsychiatric complications of COVID-19 in 153 patients: a UK-wide surveillance study. *Lancet Psychiatry* 2020, 7(10), 875-882.

Markuu, P. Sleep research in 2020: COVID-19-related sleep disorders. *The Lancet Neurology* 2021, 20(1), 15-17.

Huang, Y.; Zhao, N. Generalized anxiety disorder, depressive symptoms and sleep quality during COVID-19 outbreak in China: a web-based cross-sectional survey. *Psychiatry Res* 2020, 288, 112954.

Mazza, C.; Ricci, E.; Biondi, S.; Colasanti, M.; Ferracuti, S.; Napoli, C.; Roma, P. A nationwide survey of psychological distress among Italian people during the covid-19 pandemic: Immediate psychological responses and associated factors. *International Journal of Environmental Research and Public Health* 2020, 17(9), 3165.

Zhang, C.; Yang, L.; Liu, S.; Ma, S.; Wang, Y.; Cai, Z.; Zhang, B. Survey of insomnia and related social psychological factors among medical staff involved in the 2019 novel Coronavirus disease outbreak. *Frontiers in Psychiatry* 2020, 11, 306.

Cellini, N.; Canale, N.; Mioni, G.; Costa, S. Changes in sleep pattern, sense of time and digital media use during COVID-19 lockdown in Italy. *Journal of Sleep Research* 2020, 29(4), e13074.

Rogers, J. P.; Chesney, E.; Oliver, D.; Pollak, T A.; McGuire, P.; Fusar-Poli, P.; David, A. S. Psychiatric and neuropsychiatric presentations associated with severe coronavirus infections: A systematic review and meta-analysis with comparison to the COVID-19 pandemic. *The Lancet Psychiatry* 2020, 7, 611-627.

Partinen, M.; Kronholm, E. Epidemiology: Principles and application in sleep medicine. *In Sleep disorders medicine: Basic science, technical considerations and aspects*, 4th ed.; Chokroverty, S. Ed.; Springer, 2017; pp. 485-521.

Belleville, G.; Ouellet, M. C.; Morin, C. M. Post-traumatic stress among evacuees from the 2019 fort mcmurray wildfires: Exploration of psychological and sleep symptoms three months after the evacuation. *International Journal of Environmental Research and Public Health* 2019, 16(9), 1604.

Lavie, P. Sleep disturbances in the wake of traumatic events. *New England Journal of Medicine* 2001, 345(25), 1825-1832

Partinen, M.; Bjorvatn, B.; Holzinger, B. et al. Sleep and circadian problems during the coronavirus disease 2019 (COVID19) pandemic: the International COVID-19 Sleep Study (ICOSS). *J Sleep Res* 2020, 30e13206.

Altena, E.; Baglioni, C.; Espie, C. A. et al. Dealing with sleep problems during home confinement due to the COVID-19 outbreak: practical recommendations from a task force of the European CBT-1 Academy. *J Sleep Res* 2020, 29, e13052.

Casagrande, M.; Favieri, F.; Tambelli, R.; Forte, G. The enemy who sealed the world: effects quarantine due to the COVID19 on sleep quality, anxiety, and psychological distress in the Italian population. *Sleep Med* 2020, 75, 12-20.

Sher, L. COVID-19, anxiety, sleep disturbances and suicide. *Sleep Med* 2020, 70(124)

Esme, S.; Bhvs, O.; Souza, J. C. Sleep and immunity in times of COVID-19. *Rev Assoc Med Bras* 2020, 66(2), 143-147.

Miller, M. A.; Cappuccio, F. P. A systematic review of COVID-19 and obstructive sleep apnoea. *Sleep Med Rev* 2021, 55

Wang, S.; Xie, L.; Xu, Y.; Yu, S.; Yao, B.; Xiang D. Sleep disturbances among medical workers during the outbreak of COVID2019. *Occup Med (Lond)* 2020, 70(5), 364-369.

Marelli, S.; Castelnuovo, A.; Somma, A.; Castronovo, V.; Mombelli, S.; Bottoni, D.; Leitner, C.; Fossati, A.; Ferini-Strambi, L. Impact of COVID-19 lockdown on sleep quality in university students and administration staff. *J. Neurol* 2021, 268(1), 815.

Deng, J.; Zhou, F.; Hou, W.; Silver, Z.; Wong, C. Y.; Chang, O.; Huang, E.; Zuo, Q. K. The prevalence of depression, anxiety, and sleep disturbances in COVID-19 patients: a meta-analysis. *Ann N Y Acad Sci* 2021, 1486(1), 90-111.

Liu, Z.; Tang, H.; Jin, Q.; Wang, G.; Yang, Z.; Chen, H.; Yan, H.; Rao, W.; Owens, J. Sleep of preschoolers during the coronavirus disease 2019 (COVID-19) outbreak. *J Sleep Res* 2021, 30(1), e13142.

Martínez-de-Quel, O.; Suárez-Iglesias, D.; López-Flores, M.; Pérez, C. A. Physical activity, dietary habits and sleep quality before and during COVID-19 lockdown: A longitudinal study. *Appetite* 2021, 158, 105019.

Zhao, X.; Lan, M.; Li, H.; Yang, J. Perceived stress and sleep quality among the non-diseased general public in China during the 2019 coronavirus disease: a moderated mediation model. *Sleep Medicine* 2020, 77: 339-345.

Lucey, B. P. It's complicated: The relationship between sleep and Alzheimer's disease in humans. *Neurology of Disease* 2020, 144, 105031.

Shokri-Kojori, E.; Wang, G. J.; Wiers, C. E.; Demiral, S. B.; Guo, M.; Kim, S. W.; Lindgren, E.; Ramirez, V.; Zehra, A.; Freeman, Clara; Miller, G.; Manza, P.; Srivastava, T.; Santi, S. D.; Tomasi, D.; Benveniste, H.; Volkow, Nora D. B-Amyloid accumulation in the human brain after one night of sleep deprivation. *Proceedings of the National Academy of Sciences* 2018, 115 (17), 4483-4488.

Bishir, M.; Bhat, A.; Essa, M. M.; Ekpo, O.; Ihunwo, A. O.; Veeraraghavan, V. P.; Mohan, S. K.; Mahalakshmi, A. M.; Ray, B.; Tuladhar, S.; Chang, S.; Chidambaram, S. B.; Sakharkar, M. K.; Guillemin, G. J.; Qoronfleh, M. W.; Djcius, D. M. Sleep Deprivation and Neurological Disorders. *Hindawi BioMed Research International* 2020, 19.

Hurtado-Alvarado, G.; Becerril-Villanueva, E.; Contis-Montes, O. A.; Domínguez-Salazar E.; Salinas-Jazmín N.; Pérez Tapia, S. M.; Pavon, L.; Vélazquez-Moctezuma, J.; Gómez-González B. The yin/yang of inflammatory status: Blood-brain barrier regulation during sleep. *Brain Behav Immun* 2018, 69, 154-166.

Pan, W.; Kastin, A. J. The Blood-Brain Barrier. Regulatory Roles in Wakefulness and Sleep. *Neuroscientist* 2017, 23(2), 124136.

Cuddapah, V. A.; Zhang, Sehgal, A. Regulation of the Blood-Brain Barrier by Circadian Rhythms and Sleep. *Trends Neurosci* 2019, 42(7), 500-510.

Medina-Flores, F.; Hurtado-Alvarado G.; Contis-Montes de Oca A.; López-Cervantes S. P.; Konigsberg, M.; Deli, M. A.; Gómez-González, B. Sleep loss disrupts pericyte-brain endothelial cell interactions impairing blood-brain barrier function. *Brain Behav Immun* 2020, 89, 118-132.

Hurtado-Alvarado, G.; Domínguez-Salazar, E.; Pavon, L.; Velázquez-Moctezuma, J.; Gómez-González, B. Blood-Brain Barier Disruption Induced by Chronic Sleep Loss: Low-Grade Inflammation May Be the Link. *J Immunol Res* 2016, 4576012

Sun, J.; Wu, J.; Hua, F.; Chen, Y.; Dian, F.; Xu, G. Sleep Deprivation Induces Cognitive Impairment by Increasing BloodBrain Barrier Permeability via CD44. *Front Neurol* 2020, 11, 583916.

Lim, D. C.; Pack, A. I. Obstructive sleep apnea and cognitive impairment: addressing the blood-brain barrier. *Sleep Med Rev* 2014, 18(1), 35-48.

Daulatzai, M. A. Cerebral hypoperfusion and glucose hypometabolism: Key pathophysiological modulators promote neurodegeneration, cognitive impairment, and Alzheimer's disease. *J Neurosci Res* 2017, 95(4), 943-972.

Voirin, A. C.; Celle, S.; Perek, N.; Roche, F. Sera of elderly obstructive sleep apnea patients alter blood-brain barrier integrity in vitro: a pilot study. Sci Rep 2020, 10(1) 11309.

Hurtado-Alvarado, G.; Pavón, L.; Castillo-García, SA.; Hernández, M. E.; Domínguez-Salazar, E.; Velázquez-Moctezuma, J.; Gómez-González, B. Sleep loss as a factor to induce cellular and molecular inflammatory variations. *Clin Dev Immunol* 2013, 801341.

Benedict C.; Cedernaes J.; Giedraitis V.; Nilsson E. K.; Hogenkamp P. S.; Vågesjö E.; Massena S.; Pettersson U.; Christoffersson G.; Phillipson M.; Broman J. E.; Lannfelt L.; Zetterberg H.; Schiöth H. B. Acute sleep deprivation increases serum levels of neuron-specific enolase (NSE) and S100 calcium binding protein B (S-100B) in healthy young men. *Sleep* 2014, 37(1), 195-198.

Opp, M. R.; George, A.; Ringgold, K. M.; Hansen, K. M.; Bullock, K. M.; Banks, W A. Sleep fragmentation and sepsis differentially impact blood-brain barrier integrity and transport of tumor necrosis factoring aging. *Brain Behan. Immun* 2015, 50, 259-285.

Krueger, J. M and Majde, J. A. Humoral links between sleep and the immune system: research issues. *Ann N Y Acad Sci.* 2003, 9929-20.

Straub, R., Männel, D. How the immune system puts the brain to sleep. *Nat Med* 1999, 5, 877-879.

Hirotsu, C.; Rydlewski, M.; Aratújo, M. S.; Tufik, S.; Andersen, M. L. Sleep Loss and Cytokines Levels in an Experimental Model of Psoriasis. *PLoS ONE* 2012, 7(11), e51183.

He, J.; Hsuchou, H.; He, Y.; Kastin, A. J.; Wang, Y.; Pan, W. Sleep restriction impairs blood-brain barrier function. *The Journal of Neuroscience* 2014, 34(44), 14697-14706.

Hurtado-Alvarado, G.; Pavon, L.; Castillo-Garcia, S A. et al. Sleep loss as a factor to induce cellular and molecular inflammatory variations. *Clinical & Developmental Immunology* 2013, 14.

Ibrahim, L.; Duncan, W.; Luckenbaugh, D. A.; Yuan, P.; Machado-Vieira, R.; Zarate Jr., C. A. Rapid antidepressant changes with sleep deprivation in major depressive disorder are associated with changes in vascular endothelial growth factor (VEGF): a pilot study. *Brain Research Bulletin* 2011, 86(1-2), 129-133.

Hurtado-Alvarado, G.; Domínguez-Salazar, E.; Velázquez-Moctezuma, J.; Gómez-González, B. A2A Adenosine Receptor Antagonism Reverts the Blood-Brain Barrier Dysfunction Induced by Sleep Restriction. *PLoS ONE* 2016, 11(11), e0167236.

Gomez-Gonzalez, B.; Hurtado-Alvarado, G.; Esqueda-Leon, E.; Santana Miranda, R.; Rojas-Zamorano, J. A.; Velazquez Moctezuma, J. REM Sleep Loss and Recovery Regulates Blood-Brain Barrier Function. *Current Neurovascular Research* 2013, 10, 197-207.

Hurtado-Alvarado, G.; Velázquez-Moctezuma, J.; Gómez-González, B. Chronic sleep restriction disrupts interendothelial tight junctions in the hippocampus and increases blood-brain barrier permeability. *J. Microsc.* 2017, 268, 28-31.

Saunders, N. R.; Dziegielewska, K. M.; Mollgard, K.; Habgood, M. D. Markers for blood-brain barrier integrity: how appropriate is Evans blue in the twenty-first century and what are the alternatives. *Front. Neurosci* 2015, 9, 385.

Chennaoui, M.; Sauvet, F.; Drogou C. et al. Effect of one night of sleep loss on changes in tumor necrosis factor alpha (TNF-α) levels in healthy men. *Cytokine* 2011, 56(2), 318-324.

Zielinski, M. R.; Kim, Y.; Karpova, S. A.; McCarley, R. W.; Strecker, R. E.; Gerashchenko, D. Chronic sleep restriction elevates brain interleukin-1 beta and tumor necrosis factor-alpha and attenuates brain-derived neurotrophic factor expression. *Neuroscience Letters* 2914, 580, 27-31.

Vgontzas, A. N.; Zoumakis, M.; Papanicolaou D. A. et al. Chronic insomnia is associated with a shift of inter-leukin-6 and tumor necrosis factor secretion from night-time to daytime. *Metabolism* 2002, 51 (7), 887-892

Van Leeuwen, W. M. A. M.; Karisola L. P. et al. Sleep restriction increases the risk of developing cardiovascular diseases by augmenting proinflammatory responses through IL-17 and CRP. *PLoS ONE* 2009, 4(2), e4589.

Okun, M. L.; Coussons-Read, M.; Hall, M. Disturbed sleep is associated with increased C-reactive protein in young women. *Brain Behavior and Immunity* 2009, 23 (3), 351-354.

Cuddapah, V. A.; Zhang, S. L.; Sehgal, A. Regulation of the Blood-Brain Barrier by Circadian Rhythms and Sleep. *Trends Neurosci* 2919, 42(7), 500-510.

Carver, K. A. et al. Rhythmic expression of cytochrome P450 epoxygenases CYP4x1 and CYP2c11 in the rat brain and vasculature. *Am J Physiol Cell Physiol* 2014, 307, 989.

Gao, Y et al. Clock upregulates intercellular adhesion molecule-1 expression and promotes mononuclear cells adhesion to endothelial cells. *Biochem Biophys Res Commun* 2014, 443, 586-591.

Mohawk, J A. et al. Central and peripheral circadian clocks in mammals. *Annu Rev Neurosci* 2012, 35, 445-462.

Davidson, A. J. et al. Cardiovascular tissues contain independent circadian clocks. *Clin Exp Hypertens* 2005, 27, 307-311.

Durgan, D. J. et al. The rat cerebral vasculature exhibits time-of-day-dependent oscillations in circadian clock genes and vascular function that are attenuated following obstructive sleep apnea. *J Cereb Blood Flow Metab* 2017, 37, 2806-2819.

Shintaro H.; Mona U.; Kumiko T.; Rie H.; Yuki T.; Masaaki M.; Toshio H. How COVID-19 induces cytokine storm with high mortality. *Inflamm Regen.* 2020, 40(37).

Tay, M. Z.; Poh, C. M.; Renia, L.; MacAry, P A.; Ng, L. F. P. The trinity of COVID-19: immunity, inflammation and intervention. *Nat Rev Immunol* 2020, 20(6), 363-374.

Chen, N.; Zhou, M.; Dong, X.; Du, J.; Gong, F.; Han, Y. et al. Epidemiological and clinical characteristics of 99 cases of 2019 novel coronavirus pneumonia in Wuhan, China: a descriptive study. *Lancet* 2020, 395(10223), 507-513.

Coronaviridae Study Group of the International Committee on Taxonomy of V The species severe acute respiratory syndrome-related coronavirus: classifying 2019-nCoV and naming it SARS-CoV-2. *Nat Microbiol* 2020, 5(4), 536-544.

Huang, C.; Wang, Y.; Li, X.; Ren, L.; Zhao, J.; Hu, Y.; et al. Clinical features of patients infected with 2019 novel coronavirus in Wuhan, China. *Lancet* 2020, 395(10223), 497-506.

Zhou, F.; Yu, T.; Du, R.; Fan, G.; Liu, Y.; Liu, Z. et al. Clinical course and risk factors for mortality of adult inpatients with COVID-19 in Wuhan, China: a retrospective cohort study. *Lancet* 2020, 395(10229), 1054-1062.

Liu, B.; Li, M.; Zhou, Z.; Guan, X.; Xiang, Y. Can we use interleukin-6 (IL-6) blockade for coronavirus disease 2019 (COVID19)-induced cytokine release syndrome (CRS)? *J Autoimmun* 2020, 111, 102452.

Hirano, T.; Murakami, M. COVID-19: a new virus, but a familiar receptor and cytokine release syndrome. *Immunity* 2020, 52(5), 731-733.

Mahmudpour, M.; Roozbeh, J.; Keshavarz, M.; Farrokhi, S.; Nabipour, I. COVID-19 cytokine storm: the anger of inflammation. *Cytokine* 2020, 133, 155151.

McGonagle, D.; Sharif, K.; O'Regan, A.; Bridgewood, C. The role of cytokines including interleukin-6 in COVID-19 induced pneumonia and macrophage activation syndrome-like disease. *Autoimmun Rev* 2020, 9(6) 102537.

Pan, W. et al. Selected contribution: circadian rhythm of tumor necrosis factor-alpha uptake into mouse spinal cord. *J. Appl Physiol* 2002, 92, 62.

Pan, W.; Kastin, A. J. TNF alpha transport across the blood-brain barrier is abolished in receptor knockout mice. *Exp Neural* 2002, 174, 193-200.

Agorastos, A et al. Circadian rhythmicity, variability and correlation of interleukin-6 levels in plasma and cerebrospinal fluid of healthy men. *Psychoneuroendocrinology* 2014, 44, 71-82

Banks, W. A. et al. Penetration of interleukin-6 across the murine blood-brain barrier. *Neurosci Lett* 1994, 179, 53-56.

Banks, W. A. Diurnal uptake of circulating interleukin-1 alpha by brain, spinal cord, testis and muscle. *Neuroimmunomodulation* 1998, 5, 39-41.

Choy, E. H.; De Benedetti, F.; Takeuchi, T. et al. Translating IL-6 biology into effective treatments. *Nat Rev Rheumatol* 2020, 16, 335-345.

Maric, J.; Ravindran, A.; Mazzurana, L.; Van Acker, A.; Rao, A.; Kokkinou, E.; Ekoff, M.; Thomas, D.; Fauland, A.; Nilsson, G.; Wheelock, L E.; Dahlén, S. E.; Ferreiós, N.; Geisslinger, G.; Friberg, D.; Heinemann, A.; Konya, V.; Mjösberg, J. Cytokine induced endogenous production of prostaglandin D2 is essential for human group 2 innate lymphoid cell activation. *J Allergy Clin Immunol* 2019, 143(6), 2202-2214.e5.

O. Oyesola, O.; Duque, C; Huang, L. C.; Larson E. M.; Früh, S. P.; Webb, L. M.; Peng, S. A.; Tait Wojno, E. D. The Prostaglandin D2 Receptor CRTH2 Promotes IL-33-Induced ILC2 Accumulation in the Lung. *The Journal of Immunology* 2020, 204 (4) 10011011.

Pandey, H. P. et al. Concentration of prostaglandin D2 in cerebrospinal fluid exhibits a circadian alteration in conscious rats. *Biochem Mol Boil Int* 1997, 37, 431-437.

Ram, A. et al. CSF levels of prostaglandins, especially the level of prostaglandin D2, are correlated with increasing propensity towards sleep in rats. *Brain Res* 1997, 751, 81-89.

McNamee, E. N.; Ryan, K. M.; Griffin, E. W.; González-Reyes, R. E.; Ryan, K. J.; Harkin, A.; Connor, T. J. Noradrenaline acting at central beta-adrenoceptors induces interleukin-10 and suppressor of cytokine signaling-3 expression in rat brain: implications for neurodegeneration. *Brain Behav Immun* 2010, 24(4), 660-71.

O'Neill, E.; Harkin, A. Targeting the noradrenergic system for anti-inflammatory and neuroprotective effects: implications for Parkinson's disease. *Neural Regen Res* 2018, 13, 1332-7.

Staedtke, V.; Bai, R. Y.; Kim, K. et al. Disruption of a self-amplifying catecholamine loop reduces cytokine release syndrome. *Nature* 2018, 564, 273-277.

Pan, L.; Dong, L.; Epinephrine use in COVID-19: friend or foe? *Eur J Hosp Pharm* 2021, 28(1), e1.

Ziegler, M. C. et al. Circadian rhythm in cerebrospinal fluid noradrenaline of man and monkey. *Nature* 1976, 264, 656-658.

Manshardt, J.; Wurtman, R. Daily Rhythm in the Noradrenaline Content of Rat Hypothalamus. *Nature* 1968, 217, 574-575.

Reis, D. J.; Wurtman R. J. Diurnal changes in brain noradrenalin. *Life Sciences* 1968, 7(1), 91-98.

Reis, D. J.; Weinbren, M.; Corvelli, A. A circadian rhythm of norepinephrine regionally in cat brain: its relationship to environmental lighting and to regional diurnal variations in brain serotonin. *J. Pharmac. exp. Ther* 1968, 164, 135-145.

Freidman, A. H.; Walker, C. A. Circadian rhythms in rat mid-brain and caudate nucleus biogenic amine levels. *J. Physiol., Lond* 1968, 197, 77-85.

Lew, G. M.; Quay, W. B. The mechanism of circadian rhythms in brain and organ contents of norepinephrine: Circadian changes in the effects of methyltyrosine and 6-hydroxydopamine. *Comp. Gen. Pharmac* 1973, 4, 375-381.

Eleftheriou, B. S.; Circadian rhythm in blood and brain biogenic amines and other biochemical changes in rabbits. *Brain Res* 1974, 75, 145-152.

Mitchell, H. A.; Weinshenker, D. Good night and good luck: norepinephrine in sleep pharmacology. *Biochem Pharmacol* 2010, 79(6), 801-9.

Aston-Jones, G.; Bloom, F. E. Activity of norepinephrine-containing locus coeruleus neurons in behaving rats anticipates fluctuations in the sleep-waking cycle. *J. Neurosci* 1981, 1, 876-86.

Daneman, R.; Prat, A. The blood-brain barrier. *Cold Spring Herb Perspect Biol* 2015, 7, a020412

Abbott, J.; Patabendige, A.; Dolman, D.; Yusof, S.; Begley, D. Structure and function of the blood-brain barrier. *Neurabiol* 2010, 37, 13-25.

King, M. et al. Transport of opioids from the brain to the periphery by P-glycoprotein: peripheral actions of central drugs. *Nat Neurosci* 2001, 4, 268-274.

Loscher, W.; Potschka, H. Blood-brain barrier active efflux transporters: ATP-binding cassette gene family. *NeuroRx* 2005, 2, 86-98.

Kervezee, L et al. Diurnal variation in P-glycoprotein-mediated transport and cerebrospinal fluid turnover in the brain. *Aaps J* 2014, 16, 1029-1037.

Zhang, S. L. et al. A Circadian Clock in the Blood-Brain Barrier Regulates Xenobiotic Efflux. *Cell,* 2018, 173, 139.e10

Hindle, S. J. et al. Evolutionarily Conserved Roles for Blood-Brain Barrier Xenobiotic Transporters in Endogenous Steroid Partitioning and Behavior. *Cell Rep* 2017, 21, 1304-1316.

Baig, A. M. Neurological manifestations in COVID-19 caused by SARS-CoV-2. *Cns Neurosci* 2020, 26, 499-501.

Hoffmann, M. et al. SARS-CoV-2 cell entry depends on ACE2 and TMPRSS2 and is blocked by a clinically proven protease inhibitor. *Cell* 2020, 181, 1-16.

Walls, A. C. et al. Structure, function, and antigenicity of the SARS-CoV-2 spike glycoprotein. *Cell* 2020, 181(2), 281-292.

Hoffmann, M. et al. A multibasic cleavage site in the Spike protein of SARS-CoV-2 is essential for infection of human lung cells. *Molecular Cell* 2020, 78, 1-6.

Mayi, B. S.; Leibowitz, J. A.; Woods, A. T.; Ammon, K. A.; Liu, A. E.; Raja, A. The role of Neuropilin-1 in COVID-19. *PLoS Pathog* 2021, 17(1), e1009153.

Cantuti-Castelvetri, L.; Djha, R.; Pedro, L. D.; Djannatian, M., Franz, J.; Kuivanen, S.; van der Meer, F.; Kallio, K.; Kaya, T.; Anastasina, M.; Smura, T.; Levanov, L.; Szirovicza, L.; Tobi, A.; Kallio-Kokko, H.; Österlund, P.; Joensuu, M.; Meunier, F A.; Butcher, S. J.; Winkler, M. S.; Mollenhauer, B.; Helenius, A.; Gokce, D.; Teesalu, T.; Hepojoki, J.; Vapalahti, D.; Stadelmann, C.; Balistreri, G.; Simons, M. Neuropilin-1 facilitates SARS-CoV-2 cell entry and infectivity. *Science* 2020, 375(6518) 856-860.

Hamming, W. T.; Bulthuis, M. L. C.; Lely, A. T.; Nevis, G. J.; Goor H. Tissue distribution of ACE2 protein, the functional receptor for SARS coronavirus. A first step in understanding SARS pathogenesis. *J. Pathol* 2004, 203 (2), 631-937.

Wang, Y.; Cao, Y.; Mangalam, A. K.; Guo, Y.; LaFrance-Corey, R. G.; Gamez, J. D.; Atanga, P A.; Clarkson, B. D.; Zhang, Y.; Wang, E.; Angom, R. S.; Dutta, K.; Ji, B.; Pirko, I.; Lucchinetti, C. F.; Howe, C. L.; Mukhopadhyay, D. Neuropilin-I modulates interferon-gamma-stimulated signaling in brain microvascular endothelial cells. *J. Cell Sci* 2016, 129 (20), 3911-3921.

Paniz-Mondolfi, A.; Bryce, C.; Grimes, Z.; Gordon, R. E.; Reidy, J.; Lednicky, J.; Sordillo, E. M.; Fawkes, M. Central nervous system involvement by severe acute respiratory syndrome coronavirus-2 (SARS-CoV-2). *J. Med. Virol* 2020, 92(7), 699-702.

Burks, S. M.; Rosas-Hernandez, H.; Alenjandro Ramirez-Lee, M.; Cuevas, E.; Talpos, J. C. Can SARS-CoV-2 infect the central nervous system via the olfactory bulb or the blood-brain barrier? *Brain, Behavior, and Immunity* 2021, S0889-1591(20) 324892

Bleau, C.; Filliol, A.; Samson, M.; Lamontagne, L.; Perlman, S. Brain invasion by mouse hepatitis virus depends on impairment of tight junctions and beta interferon production in brain microvascular endothelial cells. *J. Virol* 2015, 89(19) 98969908.

Cabirac, G. F.; Soike, K. F.; Butunoi, C.; Hoel, K.; Johnson, S.; Cai, G. Y.; Murray, R. S. Coronavirus JHM OMPI pathogenesis in owl monkey CNS and coronavirus infection of owl monkey CNS via peripheral routes. *Adv. Exp. Med. Biol* 1993, 342, 347-352.

Cabirac, G. F.; Soike, K. F.; Zhang, J. Y.; Hoel, K.; Butunoi, C.; Cai, G. Y.; Johnson, S.; Murray R. S. Entry of coronavirus into primate CNS following peripheral infection. Microb. Pathog 1994, 16 (5), 349-357.

Cabirac, G. F.; Murray, R. S.; McLaughlin, L. B.; Skolnick, D. M.; Hogue, B.; Dorovini-Lis, K.; Didier, P. J. In vitro interaction of coronaviruses with primate and human brain microvascular endothelial cells. *Adv. Exp. Med Biol* 1995, 380, 79-88.

Buzhdygan, T. P.; DeOre, B. J.; Baldwin-Leclair, A.; Bullock, T. A.; McGary, H. M.; Khan, J. A.; Razmpour, R.; Hale, J. F.; Galie, P A.; Potula, R.; Andrews, A. M.; Ramirez, S. H. The SARS-CoV-2 spike protein alters barrier function in 2D static and 3D microfluidic in-vitro models of the human blood-brain barrier. *Neurobiol Dis* 2020, Preprint. bioRxiv. 2020; 2020.06.15.150912. Published 2020 Jun. 15. doi:10.1101/2020.06.15.150912

Bellon, M.; Schweblin, C.; Lambeng, N.; Cherpillod, P.; Vazquez, J.; Lalive, P. H.; Schibler, M.; Deffert C. Cerebrospinal fluid features in SARS-CoV-2 RT-PCR positive patients. Clin. Infect. Dis. 2020, ciaa1165. doi:10.1093/cid/ciaa1165.

Alam, S. B.; Willows, S.; Kulka, M.; Sandhu, J. K. Severe acute respiratory syndrome coronavirus 2 may be an underappreciated pathogen of the central nervous system. *European journal of neurology* 2020, 27(11) 2348-2360.

Robinson, C. P.; Busl, K. M. Neurologic Manifestations of Severe Respiratory Viral Contagions. *Crit Care Explor* 2020, 2.

Achar, A.; Ghosh, C. COVID-19-Associated Neurological Disorders: The Potential Route of CNS Invasion and Blood-Brain Barrier Relevance. *Cells* 2020, 9(11), 2360.

Gu, J.; Gong, E.; Zhang, B.; Zheng, J.; Gao, Z.; Zhong, Y.; Zou, W.; Zhan, J.; Wang, S.; Xie, Z.; et al. Multiple organ infection and the pathogenesis of SARS. *J. Exp. Med* 2005, 202, 415-424.

Nicholls, J. M.; Butany, J.; Poon, L. L. M.; Chan, K. H.; Beh, Poutanen, S.; Peiris, J. S. M.; Wong, M. Time course and cellular localization of SARS-CoV nucleoprotein and RNA in lungs from fatal cases of SARS. *PLoS Med.* 2006, 3, e27.

Spiegel, M.; Schneider, K.; Weber, F.; Weidmann, M.; Hufert, F. T. Interaction of severe acute respiratory syndrome-associated coronavirus with dendritic cells. *J. Gen. Virol* 2006, 87, 1953-1960.

Trojanowicz, B.; Ulrich, C.; Kohler, F.; Bode, V.; Seibert, E.; Fiedler, R.; Girndt, M. Monocytic angiotensin-converting enzyme 2 relates to atherosclerosis in patients with chronic kidney disease. *Nephrol. Dial. Transplant* 2017, 32, 287-298.

Sankowski, R.; Mader, S.; Valdés-Ferrer, S. I. Systemic Inflammation and the Brain: Novel Roles of Genetic, Molecular, and Environmental Cues as Drivers of Neurodegeneration. *Front. Cell Neurosci* 2015, 9, 28.

Pennisi, M.; Lanza, G.; Falzone, L.; Fisicaro, F.; Ferri R., Bella, R. SARS-CoV-2 and the Nervous System: From Clinical Features to Molecular Mechanisms. *Int J Mol Sci* 2020, 2(15), 5475.

Mehta, P.; McAuley, D. F.; Brown, M.; Sanchez, E.; Tattersall, R. S.; Manson, J. J.; HLH Across Specialty Collaboration, UK. COVID-19: Consider cytokine storm syndromes and immunosuppression. *Lancet Land. Engl* 2020, 395, 1033-1034.

Steardo, L.; Steardo, L. Jr.; Zorec, R.; Verkhratsky, A. Neuroinfection may contribute to pathophysiology and clinical manifestations of COVID-19. *Acta Physiol. Oxt* 2020, 229, e13473.

Varatharaj, A.; Galea I. The blood-brain barrier in systemic inflammation. *Brain Behav. Immun* 2017, 60, 1-12.

Koh, L., Zakharov, A., Johnston, M. Integration of the subarachnoid space and lymphatics: is it time to embrace a new concept of cerebrospinal fluid absorption? *Cerebrospinal fluid research* 2005, 2(1), 6.

Cserr, H. F.; Knopf, P. M. Cervical lymphatics, the blood-brain barrier and the immunoreactivity of the brain: a new view. *Immunology today* 1992, 13 (12), 507-512

Bradbury, M. Lymphatics and the central nervous system. *Trends In Neurosciences* 1981, 4, 100-101.

Ma, Q.; Ries, M.; Decker, Y.; Muller, A.; Riner, C.; "ucker, A. B.; Fass" bender, K.; Detmar, M.; Proulx S. T. Rapid lymphatic efflux limits cerebrospinal fluid flow to the brain. *Acta neuropathological* 2019, 137(1), 151-165.

Weller, R. O.; Kida, S.; Zhang, E. T. Pathways of fluid drainage from the brain-morphological aspects and immunological significance in rat and man. *Brain pathology* 1992, 2(4), 277-284.

Kida, S.; Pantazis, A.; Weller, R. Csf drains directly from the subarachnoid space into nasal lymphatics in the rat. anatomy, histology and immunological significance. *Neuropathology and applied neurobiology* 1993, 19(6), 480-488.

Johnston, M.; Zakharov, A.; Papaiconomou, C.; Salmasi, G.; Armstrong, D. Evidence of connections between cerebrospinal fluid and nasal lymphatic vessels in humans, non-human primates and other mammalian species. *Cerebrospinal fluid research* 2004, 1 (1), 2.

De Leon, M A; Li, Y.; Okamura, N.; Tsui, W. H.; Saint-Louis, L. A.; Glodzik, L.; Osorio, R. S.; Fortea, J.; Butler, T.; Pirraglia E. et al. Cerebrospinal fluid clearance in Alzheimer's disease measured with dynamic pet. *Journal of Nuclear Medicine* 2017, 58 (9), 1471-1476.

Butowt, R.; Christopher S. B. Anosmia in COVID-19: Underlying Mechanisms and Assessment of an Olfactory Route to Brain Infection. *Neuroscientist* 2020, 11:1073858420956905. doi:10.1177/1073858420956905.

Aragao, M. d. F. V. V.; Leal, M.; Cartaxo Filho, O.; Fonseca, T.; Valenc., M. Anosmia in covid-19 associated with injury to the olfactory bulbs evident on mri. *American Journal of Neuroradiology* 2020, 41(9), 1703-1706.

Baig, A. M.; Khaleeq, A.; Ali, U.; Syeda, H. Evidence of the covid-19 virus targeting the CNS: tissue distribution, host-virus interaction, and proposed neurotropic mechanisms. *ACS chemical neuroscience* 2020, 11(7), 995-998.

Briguglio, M.; Bona, A.; Porta, M.; Dell'Osso, B.; Pregliasco, F. E.; Banfi, G. Disentangling the hypothesis of host dysosmia and sars-cov 2: The bait symptom that hides neglected neurophysiological routes. *Frontiers in Physiology* 2020, 11, 671.

Gilani, S.; Roditi, R.; Naraghi, M. Covid-19 and anosmia in tehran, iran. *Medical Hypotheses* 2020, 109757.

Karimi-Galougahi, M.; Yousefi-Kama, A.; Bakhshayeshkaram, M.; Raad, N.; Haseli, S. 18fdg pet/ct scan reveals hypoactive or bitofrontal cortex in anosmia of covid-19. *Academic Radiology* 2020, 27(7):1042-1043.

Beeraka, N. M.; Sadhu, S. P.; Madhunapantula, S. V.; Pragada, R. R.; Svistunov, A. A.; Nikolenko, V. N.; Mikhaleva, L. M.; Aliev, G. Strategies for targeting sars cov-2: Small molecule inhibitors—the current status. *Frontiers in immunology* 2020.

Chassidim, Y. et al. Quantitative imaging assessment of blood-brain barrier permeability in humans. *Fluids Barriers CNS* 2013, 10, 9.

Heye, A. K.; Culling, R. D.; Váldes Hernández, M. C.; Thrippleton, M. J.; Wardlaw, J. M. Assessment of blood-brain barrier disruption using dynamic contrast-enhanced MRI. A systematic review. *NeuroImage Clin.* 2014, 6, 262-274.

Neuwelt, E. A. et al. Osmotic blood-brain barrier disruption. Computerized tomographic monitoring of chemotherapeutic agent delivery. *J. Clin. Invest* 1979, 64, 684-688.

Roman-Goldstein, S. et al. Osmotic blood-brain barrier disruption: CT and radionuclide imaging. *AJNR Am. J. Neuroradiol* 1994, 15, 581-590.

Rogosnitzky, M.; Branch, S. Gadolinium-based contrast agent toxicity: a review of known and proposed mechanisms. *Biometals* 2016, 29, 365-376.

Kaller, M. O.; An, J. Contrast Agent StatPearls [Internet]. Toxicity. [Updated 2020 May 25]. In: Treasure Island (FL): StatPearls Publishing; 2020 Jan.www.ncbi.nlm.nih.gov/books/NBK537159/

Elbeshlawi, I.; AbdelBaki, M. S. Safety of gadolinium administration in children. *Pediatr Neurol* 2018, 86, 17-32.

Perazella, M. A. Gadolinium-contrast toxicity in patients with kidney disease: nephrotoxicity and nephrogenic systemic fibrosis. *Curr Drug. Saf.* 2008, 3, 67-75.

Semyachkina-Glushkovskaya, O. et al. Phenomenon of music-induced opening of the blood-brain barrier in healthy mice. *Proceeding in the Royal Society B* 2020, 287, 20202337.

Semyachkina-Glushkovskaya, O.; Chehonin, V.; Borisova, E.; Fedosov, I.; Namykin, A.; Abdurashitov, A.; Shirokov, A.; Khlebtsov, B.; Lyubun, Y.; Navolokin, N.; et al. Photodynamic opening of the blood-brain barrier and pathways of brain clearing. *J. Biophotonics* 2018, 11, e201700287.

Lipsman, N.; Meng, Y.; Bethune, A. J.; Huang, Y.; Lam, B.; Masellis, M.; Herrmann, N.; Heyn, C.; Aubert, I.; Boutet, A.; et al. Blood-brain barrier opening in Alzheimer's disease using MR-guided focused ultrasound. *Nat. Commun* 2018, 9, 1-8.

Jordão, J. F.; Thévenot, E.; Markham-Coultes, K.; Scarcelli, T.; Weng, Y. Q.; Xhima, K.; O'Reilly, M.; Huang, Y.; McLaurin, J.; Hynynen, K.; et al. Amyloid-β plaque reduction, endogenous antibody delivery and glial activation by brain-targeted, transcranial focused ultrasound. *Exp. Neurol* 2013, 248, 16-29.

Leinenga, G.; Götz, J. Scanning ultrasound removes amyloid-β and restores memory in an Alzheimer's disease mouse model. *Sci Transl. Med* 2015, 7, 278ra33.

Burgess, A.; Dubey, S.; Yeung, S.; Hough, O.; Eterman, N.; Aubert, I; Hynynen, K. Alzheimer disease in a mouse model: MR imaging-guided focused ultrasound targeted to the hippocampus opens the blood-brain barrier and improves pathologic abnormalities and behavior. *Radiology* 2014, 273, 736-745.

Xie, L.; Kang, H.; Xu, Q.; Chen, M. J.; Liao, Y.; Thiyagarajan, M.; O'Donnell, J.; Christensen, D. J.; Nicholson, C.; Iliff, J. J.; et al. Sleep drives metabolite clearance from the adult brain. *Science* 2013, 342, 373-377.

Fultz, N E; Bonmassar, G.; Setsompop, K.; Stickgold, R. A.; Rosen, B. R.; Polimeni, J. R.; Lewis, L. D. Coupled electrophysiological, hemodynamic, and cerebrospinal fluid oscillations in human sleep. *Science* 2019, 366, 628-631.

Pavlov, A.; Dubrovsky, A.; Koronovskii, A., Jr.; Pavlova, O.; Semyachkina-Glushkovskaya, O.; Kurths, J. Extended detrended fluctuation analysis of sound-induced changes in brain electrical activity. *Chaos Solitons Fractals* 2020, 139, 109989.

Pavlov, A.; Dubrovsky, A.; Koronovskii, A., Jr.; Pavlova, D.; Semyachkina-Glushkovskaya, D.; Kurths, J. Extended detrended fluctuation analysis of electroencephalograms signals during sleep and the opening of the blood-brain barrier. *Chaos Interdiscip. J. Nonlinear Sci* 2020, 30, 073138.

Hablitz, L. M.; Vinitsky, H. S.; Sun, Q.; Stager, F. F.; Sigurdsson, B.; Mortensen, K. N.; Lilius, T. D.; Nedergaard, M. Increased glymphatic influx is correlated with high EEG delta power and low heart rate in mice under anesthesia. *Sci. Adv* 2019, 5, eaav5447.

Kiviniemi, V.; Korhonen, V.; Kortelainen, J.; Rytky, S.; Keinänen, T.; Tuovinen, T.; Isokangas, M.; Sonkajärvi, E.; Siniluoto, T.; Nikkinen, J.; et al. Real-time monitoring of human blood-brain barrier disruption. *PLoS ONE* 2017, 12, e0174072.

Shuvaev, A.; Kuvacheva, N.; Morgun, A.; Khilazheva, E.; Salmina, A. The Role of Ion Channels Expressed in Cerebral Endothelial Cells in the Functional Integrity of the Blood-Brain Barrier (Review). *Sovrem. Tehnol. V Med* 2016, 8, 241-250.

Callies, C.; Fels, J.; Liashkovich, I.; Kliche, K.; Jeggle, P.; Kusche-Vihrog, K.; Oberleithner, H. Membrane potential depolarization decreases the stiffness of vascular endothelial cells. *J. Cell Sci* 2011, 124, 1936-1942.

Vanhatalo, S.; Voipio, J.; Kaila, K. Infraslow. EEG activity. In *Niedermeyer's Electroencephalography: Basic Principles, Clinical Applications, and Related Fields*; Walter Kluwer/Lippincott Williams & Wilkins: Philadelphia Pa., USA 2011, 741-747.

Woody, C.; Marshall, W.; Besson, J.; Thompson, H.; Aleonard, P.; Albe-Fessard, D. Brain potential shift with respiratory acidosis in the cat and monkey. *Am. J. Physiol. Leg Content* 1970, 218, 275-283.

Revest, P A.; Jones, H. C.; Abbott, N. J. The transendothelial DC potential of rat blood-brain barrier vessels in situ. In *Frontiers in Cerebral Vascular Biology*; Springer Berlin/Heidelberg, Germany, 1993, 71-74.

Revest, P A.; Jones, H. C.; Abbott, N. J. Transendothelial electrical potential across pial vessels in anaesthetised rats: A study of ion permeability and transport at the blood-brain barrier. *Brain Res* 1994, 652, 76-82

Monto, S.; Palva, S.; Voipio, J.; Palva, J. M. Very slow EEG fluctuations predict the dynamics of stimulus detection and oscillation amplitudes in humans. *J. Neurosci* 2008, 28, 8268-8272.

Hiltunen, T.; Kantola, J.; Abou Elseoud, A.; Lepola, P.; Suominen, K.; Starck, T.; Nikkinen, J.; Remes, J.; Tervonen, D.; Palva, S.; et al. Infra-slow EEG fluctuations are correlated with resting-state network dynamics in fMRI. *J. Neurosci* 2014, 34, 356-382.

Brackett, A. T.; Kane, G. A.; Monari, P. K.; Briones, B. A.; Vigneron, P. A.; Barber, G. A.; Bermudez, A.; Dieffenbach, U.; Kloth, A. D.; Buschman, T. J.; et al. Evidence supporting a role for astrocytes in the regulation of cognitive flexibility and neuronal oscillations through the Ca2+ binding protein S100β. *PLoS ONE* 2018, 13, e0195726.

Bellot-Saez, A.; Cohen, G.; van Schaik, A.; Ooi, L.; Morley, J. W.; Buskila, Y. Astrocytic modulation of cortical oscillations. *Sci Rep* 2018, 8, 1-13. [CrossRef].

Henneberger, C.; Papouin, T.; Oliet, S. H.; Rusakov, D. A. Long-term potentiation depends on release of D-serine from astrocytes. *Nature* 2010, 463, 232-236.

Takata, N.; Mishima, T.; Hisatsune, C.; Nagai, T.; Ebisui, E.; Mikoshiba, K.; Hirase, H. Astrocyte calcium signaling transforms cholinergic modulation to cortical plasticity in vivo. *J. Neurosci.* 2011, 31, 18155-18165.

Bellesi, M.; de Vivo, L.; Tononi, G.; Cirelli, C. Effects of sleep and wake on astrocytes: Clues from molecular and ultrastructural studies. *BMC Biol.* 2015, 13, 66.

Semyachkina-Glushkovskaya, O.; Postnov, D.; Penzel, T.; Kurths, J. Sleep as a Novel Biomarker and a Promising Therapeutic Target for Cerebral Small Vessel Disease: A Review Focusing on Alzheimer's Disease and the Blood-Brain Barrier. *Int. J. Mol Sci.* 2020, 21, 6293.

Sleep is associated with development of immune memory, and lack of sleep may impair the ability of the immune system to effectively produce a long-lasting immunity after vaccination. Hurtado-Alvarado, Gabriela, Lenin Pavón, Stephanie Ariadne Castillo-García, María Eugenia Hernández, Emilio Domínguez-Salazar, Javier Velázquez-Moctezuma, and Beatriz Gómez-González. "Sleep loss as a factor to induce cellular and molecular inflammatory variations." Clinical and Developmental Immunology 2013 (2013); Irwin, Michael. "Effects of sleep and sleep loss on immunity and cytokines." Brain, behavior, and immunity 16, no. 5 (2002): 503-512; Opp, Mark R. "Cytokines and sleep." Sleep medicine reviews 9, no. 5 (2005): 355-384. Sleep alters cytokine profiles, and cytokines are associated with an effective response to vaccination; Krueger, James M. "The role of cytokines in sleep regulation." Current pharmaceutical design 14, no. 32 (2008): 3408-3416; García-Piñeres, Alfonso, Allan Hildesheim, Lori Dodd, Troy J. Kemp, Marcus Williams, Clayton Harro, Douglas R. Lowy, John T. Schiller, and Ligia A. Pinto. "Cytokine and chemokine profiles following vaccination with human papillomavirus type 16 L1 virus-like particles." Clinical and Vaccine Immunology 14, no. 8 (2007): 984-989; Morel, Penelope A., and Michael S. Turner. "Designing the optimal vaccine: the importance of cytokines and dendritic cells." The open vaccine journal 3 (2010): 7; De Rosa, Stephen C., Fabien X. Lu, Joanne Yu, Stephen P. Perfetto, Judith Falloon, Susan Moser, Thomas G. Evans, Richard Koup, Christopher J. Miller, and Mario Roederer. "Vaccination in humans generates broad T cell cytokine responses." The Journal of Immunology 173, no. 9 (2004): 5372-5380; Voderholzer, Ulrich, Bernd L. Fiebich, Rick Dersch, Bernd Feige, Hannah Piosczyk, Marta Kopasz, Dieter Riemann, and Klaus Lieb. "Effects of sleep deprivation on nocturnal cytokine concentrations in depressed patients and healthy control subjects." The Journal of Neuropsychiatry and Clinical Neurosciences 24, no. 3 (2012): 354-366; Irwin, Michael. "Effects of sleep and sleep loss on immunity and cytokines." Brain, behavior, and immunity 16, no. 5 (2002): 503-512.

Long-term immunity to COVID may be adversely impacted by cytokine storms, and poor sleep may increase the incidence of such cytokine storms. Mangalmurti, Nilam, and Christopher A. Hunter. "Cytokine storms: understanding COVID-19." Immunity (2020); Zheng, Yunfeng, Renfeng Li, and Shunai Liu. "Immunoregulation with mTOR inhibitors to prevent COVID-19 severity: A novel intervention strategy beyond vaccines and specific antiviral medicines." Journal of medical virology 92, no. 9 (2020): 1495-1500; Schijns, Virgil, and Ed C. Lavelle. "Prevention and treatment of COVID-19 disease by controlled modulation of innate immunity." European journal of immunology 50, no. 7 (2020): 932-938; Silva, Flavia Rodrigues da, Renato de Carvalho Guerreiro, Henrique de Araújo Andrade, Eduardo Stieler, Andressa Silva, and Marco Túlio de Mello. "Does the compromised sleep and circadian disruption of night and shiftworkers make them highly vulnerable to 2019 coronavirus disease (COVID-19)?" Chronobiology international 37, no. 5 (2020): 607-617; Kempuraj, Duraisamy, Govindhasamy Pushpavathi Selvakumar, Mohammad Ejaz Ahmed, Sudhanshu P. Raikwar, Ramasamy Thangavel, Asher Khan, Smith A. Zaheer et al. "COVID-19, mast cells, cytokine storm, psychological stress, and neuroinflammation." The Neuroscientist 26, no. 5-6 (2020): 402-414; Skibinski, David A G, Leigh Ann Jones, Yuan O. Zhu, Lin Wu Xue, Bijin Au, Bernett Lee, Ahmad Nazri Mohamed Naim et al. "Induction of human T-cell and cytokine responses following vaccination with a novel influenza vaccine." Scientific reports 8, no. 1 (2018):1-12.

There are at present three approved vaccines for COVID-19 in the LIS: Pfizer-BioNTech COVID-19 vaccine. The Pfizer-BioNTech COVID-19 vaccine, which requires two injections given 21 days apart. The second dose can be given up to six weeks after the first dose, if needed; the Moderna COVID-19 vaccine, which requires two injections given 28 days apart. The second dose can be given up to six weeks after the first dose, if needed; and Janssen/Johnson 9 Johnson COVID-19 vaccine, which requires a single dose. www-.mayoclinic.org/diseases-conditions/coronavirus/in-depth/coronavirus-vaccine/art-20484859;

Germinal centers are structures induced within the lymph nodes and spleens during infection or vaccination. In them, B cells, the immune cells that produce antibodies, mature to become long-lived "memory" cells. This process, along with controlled mutations in antibody genes, allows the immune system to select for and immortalize B cells that make the best antibodies against a particular pathogen. This creates a life-long "memory" of a pathogen which allows the body to quickly and effectively identify and attack the pathogen in the case of re-infection. Without germinal centers, there aren't enough B cells that can create a high-quality antibody response to produce long-term immunity. To form germinal centers, B cells depend on key support from another specialized type of cell called a helper T cell. In COVID-19 patients, the specialized type of helper T cell does not develop, and as a consequence B cells are not helped in the right way. A study found no germinal centers in acutely ill patients. Previous studies with infectious disease in mice have shown that high levels of cytokines, small signaling molecules unique to the immune system, can prevent the formation of these helper T cells and therefore of germinal centers. Large amounts of TNF, in particular, prevented germinal center formation. Severe COVID-19 cases were found to have massive amounts of TNF in the location where germinal centers would normally form. Lack of germinal centers has been observed in other diseases, including SARS, and does not mean there is no immune response. This finding would likely not affect vaccine-induced immunity, as vaccines do not induce cytokine storms. A vaccine-induced immune response would likely include the development of a germinal center, and the ensuing creation and immortalization of high-quality antibodies that would provide long-lasting protecting against COVID-19. See, Naoki Kaneko et al. Loss of Bcl-6-expressing T follicular helper cells and germinal centers in COVID-19. Cell, S0092-8674(20)31067-9, DOI: doi.org/10.1016/j.cell. 2020.08.0251; Massachusetts General Hospital, "Long-Term COVID-19 Immunity May Be Prevented by Cytokine Storms", Aug. 20, 2020, www.technologynetworks.com/immunology/news/long-term-covid-19-immunity-may-be-prevented-by-cytokine-storms-338817; Ciabattini, Annalisa, Paolo Garagnani, Francesco Santoro, Rino Rappuoli, Claudio Franceschi, and Donata Medaglini. "Shelter from the cytokine storm: pitfalls and prospects in the development of SARS-CoV-2 vaccines for an elderly population." In Seminars in immunopathology, pp. 1-16. Springer Berlin Heidelberg, 2020.

The ability of cytokines to steer CD4+ Th cell responses toward a Th1 or Th2 phenotype and enhance the magnitude of both CD8+ cytotoxic T lymphocytes (CTL) and antibody responses has clearly been demonstrated. There is an essential role for CD4+ Th1 helper cell induction and IFN-γ production in protection from viral challenge. Complete protection from viral challenge is achieved when the triple combination of exogenous cytokines granulocyte macrophage colony stimulating factor (GM-CSF), IL-12 and tumor necrosis factor (TNF)-α are co-administered with a peptide vaccine. In vivo depletion of CD4+ cells or immunization of IFN-γ-deficient mice abrogates protection. GM-CSF, IL-12 and TNF-α also synergize for the enhanced induction of CTL; however, adoptive transfer of a CD8+ CTL line afforded only partial protection in this viral challenge model. As a possible mechanism of in vivo protection we show that GM-CSF increases the percentage and activity of antigen-presenting dendritic cells in draining lymph nodes where the immune response is initiated. A synergy has been demonstrated between IL-12 and the proinflammatory cytokine TNF-α in driving IFN-γ production. Thus, a combination of IL-12 and TNF-α is essential for the optimal development of Th1 responses and help for CTL induction in BALB/c mice, and is complemented by a third cytokine, GM-CSF, which enhances antigen presentation. Jeffrey D. Ahlers, Igor M. Belyakov, So Matsui, Jay A. Berzofsky, Mechanisms of cytokine synergy essential for vaccine protection against viral challenge, International Immunology, Volume 13, Issue 7, July 2001, Pages 897-908, doi.org/10.1093/intimm/13.7.897.

COVID vaccines are standardized products, and are administered according to standardized protocol. Therefore, it is critical that recipients of vaccines be properly primed for receiving the vaccination, as no adaptive protocols are approved for handling exceptional cases. Further, the incidence of side effects such as coagulopathies may depend on the immune status of a vaccine recipient at the time of administration. It is therefore important to standardize response of patients to the standardized COVID vaccine. The present technology helps to normalize immune response so that the vaccination response will be more uniform, reducing the need for testing and protocol modifications.

Sleep disorders affect a significant portion of the adult population. Between 50 and 70 million adults in the U.S. have a sleep disorder. (Ohayon M. M. Epidemiology of insomnia: what we know and what we still need to learn. Sleep medicine reviews. 2002; 6(2):97-111.) Insomnia is the most common specific sleep disorder, with short-term issues reported by about 30% of adults and chronic insomnia by 10%. (Kessler R C, Berglund P A, Coulouvrat C, et al. Insomnia and the performance of US workers: results from the America insomnia survey. Sleep. 2011; 34(9):1161-1171; Sateia M J, Doghramji K, Hauri P J, Morin C M. Evaluation of chronic insomnia. An American Academy of Sleep Medicine review. Sleep. 2000; 23(2):243-308.) Chronic insomnia is associated with deterioration of memory, adverse effects on endocrine functions and immune responses, and an increase in the risk of obesity and diabetes Sateia et al. 2000; Taylor D J, Mallory L J, Lichstein K L, Durrence H H, Riedel B W, Bush A J. Comorbidity of chronic insomnia with medical problems. Sleep. 2007; 30(2):213-218). While at any age, managing insomnia is a challenge, it is especially a critical condition in the elderly due to age-related increases in comorbid medical conditions and medication use, as well as age-related changes in sleep structure, which shorten sleep time and impair sleep quality. (Ancoli-Israel S. Insomnia in the elderly: a review for the primary care practitioner. Sleep. 2000; 23:S23-30; discussion S36-28; Buysse D J. Insomnia, depression, and aging. Assessing sleep and mood interactions in older adults. Geriatrics (Basel, Switzerland). 2004; 59(2):47-51; quiz 52.) As a result, decreased sleep quality is one of the most common health complaints of older adults. Medications are widely prescribed for relief from insomnia. However, sleep-promoting agents, such as hypnotic drugs, can produce adverse effects, particularly in the elderly. (Sateia M J, Buysse D J, Krystal A D, Neubauer D N. Adverse Effects of Hypnotic Medications. J Clin Sleep Med. Jun. 15, 2017; 13(6):839.) Even natural supplements, such as melatonin, can cause some side effects, including headache, depression, daytime sleepiness, dizziness, stomach cramps, and irritability. (Buscemi N, Vandermeer B, Hooton N, et al. The efficacy and safety of exogenous melatonin for primary sleep disorders a meta-analysis. Journal of general internal medicine. 2005; 20(12):1151-1158.)

Aside from the general deterioration of sleep quality with age in adult population, the deterioration in quantity and quality of the slow-wave sleep (SWS), which is non-REM deep sleep, is particularly troubling. (Roth T. Slow wave sleep: does it matter? Journal of clinical sleep medicine: JCSM: official publication of the American Academy of Sleep Medicine. 2009; 5(2 Suppl):S4). SWS plays an important role in cerebral restoration and recovery in humans. Studies have shown that a 15% reduction in the amounts of SWS and increased number and duration of awakenings are associated with normal aging. (Chinoy E D, Frey D J, Kaslovsky D N, Meyer F R Wright Jr K R Age-related changes in slow wave activity rise time and NREM sleep EEG with and without zolpidem in healthy young and older adults. Sleep medicine. 2014; 15(9):1037-1045.) Experimental disruption of SWS have been shown to increase shallow sleep, sleep fragmentation, daytime sleep propensity, and impair daytime function. (Dijk D J. Regulation and functional correlates of slow wave sleep. J Clin Sleep Med. Apr. 15 2009; 5(2 Suppl):S6-15; Restoring Deep, Slow Wave Sleep to Enhance Health and Increase Lifespan, nutritionreview.org/2014/07/restoring-slow-wave-sleepshown-enhance-health-increase-lifespan/(2014)). Given that SWS contributes to sleep continuity, enhancement of SWS may lead to improvements in sleep quality and daytime function in patients with insomnia and the elderly. Furthermore, accumulating evidence point to the SWS is the time when short-term memory is consolidated into long-term memory. (Born J. Slow-wave sleep and the consolidation of long-term memory. The World Journal of Biological Psychiatry. 2010; 11(supl):16-21.) Recent research connects the deterioration of the SWS with early onset of Alzheimer's disease and other forms of dementia. (Petit D, Gagnon J-F, Fantini M L, Ferini-Strambi L, Montplaisir J. Sleep and quantitative EEG in neurodegenerative disorders. Journal of psychosomatic research. 2004; 56(5):487-496; McCurry S M, Ancoli-Israel S. Sleep dysfunction in Alzheimer's disease and other dementias. Current treatment options in neurology. 2003; 5(3):261-272). It is also suggested that the loss of SWS stage may play a role in these debilitating age-related diseases. (Mattis J, Sehgal A. Circadian rhythms, sleep, and disorders of aging. Trends in Endocrinology 9 Metabolism. 2019; 27(4):192-203). Unfortunately, most standard sleeping pills, while alleviating insomnia, do little to improve the SWS. (Walsh J K. Enhancement of slow wave sleep: implications for insomnia. Journal of clinical sleep medicine: JCSM: official publication of the American Academy of Sleep Medicine. 2009; 5(2 Suppl):S27.) Some evidence suggests that some hypnotic drugs change the structure of sleep, adversely affecting the SWS (Sateia et al. (2017); Walsh (2009). Hence, there is an unmet need for non-pharmacological techniques for promoting sleep, particularly, the deep non-REM sleep stage (SWS) lacking in the elderly population.

Between 50 and 70 million adults in the U.S. have a sleep disorder. Insomnia is the most common specific sleep disorder, with short-term issues reported by about 30% of adults and chronic insomnia by 10%. (Kessler et al. (2011), Sateia et al. (2000), Ancoli-Israel et al. (2000), Ancoli-Israel S, Roth T. Characteristics of insomnia in the United States: results of the 1991 National Sleep Foundation Survey. I. Sleep. 1999; 22:S347-353.). Chronic insomnia is associated with deterioration of memory, adverse effects on endocrine functions and immune responses, and an increase in the risk of obesity and diabetes. (Sateia et al. (2000)).

There is a deterioration of the slow-wave sleep (SWS) in the elderly. Aside from the general deterioration of sleep quality with age in the adult population, the deterioration in quantity and quality of the slow-wave sleep (SWS), which is the deep non-REM sleep, is particularly troubling. (Roth (2009)). SWS plays an important role in cerebral restoration and recovery in humans. It is the most prominent EEG event during sleep and appears as spontaneous large oscillations of the EEG signal occurring approximately once every second in the deepest stage of non-REM sleep. (Achermann P, Dijk D-J, Brunner D P, Borbély A A. A model of human sleep homeostasis based on EEG slow-wave activity: quantitative comparison of data and simulations. Brain research bulletin. 1993; 31(1-2):97-113.) Studies have shown that a significant decrease (~15% reduction) in the amounts of SWS and increased number and duration of awakenings are associated with normal aging. (Chinoy et al. (2014)). Given that SWS contributes to sleep continuity and experimental disruption of SWS increases shallow sleep and sleep fragmentation, enhances daytime sleep propensity, and impairs daytime function. (Dijk (2009); NutritionReview.org (2014)), enhancement of SWS may lead to improvements in sleep maintenance and daytime function in patients with insomnia and in the elderly. Furthermore, accumulating evidence point to the SWS as the time when short-term memory is consolidated into long-term memory. (Born (2010)). Recent research connects the deterioration of the SWS with early onset of Alzheimer's disease and other forms of dementia. (Petit et al. (2010); McCurry et al. (2003)). It is also suggested that the loss of SWS stage may be the culprit for these debilitating age-related diseases. (Mattis et al. (2016)).

One proposed strategy to enhance deep sleep non-pharmacologically is to stimulate the brain with light, sound, electrical currents, or magnetic fields based on artificial and synthetic stimulation paradigms. Intermittent transcranial direct-current stimulation (tDCS) applied at 0.75 Hz for 5-min intervals separated by 1-min off periods after SWS onset can increase the EEG power in the slow oscillation band (<1 Hz) during the stimulation-free intervals. (Lang N, Siebner H R, Ward N S, et al. How does transcranial DC stimulation of the primary motor cortex alter regional neuronal activity in the human brain? European Journal of Neuroscience. 2005; 22(2):495-504; Marshall L, Helgadottir H, Molle M, Born J. Boosting slow oscillations during sleep potentiates memory. Nature. Nov. 30, 2006; 444(7119):610-613). Similarly, stimulated by tDCS at the beginning of SWS accelerate the SWA homeostatic decay in subjects. (Reato D, Gasca F, Datta A, Bikson M, Marshall L, Parra L B. Transcranial electrical stimulation accelerates human sleep homeostasis. PLoS Burnout Biol. 2013; 9(2): e1002898). Furthermore, slow waves can be triggered by directly perturbing the cortex during non-REM sleep using transcranial magnetic stimulation (TMS). (Massimini M, Ferrarelli F, Esser S K, et al. Triggering sleep slow waves by transcranial magnetic stimulation. Proc Natl Acad Sci USA. May 15, 2007; 104(20):8496-8501). Other research has focused on the possibility of inducing slow waves in a more physiological natural manner. In a larger study in healthy adults, bilateral electrical stimulation of the vestibular apparatus shortened sleep onset latency in comparison to sham nights where no stimulation was provided. (Krystal A D, Zammit G K, Wyatt J K, et al. The effect of vestibular stimulation in a four-hour sleep phase advance model of transient insomnia. J Clin Sleep Med. Aug. 15 2010; 6(4): 315-321). The effect of somatosensory and auditory stimulation was also assessed (Krystal et al. 2010; Ngo H V, Martinetz T, Born J, Molle M. Auditory closed-loop stimulation of the sleep slow oscillation enhances memory. Neuron. May 8, 2013; 78(3):545-553). While the change observed with somatosensory stimulation was minor, acoustic stimulation was particularly efficacious in enhancing sleep slow waves. Specifically, using an intermittent stimulation, in which tones were played in blocks of 15 s spaced out by stimulation-free intervals, slow waves appeared remarkably large and numerous during the stimulation blocks. (Tononi G, Riedner B, Hulse B, Ferrarelli F, Sarasso S. Enhancing sleep slow waves with natural stimuli. Medicamundi. 2010; 54(2):73-79; Bellesi M, Riedner B A, Garcia-Molina G N, Cirelli C, Tononi G. Enhancement of sleep slow waves: underlying mechanisms and practical consequences. Frontiers in systems neuroscience. 2014; 8:208). In addition, high-density EEG studies (hdEEG, 256 channels) showed that the morphology, topography, and traveling patterns of induced slow waves were indistinguishable from those of spontaneous slow waves observed during natural sleep. A recent study found that EEG SWA increased following tone presentation during non-REM sleep (Arzi A, Shedlesky L, Ben-Shaul M, et al. Humans can learn new information during sleep. Nature neuroscience. 2012; 15(10):1460), and slow oscillation activity (0.5-1 Hz) was increased in response to continuous acoustic stimulation at 0.8 Hz starting 2 min before lights were turned off and lasting for 90 min. (Ngo H V, Claussen J C, Born J, Molle M. Induction of slow oscillations by rhythmic acoustic stimulation. J Sleep Res. February 2013; 22(1):22-31). Unlike the previous neurostimulation methods with artificial and synthetic stimulation paradigms, the present stimulation protocol uses source-derived waveforms, extracted from the indigenous brain activity EEG recordings of the healthy subjects, processed by statistical methods (e.g., principal component analysis, independent component analysis (Ungureanu M, Bigan C, Strungaru R, Lazarescu V. Independent component analysis applied in biomedical signal processing. Measurement Science Review. 2004; 4(2):18) or spatial principal component analysis, autocorrelation, etc.), which separates components of brain activity. These separated brain EEG activities are then modified or modulated and subsequently inverted and used for transcranial Endogenous Sleep-Derived stimulation (tESD). The application of endogenous brain waveform should not only retain the efficacy in triggering SWS but also alleviate the safety concerns that are associated with long-term brain stimulation using synthetic paradigms.

A vaccination seeks to induce an immune response that prevents or substantially abates clinical impact of infection. Immune response includes both cellular and humoral immunity.

Even the best vaccines do not work for everyone. Although vaccine efficacy depends heavily an vaccine-related factors, characteristics of the vaccinated also matter. Psychological, social, and behavioral factor's can substantially affect the immune system's vaccine response. Our lab spearheaded this line of research in the early 1990's with the initial observation that psychological factors shaped the antibody responses to vaccines, even in young and healthy people (Glaser, R., Kiecolt-Glaser, J. K. (2005). Stress-induced immune dysfunction: Implications for health. Nature Reviews Immunology, 5(3), 243-251.). Since than, studies have helped to clarify the psychological factors and poor health behaviors that increase the risk of non-responsiveness to vaccines. We will review these findings and discuss their relevance to the COVID-19 pandemic, following a brief summary of the immune system's multifaceted response to vaccines.

All vaccines challenge the immune system. Inflammatory markers rise within hours of vaccination—thanks to the immediate and nonspecific innate immune response which can produce side affects such as lethargy, malaise, and irritability. As the first prong of the immune response, the inflammatory response usually lasts a few days but can be prolonged in some individuals, such as these who are depressed. The adaptive immune system mounts the second prong of the immune response. It targets unique vaccine components and therefore takes longer to launch. Vaccines are designed to give the adaptive immune system a lasting memory of viral or bacterial components so that it can quickly and effectively respond when confronted with the actual pathogens. The adaptive immune system responds to the vaccine through (a) T cell multiplication, which can be programmed to identify and kill cells that contain the pathogen (i.e., the cell-mediated response), and (b) B cell production of antibodies, or proteins that neutralize viruses and bacteria.

One critical factor that modulates this response is whether the vaccine recipient has previously encountered the antigen—the protein on the surface of pathogen—either via infection or vaccination. If so, the body mounts a faster and fiercer antibody response—the secondary immune response—than it did during the first encounter (i.e., primary immune response). One limitation of this literature is that some studies do not fully account for prior exposure, making it difficult to decipher whether the primary or secondary immune response is reported (Cohen, S., Millar, G. E., Rabin, B. S. (2001). Psychological stress and antibody response to immunization: A critical review of the human literature. Psychosomatic Medicine, 63(1), 7-18). However, failure to account for prior exposure can mask the magnitude of the impact of stress. Especially among older adults, it is often safe to assume that they have already encountered certain antigens and therefore mount a secondary immune response. This is a key consideration for the SARS-CoV-2 vaccine, given that around 10% of Americans had prior exposure as of September 2020 (Bajema. K. L., Wiegand, R. E., Cuffe, K., Patel. S. V. Iachan, R., Lim, T., Lee, A., Moyse, D. Havers, F. P., Harding, L. (2020). Estimated SARS-CoV-2 seroprevalence in the US as of September 2020. JAMA Internal Medicine Advance online publication. doi.org/10.1001/jamainternmed. 2020.7976). Many more hays had exposure to other coronaviruses, which may influence immune responses to SARS-CoV-2 (Poland, G. A., Ovsyannikova, I. G., Kennedy, B. (2020). SARS-CoV-2 immunity: Review and applications to phase 3 vaccine card dates. The Lancet: 396(10262), 14-20. doi.org/10.1016/S0140-6736(20)32137-1), and some of the current vaccine candidates require multiple doses.

The antibody release is just one facet of the adaptive immune system response. Because the SARS-CoV-2 virus is novel, it is not yet known how different immune cells and antibodies protect against infection. Cell-mediated (T cell) immunity may play an important role in preventing COVID-19 reinfection because antibody levels naturally wane months after infection (Dan, J. M., Mateus, J., Kato, Y., Hastie, K. M., Faliti, C., Ramirez, S. I., Frazier, A., Yu, E. D., Grifoni, A., Rawlings, S. Q. Peters, B., Krammer, F., Simon, V., Saphire, E. O., Smith, D. M., Weiskopf, D., Setts, A. Crotty, S. (2020). Immunological memory to SARS-CoV-2 assessed for greater than months after infection. BioRxiv. doi.org/10.1101/2020.11.15.383323). Even so, there is little evidence that people have robust cell-mediated immunity in the absence of an antibody response (Zuo, Jianmin, Alexander C. Dowell, Hayden Pearce, Kriti Verma, Heather M. Long, Jusnara Begum, Felicity Aiano et al. "Robust SGARS-CoV-2-specific T cell immunity is maintained at E months following primary infection." Nature Immunology (2021): 1-7; Dan, Jennifer M., Jose Mateus, Yu Kato, Kathryn M. Hastie, Esther Dawen Yu, Caterina E. Faliti, Alba Grifoni et al. "Immunological memory to SARS-CoV-2 assessed for up to eight months after infection."), the peak antibody response aligned with the T cell response. Thus, antibody titers (levels) may be an important early indicator of lasting immunity. Indeed, the antibody titer is considered to be a clinically significant biomarker of protection against SARS-CoV-2 (Poland et al., 2020), although it is not the only such biomarker. It is well established that COVID-19 patients have a highly heterogenous antibody response with greater disease severity associated with azure antibody, which itself predicts clinical outcomes (Tan, W., Lu, Y., Zhang, J. Wang, J., Dan, Y., Tan, Z., He, X., Qian, C., Sun, Q., Hu, Q., Liu, H., Ye, S., Xiang, X., Zhou, Y., Zhang, W., Guo, Y., Wang, X. He, W., Wan, X, Sun. F., Wei. Q., Chen. C., Pan, G., Xia, J., Mao, Q., Shen, Y., Deng, G. (2020). Viral kinetics and antibody responses in patients with COVID-19. MedRxiv. doi.org/10.1101/2020.03.24.20042382). Antibody levels remain highly disparate months later: One study reported a 200-fold difference in SARS-CoV-2 antibody levels 6 months after infection (Zuo et al. 2021)—important variability that may map on to patient characteristics.

Mammalian immune response involves various exogenous and endogenous immune modulators. A powerful immune modulator is cortisol, produced by the adrenal cortex, and is in a family of compounds call adrenal corticosteroids. These compounds act in the nucleus of lymphocytes to suppress immune response, however, the effect is more complex, since while overt immune response is suppressed, the cells are not inactive.

Sleep plays a unique role in the maintenance of immunity; the circumstances that affect its quality have been associated with a reduction in the response to vaccines and an increase in vulnerability to infectious diseases.

Sleep is the natural periodic suspension of consciousness characterized by lessened consciousness and slowed metabolism. The sleep-wake cycle is one of the most important circadian rhythms which alternates in a lawful periodic fashion lasting for about 24 hours. Sleep is characterized by relative immobility and reduced responsiveness to environmental stimuli. This in contrast to the state of wakefulness which is characterized by presumably purposeful motor activity and ability to respond to environmental stimuli appropriately. This activity reviews the electroencephalographic (EEG) findings of normal sleep patterns as well as abnormal sleep and discusses the role of the interprofessional team in educating patients on when it may be necessary to seek professional intervention if abnormal sleep patterns develop. See, Nayak, Chetan S., and Arayamparambil C. Anilkumar. "EEG Normal Sleep." (2019).

Sleep is the natural periodic suspension of consciousness characterized by lessened consciousness and slowed metabolism. The sleep-wake cycle is one of the most important circadian rhythms which alternates in a lawful periodic fashion lasting for about 24 hours. (Aschoff J. Human circadian rhythms in activity, body temperature and other functions. Life Sci Space Res. 1967; 5:159-73.) Sleep is characterized by relative immobility and reduced responsiveness to environmental stimuli. This in contrast to the state of wakefulness which is characterized by presumably purposeful motor activity and ability to respond to environmental stimuli appropriately. Nature provides limited tolerance to the disturbance in sleep-wake cycling. (Archer S N, Oster H. How sleep and wakefulness influence circadian rhythmicity: effects of insufficient and mistimed sleep on the animal and human transcriptome. J Sleep Res. 2015 October; 24(5):476-93.)

Based on sleep macrostructure, sleep can be classified into 2 main stages: non-rapid eye movement (NREM) and rapid eye movement (REM) sleep. Typically, as one goes to sleep, the low-voltage fast EEG pattern of wakefulness gradually gives way to slower frequencies, as NREM sleep goes from stage N1 (decrease in alpha) to stage N2 (spindles, K-complexes) to stage N3 (increasing amplitude and regularity of delta rhythm). Stage N3 is referred to as slow-wave sleep (SWS). SWS is interrupted by periods of rapid eye movement (REM, i.e., active or paradoxical) sleep. Polysomnography (PSG) is a multiparametric study that has been traditionally used to assess the architecture of sleep.

Sleep goes through multiple discrete cycles of NREM and REM sleep through any given night. In normal adults, each cycle lasts for about 90 to 120 minutes and there are about 4-5 such cycles that occur during a normal 8 hour night sleep. The percentage of NREM sleep is maximum in the first part of the night, while REM sleep predominates in the second half.

Stage wake (W) is characterized by the presence of a predominant beta rhythm over the anterior leads, and there is a posterior progression to a posterior dominant alpha rhythm over the occipital regions. This anteroposterior progression is best observed with the eyes closed and is attenuated by eye-opening. Eye blinks are frequently observed in this stage which appear as conjugate eye movements consisting of 0.5 to 2 Hz. During the transition to drowsiness, one of the first things to appear is slow lateral eye movements typically less than 0.5 Hz and there is greater prominence of alpha rhythm with intermittent beta rhythm.

Stage 1 (N1) is characterized typically by the disappearance of the alpha rhythm and appearance of roving eye movements which are slow, conjugate, cyclic deflections usually lasting approximately 500 milliseconds. The EEG shows medium amplitude, mixed frequency predominantly of 4 to 7 Hz activity and irregularly spaced bursts of slow waves. There is an appearance of vertex sharp transients (VST) which are defined as sharply contoured, bilateral synchronous waves with maximum amplitude in the over the central derivations although children may show parietal dominance. The amplitude may vary on either side, and they usually last for fewer than 0.5 seconds. They are usually isolated and appear at irregular intervals both spontaneously as well as on the application of alerting stimuli. We also see the appearance of positive occipital sharp transients of sleep (POSTS) which are either mono or biphasic, positive, triangular waves most prominent in the occipital head regions. Alerting during N1 can lead to a brief recurrence of the alpha rhythm. EMG shows reduced muscle activity.

Stage 2 (N2) is characterized by the presence of bilaterally synchronous theta activity accompanied by sleep spindles or K-complexes or both. K complexes are defined by the occurrence of a complex pattern of negative sharp wave immediately followed by a positive wave (V-shaped) standing out from the background EEG, lasting=0.5 seconds, and is most prominent in the fronto-central derivations. For arousal to be associated with the K complex, it should commence no more than 1 second after the termination of the K complex. Sleep spindles are defined as distinct 12 to 14 Hz waves having frequencies of 11 to 16 Hz (most commonly 12 to 14 Hz) with the duration of greater than equal to 0.5 seconds, usually maximal in amplitude in the central derivations.

Stage 3 (N3) is characterized by high amplitude, delta slowing in the range of 0.5 to 2 Hz with amplitudes of equal to 75 µV as measured over the fronto-central derivations. K-complexes and sleep spindles may be present, but POSTs are rare. Typically, N3 sleep is scored if slowing is seen in 20% of the epoch. N3 sleep occurs most frequently during the first one-third of the night, and clinically this can be important as NREM parasomnias such as sleepwalking and night terrors are typically seen during this period. Stage REM (R) is characterized by the presence of rapid eye movements (REM) which are conjugate, irregular and sharply contoured eye movements with an initial phase deflection usually lasting less than 500 ms. We also see diminished EMG tone and is usually the lowest of the entire recording. Sawtooth waves are seen which are described as drains of sharply contoured or triangular, often serrated waves of 2 to 8 Hz with maximal amplitude over the central derivations and often, but not always preceded by a burst of rapid eye movements. The threshold for arousal by auditory stimuli tends to be the highest during REM. Typically, the R stage of sleep is present predominantly in the last one-third of the night and is the period where the REM parasomnias such as nightmares are typically seen. Stage R can be further subdivided into a phasic REM and a tonic REM stage. The phasic REM stage is a sympathetically driven sleep state characterized by the presence of rapid eye movements, intermittent muscle twitches and variations in breathing patterns. The tonic REM, on the other hand, is a parasympathetically driven sleep state and is characterized by the absence of rapid eye movements.

Transient EEG phenomena lasting less than the scoring epoch (phasic events) have been described within the sleep recordings allowing identification of what is known as the microstructure of sleep. (Terzano M G, Monge-Strauss M F, Mikol F, Spaggiari M C, Parrino L. Cyclic alternating pattern as a provocative factor in nocturnal paroxysmal dystonia. Epilepsia. 1997 September; 39(9):1015-25.) The two most commonly used methods to study the microstructure of sleep include cyclic alternating pattern (CAP) analysis and arousal paradigm.

The American Sleep Disorders Association (ASDA) proposed a definition of arousal independent of the R and K staging. (EEG arousals: scoring rules and examples: a preliminary report from the Sleep Disorders Atlas Task Force of the American Sleep Disorders Association. Sleep. 1992 April; 15(2):173-84.) According to the ASDA criteria, EEG arousals appear as sudden frequency shifts towards faster rhythms (theta, alpha, beta, but not sigma) that briefly replace the sleep stage background. In normal subjects, the mean duration of arousals remains unmodified across the lifespan (average length of about 15 seconds throughout TST), but the increase in number with age is considered as the physiological basis of sleep fragility in the elderly. (Boselli M, Parrino L, Smerieri A, Terzano M G. Effect of age on EEG arousals in normal sleep. Sleep. 1998 Jun. 15; 21(4):351-7; Carskadon M A, Brown E D, Dement W C. Sleep fragmentation in the elderly: relationship to daytime sleep tendency. Neurobiol Aging. 1982 Winter; 3(4):321-7.) In conditions of disturbed sleep, arousals have been investigated especially in sleep-related breathing disorders and in insomniac patients. There is, however, consolidated literature according to which arousals and other related phenomena represent spontaneous manifestations of physiological sleep. (Schieber J R Muzet A, Ferriere P J. "[Phases of spontaneous transitory activation during normal sleep in humans]". Arch Sci Physiol (Paris). 1971; 25(4):443-85; Halász P, Kundra O, Rajna P, Pál I, Vargha M. Microarousals during nocturnal sleep. Acta Physiol Aced Sci Hung. 1979; 54(1):1-12; McCormick L, Nielsen T, Nicolas A, Ptito M, Montplaisir J. Topographical distribution of spindles and K-complexes in normal subjects. Sleep. 1997 November; 20(10:939-41.)

Gao D, Long S, Yang H, Cheng Y, Guo S, Yu Y, Liu T, Dong L, Lu J and Yao D (2020) SWS Brain-Wave Music May Improve the Duality of Sleep: An EEG Study. Front. Neurosci. 14:67. doi: 10.3389/fnins. 2020.00067, found that the sleep efficiency increased in the SWS group but decreased in REM and WN groups. The sleep efficiency in the SWS group was ameliorated [t(10)=1.943, p=0.076]. In the EEG power spectral density analysis, the delta power spectral density in the REM group and in the control group increased, while that in the SWS group decreased [F(2,31)=7.909, p=0.005]. In the network analysis, the functional connectivity (FC), assessed with Pearson correlation coefficients, showed that the connectivity strength decreased [t(10)=1.969, p=0.073] between the left frontal lobe (F3) and left parietal lobe (C3) in the SWS group. In addition, there was a negative correlation between the FC of the left frontal lobe and the left parietal lobe and sleep latency in the SWS group (r=−0.527, p=0.064). Slow-wave sleep brainwave music may have a positive effect on sleep quality, while REM brain-wave music or WN may not have a positive effect. Furthermore, better sleep quality might be caused by a decrease in the power spectral density of the delta band of EEG and an increase in the FC between the left frontal lobe and the left parietal lobe. SWS brain-wave music could be a safe and inexpensive method for clinical use if confirmed by more data. Music can affect sleep disorders, as shown in a number of studies. Experiments with subjects listening to music before sleep have revealed that listening to soft music shortens the duration of deep sleep and prolongs the duration of deep sleep (Chang et al., 2012; Chen et al., 2014). In addition, subjects who listened to music had a longer sleep duration, greater sleep efficiency, shorter sleep latency, less sleep disturbance, and less daytime dysfunction as assessed by the Pittsburgh sleep quality index (PSQI) questionnaire (Tan, 2004). Similar results in an assessor-blinded randomized controlled trial (RCT) design showed a positive impact on sleep perception and quality of life (Jespersen et al., 2019). In electroencephalography (EEG) studies using time-frequency analysis methods, Kusumandari et al. (2018) demonstrated that music stimulation improved sleep quality.

Electroencephalography contains a wealth of information about brain activity. Scale-free brain-wave music, generated from EEG signals according to the power law of both EEG and music, possesses the characteristics of both music and EEG, and may contain physiological information that music alone may not (Wu et al., 2010, 2014; Lu et al., 2012). In recent years, brain-wave music has been shown to improve some clinical symptoms, such as pain (Levin, 1998). Levin's (1998) work, which used a combination of behavioral data and power spectral density, showed that brain-wave music incorporates factors of music therapy and biological feedback (Huang et al., 2016). Brain-wave music has been applied in the treatment of orofacial pain, and the results showed that the brain-wave music and cognitive behavioral therapy (CBT) group had lower levels of pain perception than the control group. In addition, the brain-wave music group showed lower EEG complexity and slower waves (Zhuang et al., 2009). Brain-wave music can also provide us with a new way to examine alterations in brains across various populations. The brain-wave music of healthy subjects and epilepsy patients clearly revealed differences in the two brain states, in that the brain music from the epilepsy patients was composed of unusual variations (Yao et al., 2016). Classic studies have explored neural mechanisms. Sleep staging and the PSQI questionnaire have been used to evaluate sleep quality in previous studies, and the results of the behavioral data showed that brain-wave music has a positive effect. However, the neural activities underlying the improvement in the quality of sleep by brain-wave music still need to be clarified.

As representative sleep stages, rapid eye movement (REM) sleep repairs advanced cognitive function, and N3 stage sleep, also called slow-wave sleep (SWS) or deep sleep, can relieve fatigue (Griessenberger et al., 2013). Two types of scale-free brain-wave music were used as music stimulation, one from the REM stage and the other from the SWS stage. Deep sleep can predict sleep satisfaction and is a representative indicator of sleep quality (Riedel and Lichstein, 1998), so for EEG analysis, we mainly analyzed the power spectrum of EEG during deep sleep, and explored the neural mechanisms of these two brain-wave music on sleep promotion from the perspective of EEG.

To observe the effect of brain-wave music on sleep, participants with a regular habit of staying up late were enrolled in the experiment. EEG was translated into brain-wave music (Wu et al., 2009; Lu et al., 2012). Two pieces of brain-wave music were used in the experiment. One piece was REM brain-wave music, which was generated from EEG during the REM sleep. Another piece was SWS brain-wave music, which was generated from EEG during the SWS sleep.

According to previous studies, the period of N3 stage in the proportion of total sleep time and sleep latency can predict sleep satisfaction and are representative indicators of sleep quality (Riedel and Lichstein, 1998). A sleep latency of less than 15 min is rated as an appropriate measure for indexing good sleep quality (Rayon et al., 2017). Meanwhile, sleep efficiency is also correlated to sleep quality (Jankelowitz et al., 2005), and a sleep efficiency of more than 85% is judged as an appropriate indicator of good sleep quality (Buysse et al., 1991; Åkerstedt et al., 1994; Ohayon et al., 2017). Therefore, we chose these three indicators for our behavioral data analysis.

Sleep stage assessment in the first session was based on EEG, electro-oculography (EOG), electrocardiography (ECG), and electromyography (EMG), according to the American Academy of Sleep Medicine (AASM) criteria and the identified EEG signals of deep sleep. Sleep is divided into five stages: W, R, N1, N2, and N3 in the AASM criteria, and EEG is obtained in the deep sleep stage, where fatigue is effectively relieved (Danker-Hopfe et al., 2009). According to the AASM, the delta wave accounts for more than 20% of a frame during the N3 stage. Moreover, total sleep time, sleep efficiency, sleep latency, and percentage of time in each sleep stage were calculated (Suzuki et al., 2019). Yue Yu, a physician of sleep medicine, extracted the EEG signal either from the N3 stage alone or from eight sets of N2 data, which is similar to N3 (the delta wave accounts for more than 15% of a frame), as the deep sleep data when the participant lacked the N3 stage according to the AASM criteria.

Deep sleep EEG was preprocessed by the reference electrode standardization technique (REST) with zero reference (Yao, 2001; Yao et al., 2019) and 0.5-30 Hz bandpass filtering under the Webrain platform. Consider that the delta band (0.5-4 Hz) is the dominant frequency of EEG at N3 stage and related to the quality of sleep (Danker-Hopfe et al., 2009), the power spectral density and brain network connectivity was calculated in delta band after preprocessing. The results were made clear through correlations among the total sleep time, sleep efficiency, sleep latency, percentage of time in each sleep stage, and EEG data (Guevara and Corsi-Cabrera, 1998; Chennu et al., 2018; Comsa et al., 2019).

Sleep latency in the SWS group decreased by 38.45% [t(10)=2.441, p=0.031] after listening to music. Although the sleep latency in the WN group and REM group subjects also decreased after the intervention, the differences were not significant. The sleep efficiency in the SWS group increased by 3.98% [t(10)=−1.943, p=0.076], while in the other two groups, the sleep efficiency decreased. The percentage of sleep time spent in stage N3 increased in all three groups but not to a statistically significant degree.

Some previous studies have shown that listening to the subjects' own brain-wave music could improve the quality of sleep (Levin, 1998), while another study found that listening to healthy subjects' brain-wave music might be more useful (Yao et al., 2016). There is no prior general agreement on what kinds of brain-wave music can improve the quality of sleep. REM sleep could repair advanced cognitive function, and SWS sleep could relieve fatigue (Griessenberger et al., 2013). Therefore, the study chose two kinds of EEG in different periods of sleep and generated the brain-wave music from them. As a result, the study found that SWS brain-wave music could improve sleep quality but REM brain-wave music could not. In order to understand its mechanism, further analysis on both behavioral and EEG data was performed.

Sleep latency can be interpreted as a sense of sleepiness before going to bed and is a very important part of sleep quality (Chen et al., 2014). Music intervention before bedtime may facilitate relaxation as a person falls asleep (Steelman, 1990; Updike, 1990; White, 1992). It was found that listening to SWS brain-wave music at bedtime can shorten sleep latency. In another study, listening to sedating music did not significantly alter sleep latency (Higuchi et al., 2005). Therefore, SWS brain-wave music may have a better effect with regard to relaxation than sedating music.

Normally, the delta band brainwave is generated during sleep and relaxed conditions (Kumarahirwal and Londhe, 2013). A lower power in low-frequency band EEG indicates better sleep, especially deep sleep (Svetnik et al., 2017). It was found that the power spectral density in the SWS group decreased in the delta band, which is consistent with experimental results in subjects using benzodiazepines and zolpidem (Monti et al., 2000; Bastien et al., 2003). A study also found that with increasing age, the activity in the delta band decreases in power, which may be related to an attenuation of homeostatic sleep pressure and to an increase in cortical activation during sleep (Carrier et al., 2001). Therefore, the decrease in the delta brain waves in the reported study may have been indicative of an elevated sleep propensity and a relief from homeostatic sleep pressure in the SWS group (Esposito and Carotenuto, 2014). The power spectral density in the SWS group increased, while that in the other two groups decreased in the delta band (posttest—pretest). There were significant differences between the SWS and REM groups and between the SWS and WN groups. SWS brain-wave music thus had a positive effect. However, in the delta band, the power spectral density of the REM and WN groups increased, and there was no significant difference between the two groups, indicating that REM brain-wave music and WN have similar effects on the EEG power spectrum. In Alexander's study, he found that the EEG power density in the low-frequency range (delta band) was an indicator of a progressively decreasing process during sleep (Borbély et al., 1981). It seemed that with the deepening of sleep, the power of delta frequency band decreased simultaneously. The reported study found that after REM brain-wave music or WN listening, the power of delta band increased during sleep (posttest—pretest), and suggesting that these two kinds of music may have a negative effect on the deepening of sleep.

Overnight sleep deprivation leads to reduced activation of the frontal and parietal lobes (Ghee and Tan, 2010). A meta-analysis showed brain activation in the right prefrontal cortex and medial frontal cortex was significantly reduced following sleep deprivation compared to rested wakefulness and that the activation in the frontoparietal attention network was reduced following acute total sleep deprivation compared to normal resting (Ma et al., 2015). These findings suggested that the decrease in this connectivity may be related to increased sleepiness and a greater likelihood of falling asleep. Ghee et al. (2006) found that activation of the left frontal parietal lobe after normal sleep was negatively correlated with the performance accuracy decreases observed between normal sleep conditions and sleep deprivation over 24 h. In another study, Zou et al. (2018) found that the FC in the left frontoparietal network showed strong a correlation with REM sleep percentage. It appears that the activity of the left frontal and parietal lobes is highly correlated with various aspects of sleep. In our experiment, we found that the connectivity of the left frontal (F3) and parietal (C3) lobes was linked with sleep latency, so we speculate that the connectivity of the left frontal and parietal lobes may affect sleep latency.

webrain.uestc.edu.cn/

Bastien, C. H., LeBlanc, M., Carrier, J., and Morin, C. M. (2003). Sleep EEG power spectra, insomnia, and chronic use of benzodiazepines. Sleep 26, 313-317. doi: 10.1093/sleep/26.3.313

Borbély, A. A., Baumann, F., Brandeis, D., Strauch, I., and Lehmann, D. (1981). Sleep deprivation: effect on sleep stages and EEG power density in man. Electroencephal. Clin. Neurophysiol. 51, 483-493. doi: 10.1016/0013-4694(81)90225-X Buysse, D. J., Reynolds, C. F. III, Monk, T. H., Hoch, C. C., Yeager, A. L., and Kupfer, D. J. (1991). Quantification of subjective sleep quality in healthy elderly men and women using the pittsburgh sleep quality index (PSQI). Sleep 14, 331-338. doi: 10.1093/sleep/14.4.331

Carrier, J., Land, S., Buysse, D. J., Kupfer, D. J., and Monk, T. H. (2001). The effects of age and gender on sleep EEG power spectral density in the middle years of life (ages 20-60 years old). Psychophysiology 38, 232-242 doi: 10.1111/1489-8986.3820232

Chang, E. T., Lai, H. L., Chen, P. W., Hsieh, Y. M., and Lee, L. H. (2012). The effects of music on the sleep quality of adults with chronic insomnia using evidence from polysomnographic and self-reported analysis: a randomized control trial. Int. J. Nurs. Stud. 49, 921-930. doi: 10.1016/j.ijnurstu. 2012.02.019

Chee, M. W. L., Chuah, L. Y. M., Venkatraman, V., Chan, W. Y., Philip, P., and Dinges, D. F. (2006). Functional imaging of working memory following normal sleep and after 24 and 35 h of sleep deprivation: correlations of frontoparietal activation with performance. Neuroimage 31, 419-428. doi: 10.1016/j.neuroimage. 2005.12001

Chee, M. W. L., and Tan, J. C. (2010). Lapsing when sleep deprived: neural activation characteristics of resistant and vulnerable individuals. Neuroimage 51, 835-843. doi: 10.1016/j.neuroimage. 2010.02.031

Chen, C. K., Pei, Y. C., Chen, N. H., Huang, L. T., Chou, S. W., Wu, K. P., et al. (2014). Sedative music facilitates deep sleep in young adults. J. Altern. Complement. Med. 20, 312-317. doi: 10.1089/acm. 20120050

Chennu, S., O'Connor, S., Adapa, R., Menon, D. K., and Bekinschtein, T. A. (2016). Brain connectivity dissociates responsiveness from drug exposure during propofol-induced transitions of consciousness. Plos Compu. Biol. 12:e1004669. doi: 10.1371/journal.pcbi. 1004669

Comsa, I. M., Bekinschtein, T. A., and Chennu, S. (2019). Transient topographical dynamics of the electroencephalogram predict brain connectivity and behavioural responsiveness during drowsiness. Brain Topogr. 32, 315-331. doi: 10.1007/s10548-018-0689-9

Danker-Hopfe, H., Anderer, P., Zeitlhofer, J., Boeck, M., Dorn, H., Gruber, G., et al. (2009). Interrater reliability for sleep scoring according to the Rechtschaffen & Kales and the new AASM standard. J. Sleep Res. 18, 74-84. doi: 10.1111/j. 1365-2869.2008.00700.x Esposito, M., and Carotenuto, M. (2014). Intellectual disabilities and power spectra analysis during sleep: a new perspective on borderline intellectual functioning. J. Intellect. Disabil. Res. 58, 421-429. doi: 10.1111/jir. 12036

Gozal, L. K., Gutierrez-Tobal, G. C., Martin-Montero, A., Poza, J., Alvarez, D., del Campo, F., et al. (2019). Spectral EEG differences in children with obstructive sleep apnea. Am. J. Respir. Crit. Care Med. 199, A7375. doi: 10.1164/ajrccm-conference. 2019.199.1_MeetingAbstractsA7375

Griessenberger, H., Heib, D. P. J., Kunz, A. B., Hoedlmoser, K., and Schabus, M. (2013). Assessment of a wireless headband for automatic sleep scoring. Sleep Breath 17, 747-752. doi: 10.1007/s11325-012-0757-4

Guevara, M. A., and Corsi-Cabrera, M. (1996). EEG coherence or EEG correlation? In. J. Psychophysiol. Off. J. Int. Organ. Psychophysiol. 23, 145-153. doi: 10.1016/S0167-8760(96)00038-4

Higuchi, S., Motohashi, Y., Liu, Y., and Maeda, A. (2005). Effects of playing a computer game using a bright display on presleep physiological variables, sleep latency, slow wave sleep and REM sleep. J. Sleep Res. 14, 267-273. doi: 10.1111/j. 1365-2869.2005.00463.x Huang, R., Wang, J., Wu, D., Long, H., Yang, X., Liu, H., et al. (2016). The effects of customised brainwave music on orofacial pain induced by orthodontic tooth movement. Oral Dis. 22, 766-774. doi: 10.1111/odi. 12542

Jankelowitz, L., Reid, K. J., Wolfe, L., Cullina, J., Zee, P. C., and Jain, M. (2005). Cystic fibrosis patients have poor sleep quality despite normal sleep latency and efficiency. Chest 127, 1593-1599. doi: 10.1378/chest. 127.5.1593

Jespersen, K. V., Otto, M., Kringelbach, M., Van Someren, E., and Vuust, P. (2019). A randomized controlled trial of bedtime music for insomnia disorder. J. Sleep Res. 28:e12817. doi: 10.1111/jsr. 12817 kerstedt, T., Hume, K. E. N., Minors, D., and Waterhouse, J. I. M. (1994). The meaning of good sleep: a longitudinal study of polysomnography and subjective sleep quality. J. Sleep Res. 3, 152-158. doi: 10.1111/j. 1365-2869.1994.tb00122.x Kumarahirwal, M., and Londhe, N. D. (2013). Power spectrum analysis of EEG signals for estimating visual attention. Int. J. Comput. Appl. 42, 34-40. doi: 10.5120/5769-7993

Kusumandari, D. E., Suhendra, M. A., Amri, M. F., Simbolon, A. I., Rizqyawan, M. I., Wardono, P., et al. (2018). Comparison of EEG sleep characteristic with music and aromatherapy stimuli. J. Phys. 1080:012050. doi: 10.1088/1742-6596/1080/1/012050

Levin, Y. I. (1998). "Brain music" in the treatment of patients with insomnia. Neurosci. Behav. Physiol. 28, 330-335. doi: 10.1007/BF02462965

Lu, J., Wu, D., Yang, H., Luo, C., Li, C. Y., and Yao, D. Z. (2012). Scale-free brain-wave music from simultaneously EEG and fMRI recordings. Plos One 7:e49773. doi: 10.1371/journal.pone. 0049773

Lucey, B. P., Mcleland, J. S., Toedebusch, C. D., Boyd, J., Morris, J. C., Landsness, E. C., et al. (2016). Comparison of a single-channel EEG sleep study to polysomnography. J. Sleep Res. 25, 625-635. doi: 10.1111/jsr. 12417

Ma, N., Dinges, D. F., Basner, M., and Rao, H. Y. (2015). How acute total sleep loss affects the attending brain: a meta-analysis of neuroimaging studies. Sleep 38, 233-240. doi: 10.5665/sleep. 4404

Monti, J. M., Alvarino, F., and Monti, D. (2000). Conventional and power spectrum analysis of the effects of zolpidem on sleep EEG in patients with chronic primary insomnia. Sleep 23, 1075-1084.

Ohayon, M., Wickwire, E. M., Hirshkowitz, M., Albert, S. M., Avidan, A., Daly, F. J., et al. (2017). National Sleep Foundation's sleep quality recommendations: first report. Sleep Health 3, 6-19. doi: 10.1016/j.sleh. 2016.11.006

Patterson, E. C. (2011). The Effect of Lullaby Music Versus Rain Sounds on Inducing Sleep in the First 20 Minutes of Daycare Naptime. Tallahassee, Fla.: Florida State University Libraries.

Riedel, B. W., and Lichstein, K. L. (1998). Objective sleep measures and subjective sleep satisfaction: how do older adults with insomnia define a good night's sleep? Psychol. Aging 13, 159-163. doi: 10.1037/0882-7974.13.1.159

Steelman, V. M. (1990). Intraoperative music therapy. AORN J. 52, 1026-1034. doi: 10.1016/s0001-2092(07)69164-9

Suzuki, Y., Rompré, P., Mayer, P., Kato, T., Okura, K., and Lavigne, G. J. (2019). Changes in oxygen and carbon dioxide in the genesis of sleep bruxism: a mechanism study. J. Prosthodont. Res. S1883-1958, 30446-30448. doi: 10.1016/j.jpor. 2019.04.012

Svetnik, V., Snyder, E. S., Ma, J. S., Tao, P. N., Lines, C., and Herring, W. J. (2017). EEG spectral analysis of NREM sleep in a large sample of patients with insomnia and good sleepers: effects of age, sex and part of the night. J. Sleep Res. 26, 92-104. doi: 10.1111/jsr. 12448

Tan, L. P. (2004). The Effects of background music on quality of sleep in elementary school children. J. Music Ther. 41, 128-150. doi:10.1093/jmt/41.2.128

Updike, P. (1990). Music therapy results for ICU patients. Dimens. Cri. Care Nurs. 9, 39-45. doi:10.1097/00003465-199001000-00013

White, J. M. (1992). Music therapy: an intervention to reduce anxiety in the myocardial infarction patient. Clin. Nurse Spec. G, 58-63. doi: 10.1097/00002800-199200620-00002

Wu, D., Li, C., Yin, Y., Zhou, C., and Yao, D. (2010). Music composition from the brain signal: representing the mental state by music. Intell. Neurosci. 2010:4. doi: 10.1155/2010/267671

Wu, D., Li, C. Y., Liu, J., Lu, J., and Yao, D. Z. (2014). Scale-free brain ensemble modulated by phase synchronization. J. Z. Univer. Sci. C Comput. Electron. 15, 821-831. doi:10.1631/jzus.C1400199

Wu, D., Li, C.-Y., and Yao, D.-Z. (2009). Scale-free music of the brain. PLoS One 4, e5915e5915. doi:10.1371/journal.pone. 0005915

Yao, D., Chen, M., Lu, J., and Guo, D. (2016). Neural Mass Model-Based scale-Free EEG Music. Berlin: Springer, 455-460.

Yao, D., Din, Y., Hu, S., Dong, L., Bringas Vega, M. L., and Valdés Sosa, P. A. (2019). Which reference should we use for EEG and ERP practice? Brain Topogr. 32, 530-549. doi:10.1007/s10548-019-00707-x Yao, D. Z. (2001). A method to standardize a reference of scalp EEG recordings to a point at infinity. Physiol. Meas. 22, 693-711. doi: 10.1088/0967-3334/22/4/305

Zhuang, T., Zhao, H., and Zheng, T. (2009). A study of brainwave entrainment based on EEG brain dynamics. Comput. Inform. Sci. 2:80. doi:10.5539/cis.v2n2p80

Zou, D. H., Zhou, S. O., Xu, J., Su, Z. H., Li, Y. Z., Ma, Y. D., et al. (2018). Dissociated resting-state functional networks between the dream recall frequency and REM sleep percentage. Neuroimage 174, 248-256. doi: 10.1016/j.neuroimage. 2018.03.015

Jennifer M. Johnson, and Simon J. Durrant, responded to this study in Johnson J M and Durrant S J (2021) Commentary: SWS Brain-Wave Music May Improve the Duality of Sleep: An EEG Study. Front. Neurosci. 15:609169. doi: 10.3389/fnins. 2021.609169, stating that sleep is important for maintaining health and general well-being. Improving sleep is becoming more important due to the growing prevalence of sleep disorders, with non-pharmacological sleep interventions increasing in popularity (de Niet et al., 2009; Ngo et al., 2013b). When comparing interventions, music-based were the most successful for improving subjective sleep quality (de Niet et al., 2009), using a range of music types including classical, jazz, and sedative (Chan et al., 2010; Chen et al., 2014; Shum et al., 2014), as well as sounds including white (Afshar et al., 2016) and pink noise (Zhou et al., 2012). The effect of music on specific sleep stages, however, is less well-known with relatively few studies to date using objective sleep quality measures (Cordi et al., 2019).

Sleep consists of rapid eye-movement (REM) and non-rapid eye-movement (NREM) components, with NREM comprising various stages including slow-wave sleep (SWS) (Rechtschaffen and Kales, 1998), which is dominated by slow-wave activity (SWA) (0.5-4 Hz) consisting of delta and slow waves (<2 Hz) (Dijk et al., 1993). To date, music interventions have increased the amount of SWS (Chen et al., 2014; Cordi et al., 2019) and REM sleep (Chang et al., 2012), without changing delta power during SWS (Lazio and Ogilvie, 2007). To our knowledge, Gao et al. (2020) are the first to explore the impact of brain-wave music created from EEG during REM sleep.

Gao et al. (2020) explored the impact of SWS music (n=11), REM sleep music (n=13), and white noise (n=9) played for 20 min before bedtime for 6 days on objective measures of sleep quality, including spectral power. The brain-wave music was created using the amplitude, period and average power of each sleep stage and translated into music pitch, duration, volume, and timbre using power law. Using this method, they aimed to compare the effects of each type of music on sleep quality and neural actuation. The key finding was that after SWS brain-wave music, delta power significantly reduced, which the authors interpreted as a positive effect on sleep quality.

This is an important area of research, but in this case Johnson and Durrant offer an alternative interpretation of the results. Guo et al. argue that lower delta power is indicative of improved sleep and SWS, citing previous research (Svetnik et al., 2017) and interpret the reduction in delta power as a reduced homeostatic pressure for delta power, as found in older adults (Landolt et al., 1996; Landolt and Borbély, 2001). However, Svetnik et al. (2017) actually found a reduction in delta power in younger adults (the age group in this study) was associated with insomnia, i.e., poorer sleep quality. Furthermore, while reduced delta activity could indicate a reduction in homeostatic sleep pressure, this is unlikely to be the case given that sleep latency after SWS music was significantly lower, and sleep efficiency somewhat higher, which are both associated with increased homeostatic sleep pressure (Dijk et al., 2010; Dijk and Landolt, 2019), while the duration of SWS was unchanged. These results suggest that the reduction of delta power is instead indicative of an impairment. This view results from both the positive consequences of increasing delta power and the negative consequences of prolonged delta power reduction (both clinically and cognitively), which is why research has focused on increasing delta power for optimal sleep quality (Marshall et al., 2006; Santiago et al., 2019).

SWS is the sleep stage most commonly associated with sleep quality due to its restorative nature (Åkerstedt et al., 1997; Dijk, 2009). To infer cause and effect, studies have focused on (a) enhancing SWS using stimulation, resulting in improvements to learning and health outcomes (Besedovsky et al., 2017; Johnson and Durrant, 2018); and (b) suppressing SWS, increasing the risk of type 2 diabetes through impaired insulin and glucose (Tasali et al., 2008; Herzog et al., 2013) and negatively affecting cognitive performance (Ferrara et al., 2000). These results collectively suggest that there are benefits to increasing delta power, whilst reducing delta power is problematic for a range of outcomes.

The brain-wave music intervention therefore appears to be unsuccessful and Johnson and Durrant suggest there are three possible reasons for this. Successful interventions use entrainment (Marshall et al., 2006; Ngo et al., 2013a) which may not be present in Guo et al. Auditory closed-loop stimulation entrains the sounds to the up-states of the slow-oscillations, with the slope of each individual participants slow-oscillation being measured, which then increases the amplitudes and power (Ngo et al., 2013a). The SWS brain-wave music was not, however, entrained to the SWA of each individual. Related to that, the music stimuli appeared to have no clear metrical structure and the tempo was nominally set to 120 bpm for both conditions with no consistent beat present in reality, in spite of previous findings connecting EEG periodicity to tempo (Fujioka et al., 2012). More generally, the particular mapping of EEG to music parameters is highly questionable, with no inherent relationship between average spectral power and musical timbre, for example. Finally, the stimulation was performed for only 20 min prior to sleep, when successful interventions performed prior to sleep/during sleep onset have been performed for a longer duration, e.g., 90 min (Ngo et al., 2013b). Similarly, performing auditory stimulation during SWS is more successful for improving SWA than prior to sleep/sleep onset (Ngo et al., 2013a, b). Johnson and Durrant therefore suggest that lack of entrainment, arbitrary EEG-music mapping and unfortunate stimulus timing may have contributed to the lack of success of the intervention.

Johnson and Durrant believe that this research does not show a positive effect of SWS brain-wave music on sleep quality; quite the contrary, but do agree that it is an important question and using music with characteristics specific to individual sleep stages is a positive development. The implementation in Guo et al. seems to be flawed and as such has led to inconclusive findings. Future research should, therefore, focus on improving the implementation, incorporating entrainment, appropriate stimulus timing, and a music-EEG mapping grounded in existing evidence from cognitive neuroscience.

Åkerstedt, T., Hume, K., Minors, D., and Waterhouse, J. (1997). Good sleep its timing and physiological sleep characteristics. J. Sleep Res. 6, 221-229. doi: 10.1111/j.1365-2869.1997.00221.x Afshar, F., Bahramnezhad, F., Asgari, P., and Shirt M. (2016). Effect of white noise on sleep in patients admitted to a coronary care. J. Caring Sci. 5, 103-109. doi: 10.15171/jcs. 2016.011

Besedovsky, L., Ngo, H.-V. V., Dimitrov, S., Gassenmaier, C., Lehmann, R., and Born, J. (2017). Auditory closed-loop stimulation of EEG slow oscillations strengthens sleep and signs of its immune-supportive function. Nat. Commun. 8:1984. doi: 10.1038/s41467-017-02170-3

Chan, M. F., Chan, E. A., and Mok, E. (2010). Effects of music on depression and sleep quality in elderly people: a randomised controlled trial. Complement. Ther. Med. 18, 150-159. doi:10.1016/j.ctim. 2010.02004

Chang, E. T., Lai, H. L., Chen, P. W., Hsieh, Y. M., and Lee, L. H. (2012). The effects of music on the sleep quality of adults with chronic insomnia using evidence from polysomnographic and self-reported analysis: a randomized control trial. Int. J. Nurs. Stud. 49, 921-930. doi: 10.1016/j.ijnurstu. 2012.02.019

Chen, C. K., Pei, Y. C., Chen, N. H., Huang, L. T., Chou, S. W., Wu, K. P., et al. (2014). Sedative music facilitates deep sleep in young adults. J. Altern. Complement. Med. 20, 312-317. doi:10.1089/acm. 20120050

Cordi, M. J., Ackermann, S., and Rasch, B. (2019). Effects of relaxing music on healthy sleep. Sci. Rep. 9:9079. doi: 10.1038/s41598-019-45608-y de Niet, G. J., Tiemens, B. G., Kloos, M. W., and Hutschemaekers, G. J. M. (2009). Review of systematic reviews about the efficacy of non-pharmacological interventions to improve sleep quality in insomnia. Int. J. Evid. Based. Healthc. 7, 233-242. doi:10.1111/j. 1744-1609.2009.00142.x Dijk, D.-J. (2009). Regulation and functional correlates of slow wave sleep. J. Clin. Sleep Med. 5, 13535-13539. doi: 10.5664/jcsm. 5.2S.S6

Dijk, D.-J., Hayes, B., and Czeisler, L A. (1993). Dynamics of electroencephalographic sleep spindles and slow wave activity in men: effect of sleep deprivation. Brain Res. 626, 190-199. doi: 10.1016/0006-8993(93)90579-C Dijk, D.-J., and Landolt, H.-P. (2019). "Sleep physiology, circadian rhythms, waking performance and the development of sleep-wake therapeutics," in Sleep-Wake Neurobiology and Pharmacology, eds H.-P. Landolt and D.-J. Dijk (Cham: Springer International Publishing), 441-481. doi: 10.1007/164_2019_243

Dijk, D. J., Groeger, J. A., Stanley, N., and Deacon, S. (2010). Age-related reduction in daytime sleep propensity and nocturnal slow wave sleep. Sleep 33, 211-223. doi: 10.1093/sleep/33.2.211

Ferrara, M., Gennaro, L., Casagrande, M., and Bertini, M. (2000). Selective slow-wave sleep deprivation and time-of-night effects on cognitive performance upon awakening. Psychophysiology 37, 440-446. doi:10.1111/1469-8986.3740440

Fujioka, T., Trainor, L. J., Large, E. W., and Ross, B. (2012). Internalized timing of isochronous sounds is represented in neuromagnetic beta oscillations. J. Neurosci. 32, 1791-1802 doi:10.1523/JNEUROSCI. 4107-11.2012

Gao, D., Long, S., Yang, H., Cheng, Y., Guo, S., Yu, Y., et al. (2020). SWS brain-wave music may improve the quality of sleep: an EEG study. Front. Neurosci. 14:67. doi:10.3389/fnins. 2020.00067

Herzog, N., Jauch-Chara, K., Hyzy, F., Richter, A., Friedrich, A., Benedict, L, et al. (2013). Selective slow wave sleep but not rapid eye movement sleep suppression impairs morning glucose tolerance in healthy men. Psychoneuroendocrinology 38, 2075-2082. doi: 10.1016/jpsyneuen. 2013.03.018

Johnson, J. M., and Durrant, S. J. (2018). The effect of cathodal transcranial direct current stimulation during rapid eye-movement sleep on neutral and emotional memory. R. Soc. Open Sci. 5:172353. doi:10.1098/rsos. 172353

Landolt, H. P., and Borbély, A. A. (2001). Age-dependent changes in sleep EEG topography. Db. Neurophysiol. 112, 369-377. doi: 10.1016/S1388-2457(00)00542-3

Landolt, H. P., Dijk, D. J., Achermann, P., and Borbély, A. A. (1996). Effect of age on the sleep EEG: slow-wave activity and spindle frequency activity in young and middle-aged men. Brain Res. 738, 205-212. doi: 10.1016/S0006-8993(96)00770-6

Lazic, S. E., and Ogilvie, R. D. (2007). Lack of efficacy of music to improve sleep: a polysomnographic and quantitative EEG analysis. Int. J. Psychophysiol. 63, 232-239. doi: 10.1016/j.ijpsycho. 2006.10.004

Marshall, L., Helgadóttir, H., Mölle, M., and Born, J. (2006). Boosting slow oscillations during sleep potentiates memory. Nature 444, 610-613. doi:10.1038/nature05278

Ngo, H.-V., Martinetz, T., Born, J., and Mólle, M. (2013b). Auditory closed-loop stimulation of the sleep slow oscillation enhances memory. Neuron 78, 545-553. doi: 10.1016/j.neuron. 2013.03.006

Ngo, H.-V. V., Claussen, J. C., Born, J., and Mölle, M. (2013a). Induction of slow oscillations by rhythmic acoustic stimulation. J. Sleep Res. 22, 22-31. doi: 10.1111/j. 1365-2869.2012.01039.x Rechtschaffen, A., and Kales, A. (1968). A Manual of Standardised Terminology, Techniques and Scoring System for Sleep Stages of Human Subjects. 1st Edn. Los Angeles, Calif.: Brain Information Service/Brain Research Institute: Elsevier Inc. doi: 10.1016/8978-1-4557-1267-0.00003-5

Santiago, J. C. P., Ngo, H. V., Jickeli, C., Peter, A., and Hallschmid, M. (2019). Intensifying sleep slow oscillations does not improve metabolic control in healthy men. Psychoneuroendocrinology 99, 1-7. doi:10.1016/j.psyneuen. 2018.08.028

Shum, A., Taylor, B. J., Thayala, J., and Chan, M. F. (2014). The effects of sedative music on sleep quality of older community-dwelling adults in singapore. Complement. Ther. Med. 22, 49-56. doi:10.1016/j.ctim. 2013.11.003

Svetnik, V., Snyder, E. S., Ma, J., Tao, P., Lines, C., and Herring, W. J. (2017). EEG spectral analysis of NREM sleep in a large sample of patients with insomnia and good sleepers: effects of age, sex and part of the night. J. Sleep Res. 26, 92-104. doi:10.1111/jsr. 12448

Tasali, E., Leproult, R., Ehrmann, D. A., and Van Cauter, E. (2008). Slow-wave sleep and the risk of type 2 diabetes in humans. Proc. Natl. Acad. Sci. U.S.A. 105, 1044-1049. doi: 10.1073/pnas. 0706446105

Zhou, J., Liu, D., Li, X., Ma, J., Zhang, J., and Fang, J. (2012). Pink noise: effect on complexity synchronization of brain activity and sleep consolidation. J. Theor. Biol. 306, 68-72. doi:10.1016/j.jtbi. 2012.04.006

CAP is an EEG phenomenon organized in sequences that occupy wide sections within NREM sleep. (Parrino L, Boselli M, Spaggiari M C, Smerieri A, Terzano M G. Cyclic alternating pattern (CAP) in normal sleep: polysomnographic parameters in different age groups. Electroencephalogr Clin Neurophysiol. 1998 December; 107(6):439-50.) During CAP, the EEG rhythms of sleep oscillate with periodic excitatory (phase A) and inhibitory (phase B) swings. CAP is a major marker of arousal instability that accompanies the sleep-wake transitional phases and researchers think it is a substrate for the emergence of various sleep activated neurological disorders. (Terzano M G, Parrino L, Spaggiari M C. The cyclic alternating pattern sequences in the dynamic organization of sleep. Electroencephalogr Clin Neurophysiol. 1988 May; 69(5):437-47.) Repetitive clusters of stereotyped EEG features separated by time-equivalent intervals of background activity and include at least 2 consecutive CAP cycles identify a CAP sequence. The CAP cycle consists of a phase A (composed of transient EEG elements) and a phase B (interval of theta/delta activity that separates 2 successive A phases, with an interval equal to 1 minute). Each phase of CAP may last for 2 to 60 seconds. All CAP sequences begin with phase A and ended with phase B. (Parrino L, Ferri R, Bruni O, Terzano M G. Cyclic alternating pattern (CAP): the marker of sleep instability. Sleep Med Rev. 2012 February; 16(1):27-45.) Based on the reciprocal proportion of high-voltage slow waves (EEG synchrony) and low-amplitude fast rhythms (EEG desynchrony) throughout the entire phase A duration, 3 subtypes of A phases corresponding to different levels of neurophysiologic activation are distinguished: subtype A1 (predominance of EEG synchrony), subtype A2 (balanced mixture of EEG synchrony and desynchrony), and subtype A3 (predominance of EEG desynchrony). When the interval between 2 consecutive A phases exceeds 60 seconds, the CAP sequence ends, and sleep entered into the non-CAP (NEAP) mode is characterized by stable, ongoing EEG rhythms with very few and randomly distributed arousal-related phasic events. (Smerieri A, Parrino L, Agosti M, Ferri R, Terzano M G. Cyclic alternating pattern sequences and non-cyclic alternating pattern periods in human sleep. Clin Neurophysiol. 2007 October; 118(10):2305-13.)

Sleep substantially affects immune function. People who are regularly sleep deprived are at great risk not only for vaccine non-responsiveness but also for severe illness. The relationship between disturbed sleep and lower antibody responses has been documented in both cross-sectional studies (Burns, V. E., Drayson, M., Ring, C., Carroll, D. (2002). Perceived stress and psychological well-being are associated with antibody status after meningitis C conjugate vaccination. Psychosomatic Medicine, 64(6), 963-970.) and research with experimentally induced sleep restriction (Spiegel, K., Sheridan, J. F., Van Cauter, E. (2002). Effect of sleep deprivation on response to immunization. JAMA, 288(12), 1471-1472.). For the latter, healthy young men who normally spent between 7.5 and 8.5 hr in bed were restricted to 4 hr per night in bed for 6 nights, which then lengthened to 12 hr per night for 7 nights to recover from the deprivation. On the morning after the fourth short night of sleep, they received an influenza virus vaccine. Despite the period of sleep recovery, these individuals had lower antibody production than their normally rested peers 10 days after vaccination, even accounting for baseline antibody titers. The notable between-subjects variation within each group suggested that sleep deprivation does not uniformly impair antibody responses. By three to four weeks after vaccination, their antibody levels no longer differed from those of their peers (Spiegel, K., Sheridan, J. F., Van Cauter, E. (2002). Effect of sleep deprivation on response to immunization. JAMA, 288(12), 1471-1472).

Sleep regulates immune functions. Sleep can influence immunological memory formation. In a clinical trial, twenty-seven healthy men were vaccinated against hepatitis A three times, at weeks 0, 8, and 16 with conditions of sleep versus wakefulness in the following night. Sleep was recorded polysomnographically, and hormone levels were assessed throughout the night. Vaccination-induced Th cell and Ab responses were repeatedly monitored for 1 y. Compared with the wake condition, sleep after vaccination doubled the frequency of Ag-specific Th cells and increased the fraction of Th1 cytokine-producing cells in this population. Moreover, sleep markedly increased Ag-specific IgG1. The effects were followed up for 1 y and were associated with high sleep slow-wave activity during the postvaccination night as well as with accompanying levels of immunoregulatory hormones (i.e., increased growth hormone and prolactin but decreased cortisol release). Sleep is thus shown to promote human Th1 immune responses, implicating a critical role for slow-wave sleep in this process. The proinflammatory milieu induced during this sleep stage apparently acts as adjuvant that facilitates the transfer of antigenic information from APCs to Ag-specific Th cells. Like the nervous system, the immune system takes advantage of the offline conditions during sleep to foster adaptive immune responses resulting in improved immunological memory.

The immune system and the CNS share the ability to respond to external stimuli and to form memory (Steinman L. 2004. Elaborate interactions between the immune and nervous systems. Nat. Immunol. 5: 575-581.). Vaccination induces a multistep immune response eventually leading to differentiation of Ag-specific memory T and B cells as effectors of immune protection (Seder R. A., P. A. Darrah, M. Roederer. 2008. T-cell quality in memory and protection: implications for vaccine design. Nat. Rev. Immunol. 8: 247-258.; Sallusto F., A. Lanzavecchia, K. Araki, R. Ahmed. 2010. From vaccines to memory and back. Immunity 33: 451-463.). After vaccination, APCs take up the Ag and migrate to lymphatic tissues to present part of the Ag at the cell surface to Th cells, thereby forming the so-called immunological synapse and initiating the transfer of the antigenic information into long-term storage in Ag-specific T and B cells. Formation of the immunological synapse represents an early stage in the immune response that determines quantity and quality of immunological memory, and it is at this stage adjuvants act to enhance the immunogenicity of the vaccine (Coffman R. L., A. Sher, R. A. Seder. 2010. Vaccine adjuvants: putting innate immunity to work. Immunity 33: 492-503.).

Sleep generally regulates immune functions in a supportive manner (Bence R. M., J. Quintas. 1997. Sleep and host defenses: a review. Sleep 20:1027-1037; Bryant P. A., J. Trinder, N. Curtis. 2004. Sick and tired: does sleep have a vital role in the immune system? Nat. Rev. Immunol. 4: 457-467; Lange T., S. Dimitrov, J. Born. 2010. Effects of sleep and circadian rhythm on the human immune system. Ann. N. Y. Acad. Sci. 1193: 48-59.). Sleep impacts APC and Th cell traffic and facilitates the release of endogenous adjuvants like growth hormone (GH), prolactin, and APE-derived IL-12, whereas it lowers the release of immunosuppressive hormones like cortisol (Lange T., S. Dimitrov, J. Born. 2010. Effects of sleep and circadian rhythm on the human immune system. Ann. N. Y. Acad. Sci. 1193: 48-59; Lorton D., C. L. Lubahn, C. Estus, B. A. Millar, J. L. Carter, C. A. Wood, D. L. Bellinger. 2006. Bidirectional communication between the brain and the immune system: implications for physiological sleep and disorders with disrupted sleep. Neuroimmunomodulation 13: 357-374; Dimitrov S., T. Lange, K. Nohroudi, J. Born. 2007. Number and function of circulating human antigen presenting cells regulated by sleep. Sleep 30: 401-411). In this study, an experimental vaccination approach against hepatitis A virus (HAV) was used to examine whether these effects of sleep can boost immunological memory formation. Sleep was found to enhance the vaccine-driven induction of immunological memory in the expansion, contraction, and maintenance phase as reflected by increased formation of Ag-specific Th cells and IgG1. (Tanja Lange, Stoyan Dimitrov, Thomas Bollinger, Susanne Diekelmann and Jan Born, "Sleep after Vaccination Boosts Immunological Memory", J Immunol Jul. 1, 2011, 187 (1) 283-290; DOI: doi.org/10.4049/jimmunol. 1100015.)

Among midlife adults, sleep duration also matters for vaccine efficacy. In one study, among participants who had no serological evidence of prior hepatitis B exposure, those who reported less sleep—especially on the two nights before a hepatitis B vaccination—had lower antibody titers 1 and 4 months later. Likewise, sleep duration, measured objectively via actigraphy and averaged the three nights before and three nights after the first hepatitis B inoculation, predicted subsequent antibody responses and clinical protection status after the second and third shots (Prather, A. A., Hall, M., Fury, J. M., Ross, D. C., Muldoon, M. F., Cohen, S., Marsland, A. L. (2012). Sleep and antibody response to hepatitis B vaccination. Sleep, 35(8), 1063-1069.). In fact, each additional hour of sleep tracked with a 56% increase in antibody levels. Taken together, this evidence suggests that shorter sleep duration lowers antibody responses—at least initially (e.g., Spiegel, K., Sheridan, J. F., Van Cauter, E. (2002). Effect of sleep deprivation on response to immunization. JAMA, 288(12), 1471-1472)—and fosters longer lasting deficiencies in cell-mediated immunity across a variety of vaccines and regardless of prior.

Nayyab Asif, Razia Iqbal, and Chaudhry Fahad Nazir, "Human immune system during sleep"; Am J Clin Exp Immunol. 2017; 6(6): 92-96. (Published online 2017 Dec. 20) discusses immune function and sleep. Immunity can be divided into innate immunity and adaptive immunity, both having an important component of communication, the cytokines. Cytokines are proteins produced by cells of the immune system that promote intracellular and intercellular immune responses. Some important cytokines involved in sleep and in the innate immunity are the interleukin-6 (IL-6) and Tumor Necrosis Factor-Alpha (TNF-$\alpha$). IL-6 is a pro-inflammatory cytokine that plays a role in the reduction of anabolic pathways and increase of catabolic pathways, resulting in an increased expenditure of energy to decrease the weight gain. Whereas the function of TNF-$\alpha$, which is also a pro-inflammatory cytokine, is centered on lipolysis and in changes of the adipose tissue, immunomodulation, apoptosis, proliferation, and pathological responses.

In a study with people who had chronic fatigue syndrome, those who had the worst quality of sleep were associated with higher severity of fatigue and with a higher interference in daily activities, with increased levels of pro-inflammatory interleukins (IL-1$\beta$, TNF-$\alpha$, and IL-6). Previous studies with groups of participants who got little slept (<6 h) detected a decline of T lymphocytes, lower activity of natural killer cells (NK), shorter telomere length of T-cells, and increased inflammatory markers (C-reactive protein and IL-8). Compared with people who slept seven to eight hours per day, those who slept less than five hours were more likely to report rhinopharyngitis and acute bronchitis.

The impaired mitogenic proliferation of lymphocytes, decreased HLA-DR expression, positive regulation of CD14+, and variations in CD4+ and CD8+ T lymphocytes appear to be a possible explanation for the higher susceptibility to infections after a worsening of sleep.

Sleep disorders occur due to a malfunction of its various regulatory mechanisms. Insomnia, the most common sleep-related complaint, is a multidimensional condition, reflecting the physical and mental state of an individual. It is defined as a difficulty in initiating, maintaining, and consolidating sleep or a worsened overall quality of sleep, leading to physical and mental damage. Depression and the widespread increase in anxiety are risk factors associated with the onset of insomnia. Excessive concern with the progress of the pandemic, their own health, or that of people close to them, and with financial aspects, in addition to social restrictions, collaborate to the impairment of sleep and, due to the role of sleep in emotional stabilization, this can impair mental health even further.

When associating immunity, sleep, and depression, patients with depression, which naturally go through great psychological stress, have increased pro-inflammatory markers, particularly the marker of C protein (CRP) and IL-6. In addition, an increase in inflammation increases depressive symptoms. Moreover, sleep disorders such as insomnia are linked with the incidence of depression, in addition to promoting an increase in inflammation.

Abbas A K, Lichtman A H, Pillai S. Cellular and molecular immunology. 9a ed. Philadelphia: Elsevier 2017.

Adler A B, Kim P Y, Thomas S. J., Sipos M L. Quarantine and the U.S. military response to the Ebola crisis: soldier health and attitudes. Public Health. 2018; 155:95-8.

Bacelar A. Insônia: do diagnóstico ao tratamento. São Caetano do Sul: Diffusion; 2019. p. 17-27.

Bailey M T. Psychological stress, immunity, and the effects on indigenous microflora. Adv Exp Med Biol. 2016; 874:225-46.

Besedovsky L, Lange T, Haack M. The sleep-immune crosstalk in health and disease. Physiol Rev. 2019; 99(3): 1325-80.

Choi J H, Lee B, Lee J Y, Kim C H, Park B, Kim D Y, et al. Relationship between sleep duration, sun exposure, and serum 25-hydroxyvitamin D status: a cross-sectional study. Sci Rep. 2020; 10(1)):4168.

Chokroverty S, Ferini-Strambi L. Oxford textbook of sleep disorders. Oxford: Oxford University Press; 2017.

Farhud D, Aryan Z. Circadian rhythm, lifestyle and health: a narrative review. Iran J Public Health. 2018; 47(8): 1068-76.

Holbrook J, Lara-Reyna 5, Jarosz-Griffiths H, McDermott M. Tumour necrosis factor signaling in health and disease. F1000Res. 2019; 8:F1000 Faculty Rev-111.

Ibarra-Coronado E R Pantaleón-Martínez A M, Velazquéz-Moctezuma J, Prospêro-García O, Mêndez-Díaz M, Pêrez-Tapia M, et al. The bidirectional relationship between sleep and immunity against infections. J Immunol Res. 2015; 2015:678164.

Irwin M R, Opp M R. Sleep health: reciprocal regulation of sleep and innate immunity. Neuropsychopharmacology. 2017; 42(1):129-55.

Irwin M R. Why sleep is important for health: a psychoneuroimmunology perspective. Annu Rev Psychol. 2015; 66:143-72.

Madison, Annelise A, M Rosie Shrout, Megan E Renna, Janice K Kiecolt-Glaser; "Psychological and Behavioral Predictors of Vaccine Efficacy: Considerations for COVID-19", Perspect Psychol Sci. 2021 March; 16(2): 191-203. doi: 10.1177/1745691621989243. Epub 2021 Jan. 27.

Milrad S F, Hall D L, Jutagir D R, Lattie E G, Ironson G H, Wohlgemuth W, et al. Poor sleep quality is associated with greater circulating pro-inflammatory cytokines and severity and frequency of chronic fatigue syndrome/myalgic encephalomyelitis (CFS/ME) symptoms in women. J Neuroimmunol. 2017; 303:43-50.

Morris C J, Purvis T E, Hu K, Scheer F A. Circadian misalignment increases cardiovascular disease risk factors in humans. Proc Natl Aced Sci USA. 2016; 113(10): E1402-11.

Phillips A J K Clerx W M, O'Brien C S, Sano A, Barger L K, Picard R W, et al. Irregular sleep/wake patterns are associated with poorer academic performance and delayed circadian and sleep/wake timing. Sci Rep. 2017; 7(1):3216

Prather A A, Janicki-Deverts D, Hall M H, Cohen S. Behaviorally assessed sleep and susceptibility to the common cold. Sleep. 2015; 38(9)1353-9.

Prather A A, Leung C W. Association of insufficient sleep with respiratory infection among adults in the United States. JAMA Intern Med. 2016; 176(6):850-2.

Reddy S, Reddy V, Sharma S. Physiology, circadian rhythm. In: StatPearls, Treasure Island: StatPearls Publishing; 2020. www.ncbi.nlm.nih.gov/books/NBK519507/#

Ruiz F S A, Tufik S. Aspectos imunológicos do sono. In: Paiva T, Andersen M L, Tufik S, eds. O sono e a medicine do sono. Barueri: Manole; 2014. p. 124-31.

Tempesta D, Socci V, De Gennaro L, Ferrara M. Sleep and emotional processing. Sleep Med Rev. 2018; 40:183-95.

Trochoutsou Al, Kloukina V, Semites K, Xanthou G. Vitamin-D in the immune system: genomic and non-genomic actions. Mini Rev Med Chem. 2015; 15(11):953-63.

Veronesi R, Focaccia R. Tratado de infectologia. 5a ed. São Paulo: Atheneu; 2015. p. 334-5.

Voitsidis P, Gliatas I, Bairachtari V, Papadopoulou K, Papageorgiou G, Parlapani E, et al. Insomnia during the COVID-19 pandemic in a Greek population. Psychiatry Res. 2020; 289:113076.

Wang C, Pan R, Wan X, Tan Y, Xu L, Ho C S, et al. Immediate psychological responses and associated factors during the initial stage of the 2019 coronavirus disease (COVID-19) epidemic among the general population in China. Int J Environ Res Public Health. 2020; 17(5):1729.

Promoting both cellular and humoral defense mechanisms, the Th cell response to vaccination represents a most immediate indicator of effective antigenic memory formation.

The endocrine milieu during SWS predicts the HAV-specific Th cell response to vaccination. Brain immune interactions during sleep are conveyed mainly via endocrine pathways, apart from direct neuronal influences on lymphatic tissue. Immunostimulating hormones like GH and prolactin as well as immunosuppressive hormones such as cortisol and catecholamines are strongly regulated by sleep. Sleep induced a profound increase in concentrations of GH and prolactin when compared with wakefulness ($p<0.001$). The increase in GH occurred during periods of SWS dominating the early night. In contrast, sleep was associated with decreased cortisol nadir levels during the early SWS-rich night-half ($p<0.02$). This decrease was compensated by enhanced morning cortisol levels after sleep ($p=0.008$). Sleep also diminished catecholamine levels, which was somewhat more robust for norepinephrine ($p<0.001$) than for epinephrine ($p=0.006$). To be noted, although relatively increased compared with sleep, plasma concentrations of epinephrine and norepinephrine during nocturnal wakefulness ($128\pm1.1$ and $283.7\pm18.7$ pg/ml, respectively) were still distinctly below the levels observed during daytime waking (measured before vaccinations, $32.8\pm3.3$ and $392.9\pm33.2$ pg/ml; $n=14$; $p<0.001$ for both comparisons) and were far from reaching any level commonly associated with acute stress. Nocturnal average concentrations of the primary stress hormone cortisol were closely comparable between the sleep and wake conditions ($p=0.81$), which excludes that responses to vaccination in the wake condition were substantially affected by acute stress. GH, prolactin, and cortisol significantly contributed to the fully developed HAV-specific Th cell response as measured at weeks 18-20, as well as to the response 1 y later, explaining 48% ($p=0.002$) and 56% ($p=0.02$) of the variance, respectively. Adding epinephrine or norepinephrine concentration to the analyses did not increase explained variance, which agrees with previous findings showing that the effects of catecholamines on the vaccination response are inconsistent. The combined action of GH, prolactin, and cortisol on the formation of the HAV-specific immune response is best described by an "adjuvant factor" summarizing the average hormone concentrations (0:30-2 AM) during post inoculation nights by the formula GH 3 prolactin/cortisol. This factor showed correlations as high as r=0.71 (p<0.001) and r=0.80 (p=0.002) with the percentage of HAV specific Th cells at weeks 18-20 and week 52, respectively. GH, prolactin, and cortisol synergistically contribute to the sleep-dependent enhancement of the vaccination response.

Compared with wakefulness, sleep on the nights after HBs vaccination significantly enhanced both the CD40L+ HBs-specific Th cell response and the Ab response, although overall, these effects appeared to be less consistent than for the HAV vaccination. The enhancing effect of sleep on the frequency of HBs-specific Th cells became significant after the second inoculation (p=0.05, for weeks 8-16) and continued during weeks 19-20 after the third inoculation (p=0.05). At the follow-up 1 y later, HBs-specific Th cell percentages in the sleep group were still on average distinctly higher than in the wake group, but this difference failed to reach significance (0.057±0.018 versus 0.037±0.010%, n=12; p=0.18).

Mounting an adaptive immune response that eventually results in Ag-specific memory is a slow multi-step process taking a minimum of several days. An enhanced Ag-specific Th cell response after sleep occurring within 24 h post-vaccination indicates an effect during the early stages of the immune response, most likely on APC-Th cell interactions taking place during this time window in lymphatic tissues. Analyses of sleep and endocrine activity suggest a scenario in which SWS plays a key role. SWS, a brain state hallmarked by EEG SWA, stimulates release of immune-stimulating hormones like GH and prolactin and inhibits immunosuppressive cortisol. These hormones are not only uniquely regulated by sleep but also affect the interaction between APC and Th cell and the response to vaccination, which is increased by GH and prolactin but reduced by cortisol. Interestingly, such hormonal effects appear to be most pronounced within the first 24 h after inoculation.

The sleep-associated hormonal changes prompt a shift of the type 1/type 2 cytokine balance toward enhanced activity of proinflammatory and Th1 cytokines (TNF-α, IL-12, IL-2, and IFNγ) favoring cellular aspects of adaptive immune responses over activity of anti-inflammatory or Th2 cytokines (like IL-10 and IL-4). Sleep as well as prolactin strongly enhance APC-derived IL-12 that, along with Ag stimulation, is an important signal switching Th cell differentiation toward increased Th1 cytokine production. In line, sleep during the nights following the three inoculations improved the development of adaptive Th1 immune responses at two functional levels. First, once early differentiation of IFN-γ producing HAV-specific Th cells (i.e., within 2 wk) is increased, sleep promotes IFN-γ-dependent effector functions. Second, through increased formation of IL-2 expressing HAV-specific Th cells, sleep enhances T cell survival, which enforces the induction of Ag-specific memory.

SWS establishes a unique endocrine milieu that exerts adjuvant activity by stimulating the production of proinflammatory cytokines, eventually enhancing the development of stable adaptive immunity both at the T and B cell sites. Interestingly, proinflammatory cytokines and muramyl dipeptide (like many other vaccine adjuvants) have SWS-promoting properties speaking for the presence of a feedforward loop where proinflammatory cytokines consolidate central nervous SWS during an ongoing immune response (Pabst M. J., S. Beranova-Giorgianni, J. M. Krueger. 1999. Effects of muramyl peptides on macrophages, monokines, and sleep. Neuroimmunomodulation 6: 261-283; Imeri L., M. R. Opp. 2009. How (and why) the immune system makes us sleep. Nat. Rev. Neurosci. 10: 199-210.). Animal data confirm such an assumption, because the amount of SWS predicts the survival rate after pathogen challenge in rabbits (Toth L. A. 1995. Sleep, sleep deprivation and infectious disease: studies in animals. Adv. Neuroimmunol. 5: 79-92.). Although REM sleep deprivation is known to impact immune parameters, some of which are also involved in regulating adaptive immune responses (Ruiz F. S., M. L. Andersen, R. C. Martins, A. Lager, J. D. Lopes, S. Tufik. 2010. Immune alterations after selective rapid eye movement or total sleep deprivation in healthy male volunteers. Innate. Immun. DOI: 10.1177/1753425910385962), correlation analyses of the current study argue against REM sleep playing a major role for immunological memory formation.

The observed sleep-induced increases in HAV- and HBs-specific IgG1 explain observations from two previous studies in humans in which under conditions of sleep restriction or deprivation total IgG was slightly reduced shortly after vaccination (influenza and HAV) (Spiegel K., J. F. Sheridan, E. Van Cauter. 2002. Effect of sleep deprivation on response to immunization. JAMA 288:1471-1472; Lange T., B. Perras, H. L. Fehm, J. Born. 2003. Sleep enhances the human antibody response to hepatitis A vaccination. Psychosom. Med. 65: 831-835.). Likewise, 7-8 h of sleep deprivation in rodents immediately following antigenic challenge suppressed the secondary Ab response, an effect that was completely prevented by administration of proinflammatory adjuvants like IL-1 and muramyl dipeptide (Moldofsky H. 1994. Central nervous system and peripheral immune functions and the sleep-wake system. J. Psychiatry Neurosci. 19: 368-374.). However, these human and animal studies focused on the clonal expansion phase early after vaccination and not on the contraction/maintenance phase reflecting memory formation (Sallusto F., A. Lanzavecchia, K. Araki, R. Ahmed. 2010. From vaccines to memory and back. Immunity 33: 451-463.). In addition, other animal studies could not confirm these results and if antigenic challenge took place after short-term sleep loss even an opposing (i.e., immunoenhancing) effect on early defense mechanisms became evident (Moldofsky H. 1994. Central nervous system and peripheral immune functions and the sleep-wake system. J. Psychiatry Neurosci. 19: 368-374; Toth L. A., J. E. Rehg. 1998. Effects of sleep deprivation and other stressors on the immune and inflammatory responses of influenza-infected mice. Life Sci. 63: 701-709; Renegar K. B., D. Crouse, R. A. Floyd, J. Krueger. 2000. Progression of influenza viral infection through the murine respiratory tract: the protective role of sleep deprivation. Sleep 23: 859-863.). Overall, the available data point out that experimental timing of Ag challenge, sleep deprivation, and respective immunological outcome measures is essential to uncover the adjuvant like actions of sleep on immunological memory formation.

Sleep enhances the adaptive immune response to HBs. It is difficult to explain that this enhancement was overall less robust than after HAV vaccination but could be related to differences in Ag uptake, processing, and presentation by APCs (Miller G. E., S. Cohen, S. Pressman, A. Barkin, B. S. Rabin, J. J. Treanor. 2004. Psychological stress and antibody response to influenza vaccination: when is the critical period for stress, and how does it get inside the body? Psychosom. Med. 66: 215-223.). Interestingly, in comparisons of morning and evening inoculations, Ab titers measured 4 wk later were revealed to be higher after HAV vaccination in the morning, whereas for HBs vaccination, this effect was reversed, with higher Ab titers after vaccination in the evening (Phillips A. C., S. Gallagher, D. Carroll, M. Drayson. 2008. Preliminary evidence that morning vaccination is associated with an enhanced antibody response in men. Psychophysiology 45: 663-666; Pöllmann L., B. Pöllmann. 1988. Tagesrhythmische unterschiede bei der antiköperbildung nach hepatitis-B-schutzimpfung. (Circadian differences of antibody response to hepatitis B vaccination) In Arbeitsmedizin im Gesundheitsdienst. Hofmann F., U. Stössel, eds. Gentner Verlag, Stuttgart, Germany, p. 83-87; Fleischer B. 1993. Circadian variation of antibody formation after hepatitis B vaccination (in German). Dtsch. Med. Wochenschr. 118: 999.). It is likely that sleep is most effective in supporting antigenic memory formation during a critical time window when the immunological synapse between APC and Th cell is forming. If as a result of the specific protein structure APC need a longer time for taking up and processing HAV than HBs, then sleep occurring ~15 h after a morning vaccination might optimally cover this critical window for HAV but to a lesser extent for HBs.

Immunodeficiency and poor responsiveness to vaccination in the course of aging are known to be accompanied by a particular decline in SWS, GH, prolactin, and APC-derived IL-12 (Lange T., S. Dimitrov, J. Born. 2010. Effects of sleep and circadian rhythm on the human immune system. Ann. N. Y. Acad. Sci. 1193: 48-59; Van Cauter E., R. Leproult, L. Plat. 2000. Age-related changes in slow wave sleep and REM sleep and relationship with growth hormone and cortisol levels in healthy men. JAMA 284: 861-868; Prinz P. N. 2004. Age impairments in sleep, metabolic and immune functions. *Exp. Gerontal.* 39:1739-1743; Larbi A., C. Franceschi, D. Mazzatti, R. Solana, A. Wikby, G. Pawelec. 2008. Aging of the immune system as a prognostic factor for human longevity. Physiology 23: 64-74; Panda A., F. Dian, S. Mohanty, D. van Duin, F. K. Newman, L. Zhang, S. Chen, V. Towle, R. B. Belshe, E. Fikrig, et al. 2010. Age-associated decrease in TLR function in primary human dendritic cells predicts influenza vaccine response. J. Immunol. 184: 2518-2527.).

Habitual short sleep duration is associated with an increased susceptibility to experimental rhinovirus infection and predicts poor Ab titers and poor clinical protection after three doses of hepatitis B vaccination in 125 middle-aged men and women (Cohen S., W. J. Doyle, C. M. Alper, D. Janicki-Deverts, R. B. Turner. 2009. Sleep habits and susceptibility to the common cold. Arch. Intern. Med. 169: 62-67; Prather A. A., M. Hall, J. M. Fury, D. L Ross, M. F. Muldoon, S. Cohen, A. L. Marsland. 2011. Sleep duration and antibody response to hepatitis B vaccination. Psychosom. Med. 73: A13. 47, 48).

Prolonged experimental sleep restriction consistently revealed a negative impact on immune functions (Lange et al. (2010); Everson L A., L. A. Toth. 2000. Systemic bacterial invasion induced by sleep deprivation. Am. J. Physiol. Regul. Integr. Comp. Physiol. 278: R905-R916.). However, as habitual short sleep and experimental sleep restriction may not always lead to reduced SWS or SWA (Webb W. B., H. W. Agnew Jr., 1970. Sleep stage characteristics of long and short sleepers. Science 168:146-147; Leemburg S., V. V. Vyazovskiy, U. Olcese, L L. Bassetti, G. Tononi, C. Cirelli. 2010. Sleep homeostasis in the rat is preserved during chronic sleep restriction. Proc. Natl. Acad. Sci. USA 107:15939-15944.), such immunosuppressive effects may stem rather from more pronounced endocrine changes like overall increases in cortisol levels (Lorton D., C. L. Lubahn, C. Estus, B. A. Millar, J. L. Carter, C. A. Wood, D. L. Bellinger. 2006. Bidirectional communication between the brain and the immune system: implications for physiological sleep and disorders with disrupted sleep. Neuroimmunomodulation 13: 357-374.).

Before the COVID-19 pandemic, insomnia affected about 30% of adult Americans. Since the beginning of the pandemic, many more people have difficulty falling or staying asleep. This sleep disorder, caused by stress and anxiety of pandemic and disrupted routine, is observed all over the world and reached such proportions that it deserved its own name—"Coronasomnia."

At the same time, the pandemic brought into sharp focus importance of the properly functioning immune system for protection from the serious, sometimes deadly and often long-lasting disease, caused by coronavirus infection. It is well established that one of the cornerstones supporting both innate and acquired (adaptive) immune system is adequate sleep. The central nervous system (CNS) and the immune system closely interact: a mental or physical stressor that primarily activates systems under CNS control will also induce an inflammatory response (Steptoe A, Hamer M, Chide Y. The effects of acute psychological stress on circulating factors in humans: a review and meta-analysis. Brain Behav Immun 21: 901-912, 2007. doi:10.1016/j.bbi. 2007.03.011.)

On the other hand, a microbial challenge that primarily activates the immune system will also prompt neurobehavioral, neuroendocrine, and autonomic nervous system responses (Dantzer R, O'Connor J C, Freund G G, Johnson R W, Kelley K W. From inflammation to sickness and depression: when the immune system subjugates the brain. Nat Rev Neurosci 9: 46-56, 2008. doi:10.1038/nrn2297.) The changes in behavior caused by cytokines produced as a result of active infection such as lethargy, loss of appetite, etc. are thought to promote healing, by conserving energy and directing it to the immune system.

In a long-term, dysregulated sleep can lead to an increased risk of hypertension, cardiovascular disease, diabetes, obesity, anxiety, neurodegenerative diseases, and depression. But in the context of the pandemic, the negative and almost immediate effect of sleep deregulation on immune function becomes especially worrisome. A number of studies have investigated the impact of sleep deprivation on various immune parameters, such as numbers of leukocytes and their subsets in the blood and various tissues, circulating cytokine levels, concentration of antibodies and complement factors, in and cell cytotoxicity. The sleep restriction to 4 hours for one night causes generation of inflammatory cytokines (Irwin M R, Wang M, Campomayor C O, Collado-Hidalgo A, Cole S. Sleep deprivation and activation of morning levels of cellular and genomic markers of inflammation. Arch Intern Med (2000) 166(16):1756-1762) If sleep is diminished for longer than one night to 6 hours, plasma levels of IL-6 or CRP (which is produced by the liver in response to IL-6 secretion) increase reflecting a systemic inflammatory response (Van Leeuwen W M, Lehto M, Karisola P, Lindholm H, Luukkonen R, Sallinen M, Härmä M, Porkka-Heiskanen T, Alenius H. Sleep restriction increases the risk of developing cardiovascular diseases by augmenting proinflammatory responses through IL-17 and CRP. PLoS One 4: e4589, 2009. doi:10.1371/journal.pone. 000458). The effects of sleep on other cytokines (IL-1, IL-2, IL-10, IL-12), TNF and different cytotoxic cells are complex, depending on the tissue where they are measured, time of measurement and other factors, but it seems that sleep acutely favors pro-inflammatory cytokine production over anti-inflammatory one.

Besides measuring leukocyte numbers and cytokine production, the sleep impacts functional parameters, especially NK-cell activity and lymphocyte proliferation. Normal sleep plays supportive role on lymphocyte proliferation, neutrophils and T cells, although the effects depend on the duration of sleep. Restricting the time allowed for sleep to 4 hours even for one night reduces natural killer (NK) cell activity to an average of 72%, compared with NK cell activity in participants who had a full night's sleep (Irwin M R, Mascovich A, Gillin J C, Willoughby R, Pike J, Smith T L. Partial sleep deprivation reduces natural killer cell activity in humans. (1994) Psychosom Med 56(6):493-498.).

Sleep affects antibody formation. Following selective REM sleep deprivation circulating immunoglobulins and complement level were changed, with effects depending on type of the sleep restriction (Ruiz F S, Andersen M L, Martins R D, Lager A, Lopes J D, Tufik S. Immune alterations after selective rapid eye movement or total sleep deprivation in healthy male volunteers. Innate Immun 18: 44-54, 2012. doi:10.1177/1753425910385962); Hui L, Hua F, Diandong H, Hong Y. Effects of sleep and sleep deprivation on immunoglobulins and complement in humans. Brain Behav Immun 21: 308-310, 2007. doi:10.1016/j.bbi.2006.09.005)

All those results indicate that sleep affects a variety of immune markers. An effective immune response relies on the complex interplay between several immune cells and mediators. It is essential to consider the impact of sleep on an ongoing immune response. Studies show that people who don't get quality sleep are more likely to get sick after being exposed to a virus, take longer to recover after an infection and have less robust response to a vaccine. Restricting sleep to 4 hours per night for 8 days, followed by sleep for 12 hours per night for 7 days, resulted in a greater than 50% decrease in production of antibodies to influenza vaccination (Spiegel K, Sheridan J F, Van Cauter E. Effect of sleep deprivation on response to immunization. (2002) JAMA 288(12):1471-1472) A single night without sleep on the night following vaccination against hepatitis A, hepatitis B, and H1N1 (swine flu) had the same effect on the antigen-specific antibody response (Lange T, Dimitrov S, Bollinger T, Diekelmann S, Born J. Sleep after vaccination boosts immunological memory. J Immunol 187: 283-290, 2011. doi:10.4049/jimmunol. 1100015.)

Furthermore, studies show that sleep deprivation in a particular stage of sleep affect specific marker of the immune response—some up-regulating and others down-regulating inflammatory response. The ability of the present neuro-modulation technology to stimulate specific targeted stages of sleep becomes particularly important in up- or down-regulation the inflammatory response.

Almost everything in biology is subject to change over-time. These changes occur on many different time scales, which vary greatly. For example, there are evolutionary changes that affect entire populations over time rather than a single organism. Evolutionary changes are often slower than a human time scale that spans many years (usually a human lifetime). Faster variations of the timing and duration of biological activity in living organisms occur, for example, in many essential biological processes in everyday life: in humans and animals, these variations occur, for example, in eating, sleeping, mating, hibernating, migration, cellular regeneration, etc. Other fast changes may include the transmission of a neural signal, for example, through a synapse such as the calyx of held, a particularly large synapse in the auditory central nervous system of mammals that can reach transmission frequencies of up to 50 Hz. With recruitment modulation, the effective frequencies can be higher. A single nerve impulse can reach a speed as high as one hundred meters (0.06 mile) per second (Kraus, David. Concepts in Modern Biology. New York: Globe Book Company, 1969: 170.). Myelination of axons can increase the speed of transmission by segmenting the membrane depolarization process.

Many of these changes over time are repetitive or rhythmic and are described as some frequency or oscillation. The field of chronobiology (en.wikipedia-on-ipfs.org/wiki/History_of_chronobiology.html), for example, examines such periodic (cyclic) phenomena in living organisms and their adaptation, for example, to solar and lunar-related rhythms (Patricia J. DeCoursey; Jay C. Dunlap; Jennifer J. Loros (2003). Chronobiology. Sinauer Associates Inc. ISBN 978-0-87893-149-1.) These cycles are also known as biological rhythms. The related terms chronomics and chronome have been used in some cases to describe either the molecular mechanisms involved in chronobiological phenomena or the more quantitative aspects of chronobiology, particularly where comparison of cycles between organisms is required. Chronobiological studies include, but are not limited to, comparative anatomy, physiology, genetics, molecular biology, and behavior of organisms within biological rhythms mechanics (Dunlap, J. C., Loros, J. J., & DeCoursey, P. J. (Eds.). (2004). Chronobiology: Biological timekeeping. Sinauer Associates.) Other aspects include epigenetics, development, reproduction, ecology, and evolution.

The most important rhythms in chronobiology are the circadian rhythms, roughly 24-hour cycles shown by physiological processes in all these organisms. It is regulated by circadian clocks. The circadian rhythms can be further broken down into routine cycles during the 24-hour day (Nelson R J 2005. An Introduction to Behavioral Endocrinology. Sinauer Associates, Inc.: MA Pg. 587.) All animals can be classified according to their activity cycles: Diurnal, which describes organisms active during daytime; Nocturnal, which describes organisms active in the night; and Crepuscular, which describes animals primarily active during the dawn and dusk hours (ex: white-tailed deer, some bats).

While circadian rhythms are defined as regulated by endogenous processes, other biological cycles may be regulated by exogenous signals. In some cases, multi-trophic systems may exhibit rhythms driven by the circadian clock of one of the members (which may also be influenced or reset by external factors).

Many other important cycles are also studied, including Infradian rhythms, which are cycles longer than a day. Examples include circannual or annual cycles that govern migration or reproduction cycles in many plants and animals, or the human menstrual cycle; Ultradian rhythms, which are cycles shorter than 24 hours, such as the 90-minute REM cycle, the 4-hour nasal cycle, or the 3-hour cycle of growth hormone production; Tidal rhythms, commonly observed in marine life, which follow the roughly 124-hour transition from high to low tide and back Lunar rhythms, which follow the lunar month (29.5 days). They are relevant, for example, to marine life, as the level of the tides is modulated across the lunar cycle; and Gene oscillations some genes are expressed more during certain hours of the day than during other hours.

Within each cycle, the time period during which the process is more active is called the acrophase (Refinetti, Roberto (2006). Circadian Physiology. CRC Press/Taylor & Francis Group. ISBN 0-8493-2233-2.). When the process is less active, the cycle is in its bathyphase or trough phase. The particular moment of highest activity is the peak or maximum; the lowest point is the nadir. How high (or low) the process gets is measured by the amplitude.

The normal cycle of sleep and wakefulness implies that, at specific times, various neural systems are being activated while others are being turned off. A key to the neurobiology of sleep is, therefore, to understand the various stages of sleep. In 1953, Nathaniel Kleitman and Eugene Aserinksy showed, using electroencephalographic (EEG) recordings from normal human subjects, that sleep comprises different stages that occur in a characteristic sequence.

Humans descend into sleep in stages that succeed each other over the first hour or so after retiring. These characteristic stages are defined primarily by electroencephalographic criteria. Initially, during "drowsiness," the frequency spectrum of the electroencephalogram (EEG) is shifted toward lower values, and the amplitude of the cortical waves slightly increases. This drowsy period, called stage I sleep, eventually gives way to light or stage II sleep, which is characterized by a further decrease in the frequency of the EEG waves and an increase in their amplitude, together with intermittent high-frequency spike clusters called sleep spindles. Sleep spindles are periodic bursts of activity at about 10-12 Hz that generally last 1 or 2 seconds and arise as a result of interactions between thalamic and cortical neurons. In stage III sleep, which represents moderate to deep sleep, the number of spindles decreases, whereas the amplitude of low-frequency waves increases still more. In the deepest level of sleep, stage IV sleep, the predominant EEG activity consists of low-frequency (1-4 Hz), high-amplitude fluctuations called delta waves, the characteristic slow waves for which this phase of sleep is named. The entire sequence from drowsiness to deep stage IV sleep usually takes about an hour.

These four sleep stages are called non-rapid eye movement (non-REM or NREM) sleep, and its most prominent feature is the slow-wave (stage IV) sleep. Sometimes, stages III and IV are combined and referred to jointly as the stage III sleep. It is most difficult to awaken people from slow-wave sleep; hence, it is considered to be the deepest stage of sleep. Following a period of slow-wave sleep, however, EEG recordings show that the stages of sleep reverse to reach a quite different state called rapid eye movement, or REM, sleep. In REM sleep, the EEG recordings are remarkably similar to that of the awake state. This mode is bizarre: a dreamer's brain becomes highly active while the body's muscles are paralyzed, and breathing and heart rate become erratic. After about 10 minutes in REM sleep, the brain typically cycles back through the non-REM sleep stages. Slow-wave sleep usually occurs again in the second period of this continual cycling, but not during the rest of the night. On average, four additional periods of REM sleep occur, each having longer than the preceding cycle durations.

The sleep cycle is an oscillation between the non-REM (including slow-waves) and REM phases of sleep. It is sometimes called the ultradian sleep cycle, sleep-dream cycle, or REM-NREM cycle, to distinguish it from the circadian alternation between sleep and wakefulness. In humans, this cycle takes on average between 1 and 2 hours (approximately 90 min).

The timing of sleep cycles can be observed on EEG by marked distinction in brainwaves manifested during REM and non-REM sleep. Delta wave activity, correlating with slow-wave (deep) sleep, in particular, shows regular oscillations throughout a night's sleep. Secretions of various hormones, including renin, growth hormone, and prolactin, correlate positively with delta-wave activity, whereas secretion of thyroid-stimulating hormone correlates inversely. Heart rate variability, well-known to increase during REM, also correlates inversely with delta-wave oscillations over the ~90-minute cycle.

Homeostatic functions, especially thermoregulation, normally occur during non-REM sleep, but not during REM sleep. During REM sleep, body temperature tends to drift from its mean level, and during non-REM sleep, to return to normal. The alternation between the stages, therefore, maintains body temperature within an acceptable range. In humans, the transition between non-REM and REM is abrupt; in other animals, less so.

Different models have been proposed to elucidate the complex rhythm of electrochemical processes that result in the regular alternation of REM and non-REM sleep. Monoamines are active during non-REM stages but not during REM stages, whereas acetylcholine is more active during REM sleep. The reciprocal interaction model proposed in the 1970s suggested a cyclic give and take between these two systems. More recent theories such as the "flip-flop" model proposed in the 2000s include the regulatory role of in inhibitory neurotransmitter gamma-aminobutyric acid (BABA).

The average length of the sleep cycle in an adult man is 90 minutes. N1 (NREM stage 1) is when the person is drowsy or awake to falling asleep. Brain waves and muscle activity start to decrease at this stage. N2 is when the person experiences a light sleep. Eye movement has stopped by this time. Brain wave frequency and muscle tonus is decreased. The heart rate and body temperature go down. N3 or even N4 is the most difficult stages to be awakened. Every part of the body is now relaxed, breathing is slowed, blood pressure and body temperature are reduced. REM sleep is a unique state, in which dreams usually occur. The brain is awake, and body paralyzed. This unique stage is usually when the person is in the deepest stage of sleep and dreams. The average length of a sleep cycle usually thought of as 90 min. Some sources give it 90-110 minutes or an even wider range of 80-120 minutes. A seven-eight-hour sleep usually includes five cycles, the middle two of which tend to be longer. REM takes up more of the cycle as the night goes on.

When falling asleep, a series of highly orchestrated events puts the brain to sleep in the above-mentioned stages. Technically, sleep starts in the brain areas that produce slow-wave sleep (SWS). It has been shown that two groups of cells—the ventrolateral preoptic nucleus in the hypothalamus and the parafacial zone in the brain stem—are involved in prompting SWS. When these cells are activated, it triggers a loss of consciousness. After SWS, REM sleep begins. The purpose of REM sleep remains a biological mystery, despite our growing understanding of its biochemistry and neurobiology. It has been shown that a small group of cells in the brain stem, called the subcoeruleus nucleus, control REM sleep. When these cells become injured or diseased, people do not experience the muscle paralysis associated with REM sleep, which can lead to REM sleep behavior disorder—a serious condition in which the afflicted violently act out their dreams. For reasons that are not clear, the amount of REM sleep each day decreases from about 8 hours at birth to 2 hours at 20 years, to only about 45 minutes at 70 years of age. See Mallick, B. N.; S. R. Pandi-Perumal; Robert W. McCarley; and Adrian R. Morrison (2011). *Rapid Eye Movement Sleep: Regulation and Function*. Cambridge University Press. ISBN 978-0-521-11680-0; Nir, and Tononi, "Dreaming and the Brain: from Phenomenology to Neurophysiology." *Trends in Cognitive Sciences, vol.* 14, no. 2, 2010, pp. 88-100; Varela, F., Engel, J., Wallace, B., &

Thupten, Jinpa. (1997). *Sleeping, dreaming, and dying: An exploration of consciousness with the Dalai Lama.*

Brainwaves have been widely studied in neural activity generated by large groups of neurons, mostly by EEG. In general, EEG signals reveal oscillatory activity (groups of neurons periodically firing in synchrony), in specific frequency bands: alpha (7.5-12.5 Hz) that can be detected from the occipital lobe during relaxed wakefulness and which increases when the eyes are closed; delta (1-4 Hz), theta (4-8 Hz), beta (13-30 Hz), low gamma (30-70 Hz), and high gamma (70-150 Hz) frequency bands, where faster rhythms such as gamma activity have been linked to cognitive processing. Higher frequencies imply multiple groups of neurons firing in coordination, either in parallel or in series, or both, since individual neurons do not fire at rates of 100 Hz. Neural oscillations of specific characteristics have been linked to cognitive states, such as awareness and consciousness and different sleep stages. See, Chang-Hwan Im, Computational EEG Analysis: Methods and Applications (Biological and Medical Physics, Biomedical Engineering), Sep. 11, 2019.

Alpha is the frequency range from 7 Hz to 14 Hz. This was the "posterior basic rhythm" (also called the "posterior dominant rhythm" or the "posterior alpha rhythm"), seen in the posterior regions of the head on both sides, higher in amplitude on the dominant side. It emerges with the closing of the eyes and with relaxation and attenuates with eye opening or mental exertion. The posterior basic rhythm is slower than 8 Hz in young children (therefore technically in the theta range). In addition to the posterior basic rhythm, there are other normal alpha rhythms such as the sensorimotor, or mu rhythm (alpha activity in the contralateral sensory and motor cortical areas) that emerges when the hands and arms are idle; and the "third rhythm" (alpha activity in the temporal or frontal lobes). Alpha can be abnormal; for example, an EEG that has diffuse alpha occurring in a coma and is not responsive to external stimuli is referred to as "alpha coma."

Beta is the frequency range from 15 Hz to about 30 Hz. It is usually seen on both sides in symmetrical distribution and is most evident frontally. Beta activity is closely linked to motor behavior and is generally attenuated during active movements. Low-amplitude beta with multiple and varying frequencies is often associated with active, busy, or anxious thinking and active concentration. Rhythmic beta with a dominant set of frequencies is associated with various pathologies, such as Dup15q syndrome, and drug effects, especially benzodiazepines. It may be absent or reduced in areas of cortical damage. It is the dominant rhythm in patients who are alert or anxious or who have their eyes open.

Gamma is the frequency range of approximately 30-100 Hz. Gamma rhythms are thought to represent binding of different populations of neurons together into a network to carry out a certain cognitive or motor function.

Delta wave (en.wikipedia.org/wiki/Delta_wave) is the frequency range up to 4 Hz. It tends to be the highest in amplitude and the slowest waves. It is normally seen in adults in NREM (en.wikipedia.org/wiki/NREM). It is also seen normally in babies. It may occur focally with subcortical lesions and in general distribution with diffuse lesions, metabolic encephalopathy hydrocephalus or deep midline lesions. It is, usually, most prominent frontally in adults (e.g., FIRDA-frontal intermittent rhythmic delta) and posteriorly in children (e.g., OIRDA-occipital intermittent rhythmic delta).

Theta is the frequency range from 4 Hz to 7 Hz. Theta is normally seen in young children. It may be seen in drowsiness or arousal in older children and adults; it can also be seen in meditation. Excess theta for age represents abnormal activity. It can be seen as a focal disturbance in focal subcortical lesions; it can be seen in the generalized distribution in diffuse disorder or metabolic encephalopathy or deep midline disorders or some instances of hydrocephalus. On the contrary, this range has been associated with reports of relaxed, meditative, and creative states.

Mu range is 8-13 Hz and partly overlaps with other frequencies. It reflects the synchronous firing of motor neurons in a rest state. Mu suppression is thought to reflect motor mirror neuron systems because when an action is observed, the pattern extinguishes, possibly because of the normal neuronal system and the mirror neuron system "go out of sync" and interfere with each other. (en.wikipedia.org/wiki/Electroencephalography). See Reference List 1.

All sleep stages are associated with frequencies below 13 Hz delta (1-4 Hz), theta (4-8 Hz), and alpha (8-12 Hz). While these frequencies may be reproduced in transcranial electric (or magnetic) stimulation, or via sensory stimulation with light, any attempts to reproduce these frequencies for stimulation via sound ran into problems associated with infrasound, defined as any sound below 20 Hz frequency. Firstly, it is difficult to generate infrasound through acoustic speakers. Earbuds are too small for that and so are most regular speakers. Specialized large subwoofers with circular design or sound guides may be used, but tend to be impractical.

A more serious problem is the effect of the infrasound on human health. While many animals (e.g., elephants and whales) communicate via infrasound, in humans, infrasound causes undesirable effects including send of panic, fear, and anxiety. Prolonged exposure to infrasound could be dangerous to human health. See, for example, Persinger, M. A. Nat Hazards (2014) 70: 501. doi.org/10.1007/s11069-013-0827-3. These problems are addressed using binaural beats.

One study has suggested that infrasound may cause feelings of awe or fear in humans. It has also been suggested that since it is not consciously perceived, it may make people feel vaguely that odd or supernatural events are taking place. Infrasound may affect some people's nervous system by stimulating the vestibular system, and this has shown in animal models an effect similar to sea sickness. (King, Simon (12 Jun. 2015). "Wind farm effect on balance 'akin to seasickness': scientist". News Corp Australia).

In research conducted in 2006 focusing on the impact of sound emissions from wind turbines on the nearby population, perceived infrasound has been associated to effects such as annoyance or fatigue, depending on its intensity, with little evidence supporting physiological effects of infrasound below the human perception threshold. (Rogers, Anthony; Manwell, James (2006). "Wright". Sally: 9. CiteSeerX10.1.1.362.4894). Later studies, however, have linked inaudible infrasound to effects such as fullness, pressure or tinnitus, and acknowledged the possibility that it could disturb sleep. (Salt, Alec N.; Kaltenbach, James A. (19 Jul. 2011)."Infrasound From Wind Turbines Could Affect Humans". Bulletin of Science, Technology & Society. 31(4): 296-302. doi:10.1177/0270467611412555. S2CID 110190618). Other studies have also suggested associations between noise levels in turbines and self-reported sleep disturbances in the nearby population, while adding that the contribution of infrasound to this effect is still not fully understood. (Abbasi, Milad; Monnazzam, Mohammad Reza; Zakerian, Sayed Abbolfazl; Yousefzadeh, Arsalan (June 2015). "Effect of Wind Turbine Noise on Workers' Sleep Disorder: A Case Study of Manjil Wind Farm in Northern Iran". Fluctuation and Noise Letters. 14 (2): 1550020. Bibcode:2015FNL . . . 1450020A doi:10.1142/ S0219477515500200; Bolin, Karl; Bluhm, Gösta; Eriksson, Gabriella; Nilsson, Mats E (1 Jul. 2011)."Infrasound and low frequency noise from wind turbines: exposure and health effects". Environmental Research Letters. 6 (3): 035103. Bibcode:2011ERL_6c5103B. doi:10.1088/1748-9326/6/3/035103). See, en.wikipedia.org/wiki/Infrasound.

A binaural beat is an auditory illusion perceived when two different pure-tone sine waves, both with frequencies lower than 1500 Hz, with less than a 40 Hz difference between them, are presented to a listener dichotically (one through each ear). en.wikipedia.org/wiki/Beat_(acoustics)#Binaural_beats. For example, if a 530 Hz pure tone is presented to a subject's right ear, while a 520 Hz pure tone is presented to the subject's left ear, the listener will perceive the auditory illusion of a third tone, in addition to the two pure-tones presented to each ear. The third sound is called a binaural beat, and in this example would have a perceived pitch correlating to a frequency of 10 Hz, that being the difference between the 530 Hz and 520 Hz pure tones presented to each ear. Binaural-beat perception originates in the inferior colliculus of the midbrain and the superior olivary complex of the brainstem, where auditory signals from each ear are integrated and precipitate electrical impulses along neural pathways through the reticular formation up the midbrain to the thalamus, auditory cortex, and other cortical regions. Binaural beats are widely used in brain stimulation.

EEG (electroencephalography) and MEG (magnetoencephalography) are available technologies to monitor brain electrical activity. Each generally has sufficient temporal resolution to follow dynamic changes in brain electrical activity. Electroencephalography (EEG) and quantitative electroencephalography (qEEG) are electrophysiological monitoring methods that analyze the electrical activity of the brain to measure and display patterns that correspond to cognitive states and/or diagnostic information. It is typically noninvasive, with the electrodes placed on the scalp, although invasive electrodes are also used in some cases. EEG signals may be captured and analyzed by a mobile device, often referred to as "brain wearables." There are a variety of "brain wearables" readily available on the market today. EEGs can be obtained with a non-invasive method where the aggregate oscillations of brain electric potentials are recorded with numerous electrodes attached to the scalp of a person. Most EEG signals originate in the brain's outer layer (the cerebral cortex), believed largely responsible for our thoughts, emotions, and behavior. Cortical synaptic action generates electrical signals that change in the 10 to 100-millisecond range. Transcutaneous EEG signals are limited by the relatively insulating nature of the skull surrounding the brain, the conductivity of the cerebrospinal fluid and brain tissue, relatively low amplitude of individual cellular electrical activity, and distances between the cellular current flows and the electrodes. EEG is characterized by: (1) Voltage; (2) Frequency; (3) Spatial location; (4) Interhemispheric symmetries; (5) Reactivity (reaction to state change); (6) Character of waveform occurrence (random, serial, continuous); and (7) Morphology of transient events. EEGs can be separated into two main categories. Spontaneous EEG which occur in the absence of specific sensory stimuli and evoked potentials (EPs) which are associated with sensory stimuli like repeated light flashes, auditory tones, finger pressure, or mild electric shocks. The latter is recorded, for example, by time averaging to remove effects of spontaneous EEG. Non-sensory triggered potentials are also known. EP's typically are time synchronized with the trigger, and thus have an organization principle. Event-related potentials (ERPs) provide evidence of a direct link between cognitive events and brain electrical activity in a wide range of cognitive paradigms. It has generally been held that an ERP is the result of a set of discrete stimulus-evoked brain events. Event-related potentials (ERPs) are recorded in the same way as EPs, but occur at longer latencies from the stimuli and are more associated with an endogenous brain state.

Typically, a magnetic sensor with sufficient sensitivity to individual cell depolarization or small groups is a superconducting quantum interference device (SQUID), which requires cryogenic temperature operation, either at liquid nitrogen temperatures (high-temperature superconductors, HTS) or liquid helium temperatures (low-temperature superconductors, LTS). However, current research shows the possible feasibility of room temperature superconductors (20 C). Magnetic sensing has an advantage, due to the dipole nature of sources, of having better potential volumetric localization; however, due to this added information, the complexity of signal analysis is increased.

In general, the electromagnetic signals detected represent action potentials, an automatic response of a nerve cell to depolarization beyond a threshold, which briefly opens conduction channels. The cells have ion pumps which seek to maintain a depolarized state. Once triggered, the action potential propagates along the membrane in two-dimensions, causing a brief high level of depolarizing ion flow. There is a quiescent period after depolarization that generally prevents oscillation within a single cell. Since the exon extends from the body of the neuron, the action potential will typically proceed along the length of the axon, which terminates in a synapse with another cell. While direct electrical connections between cells occur, often the axon releases a neurotransmitter compound into the synapse, which causes depolarization or hyperpolarization of the target cell. Indeed, the result may also be the release of a hormone or peptide, which may have a local or more distant effect.

The electrical fields detectable externally tend to not include signals which low-frequency signals, such as static levels of polarization, or cumulative depolarizing or hyperpolarizing effects between action potentials. In myelinated tracts, the current flows at the segments tend to be small, and therefore, the signals from individual cells are small. Therefore, the largest signal components are from the synapses and cell bodies. In the cerebrum and cerebellum, these structures are mainly in the cortex, which is largely near the skull, making electroencephalography useful, since it provides spatial discrimination based on electrode location. However, deep signals are attenuated and poorly localized. Magnetoencephalography detects dipoles, which derive from current flow, rather than voltage changes. In the case of a radially or spherically symmetric current flow within a short distance, the dipoles will tend to cancel, while net current flows long axons will reinforce. Therefore, an electroencephalogram reads a different signal than a magnetoencephalogram.

Brainwaves, e.g., EEG signals, may be acquired in various ways. Traditional signal acquisition by neurologists and encephalography/EEG technicians involves pasted-on electrodes or caps with arrays of electrodes, e.g., 20-256 electrodes positioned on the scalp. However, in some cases, especially where high spatial resolution is not required, and dominant brainwave patterns are sought, simpler and less controlled EEG acquisition systems may be employed, including through commercially available device intended to interface with smartphones. See, kokoon.io, www.thinkmindset.com/; www.choosemuse.com (Muse, Muse2); Neurosky getvi.com (Vi Sense); Strickland, Eliza, "In-Ear EEG Makes Unobtrusive Brain-Hacking Gadgets a Real Possibility", IEEE Spectrum Jul. 7, 2016; Strickland, Eliza, "Wireless Earbuds Will Record Your EEG, Send Brainwave Data To Your Phone", IEEE Spectrum May 17, 2016. The Unicorn "Hybrid Black" wearable EEG headset provides a headset with eight electrode channels and digital data acquisition electronics (24 bit, 250 Hz), intended to provide a brain-computer interface for artistic, control and other tasks. See, www.unicorn-bi.com/. Starkey Laboratories, Inc. US 20190166434 discloses an ear-worn electronic device having a plurality of sensors for EEG signals from a wearer's ear, as a brain-computer interface. A number of designs provide in-ear headphones which integrate EEG electrodes that pick up signals from the ear canal. See Reference List 11.

Another recently released application pertains to virtual reality (VR) technology. On Sep. 18, 2017 Looxid Labs launched a technology that harnesses EEG from a subject waring a VR headset. Looxid Labs intention is to factor in brainwaves into VR applications in order to accurately infer emotions. Other products such as MindMaze and even Samsung have tried creating similar applications through facial muscles recognition. (scottamyx.com/2017/10/13/looxid-labs-vr-brain-waves-human-emotions/). According to its website (looxidlabs.com/device-2/), the Looxid Labs Development Kit provides a VR headset embedded with miniaturized eye and brain sensors. It uses B EEG channels: Fp1, Fp2, AF7, AF8, AF3, AF4 in the international 10-20 system.

Light, sound or electromagnetic fields may be used to remotely convey a temporal pattern of brainwaves. See Reference List 2.

The functional relevance of brain oscillations in the alpha frequency range (8-13 Hz) has been repeatedly investigated through the use of rhythmic visual stimulation. There are two hypotheses on the origin of steady-state visual evoked potential (SSVEP) measured in EEG during rhythmic stimulation: entrainment of brain oscillations and superposition of event-related responses (ERPs). The entrainment but not the superposition hypothesis justifies rhythmic visual stimulation as a means to manipulate brain oscillations because superposition assumes a linear summation of single responses, independent from ongoing brain oscillations. Participants stimulated with the rhythmic flickering light of different frequencies and intensities, and entrainment was measured by comparing the phase coupling of brain oscillations stimulated by rhythmic visual flicker with the oscillations induced by arrhythmic jittered stimulation, varying the time, stimulation frequency, and intensity conditions. Phase coupling was found to be more pronounced with increasing stimulation intensity as well as at stimulation frequencies closer to each participant's intrinsic frequency. Even in a single sequence of an SSVEP, non-linear features (intermittency of phase locking) was found that contradict the linear summation of single responses, as assumed by the superposition hypothesis. Thus, evidence suggests that visual rhythmic stimulation entrains brain oscillations, validating the approach of rhythmic stimulation as manipulation of brain oscillations. See, Notbohm A, Kurths J, Herrmann D S, Modification of Brain Oscillations via Rhythmic Light Stimulation Provides Evidence for Entrainment but Not for Superposition of Event-Related Responses, Front Hum Neurosci. 2016 Feb. 3; 10:10 doi:10.3389/fnhum. 2016.00010 eCollection 2016. It is also known that periodic visual stimulation can trigger epileptic seizures.

Brain entrainment, also referred to as brainwave synchronization and neural entrainment, refers to the capacity of the brain to naturally synchronize its brainwave frequencies with the rhythm of periodic external stimuli, most commonly auditory, visual, or tactile. Brainwave entrainment technologies are used to induce various brain states, such as relaxation or sleep, by creating stimuli that occur at regular, periodic intervals to mimic electrical cycles of the brain during the desired states, thereby "training" the brain to consciously alter states. Recurrent acoustic frequencies, flickering lights, or tactile vibrations are the most common examples of stimuli applied to generate different sensory responses. It is hypothesized that listening to these beats of certain frequencies one can induce a desired state of consciousness that corresponds with specific neural activity. Patterns of neural firing, measured in Hz, correspond with alertness states such as focused attention, deep sleep, etc.

The term "entrainment" has been used to describe a shared tendency of many physical and biological systems to synchronize their periodicity and rhythm through interaction. This tendency has been identified as specifically pertinent to the study of sound and music generally, and acoustic rhythms specifically. The most ubiquitous and familiar examples of neuromotor entrainment to acoustic stimuli are observable in spontaneous foot or finger tapping to the rhythmic beat of a song. Exogenous rhythmic entrainment, which occurs outside the body, has been identified and documented for a variety of human activities, which include the way people adjust the rhythm of their speech patterns to those of the subject with whom they communicate, and the rhythmic unison of an audience clapping. Even among groups of strangers, the rate of breathing, locomotive, and subtle expressive motor movements, and rhythmic speech patterns have been observed to synchronize and entrain, in response to an auditory stimulus, such as a piece of music with a consistent rhythm. Furthermore, motor synchronization to repetitive tactile stimuli occurs in animals, including cats and monkeys as well as humans, with accompanying shifts in electroencephalogram (EEG) readings. Examples of endogenous entrainment, which occurs within the body, include the synchronizing of human circadian sleep-wake cycles to the 24-hour cycle of light and dark, and the frequency following response of humans to sounds and music.

Brainwaves, or neural oscillations, share the fundamental constituents with acoustic and optical waves, including frequency, amplitude, and periodicity. The synchronous electrical activity of cortical neural ensembles can synchronize in response to external acoustic or optical stimuli and also entrain or synchronize their frequency and phase to that of a specific stimulus. Brainwave entrainment is a colloquialism for such 'neural entrainment', which is a term used to denote the way in which the aggregate frequency of oscillations produced by the synchronous electrical activity in ensembles of cortical neurons can adjust to synchronize with the periodic vibration of an external stimuli, such as a sustained acoustic frequency perceived as pitch, a regularly repeating pattern of intermittent sounds, perceived as rhythm, or of a regularly rhythmically intermittent flashing light.

Changes in neural oscillations, demonstrable through electroencephalogram (EEG) measurements, are precipitated by listening to music, which can modulate autonomic arousal ergotropically and trophotropically, increasing and decreasing arousal respectively. Musical auditory stimulation has also been demonstrated to improve immune function, facilitate relaxation, improve mood, and contribute to the alleviation of stress.

The Frequency following response (FFR), also referred to as Frequency Following Potential (FFP), is a specific response to hearing sound and music, by which neural oscillations adjust their frequency to match the rhythm of auditory stimuli. The use of sound with intent to influence cortical brainwave frequency is called auditory driving, by which frequency of neural oscillation is 'driven' to entrain with that of the rhythm of a sound source. See Reference List 3

Baseline correction of event-related time-frequency measure may be made by taking pre-event baseline activity into consideration. In general, a baseline period is defined by the average of the values within a time window preceding the time-locking event. There are at least four common methods for baseline correction in time-frequency analysis. The methods include various baseline value normalizations. See, Reference List 4.

Brain entrainment may be detected through EEG or MEG activity. See Reference List 5. The entrainment hypothesis (Thut and Miniussi, 2009; Thut et al., 2011a, 2012), suggests the possibility of inducing a particular oscillation frequency in the brain using an external oscillatory force (e.g., rTMS, but also tACS). The physiological basis of oscillatory cortical activity lies in the timing of the interacting neurons; when groups of neurons synchronize their firing activities, brain rhythms emerge, network oscillations are generated, and the basis for interactions between brain areas may develop (Buzsàki, 2006). Because of the variety of experimental protocols for brain stimulation, limits on descriptions of the actual protocols employed, and limited controls, consistency of reported studies is lacking, and extrapolability is limited. Thus, while there is various consensus in various aspects of the effects of extracranial brain stimulation, the results achieved have a degree of uncertainty dependent on details of implementation. On the other hand, within a specific experimental protocol, it is possible to obtain statistically significant and repeatable results. This implies that feedback control might be effective to control implementation of the stimulation for a given purpose; however, studies that employ feedback control are lacking.

Different cognitive states are associated with different oscillatory patterns in the brain (Buzsàki, 2008; Canolty and Knight, 2010; Varela et al., 2001). Thut et al. (2011b) directly tested the entrainment hypothesis by means of a concurrent EEG-TMS experiment. They first determined the individual source of the parietal-occipital alpha modulation and the individual alpha frequency (magnetoencephalography study). They then applied rTMS at the individual alpha power while recording the EEG activity at rest. The results confirmed the three predictions of the entrainment hypothesis: the induction of a specific frequency after TMS, the enhancement of oscillation during TMS stimulation due to synchronization, and phase alignment of the induced frequency and the ongoing activity (Thut et al., 2011b).

Phase resetting or shifting can synchronize inputs and favor communication and, eventually, Hebbian plasticity (Hebb, 1949). Thus, rhythmic stimulation may induce a statistically higher degree of coherence in spiking neurons, which facilitates the induction of a specific cognitive process (or hinders that process). Here, the perspective is slightly different (coherence resonance), but the underlining mechanisms are similar to the ones described so far (stochastic resonance), and the additional key factor is the repetition at a specific rhythm of the stimulation.

Entrainment is plausible because of the characteristics of the demonstrated EEG responses to a single TMS pulse, which have a spectral composition which resembles the spontaneous oscillations of the stimulated cortex. For example, TMS of the "resting" visual (Rosanova et al., 2009) or motor cortices (Veniero et al., 2011) triggers alpha-waves, the natural frequency at the resting state of both types of cortices. With the entrainment hypothesis, the noise generation framework moves to a more complex and extended level in which noise is synchronized with on-going activity. Nevertheless, the model to explain the outcome will not change, stimulation will interact with the system, and the final result will depend on introducing or modifying the noise level. The entrainment hypothesis makes clear predictions with respect to online repetitive TMS paradigms' frequency engagement as well as the possibility of inducing phase alignment, i.e., a reset of ongoing brain oscillations via external spTMS (Thut et al., 2011a, 2012; Veniero et al., 2011). The entrainment hypothesis is superior to the localization approach in gaining knowledge about how the brain works, rather than where or when a single process occurs. TMS pulses may phase-align the natural, ongoing oscillation of the target cortex. When additional TMS pulses are delivered in synchrony with the phase-aligned oscillation (i.e., at the same frequency), further synchronized phase-alignment will occur, which will bring the oscillation of the target area in resonance with the TMS train. Thus, entrainment may be expected when TMS is frequency-tuned to the underlying brain oscillations (Veniero et al., 2011).

Binaural beats are auditory brainstem responses which originate in the superior olivary nucleus of each hemisphere. They result from the interaction of two different auditory impulses, originating in opposite ears, below 1000 Hz and which differ in frequency between one and 30 Hz. For example, if a pure tone of 400 Hz is presented to the right ear and a pure tone of 410 Hz is presented simultaneously to the left ear, an amplitude modulated standing wave of 10 Hz, the difference between the two tones, is experienced as the two wave forms mesh in and out of phase within the superior olivary nuclei. This binaural beat is not heard in the ordinary sense of the word (the human range of hearing is from 20-20,000 Hz). It is perceived as an auditory beat and theoretically can be used to entrain specific neural rhythms through the frequency-following response (FFR)—the tendency for cortical potentials to entrain to or resonate at the frequency of an external stimulus. Thus, it is theoretically possible to utilize a specific binaural-beat frequency as a consciousness management technique to entrain a specific cortical rhythm. The binaural-beat appears to be associated with an electroencephalographic (EEG) frequency-following response in the brain.

Uses of audio with embedded binaural beats that are mixed with music or various pink or background sound are diverse. They range from relaxation, meditation, stress reduction, pain management, improved sleep quality, decrease in sleep requirements, super learning, enhanced creativity and intuition, remote viewing, telepathy, and out-of-body experience and lucid dreaming. Audio embedded with binaural beats is often combined with various meditation techniques, as well as positive affirmations and visualization.

When signals of two different frequencies are presented, one to each ear, the brain detects phase differences between these signals. "Under natural circumstances, a detected phase difference would provide directional information. The brain processes this anomalous information differently when these phase differences are heard with stereo headphones or speakers. A perceptual integration of the two signals takes place, producing the sensation of a third "beat" frequency. The difference between the signals waxes and wanes as the two different input frequencies mesh in and out of phase. As a result of these constantly increasing and decreasing differences, an amplitude-modulated standing wave—the binaural beat is heard. The binaural beat is perceived as a fluctuating rhythm at the frequency of the difference between the two auditory inputs. Evidence suggests that the binaural beats are generated in the brainstem's superior olivary nucleus, the first site of contralateral integration in the auditory system. Studies also suggest that the frequency-following response originates from the inferior colliculus. This activity is conducted to the cortex where it can be recorded by scalp electrodes. Binaural beats can easily be heard at the low frequencies (<30 Hz) that are characteristic of the EEG spectrum.

Synchronized brainwaves have long been associated with meditative and hypnagogic states, and audio with embedded binaural beats has the ability to induce and improve such states of consciousness. The reason for this is physiological. Each ear is "hardwired" (so to speak) to both hemispheres of the brain. Each hemisphere has its own olivary nucleus (sound-processing center) which receives signals from each ear. In keeping with this physiological structure, when a binaural beat is perceived there are actually two standing waves of equal amplitude and frequency present, one in each hemisphere. So, there are two separate standing waves entraining portions of each hemisphere to the same frequency. The binaural beats appear to contribute to the hemispheric synchronization evidenced in meditative and hypnagogic states of consciousness. Brain function is also enhanced through the increase of cross-collosal communication between the left and right hemispheres of the brain. See Reference List 6.

Isochronic tones are regular beats of a single tone that are used alongside monaural beats and binaural beats in the process called brainwave entrainment. At its simplest level, an isochronic tone is a tone that is being turned on and off rapidly. They create sharp, distinctive pulses of sound. See Reference List 7.

There are many approaches to time-frequency decomposition of EEG data, including the short-term Fourier transform (STFT), (Gabor D. Theory of Communication. J. Inst. Electr. Engrs. 1946; 93:429-457) continuous (Daubechies I. Ten Lectures on Wavelets. Philadelphia, Pa.: Society for Industrial and Applied Mathematics; 1992:357. 21. Combes J M, Grossmann A, Tchamitchian P. Wavelets: Time-Frequency Methods and Phase Space-Proceedings of the International Conference; Dec. 14-18, 1987; Marseille, France) or discrete (Mallat S G. A theory for multiresolution signal decomposition: the wavelet representation. IEEE Trans Pattern Anal Mach Intell. 1989; 11:674-693) wavelet transforms, Hilbert transform (Lyons R G. Understanding Digital Signal Processing. 2nd ed. Upper Saddle River, N.J.: Prentice Hall PTR; 2004:6888), and matching pursuits (Mallat S, Zhang Z. Matching pursuits with time-frequency dictionaries. IEEE Trans. Signal Proc. 1993; 41(12):3397-3415). Prototype analysis systems may be implemented using, for example, MatLab with the Wavelet Toolbox, www.mathworks.com/products/wavelet.html. See Reference List 8.

Single instruction, multiple data processors, such as graphics processing units including the nVidia CNA environment or AMD Firepro high-performance computing environment are known, and may be employed for general purpose computing, finding particular application in data matrix transformations. See Reference List 9.

Statistical analysis may be presented in a form that permits parallelization, which can be efficiently implemented using various parallel processors, a common form of which is a SIMD (single instruction, multiple data) processor, found in typical graphics processors (GPUs). Artificial neural networks have been employed to analyze EEG signals. See Reference List 10.

Principal component analysis (PCA) is a statistical procedure that uses an orthogonal transformation to convert a set of observations of possibly correlated variables into a set of values of linearly uncorrelated variables called principal components. If there are n observations with p variables, then the number of distinct principal components is min(n−1,p). This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables. PCA is the simplest of the true eigenvector-based multivariate analyses. Often, its operation can be thought of as revealing the internal structure of the data in a way that best explains the variance in the data. If a multivariate dataset is visualized as a set of coordinates in high-dimensional data space (1 axis per variable), PCA can supply the user with a lower-dimensional picture, a projection of this object when viewed from its most informative viewpoint. This is done by using only the first few principal components so that the dimensionality of the transformed data is reduced. PCA is closely related to factor analysis. Factor analysis typically incorporates more domain specific assumptions about the underlying structure and solves eigenvectors of a slightly different matrix. PCA is also related to canonical correlation analysis (CEA). CEA defines coordinate systems that optimally describe the cross-covariance between two datasets while PCA defines a new orthogonal coordinate system that optimally describes variance in a single dataset. See, en.wikipedia.org/wiki/Principal_component_analysis.

SUMMARY OF THE INVENTION

In the fight against the COVID-19 pandemic boosting immunity and the immunological response to the vaccines by fighting the epidemic of insomnia, sleep deprivation, and sleep disorders is extremely important and urgent task. The present technology addressing insomnia through neuromodulation may become an important tool in combating this epidemic and infectious disease in general.

The present invention provides a system and method for improving a vaccine response of a mammal to an antigen (or antigen-producing treatment), and more particularly to a COVID vaccine. A COVID vaccine typically includes an antigen having an epitope corresponding to the SARS-Cov-2 spike protein, or a nucleic acid that generates the epitope, such as an mRNA vaccine. In contrast to COVID-19 infection, vaccination with the spike protein epitope is not typically associated with a cytokine storm, and therefore is more likely to result in long-lasting immunity. A person scheduled for a COVID vaccine may have significant apprehension, which may lead to insomnia. Likewise, after vaccination, the risk of reaction, such as malaise and fever, may also lead to sleep disorders, even if these reactions do not occur. Further, in the general population, there is a normal incidence of sleep disorders, such that these may account for at least a portion of vaccination failure.

Coronasomnia may lead adverse reactions and impaired immunity by presenting vaccination patients who are not properly receptive to the vaccine due to sleep impairment, and further have an insufficient response to the vaccine due to poor sleep during the peri-vaccination period. The present technology seeks to normalize the population to reduce the incidence of failed or reduced efficacy vaccinations.

The method comprises inducing brain states in a subject human which represent or are conducive to sleep according to a natural sleep cycle. The process may be open loop control, that is, based on a presumption of correctness of the stimulation pattern, or closed loop control, that is employing feedback of brain state or sleep stage. The method employs a non-invasive and preferably no-contact sensory stimulation, such as auditory, visual, vestibular, proprioceptive, touch, etc., in a pattern designed to induce a progression of a plurality of different sleep stages, preferably in a natural sleep stage progression cycle or plurality of cycles. Preferably, the technology employs the principles of binaural beats, though perhaps through various sensory modalities other than hearing, to achieve entrainment of brainwaves with low frequencies while simulating at higher frequencies, due to a virtual beat frequency observed in the brain.

During sleep, in a mass deployment, simplicity and safety of the apparatus and method, as well as high efficacy, are required. During initial sleep induction when a person is awake, visual stimulation is possible. However, after sleep is induced, use of visual stimulation to maintain sleep or control progression of sleep stages is difficult or unavailable. Therefore, auditory stimulation is preferred. Note that during sleep, aspects of hearing remain intact, while some other senses are attenuated or blocked.

Because sleep brainwaves are associated with low frequencies, in the infrasound range, direct stimulation with acoustic waves would be expected to lead to adverse effects as discussed above, including insomnia, the opposite of the desired effect. On the other hand, using neuropsychological techniques, such as binaural beats and isochronic tones, brainwave entrainment at low frequencies may be achieved without use of infrasound.

In an open loop embodiment, a prototype sleep cycle is defined, and a sensory stimulation provided which seeks to entrain brainwaves corresponding to the sequence of sleep cycles. In a closed loop embodiment, EEG or patient vital signs (e.g., respiratory rate and variability, heart rate and variability, movement and/or muscle tone, rapid eye movements, such as through video monitoring or electrooculography) are monitored to assess a current state of the patient, and the stimulation provided adaptively to progress the patient through a desired sleep cycle or specific stages of sleep.

The stimulation of the subject may seek to induce EEG patterns that are representative of a target sleep state. The sequence of sleep states may be drawn from the species population statistics, individual characteristics, or designed according to an algorithm designed or optimized to achieve the overall sleep pattern comprising the desired sequence of sleep states. Advantageously, the subject is monitored during stimulation to measure response to the stimulation, and/or interruption of the target sleep cycle. In case of interruption of the sleep cycle, the stimulation is restarted based on the state of the subject and, therefore, progresses again through a natural sequence of sleep states.

The preferred stimulation is non-invasive, and also preferably not electrical (galvanic). However, transcranial magnetic stimulation, e.g., subthreshold PEMF, may be employed, alone or with auditory, visual, or other stimulation. For example, while visual stimulation may be contraindicated for entry into respectively deeper sleep states, it may be advantageously used for moving the subject to a shallower sleep state, and to awaken the subject, in order to achieve repeated cycles. However, such auditory or visual stimulation preferably is modulated to synchronize or control brainwave patterns, in addition to any overt sensory effects that may be provided. The measurement of brain activity, and brain stimulation may be according to the known methods described hereinabove, without limitation, though the preferred implementation is such that the subject need not be encumbered by bulky, uncomfortable, expensive, or exotic equipment, and can be used unmonitored in a home environment. However, the invention is not limited by such constraints, so long as the sleep pattern is effectively controlled. In some cases, the invention is used for other than sleep induction, and may also be used to control other stages of consciousness or other mental or emotional states, and preferably a desired sequence of states based on subject biology.

Human trials conducted by the Inventor and assignee, Neuroenhancement Lab in collaboration with the Neuromodulation Laboratory at The City College of New York (CUNY) showed promise in replicating the desired sleep stage of a healthy donor in other subjects (recipients). Electroencephalogram (EEG) of healthy volunteers were recorded as they dozed off entering stage I of sleep, as evidenced by the predominance of alpha waves. These EEG recordings were subsequently filtered from noise, inverted, and used for transcranial Endogenous Sleep-Derived stimulation (tESD). Volunteer subjects stimulated with tESD modulated with the indigenous brainwaves recorded in a sleeping donor, quickly dozed off and entered stage I of sleep, as evidenced by EEG, heart rate, respiration rate, and post-sleep cognitive test. These results were better as compared to the control arms of the study that included sham stimulation, tDCS, and tACS (10 Hz). These preliminary results suggest that tACS modulated with indigenous brainwaves recorded from a healthy sleeping donor can be used to replicate the desired sleep stage of a healthy donor in another subject.

EEG recordings of brainwaves were obtained and preprocessed from healthy human subjects during various stages of sleep. EEG recordings of three stages of sleep, and while being awake from at least ten healthy subjects (e.g., through public EEG database), which are then smoothed and filtered. The EEG recordings were then analyzed to identify statistically significant waveform components correlated with specific sleep stages. A model (e.g., a linear multivariate model) is developed for the coefficients of the components of the EEG, based on sleep stage/wakefulness status; and the statistical significance of the model is measured. Stimulation protocols are developed that can provide safe and effective neurostimulation to induce desired sleep stage.

In general, the present technology is directed toward inducing sleep in order to normalize immune status of a person during a peri-COVID vaccination period. Note that certain kinds of content are known to assist in induction of sleep, e.g., a lullabies. However, the present technology encompasses both human comprehensible signals and incomprehensible (noise-like) signals. Further, the stimulation preferably comprises a non-infrasonic auditory stimulation seeking to entrain brainwaves associated with infrasonic frequencies.

More generally, a stimulation may be conveyed or induced non-invasively via light (visible or infrared), sound (or infrasound, though preferably avoiding infrasound). Alternately, non-sensory stimulation may be employed, e.g., PEMF, transcranial direct or alternating current stimulation (tDCS or tACS), transcranial magnetic stimulation (TMS), Deep transcranial magnetic stimulation (Deep TMS, or dTMS), Repetitive Transcranial Magnetic Stimulation (rTMS) olfactory stimulation, tactile stimulation, or any other means capable of conveying frequency patterns. In a preferred embodiment, normal human senses are employed to stimulate the subject, such as light, sound, smell, and touch. Combinations of stimuli may be employed. In some cases, the stimulus or combination is innate, and therefore largely pan-subject. In other cases, response to a context is learned, and therefore subject-specific. Therefore, feedback from the subject may be appropriate to determine the triggers and stimuli appropriate to achieve a mental state.

In order to facilitate large scale usage, the preferred stimulation modality is sensory, e.g., auditory or visual. This may be augmented by tactile or proprioceptive sensory stimulation, and possibly transcranial PEMF. Preferably, the system avoids galvanic skin contact. If galvanic skin contact is established, it is preferably used for detecting EEG or EMG signals.

A radar sensor may be used to monitor respiration and/or cardiac activity. Radar can detect movement through radio frequency Doppler backscatter, or changes in range/position due to time or phase differences in scattered radiation. See:

Gu, Changzhan, Ruijiang Li, Hualiang Zhang, Albert Y C Fung, Carlos Torres, Steve B. Jiang, and Changzhi Li. "Accurate respiration measurement using DC-coupled continuous-wave radar sensor for motion-adaptive cancer radiotherapy." IEEE Transactions on biomedical engineering 59, no. 11 (2012): 3117-3123.

Rahman, Ashikur, Victor M. Lubecke, Olga Boric-Lubecke, Jan H. Prins, and Takuya Sakamoto. "Doppler radar techniques for accurate respiration characterization and subject identification." IEEE Journal on Emerging and Selected Topics in Circuits and Systems 8, no. 2 (2018): 350-359.

Islam, Shekh M M, Ashikur Rahman, Narayana Prasad, Olga Boric-Lubecke, and Victor M. Lubecke. "Identity authentication system using a support vector machine (SVM) on radar respiration measurements." In 2019 93rd ARFTG Microwave Measurement Conference (ARFTG), pp. 1-5. IEEE, 2019.

Rahman, Ashikur, Victor M. Lubecke, Olga Boric-Lubecke, Jan H. Prins, and Takuya Sakamoto. "Doppler radar techniques for accurate respiration characterization and subject identification." IEEE Journal on Emerging and Selected Topics in Circuits and Systems 8, no. 2 (2018): 350-359.

Shen, Hongming, Chen Xu, Yongjie Yang, Ling Sun, Zhitian Cai, Lin Bai, Edward Clancy, and Xinming Huang. "Respiration and heartbeat rates measurement based on autocorrelation using IR-UWB radar." IEEE Transactions on Circuits and Systems 11: Express Briefs 65, no. 10 (2018): 1470-1474.

Kim, Jong Deok, Won Hyuk Lee, Yonggu Lee, Hyun Ju Lee, Teahyen Cha, Seung Hyun Kim, Ki-Min Song et al. "Non-contact respiration monitoring using impulse radio ultrawideband radar in neonates." Royal Society open science 6, no. 6 (2019): 190149.

Kim, Seong-Hoon, and Gi-Tae Han. "ID CNN based human respiration pattern recognition using ultra wideband radar." In 2019 International Conference on Artificial Intelligence in Information and Communication (ICAIIC), pp. 411-414. IEEE, 2019.

Park, Jun-Young, Yonggu Lee, Yeon-Woo Choi, Ran Heo, Hyun-Kyung Park, Seok-Hyun Cho, Sung Ho Cho, and Young-Hyo Lim. "Preclinical evaluation of a noncontact simultaneous monitoring method for respiration and carotid pulsation using impulse-radio ultra-wideband radar." Scientific reports 9, no. 1 (2019): 1-12.

Xiang, Junjun, Hong Hong, Hongqiang Zhang, Ning Wang, Hui Chu, and Xiaohua Zhu. "Multitarget respiration detection with adaptive digital beamforming technique based on SIMO radar." IEEE Transactions on Microwave Theory and Techniques 68, no. 11 (2020): 4814-4824.

Walterscheid, Ingo, Oliver Biallawons, and Patrick Berens. "Contactless respiration and heartbeat monitoring of multiple people using a 2-D imaging radar." In 2019 41st Annual International Conference of the IEEE Engineering in Medicine and Biology Society (EMBC), pp. 3720-3725. IEEE, 2019.

Hong, Hong, Li Zhang, Heng Zhao, Hui Chu, Chen Gu, Michael Brown, Xiaohua Zhu, and Changzhi Li. "Microwave sensing and sleep: Noncontact sleep-monitoring technology with microwave biomedical radar." IEEE Microwave Magazine 20, no. 8 (2019): 18-29.

Tran, Vinh Phuc, Adel Ali Al-Jumaily, and Syed Mohammed Shamsul Islam. "Doppler radar-based non-contact health monitoring for obstructive sleep apnea diagnosis: A comprehensive review." Big Data and Cognitive Computing 3, no. 1 (2019): 3.

Rang, Yu, Alex R. Chiriyath, Arindam Dutta, and Daniel W. Bliss. "Active breathing suppression for improved sleep monitoring heartbeat detection using UWB radar." In 2019 IEEE 8th International Workshop on Computational Advances in Multi-Sensor Adaptive Processing (CAMSAP), pp. 161-165. IEEE, 2019.

Baboli, Mehran, Aditya Singh, Bruce Soll, Olga Boric-Lubecke, and Victor M. Lubecke. "Wireless sleep apnea detection using continuous wave quadrature Doppler radar." IEEE Sensors Journal 20, no. 1 (2019): 538-545.

Du, Na, Kewen Liu, Linfei Ge, and Jin Zhang. "ApneaRadar: A 24 GHz radar-based contactless sleep apnea detection system." In 2017 2nd International Conference on Frontiers of Sensors Technologies (UST), pp. 372-376. IEEE, 2017.

Dixon, Michael, Logan Schneider, Jeffrey Yu, Jonathan Hsu, Anupam Pathak, D. Shin, Reena Singhal Lee et al. "Sleep-wake Detection With a Contactless, Bedside Radar Sleep Sensing System." (2021).

Tsang, Ing Jyh, Federico Corradi, Manolis Sifalakis, Werner Van Leekwijck, and Steven Latré. "Radar-Based Hand Gesture Recognition Using Spiking Neural Networks." Electronics 10, no. 12 (2021): 1405.

Ahmed, Shahzad, Karam Dad Kallu, Sarfaraz Ahmed, and Sung Ho Cho. "Hand gestures recognition using radar sensors for human-computer-interaction: A review." Remote Sensing 13, no. 3 (2021): 527.

Islam, Shekh Md Mahmudul. "Radar-Based Non-Contact Physiological Sensing." In Vision, Sensing and Analytics: Integrative Approaches, pp. 177-212 Springer, Cham, 2021.

Saluja, Justin, Joaquin Casanova, and Jenshan Lin. "A supervised machine learning algorithm for heart-rate detection using doppler motion-sensing radar." IEEE Journal of Electromagnetics, RE and Microwaves in Medicine and Biology 4, no. 1 (2019): 45-51.

Islam, Shekh M M, F. Fioranelli, and V. M. Lubecke. "Can Radar Remote Life Sensing Technology Help to Combat COVID-19?." Front. Comms. Net 2: 648181. doi: 10.3389/frcmn (2021).

Sakamoto, Takuya. "Ultra-Wideband Radar and Wireless Human Sensing." arXiv preprint arXiv:2012.01746 (2020).

Ahmed, S., K. D. Kallu, S. Ahmed, and S. H. Cho. "Hand Gestures Recognition Using Radar Sensors for Human-Computer-Interaction: A Review. Remote Sens. 2021, 13, 527." (2021).

Gu, Changzhan, Jian Wang, and Jaime Lien. "Motion sensing using radar: Gesture interaction and beyond." IEEE Microwave Magazine 20, no. 8 (2019): 44-57.

Ravichandran, Ruth, Sang-Wha Sien, Shwetak N. Patel, Julie A. Kientz, and Laura R. Pina. "Making sense of sleep sensors: How sleep sensing technologies support and undermine sleep health." In Proceedings of the 2017 CHI Conference on Human Factors in Computing Systems, pp. 6864-6875. 2017.

When the technology is integrated into a mobile device, such as a smartphone, the functionality may be provided by an app, which is downloaded from a remote server, and may be updated or automatically updated from the remote server. The same app or a related app may provide contact tracing, i.e., use of a short range transceiver, such as a Bluetooth personal area network transceiver, which can pass or exchange identifications, such as MAC address or persistent IP address or telephone number or other unique or quasi-unique identifier of a counterpart device, which is persistently associated with a person. Smartphone have GPS receivers, and therefore the contact tracing may be geolocation-assisted. Therefore, if a person with such a device is diagnosed with an infections disease, others who have been in contact with the person can be identified, to warn or quarantine them. See, Hernández-Orallo, Enrique, Pietro Manzoni, Carlos Tavares Calafate, and Juan-Carlos Cano. "Evaluating how smartphone contact tracing technology can reduce the spread of infectious diseases: the case of COVID-19." Ieee Access 8 (2020): 99083-99097.

Hernández-Orallo, Enrique, Carlos T. Calafate, Juan-Carlos Cano, and Pietro Manzoni. "Evaluating the effectiveness of COVID-19 Bluetooth-Based smartphone contact tracing applications." Applied Sciences 10, no. 20 (2020): 7113.

Kindt, Philipp H., Trinad Chakraborty, and Samarjit Chakraborty. "How reliable is smartphone-based electronic contact tracing for covid-19?." arXiv preprint arXiv:2005.05625 (2020).

Yasaka, Tyler M., Brandon M. Lehrich, and Ronald Sahyouni. "Peer-to-peer contact tracing: development of a privacy-preserving smartphone app." JMIR mHealth and uHealth 8, no. 4 (2020): e18936.

Ng, Pai Chet, Petros Spachos, and Konstantinos N. Plataniotis. "COVID-19 and your smartphone: BLE-based smart contact tracing." IEEE Systems Journal (2021).

McLachlan, Scott, Peter Lucas, Kudakwashe Dube, Graham A. Hitman, Magda Osman, Evangelia Kyrimi, Martin Neil, and Norman E. Fenton. "Bluetooth Smartphone Apps: Are they the most private and effective solution for COVID-19 contact tracing?." arXiv preprint arXiv:2005.06621 (2020).

Rahman, Md Tanvir, Risala T. Khan, Muhammad R A Khandaker, Mathini Sellathurai, and Md Sifat A. Salan. "An automated contact tracing approach for controlling COVID-19 spread based on geolocation data from mobile cellular networks." IEEE Access 8 (2020): 213554-213565.

Cohen, I. Glenn, Lawrence O. Gostin, and Daniel J. Weitzner. "Digital smartphone tracking for COVID-19: public health and civil liberties in tension." Jama 323, no. 23 (2020): 2371-2372.

Wang, Shaoxiong, Shuizi Ding, and Li Xiong. "A new system for surveillance and digital contact tracing for COVID-19: spatiotemporal reporting over network and BPS." JMIR mHealth and uHealth 8, no. 6 (2020): e19457.

Maghdid, Halgurd S., and Kayhan Zrar Ghafoor. "A smartphone enabled approach to manage COVID-19 lockdown and economic crisis." SN Computer Science 1, no. 5 (2020): 1-9.

Jacob, Steve, and Justin Lawarée. "The adoption of contact tracing applications of COVID-19 by European governments." Policy Design and Practice 4, no. 1 (2020:44-58.

Bradshaw, William J., Ethan C. Alley, Jonathan H. Huggins, Alun L. Lloyd, and Kevin M. Esvelt. "Bidirectional contact tracing could dramatically improve COVID-19 control." Nature communications 12, no. 1 (2021): 1-9.

Ramakrishnan, Abinaya Megan, Aparna Nicole Ramakrishnan, Sarah Lagan, and John Torous. "From Symptom Tracking to Contact Tracing: A Framework to Explore and Assess COVID-19 Apps." Future Internet 12 no. 9 (2020): 153.

Abuhammad, Sawsan, Omar F. Khabour, and Karem H. Alzoubi. "COVID-19 contact-tracing technology: acceptability and ethical issues of use." Patient preference and adherence 14 (2020): 1639.

Nguyen, Khuong An, Zhiyuan Luo, and Chris Watkins. "Epidemic contact tracing with smartphone sensors." Journal of Location Based Services 14, no. 2 (2020): 92-128.

Collado-Barrell, Roberto, Vicente Escudero-Vilaplana, Cristina Villanueva-Buena, Ana Herranz-Alonso, and Maria Sanjurjo-Saez. "Features and functionalities of smartphone apps related to COVID-19: systematic search in app stores and content analysis." Journal of medical Internet research 22, no. 8 (2020): e20334.

Huang, Milian, Huiling Guo, Yee-Mun Lee, Eu Chin Ho, Hou Ang, and Angela Chow. "Performance of digital contact tracing tools for COVID-19 response in Singapore: cross-sectional study." JMIR mHeafth and uHealth 8, no. 10 (2020): e23148.

Kleinman, Robert A., and Colin Merkel. "Digital contact tracing for COVID-19." CMAJ 192, no. 24 (2020): E653-E656.

Colizza, Vittoria, Eva Grill, Rafael Mikolajczyk, Ciro Cattuto, Adam Kucharski, Steven Riley, Michelle Kendall et al. "Time to evaluate COVID-19 contact-tracing apps." Nature Medicine 27, no. 3 (2021): 361-362.

Braithwaite, Isobel, Thomas Callender, Miriam Bullock, and Robert W. Aldridge. "Automated and partly automated contact tracing: a systematic review to inform the control of COVID-19." The Lancet Digital Health (2020).

Ahmed, Nadeem, Regio A. Michelin, Wanli Xue, Sushmita Ruj, Robert Malaney, Salil S. Kanhere, Aruna Seneviratne, Wen Hu, Helge Janicke, and Sanjay K. Jha. "A survey of COVID-19 contact tracing apps." IEEE access 8 (2020): 134577-134601.

U.S. Pub. App. And Pat. Nos. 20210204886; 20210152910; 20210151198; 20210142885; 20210142874; 20210105353; 20210086005; 20210082583; 20210079067; 20210052221; 20210050116; 20210044925; 20210014654;

20210007179; 20210006933; 20210001157; 20200394728; 20200381130; 20200380957; 20200374608; 20200357512; 20200357510; 20200350989; 20200335223; 20200334945; 20200304944; 20200302452; 20200279464; 20200200749; 20190071489; 20180366221; 20180308585; 20180291088; 20180180614; 20180046766; 20170053091; 20150100345; 20110093249; 20080036619; 11,056,242; 11,054,423; 11,045,271; 11,031,119; 11,013,472; 11,011,277; 10,984,496; 10,966,059; 10,945,055; 10,923,216; 10,902,955; 10,887,104; 10,841,737; 10,706,970, 10,620,204; 10,528,875; 10,273,288; 10,160,795; 9,480,263; and 8,862,448.

The present technology, in an EEG feedback embodiment, may employ an event-correlated EEG time and/or frequency analysis performed on neuronal activity patterns. In a time-analysis, the signal is analyzed temporally and spatially, generally looking for changes with respect to time and space. In a frequency analysis, over an epoch of analysis, the data, which is typically a time-sequence of samples, is transformed, using e.g., a Fourier transform (FT, or one implementation, the Fast Fourier Transform, FFT), into a frequency domain representation, and the frequencies present during the epoch are analyzed. The window of analysis may be rolling, and so the frequency analysis may be continuous. In a hybrid time-frequency analysis, for example, a wavelet analysis, the data during the epoch is transformed using a "wavelet transform", e.g., the Discrete Wavelet Transform (DWT) or continuous wavelet transform (MT), which has the ability to construct a time-frequency representation of a signal that offers very good time and frequency localization. Changes in transformed data over time and space may be analyzed. In general, the spatial aspect of the brainwave analysis is anatomically modeled. In most cases, anatomy is considered universal, but in some cases, there are significant differences. For example, brain injury, psychiatric disease, age, race, native language, training, sex, handedness, and other factors may lead to distinct spatial arrangement of brain function, and therefore when transferring mood from one individual to another, it is preferred to normalize the brain anatomy of both individuals by experiencing roughly the same experiences, and measuring spatial parameters of the EEG or MEG. Note that spatial organization of the brain is highly persistent, absent injury or disease, and therefore, this need only be performed infrequently. However, since electrode placement may be inexact, a spatial calibration may be performed after electrode placement.

Different aspects of EEG magnitude and phase relationships may be captured, to reveal details of the neuronal activity. The "time-frequency analysis" reveals the brain's parallel processing of information, with oscillations at various frequencies within various regions of the brain reflecting multiple neural processes co-occurring and interacting. See, Lisman J, Buzsaki G. A neural coding scheme formed by the combined function of gamma and theta oscillations. Schizophr Bull. Jun. 16, 2008; doi:10.1093/schbul/sbn060. Such a time-frequency analysis may take the form of a wavelet transform analysis. This may be used to assist in integrative and dynamically adaptive information processing. Of course, the transform may be essentially lossless and may be performed in any convenient information domain representation. These EEG-based data analyses reveal the frequency-specific neuronal oscillations and their synchronization in brain functions ranging from sensory processing to higher-order cognition. Therefore, these patterns may be selectively analyzed, for transfer to or induction in, a subject.

A statistical clustering analysis may be performed in high dimension space to isolate or segment regions (e.g., spatial regions, or pseudo-spatial regions) which act or appear to act as signal sources, and to characterize the coupling between various regions. This analysis may also be used to establish signal types within each brain region and decision boundaries characterizing transitions between different signal types. These transitions may be state dependent, and therefore the transitions may be detected based on a temporal analysis, rather than merely a concurrent oscillator state. Thus, the present invention is not limited to whole brain entrainment, and may target brain regions. This may permit sequential recruitment of regions to the desired state, which may be easier that concurrent recruitment. Further, in case of coronasomnia, certain brain regions may be abnormally active, and by targeting and addressing other brain regions, the impact of the active region(s) may be minimized.

The entrainment may be achieved by phase-coupling of brain oscillations (e.g., brainwaves or their physiological correlates) with a pulsed stimulus, according to the Arnold Tongue. See, mathworld.wolfram.com/ArnoldTongue.html; en.wikipedia.org/wiki/Arnold_tongue. Phase coupling of brain oscillations stimulated by rhythmic visual flicker is stronger when the stimulus is closer to the intrinsic frequency of brain oscillations of the person. Therefore, by determining or predicting the brain oscillation frequency, and initially matching the stimulation frequency to the existing frequency, the brain frequency may be entrained, and thereafter more readily modified. The Arnold tongue predicts the degree of synchronization (entrainment) of an oscillator coupled to a rhythmic driving force, depending on two parameters: the amplitude of the driving force (here: light intensity) and driving frequency. With a driving frequency that approaches the intrinsic frequency, entrainment is more likely to occur. With increasing intensity, the window of entrainment widens around the intrinsic frequency, allowing more distant stimulation frequencies to entrain the intrinsic oscillator compared to weaker stimulation intensities. This prediction results in a triangular shaped area of entrainment when plotted as a function of driving intensity and frequency. At the border of this triangular shaped Arnold tongue, entrainment is intermitted by uncoupled time periods, so called phase slips. In other words, the intrinsic oscillator is coupled to the external stimulation phase for certain time periods, until, during constant prevailing stimulation, the internal oscillator slips back to the intrinsic frequency until it is again driven by the external stimulation. As opposed to the superposition of ERPs, the Arnold tongue predicts a non-linear response that clearly identifies entrainment.

Regan, D. (1982). Comparison of transient and steady-state methods*. Ann. N.Y. Acad. Sci. 388, 45-71. doi: 10.1111/j. 1749-6632.1982.tb50784.x.

Pikovsky, A., Rosenblum, M., and Kurths, J. (2003). Synchronization: A Universal Concept in Nonlinear Sciences, Vol. 12 Cambridge, UK: Cambridge University Press.

Notbohm, Annika, Jürgen Kurths, and Christoph S. Herrmann. "Modification of brain oscillations via rhythmic light stimulation provides evidence for entrainment but not for superposition of event-related responses." Frontiers in human neuroscience 10 (2016): 10.

Escalona, Joaquín, Jorge V. José, and Paul Tiesinga. "Entrainment, Arnold tongues, and duality in a periodically driven integrate-and-fire model." Neurocomputing 44 (2002): 91-96.

Fröhlich, Flavin. "Tuning out the blues-thalamo-cortical rhythms as a successful target for treating depression."

Brain Stimulation: Basic, Translational, and Clinical Research in Neuromodulation 8, no. 6 (2015): 1007-1009.

Snari, Razan. Synchronization of coupled and periodically forced chemical oscillators. West Virginia University, 2015.

Henan, David, Miguel Navarrete, Mario Valderrama, and Michel Le Van Quyen. "Entrainment and synchronization of brain oscillations to auditory stimulations." Neuroscience research (2020).

Obleser, Jonas, and Christoph Kayser. "Neural entrainment and attentional selection in the listening brain." Trends in cognitive sciences 23, no. 11 (2019): 913-926.

Sasi, Swapna, and Basabdatta Sen Bhattacharya. "Phase Entrainment by Periodic Stimuli In Silica: A Quantitative Study." arXiv preprint arXiv:2105.10676 (2021).

Singer, Wolf. "Neuronal oscillations: unavoidable and useful?." European Journal of Neuroscience 48, no. 7 (2018): 2389-2398.

Ali, Mohsin M., Kristin K. Sellers, and Flavin Fróhlich. "Transcranial alternating current stimulation modulates large-scale cortical network activity by network resonance." Journal of Neuroscience 33, no. 27 (2013): 11262-11275.

van der Has, Mircea, and Simon Hanslmayr. "Entraining neurons via noninvasive electric stimulation improves cognition." PLoS Biology 18, no. 10 (2020): e3000931.

The various measures make use of the magnitude and/or phase angle information derived from the complex data extracted from the EEG during spectral decomposition and/or temporal/spatial/spectral analysis. Some measures estimate the magnitude or phase consistency of the EEG within one channel across trials, whereas others estimate the consistency of the magnitude or phase differences between channels across trials. Beyond these two families of calculations, there are also measures that examine the coupling between frequencies, within trials and recording sites. Of course, in the realm of time-frequency analysis, many types of relationships can be examined beyond those already mentioned.

It is believed that brainwaves represent, or are formed as a result of a resonance, where ensembles of neurons interact in a coordinated fashion. The frequency of the wave is related to neural responsiveness to neurotransmitters, distances along neural pathways, diffusion limitations, etc. That is, the same sleep stage may be represented by slightly different frequencies in two different individuals, based on differences in the size of their brains, neuromodulators present, other anatomical, morphological and physiological differences, etc. These differences may be measured in microseconds or less, resulting in small changes in frequency. However, in a normal individual under non-pathologic circumstances, the low frequency brainwaves tend to encompass the entire brain, and the resonance is global.

Therefore, a model component of a controller can determine the parameters of neural transmission and ensemble characteristics, vis-à-vis stimulation, and synthesize a stimulus signal to match the correct frequency and phase of the subject's brainwave, with the optimization of the waveform adaptively determined. This may not be as simple as speeding up or slowing down playback of a signal, as different elements of the various brainwaves representing neural correlates of a sleep stage may have different relative differences between subjects. As noted above, a non-feedback or minimal feedback (e.g., respiratory monitoring through use of a microphone to analyze breath sounds) embodiment does not benefit from the luxury of reading brainwave patterns directly, and therefore must use open loop control paradigms and inferential feedback to achieve the results.

Typically, the goal of the process is to improve sleep in a recipient by inducing the desired sleep stages, or a sequence of stages, by inducing neural correlates of the respective sleep stage (or a sequence of stages), through the use of stimulation parameters comprising a waveform (or in the case of binaural beats, a set of stimulation parameters) over a period of time derived from the neural correlates of the respective sleep stage of the subject or a patient population.

The sleep, for example, precedes vaccination, in order to normalize and improve immune response. However, the Coronavirus-induced or associated sleep disorders may induce immunosuppression or immune disorders regardless of vaccination, and the present technology may provide benefit in either case.

The method of therapy comprises, for example, providing a device (or a downloadable software application for a smartphone, or program delivered through a smart speaker), which is provided near a subject on the night or nights prior to or after a scheduled vaccination. The device presents binaural auditory stimulation, preferably through earbuds, but also possibly through stereo speakers, which include sounds having difference frequencies corresponding to sleep patterns. While open loop control over the process is possible, certain types of monitoring are cost efficient and minimally obtrusive. For example, microphones in smartphones or smart speakers can be monitored to listen for breath sounds, which permit extraction of respiratory rate and an assessment of variability. Likewise, other sounds, such as from movement or voices, may be monitored for indicial of sleep stage. (Douglas, Neil J., David P. White, Cheryl K. Pickett, John V. Weil, and L W. Zwillich. "Respiration during sleep in normal man." Thorax 37, no. 11 (1982): 840-844; Snyder, Frederick, J. Allan Hobson, Donald F. Morrison, and Frederick Goldfrank. "Changes in respiration, heart rate, and systolic blood pressure in human sleep." Journal of applied physiology 19, no. 3 (1964): 417-422; Lee-Chiang Jr, Teofilo L. "Monitoring respiration during sleep." Clinics in chest medicine 24, no. 2 (2003): 297-306; Carskadon, Mary A., and William L Dement. "Respiration during sleep in the aged human." Journal of gerontology 36, no. 4 (1981): 420-423; Zhu, Xin, Wenxi Chen, Tetsu Nemoto, Yumi Kanemitsu, Kei-ichiro Kitamura, Ken-ichi Yamakoshi, and Daming Wei. "Real-time monitoring of respiration rhythm and pulse rate during sleep." IEEE transactions on biomedical engineering 53, no. 12 (2006): 2553-2563; Hobson, J. Allan, Frederick Goldfrank, and Frederick Snyder. "Respiration and mental activity in sleep." Journal of Psychiatric Research 3, no. 2 (1965): 79-90; Rum, Stuart F., Michael E. Griswold, Conrad Iber, F. Javier Nieto, David M. Rapoport, Susan Redline, Mark Sanders, and Terry Young. "Short-term variability of respiration and sleep during unattended nonlaboratory polysomnography—the Sleep Heart Health Study." Sleep 25, no. 8 (2002): 8-14.)

While simple frequency generators may be used to produce pure tones, the results may be obtrusive and unnatural. Rather, a musical sequence may be presented, for example generated by a Musical Instrument Digital Interface (MIDI) synthesizer device or other synthesizer, encoded to provide difference frequencies between left and right channels. In order to increase spatial separation of binaural sounds, spatialized audio may be employed. (en.wikipedia.org/wiki/3D_audio_effect; creator.oculus.com/learn/spatial-audio/; developer.oculus.com/learn/audio-intro-spatialization/;

Méaux Eric, and Sylvain Marchand. "Synthetic Transaural Audio Rendering (STAR): a Perceptive Approach for Sound Spatialization." In International Conference on Digital Audio Effects (DAFx). 2019. Normandeau, Robert, Olivier Bélanger, Christophe Lengelé, and David Ledoux. "SPAT-GRIS/SERVERGRIS, Creative Tools for 2D and 3D Sound Spatialization." In ICMC. 2018; Melvin, Adam, B. Bridges, and Enda Bates. "Sound Spatialization." In Foundations in Sound Design for Interactive Media: A Multidisciplinary Approach, pp. 141-160. Routledge Taylor 9 Francis Group, 2019; Geronazzo, Michele. "Sound Spatialization." (2019); Kunchur, Milind. "Three-Dimensional Spatialization in Two-Channel Stereo Sound." Bulletin of the American Physical Society (2020); Arevalo, Camilo, M. Sarria, and M. Gerardo. "Accurate Spatialization of VR Sound Sources in the Near Field." In Audio Engineering Society Conference: 2018 AES International Conference on Spatial Reproduction-Aesthetics and Science. Audio Engineering Society, 2018.)

The binaural sounds may be harmonic, for example major chords, using tremolo/isochronic tones, binaural beats, etc. to achieve brain entrainment a desired EEG pattern corresponding to a sleep stage. In order to initially induce sleep, the system may generate a lullaby, or other somnolescent music, with semantic or abstract content. Since the target is awake, higher level brain functions may be accessed, and sounds without semantic or abstract content may actually prevent sleep progression. After induction of sleep, the tones or sounds may become more technical in nature. However, when more than one person is within the soundscape, the tones may remain complex, in order to avoid disrupting the other person. However, assuming that the sleep sequence is non-pathological, the system may seek to synchronize sleep cycles for the people. Using spatialized audio, sleep inducing sounds may be distinctly targeted to different target people within an environment.

Note that, since the intent of the audio signal is to induce a synthetic subsonic signal in the brain based of difference frequencies in the audio stimulation, the fundamental frequencies are less relevant. Further, the beat of the music, and especially percussion, may be timed to reinforce the desired brainwave pattern.

The waking state with the eyes open is characterized by high-frequency (15-60 Hz), low-amplitude activity (~-30 µV) activity. This pattern is called beta activity. Descent into stage I non-REM sleep is characterized by decreasing EEG frequency (4-8 Hz) and increasing amplitude (50-100 µV), called theta waves. Descent into stage II non-REM sleep is characterized by 10-15 Hz oscillations (50-150 µV) called spindles, which occur periodically and last for a few seconds. Stage III non-REM sleep is characterized by slower waves at 2-4 Hz (100-150 µV). Stage IV sleep is defined by slow waves (also called delta waves) at 0.5-2 Hz (100-200 µV). After reaching this level of deep sleep, the sequence reverses itself and a period of rapid eye movement sleep, or REM sleep, ensues. REM sleep is characterized by low-voltage, high-frequency activity similar to the EEG activity of individuals who are awake. (Hobson, J. A. (1989) Sleep. New York: Scientific American Library.) In order to achieve these low frequencies, it is preferred to start with bass range signals. Due to issues of reproduction efficiency and directionality, it is preferred that the audio signals have a fundamental frequency in the range of 40-200 Hz if open air speakers, and 25-200 Hz if headphones are used. Thus, for example, to induce a 4 While it is desired to synchronize brain activity to a desired sequence of sleep states, it is not necessary to continuously steer the brain activity, and therefore the acoustic stimulator may stop emitting, or simply continue emitting, but avoiding frequencies and combinations that would tend to entrain the brainwaves away from the target frequency range. For example, it may be sufficient to generate a binaural beat entrainment signal for ten continuous seconds per minute, with the remaining program avoiding any binaural beats at all. The technology may also encode the binaural beats in a phase modulation encoding of the sound source, in which the frequencies themselves remain nominally the same, but the phase relationship is steered to create an interference pattern that temporally corresponds to the targeted brainwave frequency.

A typically process performed on the neural correlates is filtering to remove noise. In some embodiments, noise filters may be provided, for example, at 50 Hz, 60 Hz, 100 Hz, 120 Hz, and additional overtones (e.g., tertiary and higher harmonics). The stimulator associated with the second subject (recipient) would typically perform decoding, decompression, decryption, inverse transformation, modulation, etc.

A method of sleep stage modification, e.g., brain entrainment, is provided, comprising: ascertaining a sleep stage in a plurality of first subjects (donors); acquiring brainwaves of the plurality of first subjects (donors), e.g., using one of EEG and MEG, to create a dataset containing brainwaves corresponding to different sleep stages. The database may be encoded with a classification of sleep stages, activities, environment, and stimulus patterns, applied to the plurality of first subjects, and the database may include acquired brainwaves across a large number of sleep stages, activities, environment, or stimulus patterns, for example. In many cases, the database records will reflect a characteristic or dominant frequency of the respective brainwaves.

The record(s) thus retrieved are used to define a stimulation pattern for the second subject (recipient). As a relatively trivial example, a female recipient could be stimulated principally based on records from female donors. Similarly, a child recipient of a certain age could be stimulated principally based on the records from children donors of a similar age. Likewise, various demographic, personality, and/or physiological parameters may be matched to ensure a high degree of correspondence to between the source and target subjects. In the target subject, a guided or genetic algorithm may be employed to select modification parameters from the various components of the signal, which best achieve the desired target state based on feedback from the target subject.

The process of stimulation typically seeks to target the desired sleep stage in the recipient, which is automatically or semi-automatically determined or manually entered. In one embodiment, the records are used to define a modulation waveform of a synthesized carrier or set of carriers, and the process may include a frequency domain multiplexed multi-subcarrier signal (which is not necessarily orthogonal). A plurality of stimuli may be applied concurrently, through the different subchannels and/or though different stimulator electrodes, electric current stimulators, magnetic field generators, mechanical stimulators, sensory stimulators, etc. The stimulus may be applied to achieve brain entrainment (i.e., synchronization) of the second subject (recipient) with one or more first subjects (donors). If the plurality of donors are mutually entrained, then each will have a corresponding brainwave pattern dependent based on brainwave entrainment. This link between donors may help determine compatibility between a respective donor and the recipient. For example, characteristic patterns in the entrained brainwaves may be determined, even for different target sleep stages, and the characteristic patterns may be correlated to find relatively close matches and to exclude relatively poor matches.

As discussed above, the plurality of first subjects (donors) may have their respective brainwave patterns stored in separate database records. However, they may also be combined into a more global model. One such model is a neural network or a deep neural network. Typically, such a network would have recurrent features. Data from a plurality of first subjects (donors) is used to train the neural network, which is then accessed by inputting the target stage and/or feedback information, and which outputs a stimulation pattern or parameters for controlling a stimulator(s). When multiple first subjects (donors) form the basis for the stimulation pattern, it is preferred that the neural network output parameters of the stimulation, derived from and comprising features of the brainwave patterns or other neural correlates of sleep stage from the plurality of first subject (donors), which are then used to control a stimulator which, for example, generates its own carrier wave(s) which are then modulated based on the output of the neural network. A trained neural network need not periodically retrieve records and, therefore, may operate in a more time-continuous manner, rather than the more segmented scheme of record-based control.

In any of the feedback dependent methods, the brainwave patterns or other neural correlates of sleep stages may be processed by an artificial neural network (or deep neural network), to produce an output that guides or controls the stimulation. The stimulation, is, for example, at least one of a light signal, a sound signal, an electric signal, a magnetic field, and vibration or mechanical stimulus. The process may employ a relational database of sleep stages and brainwave patterns, e.g., frequencies/neural correlate waveform patterns associated with the respective sleep stages. The relational database may comprise a first table, the first table further comprising a plurality of data records of brainwave patterns, and a second table, the second table comprising a plurality of sleep stages, each of the sleep stages being linked to at least one brainwave pattern. Data related to sleep stages and brainwave patterns associated with the sleep stages are stored in the relational database and maintained. The relational database is accessed by receiving queries for selected (existing or desired) sleep stages, and data records are returned representing the associated brainwave pattern. The brainwave pattern retrieved from the relational database may then be used for modulating a stimulator seeking to produce an effect selectively dependent on the desired sleep stage.

A further aspect of the technology provides a computer apparatus for creating and maintaining a relational database of sleep stages and frequencies associated with the sleep stage, and may include set of music or musical stimuli that produce desired binaural beat stimulation. The computer apparatus may comprise a non-volatile memory for storing a relational database of sleep stages and neural correlates of brain activity associated with the sleep stages, the database comprising a first table comprising a plurality of data records of neural correlates of brain activity associated with the sleep stages, and a second table comprising a plurality of sleep stages, each of the sleep stages being linked to one or more records in the first table; a processor coupled with the non-volatile memory, and is configured to process relational database queries, which are then used for searching the database; RAM coupled with the processor and the non-volatile memory for temporary holding database queries and data records retrieved from the relational database; and an IO interface configured to receive database queries and deliver data records retrieved from the relational database. A structured query language (SQL) or alternate to SQL (e.g., noSQL) database may also be used to store and retrieve records. A relational database described above, maintained and operated by a general-purpose computer, improves the operations of the general-purpose computer by making searches of specific sleep stages and brainwaves associated therewith more efficient thereby, inter alia, reducing the demand on computing power.

A further aspect of the technology provides a method of brain entrainment comprising: ascertaining a sleep stage in at least one first subject (donor), applying an aliased stimulus signal pattern designed to generate a brainwave pattern associated with the respective targeted sleep stage via sensory stimulation, whereby the sleep stage desired by the second subject (recipient) is achieved. One of the advantages of transforming the data is the ability to select a transform that separates the information of interest represented in the raw data, from noise or other information. Some transforms preserve the spatial and state transition history and may be used for a more global analysis. Another advantage of a transform is that it can present the information of interest in a form where relatively simple linear or statistical functions of a low order may be applied. In some cases, it is desired to perform an inverse transform on the data. For example, if the raw data includes noise, such as 50 or 60 Hz interference, a frequency transform may be performed, followed by a narrow band filtering of the interference and its higher order intermodulation products. An inverse transform may be performed to return the data to its time-domain representation for further processing. (In the case of simple filtering, a finite impulse response (FIR) or infinite impulse response (IIR) filter could be employed). In other cases, the analysis is continued in the transformed domain.

Artificial intelligence (AI) and machine learning methods, such as artificial neural networks, deep neural networks, etc., may be implemented to extract the signals of interest. Neural networks act as an optimized statistical classifier and may have arbitrary complexity. A so-called deep neural network having multiple hidden layers may be employed. The processing is typically dependent on labeled training data, such as EEG data, or various processed, transformed, or classified representations of the EEG data. The label represents the sleep stage of the subject during acquisition. In order to handle the continuous stream of data represented by the EEG, a recurrent neural network architecture may be implemented. Depending preprocessing before the neural network, formal implementations of recurrence may be avoided. A four or more dimensional data matrix may be derived from the traditional spatial-temporal processing of the EEG and fed to a neural network. Since the time parameter is represented in the input data, a neural network temporal memory is not required, though this architecture may require a larger number of inputs. Principal component analysis (PCA, en.wikipedia.org/wiki/Principal_component_analysis), spatial PCA (arxiv.org/pdf/1501.03221v3.pdf, adegenet.r-forge.r-project.org/files/tutorial-spca.pdf, www.ncbi.nlm.nih.gov/pubmed/1510870); and clustering analysis may also be employed (en.wikipedia.org/wiki/Cluster_analysis, see U.S. Pat. Nos. 9,336,302, 9,607,023).

The technology may be embodied in apparatuses for acquiring the brain activity information from the source, processing the brain activity information to reveal a target brain activity state and a set of stimuli, which seek to achieve that state in a recipient, and generating stimuli for the recipient to achieve and maintain the target brain activity state over a period of time and potential state transitions. A general-purpose computer may be used for the processing of the information, a microprocessor, an FPGA, an ASIC, a system-on-a-chip, or a specialized system, which employs a customized configuration to efficiently achieve the information transformations required. Typically, the source and recipient act asynchronously, with the brain activity of the source recorded and later processed. However, real-time processing and brain activity transfer are also possible. In the case of a general purpose programmable processor implementation or portions of the technology, computer instructions may be stored on a nontransitory computer readable medium. Typically, the system will have special-purpose components, such as a sensory stimulator, or a modified audio and/or display system, and therefore the system will not be a general purpose system. Further, even in a general purpose system, the operation per se is enhanced according to the present technology.

According to one embodiment, the brainwave pattern is induced based on an actual subject, subjects, or population, and not merely a synthetic sine wave. Therefore, information which is modulated on the neural correlates (e.g., EEG) will be transferred to the recipient.

The source brain wave pattern may be acquired through multichannel EEG or MEG, from a human in the desired brain state. A computational model of the brain state is difficult to create. However, such a model is not required according to the present technology. Rather, the signals may be processed by a statistical process (e.g., PCA or a related technology), or a statistically trained process (e.g., a neural network). The processed signals preferably retain information regarding signal source special location, frequency, and phase. In stimulating the recipient's brain, the source may be modified to account for brain size differences, electrode locations, etc. Therefore, the preserved characteristics are normalized spatial characteristics, frequency, phase, and modulation patterns.

The normalization may be based on feedback from the target subject, for example, based on a comparison of a present state of the target subject and a corresponding state of the source subject, or another comparison of known states between the target and source. Typically, the excitation electrodes in the target subject do not correspond to the feedback electrodes or the electrodes on the source subject. Therefore, an additional type of normalization is required, which may also be based on a statistical or statistically trained algorithm.

In some cases, the target has an abnormal or unexpected response to stimulation based on a model maintained within the system. In this case, when the deviance from the expected response is identified, the system may seek to a new model, such as from a model repository that may be online, such as through the Internet. If the models are predictable, a translation may be provided between an applicable model of a source or trainer, and the applicable model of the target, to account for differences. In some cases, the desired mental state is relatively universal, such as sleep and awake. In this case, the brain response model may be a statistical model, rather than a neural network or deep neural network type implementation.

Thus, in one embodiment, a hybrid approach is provided, with the use of donor-derived brainwaves, on the one hand, which may be extracted from the brain activity readings (e.g., EEG or MEG) of the first at least one subject (donor), preferably processed by principal component analysis, or spatial principal component analysis, autocorrelation, or other statistical processing technique (clustering, PCA, etc.) or statistically trained technique (backpropagation of errors, etc.) that separates components of brain activity, which can then be modified or modulated based on high-level parameters, e.g., abstractions. See, ml4a.github.io/ml4a/how_neural_networks_are_trained/. Thus, the stimulator may be programmed to induce a series of brain states defined by name (e.g., sleep stage 1, sleep stage 2, etc.) or as a sequence of "abstract" semantic labels, icons, or other representations, each corresponding to a technical brain state or sequence of sub-states. The sequence may be automatically defined, based on biology and the system training, and thus relieve the programmer of low-level tasks. However, in a general case, the present technology maintains the use of components or subcomponents of the donor's brain activity readings, e.g., EEG or MEG, and does not seek to characterize or abstract them to a semantic level.

According to the present technology, a neural network system or statistical classifier may be employed to characterize the brain wave activity and/or other data from a subject, e.g., respiratory or muscular response to stimulation. In addition to the classification or abstraction, a reliability parameter is presented, which predicts the accuracy of the output. Where the accuracy is high, a model-based stimulator may be provided to select and/or parameterize the model and generate a stimulus for a target subject. Where the accuracy is low, a filtered representation of the signal may be used to control the stimulator, bypassing the model(s). The advantage of this hybrid scheme is that when the model-based stimulator is employed, many different parameters may be explicitly controlled independently of the source subject. On the other hand, where the data processing fails to yield a highly useful prediction of the correct model-based stimulator parameters, the model itself may be avoided, in favor of a direct stimulation type system.

In some cases, the base frequency, modulation, coupling, noise, phase jitter, or another characteristic of the signal may be substituted. For example, if the first subject is listening to music, there will be significant components of the neural correlates that are synchronized with the particular music. On the other hand, the music per se may not be part of the desired stimulation of the target subject. Therefore, through signal analysis and decomposition, the components of the signal from the first subject, which have a high temporal correlation with the music, may be extracted or suppressed from the resulting signal. Further, the target subject may be in a different acoustic environment, and it may be appropriate to modify the residual signal dependent on the acoustic environment of the target subject, so that the stimulation is appropriate for achieving the desired effect, and does not represent phantoms, distractions, or irrelevant or inappropriate content. In order to perform processing, it is convenient to store the signals or a partially processed representation, though a complete real-time signal processing chain may be implemented. Such a real-time signal processing chain is generally characterized in that the average size of a buffer remains constant, i.e., the lag between output and input is relatively constant, bearing in mind that there may be periodicity to the processing.

A self-learning or genetic algorithm may be used to tune the system, including both or either the signal processing at the donor system and the recipient system. In a genetic algorithm feedback-dependent self-learning system, the responsivity of a subject, e.g., the target, to various kinds of stimuli may be determined over a stimulus space. This stimulation may be in the context of use, with a specific target sleep stage provided, or unconstrained. The stimulator may operate using a library of stimulus patterns, or seek to generate synthetic patterns or modifications of patterns.

Over some time, the system will learn to map the desired sleep stage to optimal context-dependent parameters of the stimulus pattern.

The technology may be used for both creation of a desired sleep stages in the recipient, elimination of existing sleep stages in the recipient. In the latter case, a decision of what end state is to be achieved is less constrained, and therefore, the optimization is distinct. For example, in the former case, it may be hard to achieve a particular sleep stage that is desired, requiring a set of transitions to cause the brain of the recipient to be enabled/prepared to enter the target state. In the case of a system seeking to eliminate an undesired sleep stage, the issue is principally what path to take to most efficiently leave the current state, bearing in mind the various costs, such as the comfort/discomfort of the stimulation, the time value cost, etc. Therefore, the series of states may differ in the implementation of these distinct goals, even if the endpoints are identical, i.e., the optimal algorithm to achieve state B from state A, may be different from the optimal algorithm to exist state A, and end up at state B.

It is therefore an object to provide a method of treating coronasomnia during a SARS-Cov-2 perivaccination period, comprising: determining a current awake or sleep stage of a person; automatically defining a desired sleep cycle pattern, dependent on the current awake or sleep stage of the person; generating infrasonic binaural beats in the person by presenting audio frequency stimulation with different audio signals in each ear generated by an automated processor, entraining brainwaves of the brain of the person with the infrasonic binaural beats according to a pattern corresponding to the desired sleep cycle pattern, to thereby induce a sleep cycle in the person according to the sleep cycle pattern; and administering the SARS-Cov-2 vaccination to the person. The sleep cycle may be induced in a prevaccination period, and/or a postvaccination period. The generation of infrasonic binaural beats may comprise synthesizing a musical program having distinct binaural components, the binaural components being encoded with respective dominant components having respective frequencies which differ according to the pattern of infrasonic binaural beats.

It is also a method of treating a SARS-Cov-2 related sleep disorder to a person, comprising: defining a desired sleep cycle pattern for the person; presenting, under control of an automated processor, a stimulation pattern to the person through of at least one of binaural beats, isochronic tones, and optical pulses to a person, the stimulation pattern representing a series of brainwave patterns progressing dependent on a current awake or sleep stage of the person and the defined desired sleep cycle pattern; entraining brainwaves of the person with the presented stimulation pattern, to thereby induce a sleep cycle in the person according to the sleep cycle pattern; and administering a SARS-Cov-2 vaccine to the person, wherein the sleep cycle enhances immune response to the SARS-CoV-2 vaccine as compared to the SARS-Cov-2 related sleep disorder. The presenting, and entraining steps may be continued in a postvaccination period. The current awake or sleep stage of the person may be determined based on a monitoring at least one of a respiratory pattern, a heartrate, a heart rate variability, a temperature, and a movement pattern of the person. The stimulation pattern may be presented as at least one of an optical signal and a near-infrared signal to the person. The stimulation pattern may be presented based on signals defined by an app executing on a smartphone, the app being downloadable and upgradable from a remote server. The stimulation pattern may have a modulated pattern corresponding to a brainwave signal obtained from the at least one other person. The stimulation pattern may comprises different audio signals presented in each ear by a spatialized audio transducer system. The method may further comprise detecting an awakening of the person outside of the desired sleep cycle pattern, and resetting the sleep cycle pattern presentation dependent on the detected awakening.

It is a further object to provide a method of improving vaccine response in a person administered a vaccine, e.g., SARS-Cov-2 vaccine, comprising: generating, by an automated processor, an excitation pattern adapted to induce neural correlates of sleep stage I having frequencies in the alpha band, followed by neural correlates of sleep stage 2 having frequencies in the theta band, followed by neural correlates of sleep stage 3 or 4 having frequencies in the delta band below 4 Hz, corresponding to a desired sleep cycle pattern; entraining brainwaves of the person with the excitation pattern according to the desired sleep cycle pattern, to enhance sleep and thereby enhance vaccine immune responsivity of the person; and administering the vaccine, e.g., the SARS-Cov-2 vaccine to the person. The excitation pattern may be conveyed to the person in a spatialized audio soundfield, e.g., from earbuds or from a speaker remote from the person. The method may further comprise detecting at least one of sounds and scattered radio frequency waves from the person indicative of a sleep state, and synchronizing the sleep cycle pattern based on the detected sounds or scattered radio frequency waves.

Another object provides a system for improving vaccine response in a person, comprising: at least one sensor configured to determine a current brain state of a person being one of a waking state and a sleeping state; at least one microprocessor, configured to: define a desired sleep cycle pattern, dependent on the determined current brain state of the person; and generate at least one of an audio or optical stimulation pattern modulated with a waveform derived from cortical signatures extracted from EEG recordings of at least one sleeping donor and adapted to entrain brainwaves in the brain of the person with the stimulation pattern corresponding to the desired sleep cycle pattern, to thereby induce a sleep cycle in the person according to the sleep cycle pattern. The person may have a coronavirus pandemic-induced insomnia and the stimulation pattern may be adapted to reduce the coronavirus pandemic-induced insomnia. The sensor may comprise at least one of: a microphone configured to receive respiratory sounds of the person; a radar sensor configured to detect at least one of respiratory and cardiac signals, and an electroencephalography sensor for receiving brainwaves of the person. The stimulation pattern may comprise a modulated visual or near-infrared signal. The system may further comprise a database configured to store a plurality of stimulation pattern portions corresponding to different sleep stages, wherein the at least one automated processor is further configured to detect an awakening of the person outside of the desired sleep cycle pattern, and to reset the desired sleep cycle pattern dependent on the detected awakening. The stimulation pattern may be generated based on signals defined by an app executing on the smartphone, the app being downloadable and upgradable from a remote server.

A further object provides a method of treating a person suffering from a SARS-Cov-2 related sleep disorder, comprising: selecting a waveform derived from cortical signatures extracted from EEG recordings of a healthy sleeping donor; modulating the waveform on at least one stimulus using a microprocessor, wherein the stimulus is at least one of a visual stimulus, an auditory stimulus, and tactile stimulus; stimulating the person with said at least one stimulus to adapted to achieve brain entrainment; entraining brainwaves of the person with the cortical signatures extracted from EEG recordings of the healthy sleeping donor, to induce sleep in the person and thereby treat the SARS-Cov-2 related sleep disorder and improve immunity in the person; monitoring at least one physiological parameter of the person to determine a brain state of the person; and upon determining that the brain state of the person is the state of sleep, automatically modifying the stimulation. The stimulation may be modified by cessation when the brain state of the person indicates a sleep state. The effectiveness of a SARS-Cov-2 related vaccine in the person is improved by treating the SARS-Cov-2 related sleep disorder. The SARS-Cov-2 related sleep disorder may be caused by at least one of a SARS-Cov-2 pandemic-related anxiety, a SARS-Cov-2 pandemic-related stress, a SARS-Cov-2 infection, and a persistent COVID disease. The waveform may be modulated on said at least one stimulus by varying at least one of a frequency and an amplitude of said at least one stimulus corresponding at least one of a frequency and an amplitude of the cortical signatures. The entraining of brainwaves may involve locking phase with the person's endogenous brainwaves and establishing an Arnold tongue condition. The stimulus may be selected from the group consisting of at least one of a red light stimulus, a near-infrared light stimulus, an isochronic tone stimulus, and a binaural beats stimulus. The method may further comprise administering at least one dose of a SARS-Cov-2-related vaccine, after determining that the brain state of the person was in the state of sleep.

It is also an object to provide a system for treating coronasomnia, comprising: a sensor configured to determine a current awake or sleep stage of a person; at least one automated processor, configured to: define a desired sleep cycle pattern, dependent on the determined current awake or sleep stage of the person; and generate infrasonic binaural beats in the person by presenting audio frequency stimulation with different audio signals in each ear generated by an automated processor, the generated infrasonic binaural beats being adapted to entrain brainwaves in the brain of the person with the infrasonic binaural beats according to a pattern corresponding to the desired sleep cycle pattern, to thereby induce a sleep cycle in the person according to the sleep cycle pattern.

It is another object to provide a method of improving vaccine response in a person administered a SARS-Cov-2 vaccine, comprising: defining a sleep cycle pattern; generating by an automated processor an audio excitation pattern adapted to induce infrasonic binaural beats in a person comprising binaural audio frequency stimulation with different audio signals in each ear of the person; entraining brainwaves of the brain of the person with the infrasonic binaural beats according the desired sleep cycle pattern, to thereby enhance immune responsivity of the person; and administering the SARS-Cov-2 vaccine to the person.

The current awake or sleep stage of the person may be determined based on a respiratory pattern of the person monitored through a microphone configured to receive respiratory sounds of the person and/or a brainwave pattern of the person monitored through electroencephalography for receiving brainwaves of the person.

The automated processor may be part of a smartphone or smart speaker, and the infrasonic binaural beats generated based on signals defined by an app executing on the smartphone or smart speaker, the app being downloadable and upgradable from a remote server.

The audio frequency stimulation may be generated based on at least a brainwave signal from at least one other person.

The method may further comprise detecting an awakening of the person outside of the desired sleep cycle pattern, wherein the automatically defined desired sleep cycle pattern is reset dependent on the detected awakening.

The audio frequency stimulation with different audio signals may be presented in each ear by a spatialized audio transducer system.

The system may further comprise a database configured to store a plurality of stimulation patterns corresponding to different sleep stages.

The at least one automated processor may further be configured to detect an awakening of the person outside of the desired sleep cycle pattern, and to reset the automatically defined desired sleep cycle pattern dependent on the detected awakening.

The audio excitation pattern may be conveyed to the person in a spatialized audio soundfield.

The method may further comprise detecting sounds emitted from the person, and synchronizing the sleep cycle pattern based on the detected sounds.

It was suggested (Blagrove) that if we attempt to hack our dreams by artificially increasing theta waves, it might lead to the incorporation of more waking experiences into our dreams. (See "Dreams act as overnight therapy" New Scientist magazine on 5 May 2018). Transplanting theta frequency brainwaves from a vivid dreamer may also help achieve the same effect. Moreover, instead of stimulating the subject's brain with a synthetic theta frequency (e.g., isotonic tones or ambient sound beats), stimulating the recipient's brain using donor's brainwaves carrying secondary (and higher) harmonics, in addition to the dominant theta frequency, may induce the same category of dreams, i.e., if the donor dreamed of people, the recipient will be more likely to dream of people, albeit different people, because the donor's brainwaves will stimulate the visual cortex of the recipient. This may be helpful in the treatment of PTSD, stress management, phobias and some psychiatric diseases.

It is an object to provide a method of brain entrainment to facilitate sleep in a subject using a sleep app executing on a user device, the method comprising: executing the sleep app on the user device, configured to select at least one stimulus selected from the group consisting of at least one of a light signal and a sound signal; selecting a waveform from a menu having a plurality of waveforms derived from brainwaves of at least one sleeping donor, wherein said waveform corresponds to at least one specific stage of sleep; and stimulating the subject with said at least one stimulus, wherein said at least one stimulus is modulated with the selected waveform, to thereby entrain the brain of the subject with the selected waveform to facilitate sleep in the subject. The user device may be, e.g., a mobile device, a wearable device, or an implantable device. The stimulus may be a sound signal, comprising at least one of a predetermined soundtrack, a tone, and white noise. The sound signal may comprise a soundtrack representing at least one of a sound of rainfall, a sound of a waterfall, a sound of ocean waves, a lullaby, a melody, and a polyphony.

The effect of the stimulus may be monitored by feedback e.g., EEG, body temperature, heart rate, respiration rate, facial expression, muscle tone, vasodilation, which may be measured by non-contact sensors or wearable devices, and other electronic sensors embedded in the bed, blanket, mattress, sheets, pillow, etc. Body movement and eye movement may be observed by a video camera or webcam. The sensor signals are advantageously transmitted back to the user device to adjust the regime of stimulation. Of course, the communication path may be indirect to the user device, or the analysis of the signals may be remote from the user device, e.g., in a cloud computing center. An important aspect of the system is synchronizing the cycles with the context and current state of the subject. For example, if the subject got up to go to the bathroom or woke up for other reasons, the modulation cycle would generally need to restart from sleep stage I. However, depending on the mental state of the subject, the progression through the sleep states may be varied.

The sound may be amplitude modulated on a carrier waveform, which would generally have higher frequencies than the modulation waveform (typically <100 Hz), and/or frequency modulated. When the sound separation between ears is present, the amplitude, frequency, phase, timing, etc. between ears may be modulated. Similarly, optical signals may be modulated by intensity, color, frequency, phase, etc., in addition to morphological objects and dynamic changes in real time.

The at least one waveform may be derived from an EEG recordings of brainwaves of at least one sleeping donor, processed using at least one of a principal component analysis (PCA), a correspondence analysis (CA), a factor analysis, a K-means clustering, a non-negative matrix factorization (NMF), a sparse PCA, a non-linear PCA, a robust PCA, an independent component analysis (ICA), a network component analysis, and a singular spectral analysis.

The user device may comprise at least one speaker and wherein the stimulus comprises a sound signal delivered through said at least one speaker, and comprises an isochronic tone. The sound signal may be delivered to the subject through a pair of wireless earbuds, e.g., the modulated selected waveform may comprise binaural beats. Spatialized audio may be used, based on a head-related transfer function, to provide high source separation between ears without contacting headphones.

The user device may be configured to control an ambient light, which is selectively controllable to change at least one of brightness and color, and wherein the stimulus comprises a light signal which is presented to the subject through the ambient light. The light signal may be generated by at least one light emitting diode (LED). The LED may be disposed in proximity to the subject's eyes, e.g., in a sleep mask. The user device may comprise at least one biometric sensor, further comprising the step of monitoring and collecting biometric data of the subject from said at least one biometric sensor.

The method may further comprise monitoring movement of the subject using at least one of a camera in the user device and a webcam coupled with the user device, processed with a neural network configured to classify a subject's sleep as one of a REM sleep, non-REM sleep, and a slow-wave sleep; and adjusting the stimulating of the subject upon determining whether the classification.

The method may further comprise monitoring a facial expression of the subject to determine if the subject is asleep or awake, and controlling a sequence of sleep stages induced by said stimulating in dependence on at least the monitored facial expression. The stimulating may be controlled to progress according to a natural series of sleep stages, further comprising resetting the progress according to the natural series of sleep stages in dependence on an awakening of the subject determined based on the monitored facial expression. The facial expression may be monitored by at least one of a camera in the user device and a webcam communicating with the user device. The facial expression may be monitored according to a signal present in at least one electromyographic electrode. The method may further comprise obtaining biofeedback from the subject in real time and adjusting the stimulation of the subject in real time according to a biofeedback loop implemented by the user device.

It is also an object to provide a mobile device, comprising a housing; a microprocessor disposed within the housing; and a non-volatile memory disposed within the housing and electrically coupled with the processor, configured to store at least one app for controlling the microprocessor; the at least one app being configured to: (a) select a waveform from a plurality of waveforms derived from brainwaves of at least one sleeping donor, wherein said waveform corresponds to at least one specific stage of sleep; and (b) stimulate a subject with said at least one stimulus, wherein at least one stimulus selected from the group consisting of at least one of an auditory stimulus and a visual stimulus is modulated with the selected waveform, to thereby entrain the brain of the subject with the selected waveform to facilitate sleep in the subject. The mobile device may further comprise a battery electrically coupled with the processor; a display, disposed within the housing, electrically coupled with the microprocessor; a wireless communication transceiver disposed within the housing, electrically coupled with the microprocessor; at least one microphone, electrically coupled with the processor; at least one speaker disposed within the housing, electrically coupled with the processor; and at least one camera electrically coupled with the processor. The mobile device may be wirelessly coupled with a wearable device, wherein said wearable device comprises at least one biometric sensor configured to communicate biometric data from the subject to the mobile device through the wireless communication transceiver. The housing may be wearable by the subject and/or maintained close to the skull of the subject with a headband.

Another object provides a method of brain entrainment to facilitate sleep in a subject using a sleep app, comprising opening the sleep app on a programmable device; choosing at least one stimulus, wherein said at least one stimulus is one of a light signal and a sound signal choosing a waveform from a menu having a plurality of waveforms derived from brainwaves of at least one sleeping donor, wherein said waveform corresponds to at least one specific stage of sleep; and stimulating the subject's brain with said at least one stimulus, wherein said at least one stimulus is modulated with the chosen waveform to entrain the brain of the subject with frequencies of the brainwaves of the at least one sleeping donor, to facilitate sleep in the subject. The method may further comprise recording a subject's electroencephalogram (EEG) during sleep while stimulated; and adjusting the stimulating based on the subject's electroencephalogram (EEG) in real time using a neurofeedback loop.

A further object provides a method of brain entrainment to facilitate sleep in a subject, comprising: providing a programmable device having a sleep app stored in a non-volatile memory; providing a stimulator, selected from one or more of a light stimulator and a sound stimulator; defining a waveform, by the sleep app, from a plurality of waveforms, each respective waveform being derived from brainwaves of at least one sleeping donor, wherein said waveform corresponds to at least one specific stage of sleep; stimulating the subject with the stimulator, having at least one of a light output or a sound output modulated with the defined waveform, to entrain the brain of the subject with the brainwaves of the at least one sleeping donor, to facilitate sleep in the subject. The method may further comprise recording an electroencephalogram (EEG) from the subject during sleep while being stimulated, and defining at least one new waveform for stimulation, said waveform being selectively dependent on the uploaded recorded electroencephalogram. The at least one new waveform may be used to stimulate the subject one day after the electroencephalogram is recorded. The recorded electroencephalogram may be uploaded to a remote server, and the new waveform for stimulation subsequently downloaded from the remote server.

Another object provides a non-transitory computer readable medium storing instructions for controlling a processor to perform a method comprising: instructions to select a waveform from a plurality of waveforms derived from brainwaves of at least one sleeping donor, wherein said waveform corresponds to at least one specific stage of sleep; and instructions to stimulate a subject with said at least one stimulus, wherein at least one stimulus selected from the group consisting of at least one of an auditory stimulus and a visual stimulus is modulated with the selected waveform, to thereby entrain the brain of the subject with the selected waveform to facilitate sleep in the subject.

A still further object provides a method of generating a waveform for neuromodulation to improve sleep in a subject, the method comprising: collecting EEG recording from at least one sleeping donor; identifying portions of the EEG recordings corresponding to a specific sleep stage; grouping a plurality of portions of the EEG recordings corresponding to the specific sleep stage, each group corresponding to the specific sleep stage; analyzing each group corresponding to the specific sleep stage using a statistical analysis; extracting a cortical signature corresponding to each specific sleep stage; generating a waveform based on the cortical signature for each sleep stage; and modulating a stimulus for the subject according to the waveform. The modulating of the stimulus may be performed under control of a sleep app executing on a mobile or wearable device. The statistical analysis may be at least one of a principal component analysis (PCA), a correspondence analysis (CA), a factor analysis, a K-means clustering, a non-negative matrix factorization (NMF), a sparse PCA, a non-linear PCA, a robust PCA, an independent component analysis (ICA), a network component analysis, and a singular spectral analysis.

It is, therefore, an object to provide a method of inducing sleep in a second subject comprising: recording brain activity patterns of a first subject (donor) who is asleep; and inducing sleep in the second subject (recipient) by replicating the brain activity patterns of the donor in the recipient. It is further an object to provide a method of inducing sleep in a second subject (recipient) comprising: identifying the mental state of a first subject (donor); if the donor is asleep, recording brain activity patterns of the donor; and inducing sleep in the recipient by replicating the brain activity patterns of the donor in the recipient. The method may further comprise verifying that the recipient is asleep. Another object is a method of transplanting a desired sleep stage from a first subject (donor) to a second subject (recipient) comprising: identifying a sleep stage of the donor; capturing a sleep stage of the donor by recording brain activity patterns; saving the brain activity patterns in a non-volatile memory; retrieving the brain activity patterns from the non-volatile memory; and transplanting the desired sleep stage of the donor to the recipient by inducing the brain activity patterns in the recipient, wherein the desired sleep stage is one sleep stage 1, 2, and 3 or wherein the desired sleep stage is one of a REM sleep stage and non-REM sleep stage, or wherein the desired sleep stage is a slow-wave deep non-REM sleep. The stimulus may be a light signal, a sound signal, or a combination thereof. The light stimulation may be an ambient light or a direct light. The sound stimulation may be binaural beats or isochronic tones. The apparatus for stimulation may be a light source capable of modulating said at least one dominant frequency on the light, a sound source capable of modulating said at least one dominant frequency on the sound, or a combination thereof. The sound source may be binaural beats source or isochronic tones source. The technology may be used to modify or alter a mental state (e.g., from waking to sleep) in a subject. Typically, the starting mental state, brain state, or brainwave pattern is assessed, such as by EEG, MEG, observation, stimulus-response amplitude and/or delay, or the like. Of particular interest in uncontrolled environments are automated mental state assessments, which do not rely on human observation or EEG signals, and rather may be acquired through MEG (e.g., SQID, optically-pumped magnetometer), EMG, MMG (magnetomyogram), mechanical (e.g., accelerometer, gyroscope, etc.), data from physiological sensors (e.g., EKG, heartrate, respiration rate, temperature, galvanic skim potential, etc.), or automated camera sensors.

Advantageously, a characteristic delay between application of stimulus and determination of response varies with the brain or mental state. For example, some mental states may lead to an increased delay or greater variability in delay, while others may lead to decreased or lower variability. Further, some states may lead to attenuation of response, while others may lead to an exaggerated response. In addition, different mental states can be associated with qualitatively different responses. Typically, the mere assessment of the brain or mental state should not itself alter the state, though in some cases the assessment and transition influence may be combined. For example, in seeking to assist in achieving a deep sleep state, the excitation that disturbs sleep is contraindicated. A predictive model may be used to determine the current mental state, optimal transition to a desired mental state, when the subject has achieved the desired mental state, and how to maintain the desired mental state. The desired mental state itself may represent a dynamic sequence (e.g., stage 1→stage 2→stage 3, etc.), such that the subject's mental state is held for the desired period in a defined condition. Accordingly, the stimulus may be time-synchronized with respect to the measured brainwave pattern.

A further object provides a system and method for enhancing deep non-REM sleep, comprising statistically separating slow-wave sleep components from acquired brainwave patterns; defining a stimulation pattern based on the statistically separating slow-wave sleep components, and stimulating a subject with the defined stimulation pattern. The neurological stimulator comprises a memory configured to store acquired brainwave patterns; at least one processor configured to: statistically separate slow-wave non-REM sleep components from the acquired brainwave patterns; and define a brain stimulation pattern based on the statistically separating slow-wave non-REM deep sleep components; and an output signal generator configured to defined brain stimulation pattern.

A still further object provides a system and method for enhancing deep sleep, comprising: extracting brainwave patterns representing a deep sleep state comprising slow wave sleep, from endogenous brain activity EEG recordings of at least one subject; processing the extracted brainwave patterns using a statistical processing algorithm to separate slow wave sleep components from the indigenous brain activity EEG recordings of the at least one subject; inverting the processed extracted brainwave patterns; and stimulating a subject with the inverted processed extracted brainwave patterns. The corresponding system for enhancing deep sleep comprises a memory configured to store brainwave patterns representing a deep sleep state comprising slow wave sleep, from indigenous brain activity EEG recordings of at least one subject; at least one processor configured to process the extracted brainwave patterns using a statistical processing algorithm to separate slow wave sleep components from the indigenous brain activity EEG recordings of the at least one subject; and a stimulator, configured to generate a stimulation signal based on the processed extracted brainwave patterns. The stimulator may comprise a sensory stimulator (e.g., sight, sound, vestibular, touch, taste, smell, etc.). In order to format the signal for stimulating the brain, it may be inverted. Normalization of brain activity information may be spatial and/or temporal.

It is also an object to provide a method of generating a waveform for neuromodulation to improve sleep in a subject, the method comprising: collecting EEG recordings from at least one sleeping donor for a plurality of sleep stages; grouping a plurality of portions of the EEG recordings corresponding to the plurality of sleep stages, into a plurality of groups corresponding to the plurality of sleep stages; analyzing each group using a statistical analysis; extracting a cortical signature corresponding characteristic of each analyzed group; generating a waveform based on the characteristic cortical signature for each of the plurality of sleep stages; and modulating a stimulus for the subject according to the generated waveforms for the plurality of sleep stages.

It is a further object to provide a mobile device contained within a housing, comprising: a microprocessor; an electrical power source, electrically coupled with the microprocessor; a wireless communication transceiver, electrically coupled with the microprocessor, at least one microphone port, electrically coupled with the microprocessor, configured to receive an electrical signal corresponding to a sound; at least one camera port electrically coupled with the microprocessor, configured to receive an electrical signal corresponding to an image; a display, electrically coupled with the microprocessor; at least one speaker port, electrically coupled with the microprocessor, configured to generate an electrical signal corresponding to a sound; a non-volatile memory and electrically coupled with the microprocessor, configured to store at least one app downloadable through the wireless communication transceiver for controlling the microprocessor, said at least one downloadable app being configured to: (a) select a waveform from a plurality of waveforms derived from brainwaves of at least one sleeping donor, wherein said waveform corresponds to at least one a specific stage of sleep, a gender, and an age group; and (b) define a stimulus for stimulation of a subject, selected from the group consisting of at least one of an auditory stimulus generated through the at least one speaker, and a visual stimulus generated through the display, modulated with the selected waveform, and adapted to entrain the brain of the subject with the selected waveform to facilitate sleep in the subject; wherein at least one of the selection of the waveform and the definition of the stimulus is responsive to the at least one microphone or the at least one camera.

It is another object to provide a method of facilitating sleep, comprising: providing data defining a plurality of waveforms in a memory retrieving a selected waveform from the memory, selectively dependent on at least one of a determined sleep phase of a human subject and a predetermined sequence; and stimulating the human subject with a stimulus modulated according to the selected waveform; to thereby entrain the brain of the human subject with the selected waveform to facilitate sleep in the subject.

The method may further comprise adaptively defining a sequence of sleep stages dependent on biometric information received from a sleeping human subject; and selecting waveforms from the memory in dependence on a correspondence to a respective sleep stage of the adaptively defined sequence of sleep stages; wherein said stimulating the human subject comprises altering a sleep stage of the human subject dependent on both the determined sleep phase of a human subject and the adaptively defined sequence of sleep stages.

The human subject may be stimulated with at least one audio transducer and wherein the stimulus comprises at least one of an isochronic tone and binaural beats or with an ambient light stimulus, selectively modulated according to the selected waveform to change at least one of brightness and color. The ambient light stimulus may be emitted by at least one light emitting diode disposed in a sleep mask proximate the human subject's eyes.

The method may further comprise providing at least one sensor to determine at least one of an eye movement and a facial expression of the human subject, to at least one of determine a current determined sleep phase of a human subject or select the predetermined sequence.

The predetermined sequence may be a natural series of sleep stages, the method further comprising resetting the progress according to the natural series of sleep stages in dependence on an awakening of the human subject.

BRIEF DESCRIPTION OF THE DRAWINGS

The detailed description is described with reference to the accompanying figures.

FIG. 1 shows a flowchart according to one embodiment of the invention illustrating a process of replicating a sleep state from one subject to another subject.

FIG. 2 shows a flowchart according to one embodiment of the invention illustrating a process of replicating a waking stage from one subject to another subject by recording and replicating brainwaves associated with the waking stage, according to one embodiment of the invention.

DETAILED DESCRIPTION OF THE PREFERRED EMBODIMENTS

Figures 3, 4:
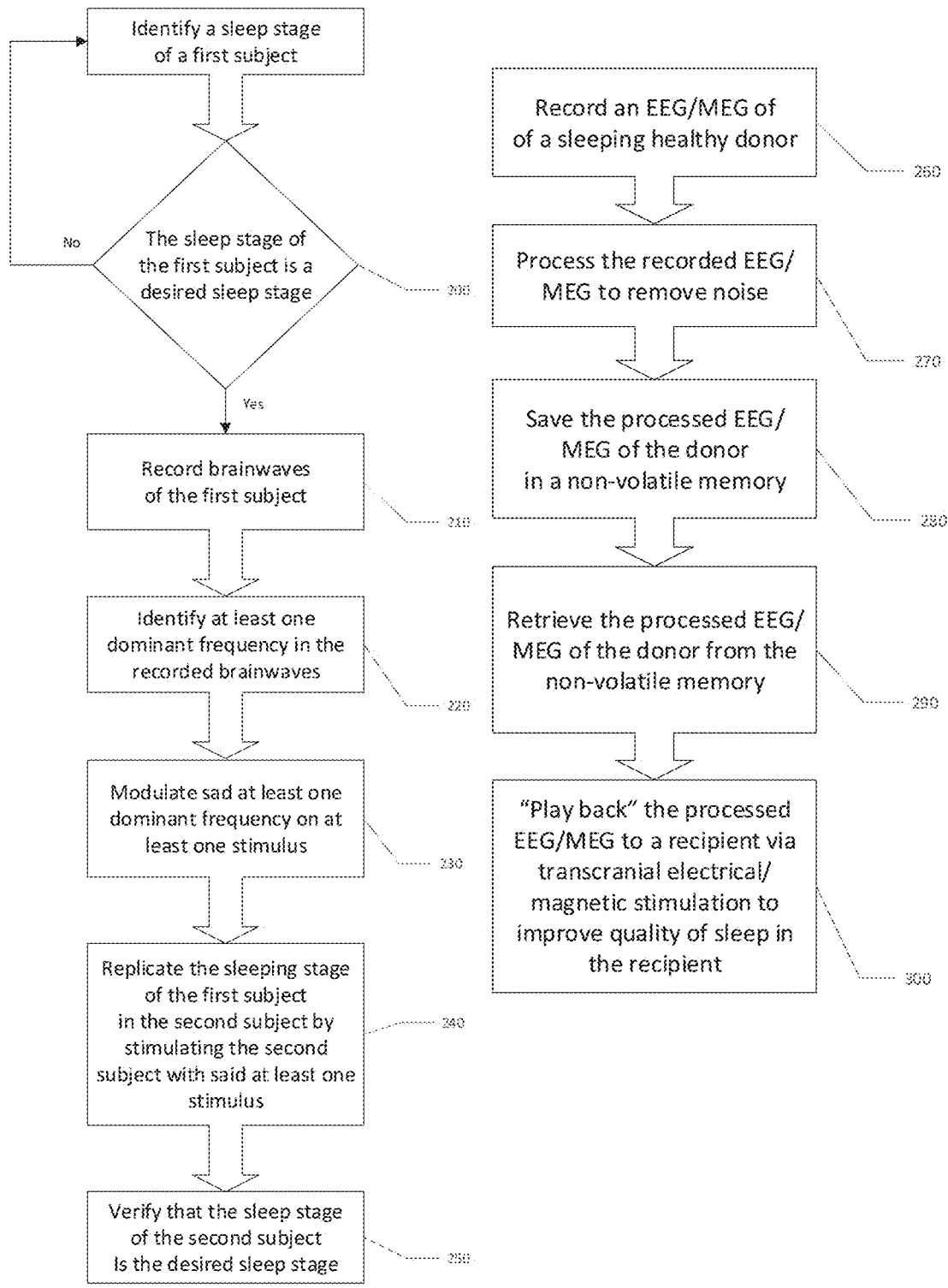
FIG. 3 shows a flowchart according to one embodiment of the invention illustrating a process of replicating a sleep stage from at least one first subject to another subject by recording electroencephalogram (EEG) of said least one first subject, extracting at least one dominant frequency from the EEG and replicating the sleep stage of said at least one first subject in a second subject by stimulating the second subject with stimuli having the dominant frequency associated with the desired sleep stage, according to one embodiment of the invention.
FIG. 4 shows a flowchart according to one embodiment of the invention illustrating a method of improving sleep in a recipient by recording EEG or MEG of a healthy donor and "playing it back" to the recipient via transcranial stimulation.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

FIG. 1 shows a flowchart of a first embodiment according to the present invention. A first subject (donor), having a mental state, is interrogated, observed or sensed, to determine or identify his or her mental state 100. The first subject is typically human, though this is not a limit of the technology and the subject may be an animal. In this embodiment, the process seeks to identify a characteristic sleep pattern, and therefore the mental state of the first subject is monitored until a sleep state occurs 110. When the first subject (donor) is asleep, brain activity patterns reflecting or characterizing the sleep state are captured 120. This step may be done by recording EEG or MEG of the first subject (donor). And the brain activity patterns are stored in a non-volatile memory 130. These stored patterns may be optionally processed, statistically aggregated, analyzed for perturbations or anomalies, filtered, compressed, etc. Stages of sleep may be determined. It is noted that brain activity patterns change over time during sleep from stage to stage, and therefore, the stored patterns may encompass one or more stages of sleep.

The stored data from the first subject (donor) is then used to induce sleep in a second subject (a recipient—also typically a human, but may be an animal) by replicating the brain activity patterns (or sequences of brain activity patterns) of the first subject (donor) in the second subject (recipient) 150. The replication of brain activity patterns, dependent on the stored patterns, typically seeks to stimulate or induce the brain of the second subject (recipient) by modulating a stimulus (or several stimuli) in a manner synchronized with the frequency, phase and/or waveform pattern represented in the brain activity patterns of the first subject (donor) in the sleep state. Typically, when the second subject (recipient) achieves the sleep state 160 (assuming that the first subject and second subject are physiologically compatible—a donor and a recipient should both be either human or animals), the brain activity patterns of the first and second subject will be corresponding.

According to the present technology, the modulation of stimulation, which is, for example, a sensory stimulation, whose waveform is modulated to correspond to the raw or processed brainwave pattern of the first subject (donor) for the brain region associated with the stimulation electrode.

For example, the brain activity pattern of the first subject (donor) is measured by EEG electrodes. In a sleep state, it may assume various wave patterns, over the range <1 Hz to about 25 Hz, which vary in amplitude, frequency, spatial location, and relative phase. For example, the first stage of sleep is initially dominated by alpha brainwaves with a frequency of 8 Hz to 13 Hz. Typically, brain activity pattern measurement from the first subject (donor) has a higher spatial resolution, e.g., 64 or 128 electrode EEGs, than the stimulator for the second subject (recipient), and the stimulus electrodes tend to be larger than the EEG electrode. The stimulus for the second subject (recipient) is therefore processed using a dimensionality (or spatial) reduction algorithm to account for these differences, which will tend to filter the stimulus signal. By applying this stimulus modulated with the brain activity of the first subject (donor), the second subject (recipient) is made susceptible to synchronization with the brain activity pattern of the first subject (donor). For example, by temporally modulating the polarization level of the cells near the electrode, the cells will better couple to excitation stimuli in the brain of the second subject (recipient) having the characteristics of the brain activity pattern of the first subject (donor).

The donor's indigenous brainwaves may be modulated on light, sound, vibrations or any number of other stimuli amenable to frequency modulation. For example, donor's brainwaves may be modulated on ambient light, on binaural beats, or isochronic tones.

The verification that the recipient has achieved the desired sleep state may optionally be done by visual observation, by ER EKG, measuring heart and/or respiration rate, body temperature or any number of other physiological parameters that will be well understood by a person skilled in the art. These measurements should be, preferably, done automatically via biosensors.

FIG. 2 shows a flowchart of the second embodiment according to the present invention. A first subject (donor), having a mental state, is interrogated, observed or sensed, to determine or identify of his or her mental state 100. The first subject is typically human, though this is not a limit of the invention (which equally applies to any animal). In this embodiment, the interrogation seeks to identify a characteristic alert/awake pattern, and therefore the mental state of the first subject is monitored until an alert state occurs 111. When the first subject (donor) is awake, brain activity patterns reflecting or characterizing the waking state are captured 120, and stored in a non-volatile memory 130. For example, one may seek to capture the patterns that represent awakening, and therefore, the monitoring commences on a sleeping subject. These stored patterns may be optionally processed, statistically aggregated, analyzed for perturbations or anomalies, filtered, compressed, etc. Stages of awakening may be determined. It is noted that the brain activity patterns change overtime during awakening, and therefore, the stored patterns may encompass one or more stages of the waking process.

The stored data from the first subject (donor) is then retrieved from the non-volatile memory 140 and used to "transplant" the state of alertness to prevent sleep, or maintain alertness, in a second subject (a recipient—also typically, but not necessarily, a human) by replicating the awake brain activity patterns of the first subject (donor), or sequences of brain activity patterns, in the second subject (recipient) 170. The replication of brain activity patterns, dependent on the stored patterns, typically seeks to stimulate or induce the brain of the second subject (recipient) by modulating indigenous brainwaves of the donor on a stimulus in a manner synchronized with the frequency, and preferably phase and/or waveform pattern represented in the brain activity patterns of the first subject (donor) in the awake or wakening state. Typically, when the second subject is awake or wakes up, 180, the brain activity patterns of the first and second subject will be corresponding.

FIG. 3 shows a flowchart of a third embodiment, in which the technology is generalized. A first subject (donor), having a mental state, is interrogated, observed or sensed, to determine or identify his or her mental state 190. The mental state of the first subject is monitored until the desired state is achieved 200. When the first subject achieves that state, brain activity patterns reflecting or characterizing the state are captured 210 by, for example, recording EEG or MEG of the first subject, and optionally stored in non-volatile memory. The brain activity pattern is, e.g., brainwaves (e.g., EEG) 210.

The brainwaves are analyzed using statistical data mining techniques such as principal component analysis (PCA) to determine a set of linearly-uncorrelated variables—principal components. At least one dominant frequency in the recorded brainwaves is identified 220. Optionally, secondary and higher harmonics may be identified as well. It will be well-understood by a person skilled in the art that any number of similar statistical data analysis technics may be used, such as signal processing, independent component analysis, network component analysis, correspondence analysis, multiple correspondence analysis, factor analysis, canonical correlation, functional principal component analysis, independent component analysis, singular spectrum analysis, weighted PCA, sparse PCA, principal geodesic analysis, eigenvector-based multivariate analyses, etc.

The stored data from the first subject is then retrieved, at least the dominant frequency is modulated on at least one stimulus and used to "transplant" the desired mental state of the donor in a second subject (recipient) by seeking to replicate the brain activity patterns of the first subject (donor), or sequences of brain activity patterns, in the second subject (recipient) 240. The second subject (recipient) is then monitored for induction of the desired mental state 250.

FIG. 4 shows a flowchart according to the fourth embodiment, in which an EEG or EMG of a first subject (healthy donor), while in a state of sleep, is recorded 280, optionally processed to remove noise 270, and stored 280. The data may optionally be compressed. The stored data is retrieved 290 and decompressed as necessary. The data is then played back to a second subject (recipient), to improve the quality of sleep 300.

Figures 5, 6:
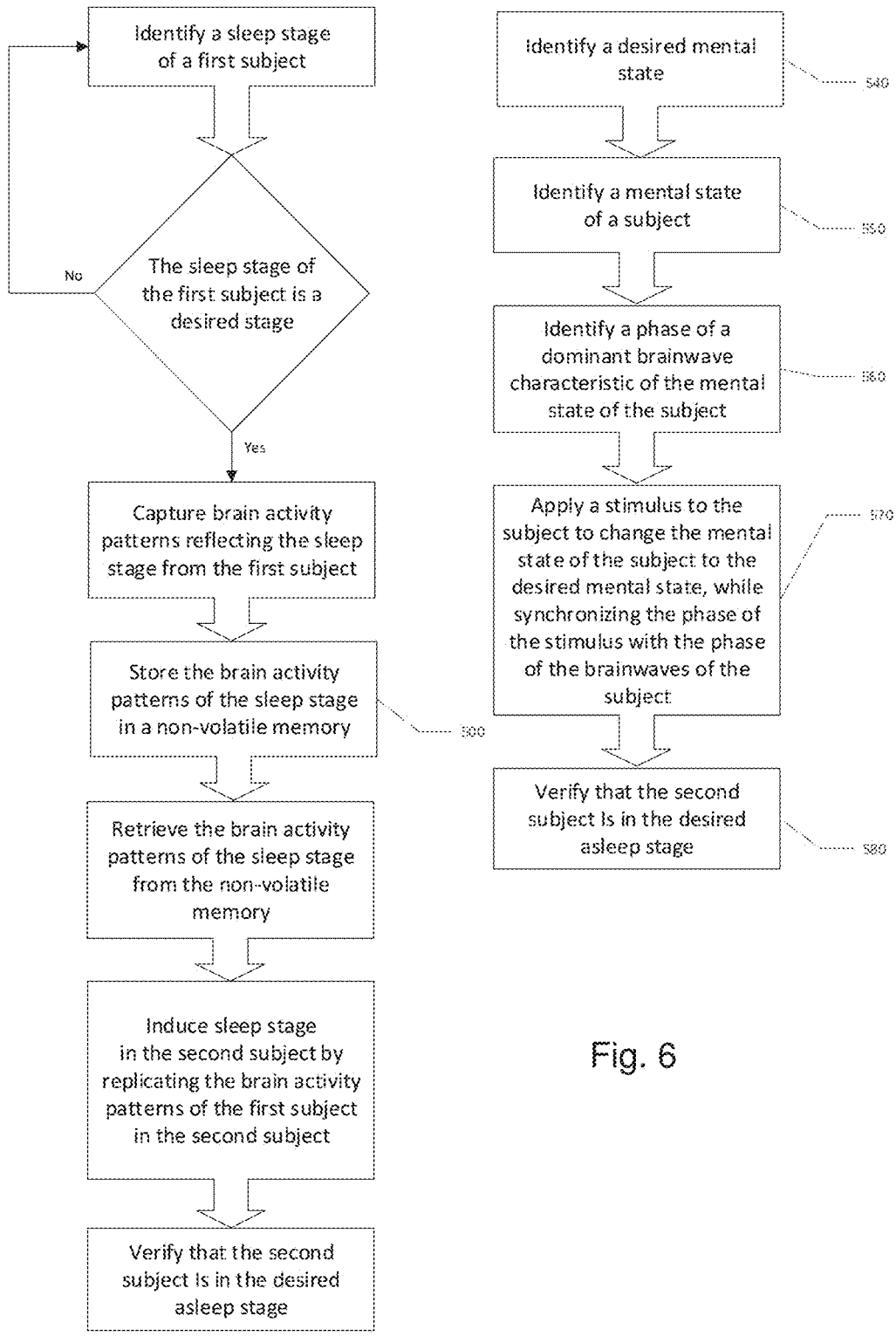
FIG. 5 shows a flowchart according to a further embodiment of the invention.
FIG. 6 shows a flowchart according to one embodiment of the invention illustrating a process of replicating the desired sleep stage from one subject to another subject.

FIG. 5 shows a flowchart according to a further embodiment of the present invention illustrating a process of replicating the desired sleep stage from one subject (donor) to another subject (recipient). In general, the sleep stage of the source subject is determined in a traditional manner, which may include brain signal analysis, other biometrics, and/or observation. The data may be acquired 400 over one or more sleep cycles, and during or after different types of environmental conditions or stimulation. For example, various types of music may be played, seeking to entrain a conscious or subconscious rhythm. Lights can flash, and various other sensory stimulation may occur. The brain signal readings are synchronized and tagged with the stimulation parameters 410 so that the stimulation is associated with its respective effect. Similarly, before sleep, the subject may be presented with certain experiences, such that during sleep, the memory processing within the brain is dependent on these experiences.

After the various data is acquired from the subject 400, along with information about the pre-sleep experience and or context 410, and sensory stimulation during sleep, a memory, database, statistical model, the rule-based model is generated, and/or neural network is trained, reflecting the subject (donor). Data may be aggregated from a plurality of subjects (donors), but typically, these are processed for the particular subject before aggregation. Based on single or multiple subject data, a normalization process may occur 420. The normalization may be spatial and/or temporal. For example, the EEG electrodes between sessions or for the different subject may be in different locations, leading to a distortion of the multichannel spatial arrangement. Further, the head size and shape of different individuals are different, and this needs to be normalized and/or encoded as well. The size and shape of the head/skull and/or brain may also lead to temporal differences in the signals, such as characteristic time delays, resonant or characteristic frequencies, etc.

One way to account for these effects is through the use of a time-space transform, such as a wavelet-type transform. It is noted that, in a corresponding way that statistical processes are subject to frequency decomposition analysis through Fourier transforms, they are also subject to time-frequency decomposition through wavelet transforms. Typically, the wavelet transform is a discrete wavelet transform (DWT), though more complex and less regular transforms may be employed. As discussed above, principal component analysis (PCA) and spatial PCA may be used to analyze signals, presuming linearity (linear superposition) and statistical independence of components. However, these presumptions technically do not apply to brainwave data, and practically, one would normally expect interaction between brain wave components (non-independence) and lack of linearity (since "neural networks" by their nature are non-linear), defeating the use of KA or spatial PCA unmodified. However, a field of nonlinear dimensionality reduction provides various techniques to permit corresponding analyses under the presumptions of non-linearity and non-independence. See, en.wikipedia.org/wiki/Nonlinear_dimensionality_reduction, www.image.ucar.edu/pub/toyIV/monahan_5_16.pdf (An Introduction to Nonlinear Principal Component Analysis, Adam Monahan), Nonlinear PCA toolbox for MATLAB (www.nlpca.org), Nonlinear Principal Components Analysis: Introduction and Application (open-access.leidenuniv.nl/bitstream/handle/1887/12386/Chapter2.pdf?sequence=10, 2007), Nonlinear PCA (www-.comp.nus.edu.sg/~cs5240/lecture/nonlinear-pca.pdf), Nonlinear Principal Component Analysis: Neural Network Models and Applications (pdfs.semanticscholar.org/9d31/23542031a227d2f4c4602066cf8ebceaeb7a.pdf), Karl Friston, "Nonlinear PCA: characterizing interactions between modes of brain activity" (www.fil.ion.ucl.ac.uk/~karl/Nonlinear PCA.pdf, 2000), Howard et al., "Distinct Variation Pattern Discovery Using Alternating Nonlinear Principal Component Analysis", IEEE Trans Neural Network Learn Syst. 2018 January; 29(1):156-166. doi: 10.1109/TNNLS.2016.2616145. Epub 2016 Oct. 26 (www.ncbi.nlm.nih.gov/pubmed/27810837); Jolliffe, I. T., "Principal Component Analysis, Second Edition", Springer 2002 cda.psych.u-iuc.edu/statistical_learning_course/Jolliffe I. Principal Component Analysis (2ed., Springer, 2002) (518s) MVsa_.pdf, Stone, James V. "Blind source separation using temporal predictability." Neural computation 13, no. 7 (2001): 1559-1574.; Barros, Allan Kardec, and Andrzej Cichocki. "Extraction of specific signals with temporal structure." Neural computation 13, no. 9 (2001): 1995-2003.; Lee, Soo-Young. "Blind source separation and independent component analysis: A review." Neural Information Processing-Letters and Reviews 6, no. 1 (2005): 1-57.; Hyvärinen, Aapo, and Patrik Hoyer. "Emergence of phase- and shift-invariant features by decomposition of natural images into independent feature subspaces." Neural computation 12, no. 7 (2000): 1705-1720.; Wahlund, Björn, Wlodzimierz Klonowski, Pawel Stepien, Robert Stepien, Tatjana von Rosen, and Dietrich von Rosen. "EEG data, fractal dimension and multivariate statistics." Journal of Computer Science and Engineering 3, no. 1 (2010): 10-14.; Yu, Xianchuan, Dan Hu, and Jindong Xu. Blind source separation: theory and applications. John Wiley & Sons, 2013; Parida, Shantipriya, Satchidananda Dehuri, and Sung-Bae Cho. "Machine Learning Approaches for Cognitive State Classification and Brain Activity Prediction: A Survey." Current Bioinformatics 10, no. 4 (2015): 344-359.; Friston, Karl J., Andrew P. Holmes, Keith J. Worsley, J-P. Poline, Chris D. Frith, and Richard S J Frackowiak. "Statistical parametric maps in functional imaging: a general linear approach." Human brain mapping 2, no. 4 (1994): 189-210.; Wang, Yan, Matthew T. Sutherland, Lori L. Sanfratello, and Akaysha C. Tang. "Single-trial classification of ERPS using second-order blind identification (SOBI)." In Machine Learning and Cybernetics, 2004. Proceedings of 2004 International Conference on, vol. 7, pp. 4246-4251. IEEE, 2004.; Jutten, Christian, and Massoud Babaie-Zadeh. "Source separation: Principles, current advances and applications." IAR Annu Meet Nancy Fr 110 (2006).; Saproo, Sameer, Victor Shih, David C. Jangraw, and Paul Sajda. "Neural mechanisms underlying catastrophic failure in human-machine interaction during aerial navigation." Journal of neural engineering 13, no. 6 (2016): 066005.; Valente, Giancarlo. "Separazione cieca di sorgenti in ambienti reali: nuovi algoritmi, applicazioni e implementazioni." (2006).; SAPIENZA, L A. "Blind Source Separation in real-world environments: new algorithms, applications and implementations Separazione cieca di sorgenti in ambienti reali: nuovi algoritmi, applicazioni e."; Ewald, Arne. "Novel multivariate data analysis techniques to determine functionally connected networks within the brain from EEG or MEG data." (2014).; Friston, Karl J. "Basic concepts and overview." SPMcourse, Short course; Crainiceanu, Ciprian M., Ana-Maria Staicu, Shubankar Ray, and Naresh Punjabi. "Statistical inference on the difference in the means of two correlated functional processes: an application to sleep EEG power spectra." Johns Hopkins University, Dept. of Biostatistics Working Papers (2011): 225.; Konar, Amit, and Aruna Chakraborty. Emotion recognition: A pattern analysis approach. John Wiley & Sons, 2014.; Kohl, Florian. "Blind separation of dependent source signals for MEG sensory stimulation experiments." (2013).; Iiken, Arno, Jian K. Liu, P P Chamanthi R. Karunasekara, Ioannis Delis, Tim Gollisch, and Stefano Panzeri. "Using matrix and tensor factorizations for the single-trial analysis of population spike trains." PLoS computational biology 12, no. 11 (2016): e1005189.; Tressoldi, Patrizio, Luciano Pederzoli, Marco Bilucaglia, Patrizio Caini, Pasquale Fedele, Alessandro Ferrini, Simone Melloni, Diana Richeldi, Florentine Richeldi, and Agostino Accardo. "Brain-to-Brain (Mind-to-Mind) Interaction at Distance: A Confirmatory Study." (2014). f1000researchdata.s3.amazonaws.com/manuscripts/5914/5adbf847-787a-4fcl-ac04-2elcd61ca972_4336_-_patrizio_tressoldi_v3.pdf?doi=10.12688/f1000research. 4336.3; Tsiaparas, Nikolaos N. "Wavelet analysis in coherence estimation of electroencephalographic signals in children for the detection of dyslexia-related abnormalities." PhD diss., 2006.

FIG. 6 shows a flowchart of an embodiment of the invention. A sleep stage of a first subject is identified, and then it is determined whether the sleep stage is the desired sleep stage. If not, the first subject is further monitored. If the sleep stage is the one desired, the brain activity of the first subject is captured, reflecting the sleep stage, and the brain activity patterns of the first subject while in the desired sleep stage stored in non-volatile memory 500. The stored brain activity patterns are subsequently retrieved and used to induce the sleep stage in a second subject by replicating the brain activity patterns of the first subject in the second subject by appropriate stimulation of the second subject. The second subject may be monitored to verify that the second subject is in the desired sleep stage.

Figure 7:
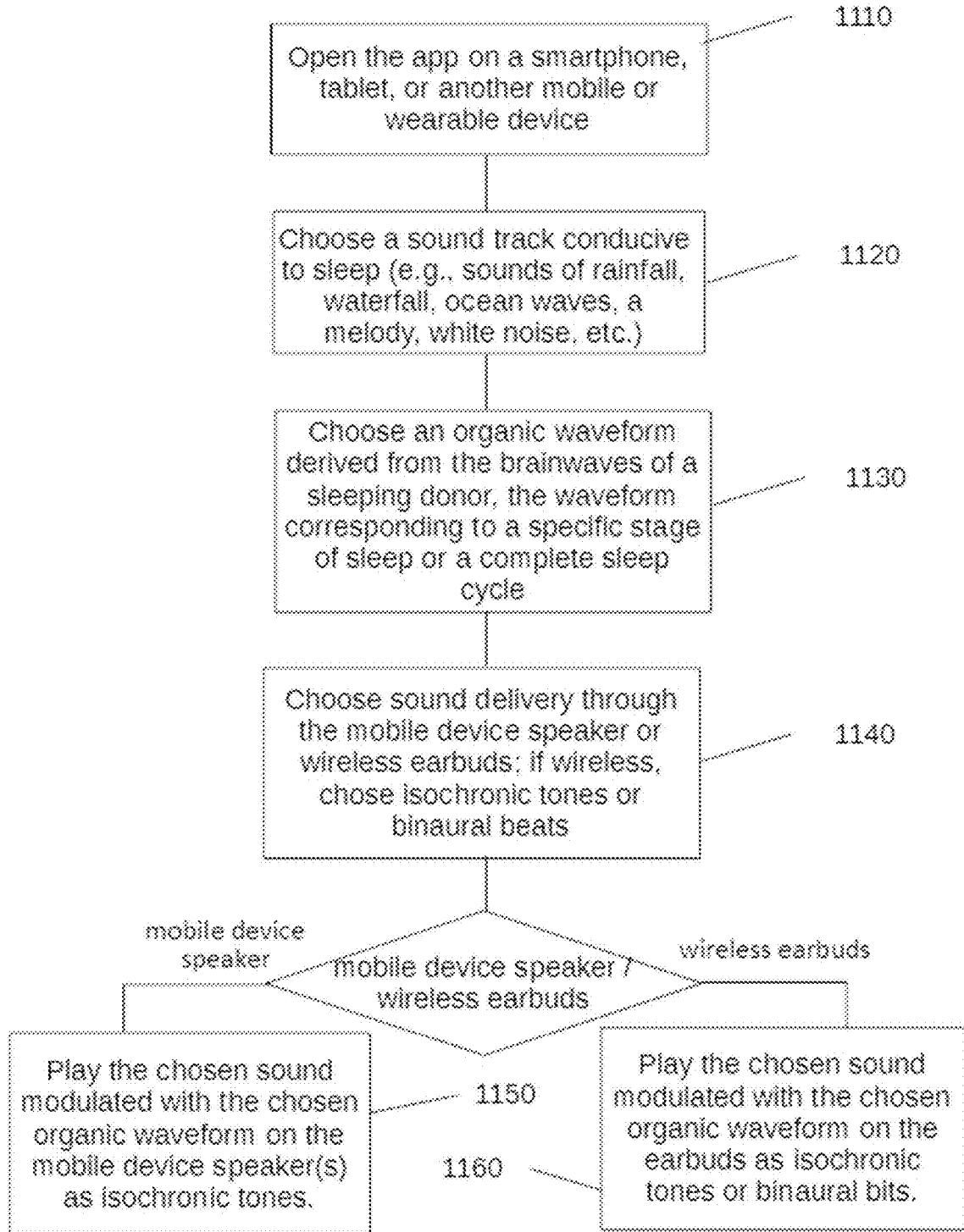
FIG. 7 shows a flowchart according to an embodiment of the invention.

As shown in FIG. 7, a human brain state or mental state in a subject is modified or altered. In some implementations, a current brainwave pattern of the subject, a phase of a characteristic wave of the current brainwave pattern of the subject, a characteristic timing of a stimulus-response dependent on the mental state, or temporal relationships in monitored neurological or motor patterns of the subject is determined. The desired change in the current brain wave pattern of the subject is determined or defined. A stimulus is applied, e.g., electrical, magnetic, acoustic or ultrasound, sensory, etc., which can be for determining the current state, changing the state, or both. For example, a characteristic timing of a stimulus-response dependent on the mental state may be extracted, or temporal relationships in monitored neurological or motor patterns of the subject determined. The stimulus may be asynchronous, or time-synchronized with respect to the phase state, or dependent on at least the determined temporal relationships. In a closed-loop excitation, the brain wave pattern of the subject after at least one stimulus is monitored or the response parameters, e.g., characteristic timing measured or assessed. The stimulus may be controlled dependent on the observed or monitored changes, indicative of an effective alteration or modification of the brain state or mental state in the subject. FIG. 6 thus shows a flowchart of an embodiment of the invention. A desired mental state is identified 540. The mental state of a subject identified 550, and a phase of a dominant brainwave, characteristic of the mental state of the subject identified 560. A stimulus is applied to the subject to change the mental state of the subject to the desired mental state, while synchronizing the phase of the stimulus with the phase of the dominant brainwave of the subject 570. The subject is monitored to determine if the desired mental state is achieved. If the desired mental state is sleep, the sleep state of the subject may be verified 580.

FIG. 7 shows a flowchart of a further embodiment of the invention. An app is opened on a smartphone, tablet or another mobile or wearable device 1110. Note that in some applications, the device need not be mobile, and for example may be part of a headboard, nightstand, clock radio, etc. A soundtrack conducive to sleep, e.g., sounds of rainfall, waterfall, ocean waves, a melody, white noise, pink noise, etc., is chosen 1120. An organic waveform is chosen, derived from brainwaves of a sleeping donor, corresponding to a specific stage of a sleep cycle or a complete sleep cycle 1130. The sound delivery may be chosen to be through a mobile device speaker, earphones, wireless earbuds. If separate sound delivery to each ear, the sound may be isochronic tones or binaural beats 1140, while if not isolated, isochronic tones may be played 1160.

Figures 8, 9:
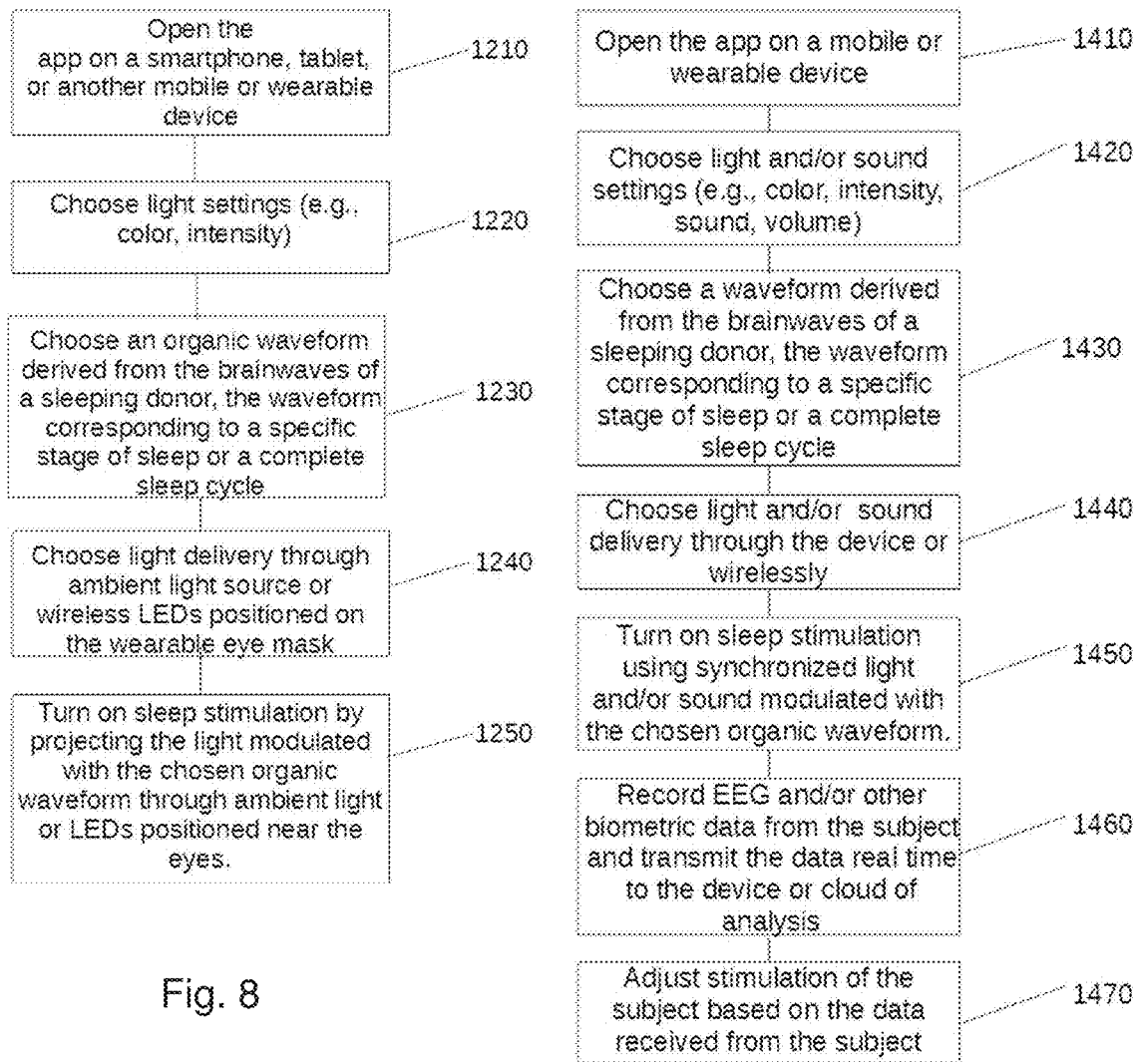
FIG. 8 shows a flowchart according to an embodiment of the invention.
FIG. 9 shows a flowchart according to an embodiment of the invention.

FIG. 8 shows a flowchart of a still further embodiment of the invention. An app may be opened on a smartphone, tablet or wearable device 1210. Light settings, such as color and intensity, are chosen 1220. An organic waveform derived from brainwaves of a sleeping donor, corresponding to a specific stage or stages of sleep, or a complete sleep cycle is chosen 1230. Light delivery may be chosen through an ambient light source or e.g., LEDs positioned on a wearable eye mask 1240, which is wirelessly connected to the device. Sleep stimulation is turned on by projecting the light modulated with the chosen organic waveform through ambient light or LEDs positioned near the eyes 1250.

FIG. 9 shows a flowchart of an embodiment of the invention. The subject opens an app on, e.g., a mobile or wearable device and logs in to a personal account 1510. A new waveform, modified from the last waveform used based on biometric sleep data received from the subject during a previous stimulation session 1520. Light and/or sound delivery through the device or through a wireless peripheral is chosen 1540. Sleep stimulation is turned using synchronized light and/or sound modulated with the chosen organic waveform 1550. EEG and/or other biometric data is recorded from the subject and transmitted to a remote for analysis 1590. The received biometric data from the subject is analyzed, to measure the effectiveness of the stimulation and to adjust the waveform accordingly, to improve the effect of the stimulation 1570.

Therefore, statistical approaches are available for separating EEG signals from other signals, and for analyzing components of EEG signals themselves. According to the present invention, various components that might be considered noise in other contexts, e.g., according to prior technologies, such as a modulation pattern of a brainwave, are preserved. Likewise, interactions and characteristic delays between significant brainwave events are preserved. This information may be stored either integrated with the brainwave pattern in which it occurs or as a separated modulation pattern that can then be recombined with an unmodulated brainwave pattern to approximate the original subject.

According to the present technology, lossy "perceptual" encoding (i.e., functionally optimized with respect to a subjective response) of the brainwaves may be employed to process, store, and communicate the brainwave information. In a testing scenario, the "perceptual" features may be tested, so that important information is preserved over information that does not strongly correspond to the effective signal. Thus, while one might not know a priori which components represent useful information, a genetic algorithm may empirically determine which features or data reduction algorithms or parameter sets optimize retention of useful information vs. information efficiency. It is noted that subjects may differ in their response to signal components, and therefore the "perceptual" encoding may be subjective with respect to the recipient. On the other hand, different donors may have different information patterns, and therefore, each donor may also require individual processing. As a result, pairs of donor and recipient may require optimization, to ensure accurate and efficient communication of the relevant information. According to the present invention, sleep/wake mental states and their corresponding patterns are sought to be transferred. In the recipient, these patterns have characteristic brainwave patterns. Thus, the donor may be used, under a variety of alternate processing schemes, to stimulate the recipient, and the sleep/wake response of the recipient determined based on objective criteria, such as resulting brainwave patterns or expert observer reports, or subjective criteria, such as recipient self-reporting, survey or feedback. Thus, after a training period, optimized processing of the donor, which may include filtering, dominant frequency resynthesis, feature extraction, etc., may be employed, which is optimized for both donor and recipient. In other cases, the donor characteristics may be sufficiently normalized, that only recipient characteristics need be compensated. In a trivial case, there is only one exemplar donor, and the signal is oversampled and losslessly recorded, leaving only recipient variation as a significant factor.

Because dominant frequencies tend to have low information content (as compared to the modulation of these frequencies and interrelation of various sources within the brain), one efficient way to encode the main frequencies is by location, frequency, phase, and amplitude. The modulation of a wave may also be represented as a set of parameters. By decomposing the brainwaves according to functional attributes, it becomes possible, during stimulation, to modify the sequence of "events" from the donor, so that the recipient need not experience the same events, in the same order, and in the same duration, as the donor. Rather, a high-level control may select states, dwell times, and transitions between states, based on classified patterns of the donor brainwaves. The extraction and analysis of the brainwaves of the donors, and response of the recipient, may be performed using statistical processes, such as principal components analysis (PCA), independent component analysis (ICA), and related techniques; clustering, classification, dimensionality reduction and related techniques; neural networks and other known technologies. These algorithms may be implemented on general purpose CPUs, array processors such as CPUs, and other technologies.

In practice, a brainwave pattern of the first subject may be analyzed by a PCA technique that respects the non-linearity and non-independence of the brainwave signals, to extract the major cyclic components, their respective modulation patterns, and their respective interrelation. The major cyclic components may be resynthesized by a waveform synthesizer, and thus may be efficiently coded. Further, a waveform synthesizer may modify frequencies or relationships of components from the donor based on normalization and recipient characteristic parameters. For example, the brain of the second subject (recipient) may have characteristic classified brainwave frequencies 3% lower than the donor (or each type of wave may be separately parameterized), and therefore the resynthesis may take this difference into account. The modulation patterns and interrelations may then be reimposed onto the resynthesized patterns. The normalization of the modulation patterns and interrelations may be distinct from the underlying major cyclic components, and this correction may also be made, and the normalized modulation patterns and interrelations included in the resynthesis. If the temporal modifications are not equal, the modulation patterns and interrelations may be decimated or interpolated to provide a correct continuous time sequence of the stimulator. The stimulator may include one or more stimulation channels, which may be implemented as electrical, magnetic, auditory, visual, tactile, or another stimulus, and/or combinations.

The stimulator is preferably feedback controlled. The feedback may relate to the brainwave pattern of the recipient, and/or context or ancillary biometric basis. For example, if the second subject (recipient) begins to awaken from sleep, which differs from the first subject (donor) sleep pattern, then the stimulator may resynchronize based on this finding. That is, the stimulator control will enter a mode corresponding to the actual state of the recipient, and seek to guide the recipient to the desired state from a current state, using the available range and set of stimulation parameters. The feedback may also be used to tune the stimulator, to minimize error from a predicted or desired state of the recipient subject based on the prior and current stimulation.

The control for the stimulator is preferably adaptive and may employ a genetic algorithm to improve performance overtime. For example, if there are multiple first subjects (donors), the second subject (recipient) may be matched with those donors from whose brainwave signals (or algorithmically modified versions thereof) the predicted response in the recipient is best, and distinguished from those donors from whose brainwave signals the predicted response in the recipient subject poorly corresponds. Similarly, if the donors have brainwave patterns determined over a range of time and context and stored in a database, the selection of alternates from the database may be optimized to ensure best correspondence of the recipient subject to the desired response.

It is noted that a resynthesizer-based stimulator is not required, if a signal pattern from a donor is available that properly corresponds to the recipient and permits a sufficiently low error between the desired response and the actual response. For example, if a donor and a recipient are the same subject at different times, a large database may be unnecessary, and the stimulation signal may be a minimally processed recording of the same subject at an earlier time. Likewise, in some cases, a deviation is tolerable, and an exemplar signal may be emitted, with relatively slow periodic correction. For example, a sleep signal may be derived from a single subject and replayed with a periodicity of 90 minutes or 180 minutes, such as a light or sound signal, which may be useful in a dormitory setting, where individual feedback is unavailable or unhelpful.

In some cases, it is useful to provide a stimulator and feedback-based controller on the donor. This will better match the conditions of the donor and recipient, and further allow determination of not only the brainwave pattern of the donor but also responsivity of the donor to the feedback. One difference between the donors and the recipients is that in the donor, the natural sleep pattern is sought to be maintained and not interrupted. Thus, the adaptive multi-subject database may include data records from all subject, whether selected ab initio as a useful exemplar or not. Therefore, the issue is whether a predictable and useful response can be induced in the recipient from the database record and, if so, that record may be employed. If the record would produce an unpredictable result or a non-useful result, the use of that record should be avoided. The predictability and usefulness of the responses may be determined by a genetic algorithm or other parameter-space searching technology.

Extending the sleep signal illumination example, an illuminator (e.g., red LED lightbulb) may have an intensity modulated based on a donors' brainwave pattern. The illuminator may have a flash memory module with tens or hundreds of different brainwave patterns available. The illuminator may further include a sensor, such as a camera or non-imaging optical or infrared sensor, and speech control, similar to Amazon Alexa. The illuminator may also include an associated speaker, to play synchronized sounds or music. When a sleep cycle is commenced, the illuminator begins displaying (and playing and associated audio) the brainwave pattern as a program, seeking to induce a predetermined sleep pattern. The sensors may be used to determine whether the recipient is in the predicted sleep state based on the program. If the recipient has a sleep state that deviates from the program, then the program may be reset to a portion that corresponds to the actual state of the recipient or reset to a guiding state that seeks to guide the sleep state of the recipient back to the desired program. If the target subject cannot be efficiently synchronized or guided, then the illuminator may adopt a different source subject brainwave pattern. In this case, no electrical stimulation or electrical feedback is employed, and the entire operation may be non-contact.

Figure 10:
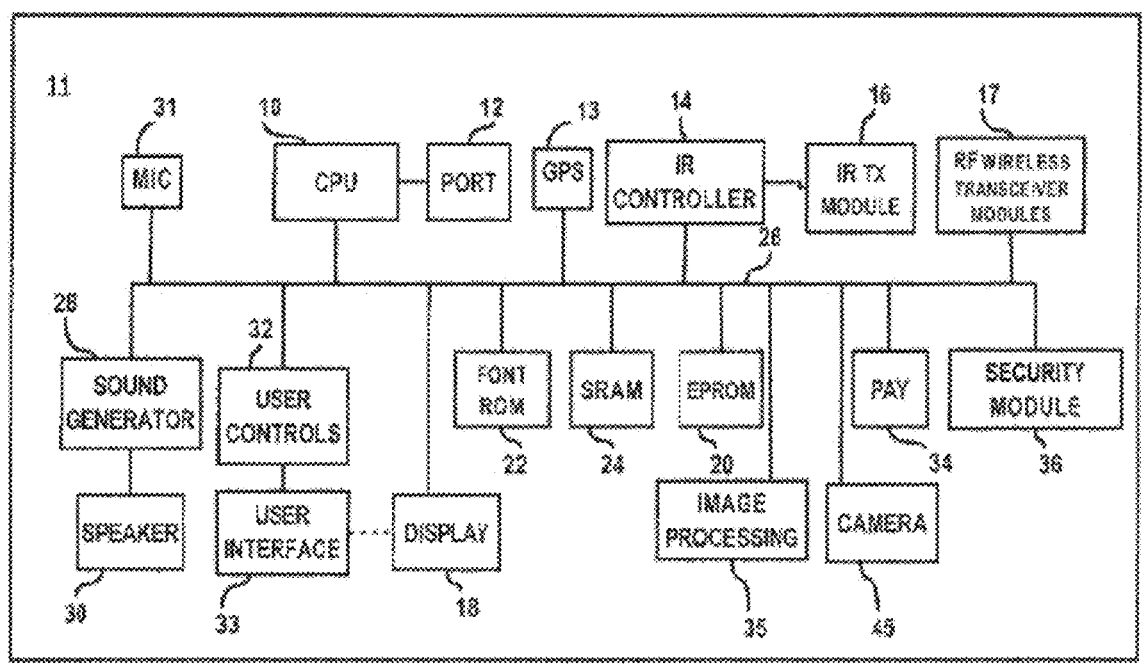
FIG. 10 shows a schematic representation of a smartphone for executing apps.

FIG. 10 shows a representation of a mobile device 11. The mobile device is shown in a familiar "smartphone" form factor. Data can be transferred to and from the mobile device 11 via wireless data communications. In general, the mobile device 11 can include a touch-sensitive display screen 18, a speaker 30, a microphone 31, and one or more control buttons 32 for controlling some operations of device 11. The device 11 depicted in FIG. 10 can be a device, such as, for example, a smartphone capable of communicating with a wireless local area network, and so forth. In this respect, the mobile device 11 can be implemented with touch screen capabilities associated with the display screen 18. Display screen 18 can be configured to display data including video and text and icons 33 operable as soft buttons providing options and action by the mobile device 11 when selected by a user. The mobile device 11 can be capable of carrying out a variety of functionalities. For example, microprocessor shown as CPU 10 of the mobile device 11 can function as the main controller operating under the control of operating clocks supplied from a clock oscillator. CPU 10 can be configured as, for example, a microprocessor. Such a microprocessor can be configured to facilitate the operations of and communicate by the electronic wireless hand-held multimedia device 11. External pins of CPU 10 can be coupled to an internal bus 26 so that it can be interconnected to respective components. The mobile device 11 can also be configured to include memories such as, for example, SRAM 24 which can be provided as a writeable memory that does not require a refresh operation and can be generally utilized as a working area of CPU 10, SRAM (Static RAM) is generally a form of semiconductor memory (RAM) based on a logic circuit known as a flip-flop, which retains information as long as there is enough power to run the device. Font ROM 22 can be configured as a read only memory for storing character images (e.g., icons and font) displayable on a display 18, which can be implemented as, for example, a touch-sensitive display screen. Example types of displays that can be utilized in accordance with display 18 include, for example, a TFT active matrix display, an illuminated LCD (Liquid Crystal Display), or other small-scaled displays being developed or available in the art in compact form. CPU 10 can be utilized to drive display 18 utilizing, among other media, font images from Font ROM 22 and images transmitted as data through wireless unit 17 and processed by image-processing unit 35. EPROM 20 can be configured as a read-only memory that is generally erasable under certain conditions and can be utilized for permanently storing control codes for operating respective hardware components and security data, such as a serial number. A camera capable of capturing video and pictures can be provided and can also work in conjunction with the image processing unit 35.

IR controller 14, when provided, can be generally configured as a dedicated controller for processing infrared codes transmitted/received by an IR transceiver module 15 and for capturing the same as computer data. Wireless unit 17 can be generally configured as a dedicated controller and transceiver module for processing all wireless data transmitted from and to a wireless communications network. It can be appreciated that other variations for wireless transceiver module 17 can also be provided, such as standardized Bluetooth, NFC, Zigbee, etc., and proprietary RF protocols that may be developed for specialized applications.

Port 12 can be connected to CPU 10 and can be temporarily attached, for example, to a docking station to transmit information to and from the mobile device 11 to other devices, such as personal computers. In light of the present invention, port 12 can also be connected to external probes and external sensors for monitoring or providing data. Port 12 can also be configured, for example to link with a battery charger, data communication device, and can permit network devices, a personal computer, or other computing devices to communicate with mobile device 11.

User controls 32 can permit a user to enter data to mobile device 11 and/or initiate particular processing operations via CPU 10. A user interface 33 can be linked to user controls 32 to permit a user to access and manipulate electronic wireless hand held multimedia device 11 for a particular purpose, such as, for example, viewing video images on display 18. User interface 33 can be implemented as a touch screen manipulated user interface, as indicated by the dashed lines linking display 18 with user interface 33. User interface 33 can be configured to accept user input into the mobile device 11. In addition, CPU 10 can cause a sound generator 28 to generate sounds of predetermined frequencies from a speaker 30. Speaker 30 can be utilized to produce music and other audio information associated with video data transmitted to mobile device 11 from an outside source.

A GPS (Global Positioning System) module 13 can be included in the mobile device and can be connected to bus 26. GPS module 13 can be configured to provide location information for the mobile device 11 and can operate with mapping software and resources to provide navigable directions on the display screen 18 to the user, which can be referred to as GPS mapping. The CPU 10 can execute "apps", which are downloadable programs that provide a user interface, and access to various application programming interface (API) calls made available through the operating system, but are generally limited to executing in a low privilege mode and without direct hardware or driver level access. The aps may be downloaded from the Internet, or an on-line service (e.g., iTunes store, Google Play) or through a wireless transceiver.

Figure 11:
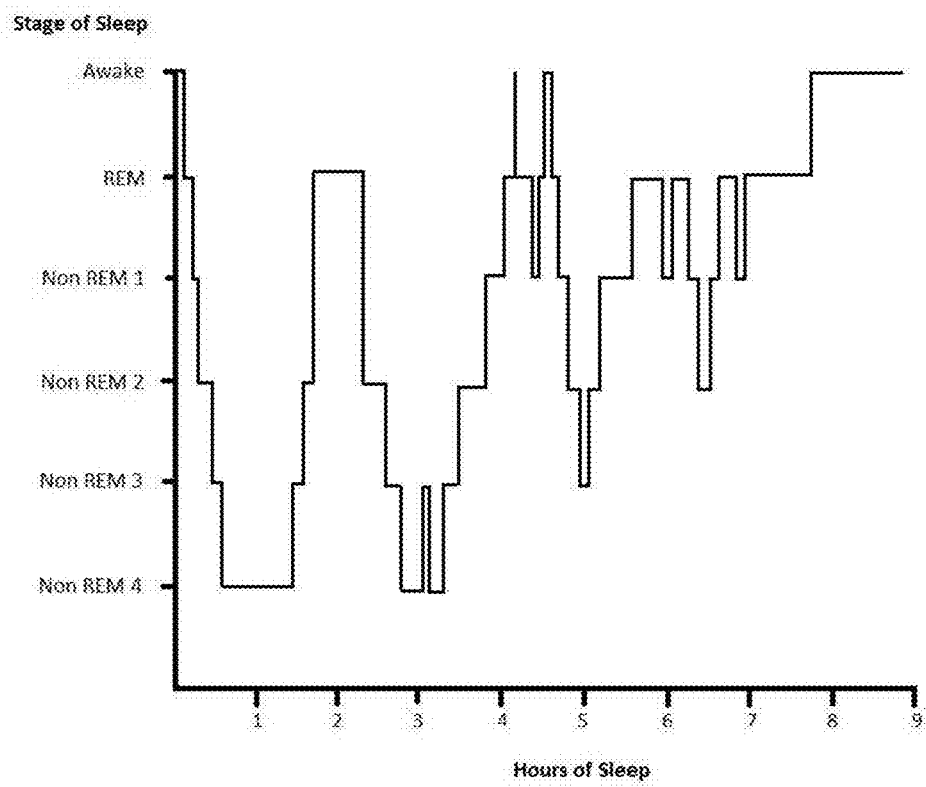
FIG. 11 shows a hypnogram of a healthy adult.

FIG. 11 shows a hypnogram of a healthy adult. As shown, the sleep cycle progresses non-monotonically through a series of stages.

Figure 12:
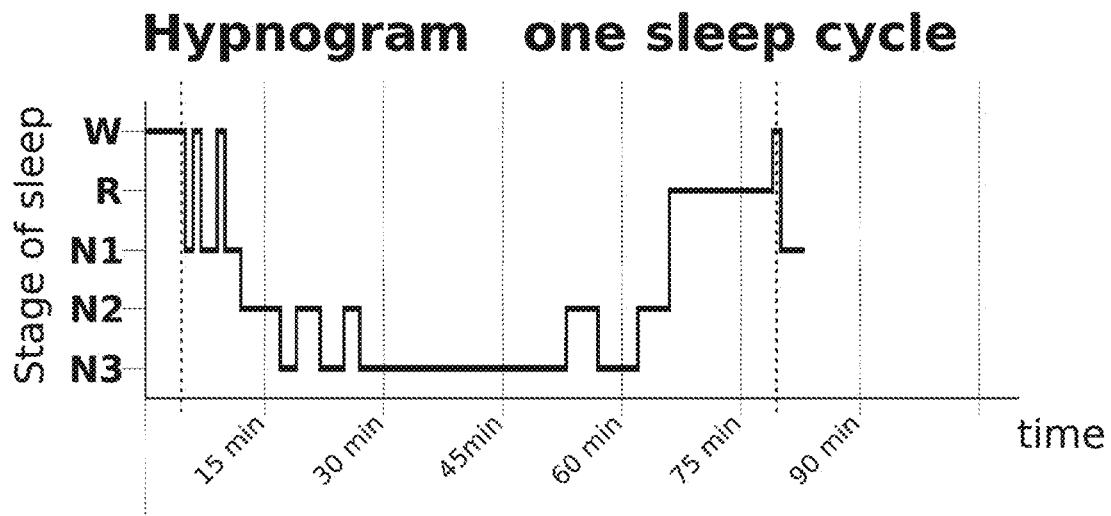
FIG. 12 shows a hypnogram of a healthy adult.

FIG. 12 shows a hypnogram of a healthy adult. As shown, one sleep cycle lasting approximately 90 min is comprised of several sleep stages, including REM sleep (R), first non-REM stage (N1), second non-REM stage (N2), and third non-REM stage (N3), also known as slow-wave sleep, having different duration and periodicity. The waking stage is indicated on the hypnogram as W.

Figure 13:
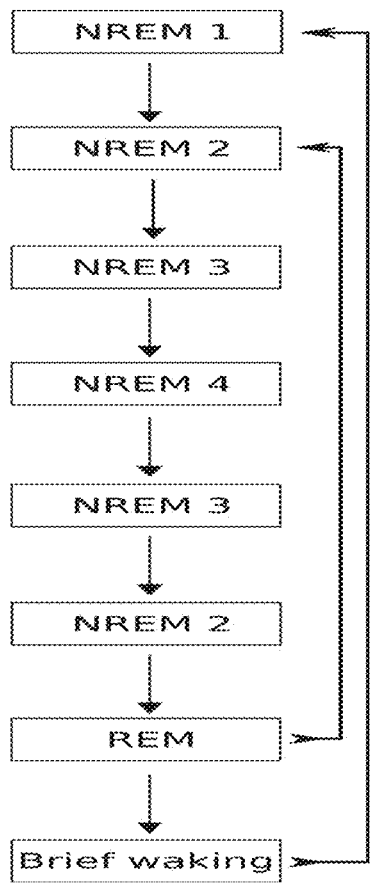
FIG. 13 shows a sequence of sleep stages in a healthy adult.

FIG. 13 shows a flowchart indicating the sequence of sleep stages.

Figure 14:
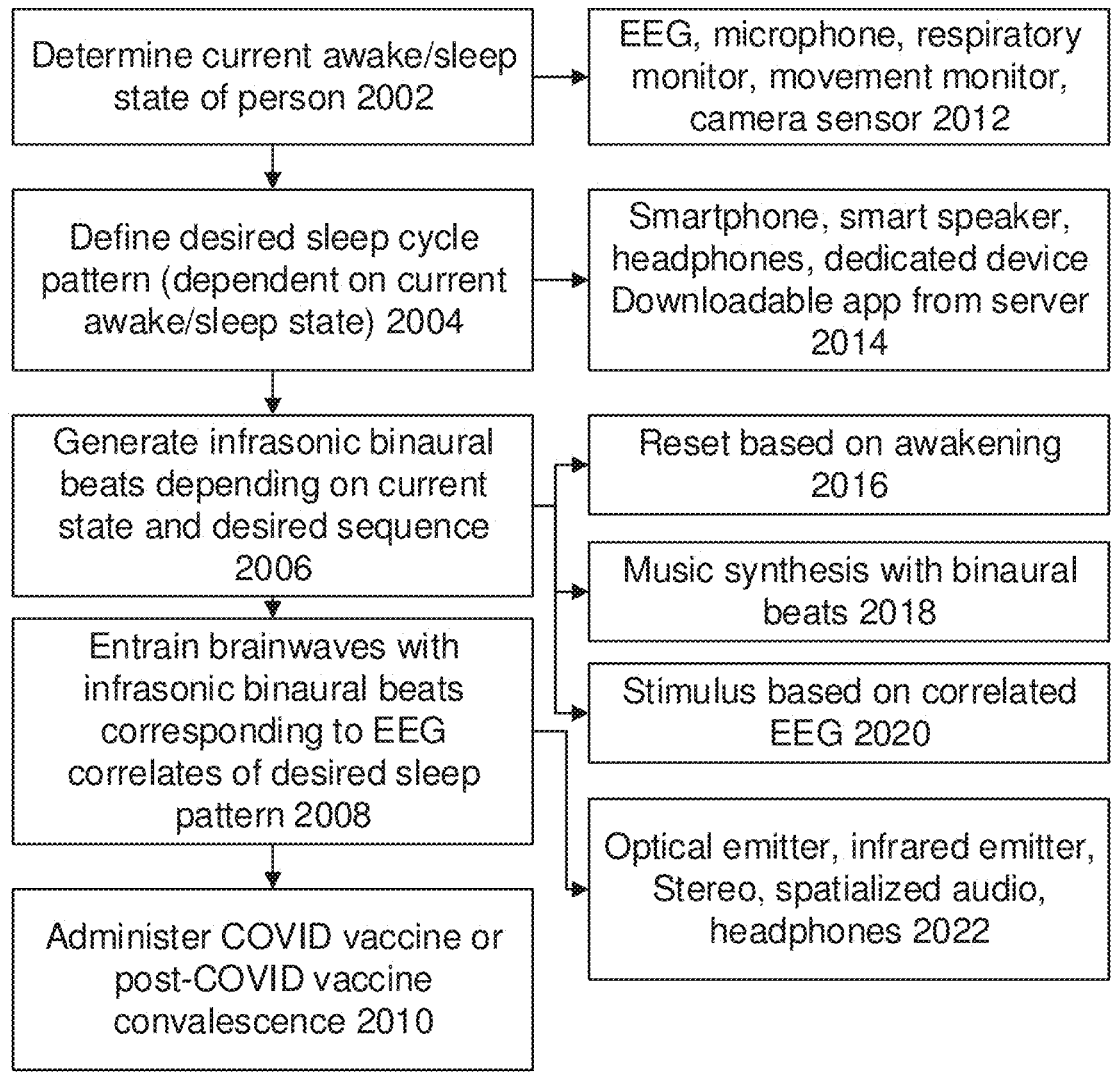
FIG. 14 shows a flowchart according to an embodiment of the invention.

FIG. 14 shows a schematic flowchart of a preferred embodiment of the invention. A current awake or sleep stage of a person is detected 2002, using EEG, microphone, respiratory monitor, movement monitor (e.g., accelerometer), and/or a camera 2012. A desired sleep cycle pattern is defined 2004, dependent on the current awake or sleep stage of the person, with a device which may be a smartphone, a smart speaker, intelligent headphones, etc., which may be dependent on a downloadable app and/or date from a remote server 2014. A frequency-following response for low frequency EEG signals is generated in the person by presenting binaural beats, isochronic tones, or optical stimulation, e.g., audio frequency stimulation with different audio signals in each ear 2006 to stimulate infrasonic EEG response, using stereo speakers, earphones or earbuds, spatialized audio, etc., 2022. The cycle may be reset upon awakening 2016, and the source material which generates binaural beats may be encoded onto a musical work 2018 or audiovisual work. The stimulus pattern may be dependent on a previously recorded EEG, from the subject or one or more other persons 2020. Brainwaves of the brain of the person are entrained with the stimulation pattern according to the desired sleep cycle pattern, to thereby induce a sleep cycle in the person according to the sleep cycle pattern 2008. The SARS-Cov-2 vaccination may be administered after a good night's sleep, or the process used to improve sleep during the postvaccination convalescence 2010.

The aspects of the invention are intended to be separable and may be implemented in combination, sub-combination, and with various permutations of embodiments. Therefore, the various disclosure herein, including that which is represented by acknowledged prior art, may be combined, sub-combined and permuted in accordance with the teachings hereof, without departing from the spirit and scope of the invention. All references and information sources cited herein are expressly incorporated herein by reference in their entirety.

REFERENCE LIST 1

Abeles M, Local Cortical Circuits (1982) New York: Springer-Verlag.

Braitenberg V and Schuz A (1991) Anatomy of the Cortex. Statistics and Geometry. New York: Springer-Verlag.

Ebersole J S (1997) Defining epileptogenic foci: past, present, future. J. Clin. Neurophysiology 14: 470-483.

Edelman G M and Tononi G (2000) A Universe of Consciousness, New York: Basic Books.

Freeman W J (1975) Mass Action in the Nervous System, New York: Academic Press.

Gevins A S and Cutillo B A (1995) Neuroelectric measures of mind. In: P L Nunez (Au), Neocortical Dynamics and Human EEG Rhythms. NY: Oxford U. Press, pp. 304-338.

Gevins A S, Le J, Martin N, Brickett P, Desmond J, and Reutter B (1994) High resolution EEG: 124-channel recording, spatial enhancement, and MRI integration methods. Electroencephalography and Clin. Neurophysiology 90: 337-358.

Gevins A S, Smith M E, McEvoy L and Yu D (1997) High-resolution mapping of cortical activation related to working memory effects of task difficulty, type of processing, and practice. Cerebral Cortex 7: 374-385.

Haken H (1983) Synergetics: An Introduction, 3rd Edition, Springer-Verlag.

Haken H (1999) What can synergetics contribute to the understanding of brain functioning? In: Analysis of Neurophysiological Brain Functioning, C Uhl (Ed), Berlin: Springer-Verlag, pp 7-40.

Ingber L (1995) Statistical mechanics of multiple scales of neocortical interactions. In: P L Nunez (Au), Neocortical Dynamics and Human EEG Rhythms. NY: Oxford U. Press, 628-681.

Izhikevich E M (1999) Weakly connected quasi-periodic oscillators, FM interactions, and multiplexing in the brain, SIAM J. Applied Mathematics 59: 2193-2223.

Jirsa V K and Haken H (1997) A derivation of a macroscopic field theory of the brain from the quasi-microscopic neural dynamics. Physica D 99: 503-526.

Jirsa V K and Kelso J A S (2000) Spatiotemporal pattern formation in continuous systems with heterogeneous connection topologies. Physical Review E 62: 8462-8465.

Katznelson R D (1981) Normal modes of the brain: Neuroanatomical basis and a physiological theoretical model. In PL Nunez (Au), Electric Fields of the Brain: The Neurophysics of EEG, 1st Edition, NY: Oxford U. Press, pp 401-442.

Klimesch W (1996) Memory processes, brain oscillations and EEG synchronization. International J. Psychophysiology 24: 61-100.

Law S K, Nunez P L and Wijesinghe R S (1993) High resolution EEG using spline generated surface Laplacians on spherical and ellipsoidal surfaces. IEEE Transactions on Biomedical Engineering 40:145-153.

Liley D T J, Cadusch P J and Dafilis M P (2002) A spatially continuous mean field theory of electrocortical activity network. Computation in Neural Systems 13: 67-113.

Malmuvino J and Plonsey R (1995) Bioelectromagetism. NY: Oxford U. Press.

Niedermeyer E and Lopes da Silva F H (Eds) (2005) Electroencephalography. Basic Principals, Clin. Applications, and Related Fields. 5th Edition. London: Williams and Wilkins.

Nunez P L (1989) Generation of human EEG by a combination of long and short range neocortical interactions. Brain Topography 1: 199-215.

Nunez P L (1995) Neocortical Dynamics and Human EEG Rhythms. NY: Oxford U. Press.

Nunez P L (2000) Toward a large-scale quantitative description of neocortical dynamic function and EEG (Target article), Behavioral and Brain Sciences 23: 371-398.

Nunez P L (2000) Neocortical dynamic theory should be as simple as possible, but not simpler (Response to 18 commentaries on target article), Behavioral and Brain Sciences 23: 415-437.

Nunez P L (2002) EEG. In VS Ramachandran (Ed) Encyclopedia of the Human Brain, La Jolla: Academic Press, 169-179.

Nunez P L and Silberstein R B (2001) On the relationship of synaptic activity to macroscopic measurements: Does co-registration of EEG with fMRI make sense? Brain Topog. 13:79-96.

Nunez P L and Srinivasan R (2006) Electric Fields of the Brain: The Neurophysics of EEG, 2nd Edition, NY: Oxford U. Press.

Nunez P L and Srinivasan R (2006) A theoretical basis for standing and traveling brain waves measured with human EEG with implications for an integrated consciousness. Clin. Neurophysiology 117: 2424-2435.

Nunez P L, Srinivasan R, Westdorp A F, Wijesinghe R S, Tucker D M, Silberstein R B, and Cadusch P (1997) EEG coherency I: Statistics, reference electrode, volume conduction, Laplacians, cortical imaging, and interpretation at multiple scales. Electroencephalography and Clin. Neurophysiology 103: 516-527.

Nunez P L. Wingeier B M and Silberstein R B (2001) Spatial-temporal structures of human alpha rhythms: theory, micro-current sources, multiscale measurements, and global binding of local networks, Human Brain Mapping 13:125-164.

Nuwer M (1997) Assessment of digital EEG, quantitative EEG and EEG brain mapping: report of the American Academy of Neurology and the American Clin. Neurophysiology Society. Neurology 49: 277-292

Penfield W and Jasper H D (1954) Epilepsy and the Functional Anatomy of the Human Brain. London: Little, Brown and Co.

Robinson P A, Rennie C J Rowe D L and O'Conner S C (2004) Estimation of multiscale neurophysiologic parameters by electroencephalographic means. Human Brain Mapping 23: 53-72

Scott A C (1995) Stairway to the Mind. New York: Springer-Verlag.

Silberstein R B, Danieli F and Nunez P L (2003) Frontoparietal evoked potential synchronization is increased during mental rotation, NeuroReport 14: 67-71.

Silberstein R B, Song J, Nunez P L and Park W (2004) Dynamic sculpting of brain functional connectivity is correlated with performance, Brain Topography 16: 240-254.

Srinivasan R and Petrovic S (2006) MEG phase follows conscious perception during binocular rivalry induced by visual stream segregation. Cerebral Cortex, 16: 597-608.

Srinivasan R, Nunez P L and Silberstein R B (1998) Spatial filtering and neocortical dynamics: estimates of EEG coherence. IEEE Trans. on Biomedical Engineering, 45: 814-825.

Srinivasan R, Russell D P, Edelman G M, and Tononi G (1999) Frequency tagging competing stimuli in binocular rivalry reveals increased synchronization of neuromagnetic responses during conscious perception. J. Neuroscience 19: 5435-5448.

Uhl C (Ed) (1999) Analysis of Neurophysiological Brain Functioning. Berlin: Springer-Verlag, Wingeier B M, Nunez P L and Silberstein R B (2001) Spherical harmonic decomposition applied to spatial-temporal analysis of human high-density electroencephalogram. Physical Review E 64: 051916-1 to 9.

en.wikipedia.org/wiki/Electroencephalography

REFERENCE LIST 2

U.S. Pat. Nos. 5,293,187; 5,422,689; 5,447,166; 5,491,492; 5,546,943; 5,622,168; 5,649,061; 5,720,619; 5,740,812; 5,983,129; 6,050,962; 6,092,058; 6,149,586; 6,325,475; 6,377,833; 6,394,963; 6,428,490; 6,482,165; 6,503,085; 6,520,921; 6,522,906; 6,527,730; 6,556,695; 6,565,518; 6,652,458; 6,652,470; 6,701,173; 6,726,624; 6,743,182; 6,746,409; 6,758,813; 6,843,774; 6,896,655; 6,996,261; 7,037,260; 7,070,571; 7,107,090; 7,120,486; 7,212,851; 7,215,994; 7,260,430; 7,269,455; 7,280,870; 7,392,079; 7,407,485; 7,463,142; 7,478,108; 7,488,294; 7,515,054; 7,587,693; 7,647,097; 7,740,592; 7,751,877; 7,831,305; 7,856,264; 7,881,780; 7,970,734; 7,972,278; 7,974,787; 7,991,461; 8,012,107; 8,032,486; 8,033,996; 8,060,194; 8,095,209; 8,209,224; 8,239,030; 8,262,714; 8,320,649; 8,358,818; 8,376,965; 8,380,316; 8,386,312; 8,386,313; 8,392,250; 8,392,253; 8,392,254; 8,392,255; 8,437,844; 8,464,288; 8,475,371; 8,483,816; 8,494,905; 8,517,912; 8,533,042; 8,545,420; 8,580,041; 8,655,428; 8,672,852; 8,682,687; 8,684,742; 8,694,157; 8,706,241; 8,706,518; 8,738,395; 8,753,296; 8,762,202; 8,764,673; 8,768,022; 8,788,030; 8,790,255; 8,790,297; 8,821,376; 8,838,247; 8,864,310; 8,872,640; 8,888,723; 8,915,871; 8,938,289; 8,938,301; 8,942,813; 8,955,010; 8,955,974; 8,958,882; 8,964,298; 8,971,936; 8,989,835; 8,992,230; 8,998,828; 9,004,687; 9,080,671; 9,101,279; 9,135,221; 9,142,145; 9,165,472; 9,173,582; 9,179,855; 9,208,558; 9,215,978; 9,232,984; 9,241,665; 9,242,067; 9,254,099; 9,271,660; 9,275,191; 9,282,927; 9,292,858; 9,292,920; 9,320,450; 9,326,705; 9,330,206; 9,357,941; 9,396,669; 9,398,873; 9,414,780; 9,414,907; 9,424,781; 9,445,739; 9,445,763; 9,451,303; 9,451,899; 9,454,646; 9,482,977; 9,468,541; 9,483,117; 9,492,120; 9,504,420; 9,504,788; 9,526,419;

9,541,383; 9,545,221; 9,545,222; 9,545,225; 9,560,967; 9,560,984; 9,583,740; 9,582,072; 9,596,224; 9,615,746; 9,622,702; 9,622,703; 9,626,756; 9,629,568; 9,642,699; 9,649,030; 9,651,388; 9,655,573; 9,668,694; 9,672,302; 9,672,617; 9,682,232; 9,693,734; 9,694,155; 9,704,205; 9,706,910; 9,710,788; RE44408; RE45766; 20020024450; 20020103428; 20020103429; 20020112732; 20020128540; 20030028081; 20030028121; 20030070685; 20030083596; 20030100844; 20030120172; 20030149351; 20030158496; 20030158497; 20030171658; 20040019257; 20040024287; 20040068172; 20040092809; 20040101146; 20040116784; 20040143170; 20040267152; 20050010091; 20050019734; 20050025704; 20050038354; 20050113713; 20050124851; 20050148828; 20050228785; 20050240253; 20050245796; 20050267343; 20050267344; 20050283053; 20060020184; 200060061544; 20060078183; 20060087746; 20060102171; 20060129277; 20060161218; 20060189866; 20060200013; 20060041718; 20060052978; 200060252979; 20070050715; 20070179534; 20070191704; 20070238934; 20070273611; 20070282228; 20070299371; 20080004550; 20080009772; 20080058668; 20080081963; 20080119763; 20080123927; 20080132383; 20080228239; 20080234113; 20080234601; 20080242521; 20080255949; 20090018419; 20090058660; 20090062698; 20090076406; 20090099474; 20090112523; 20090221928; 20090267758; 20090270687; 20090270688; 20090270692; 20090270693; 20090270694; 20090270786; 20090281400; 20090287108; 20090297000; 20090299169; 20090311655; 20090312808; 20090312817; 20090318794; 20090326604; 20100004977; 20100010289; 20100010366; 20100041949; 20100069739; 20100069780; 20100163027; 20100163028; 20100163035; 20100165593; 20100188525; 20100168529; 201001680602; 20100268055; 20100293115; 20110004412; 20110009777; 20110015515; 20110015539; 20110043759; 20110054272; 20110077548; 20110092882; 20110105859; 20110130643; 20110172500; 20110218456; 20110256520; 20110270074; 20110301488; 20110307079; 20120004579; 20120021394; 20120036004; 20120071771; 20120108909; 20120108995; 20120136274; 20120150545; 20120203130; 20120262558; 20120271377; 20120310106; 20130012804; 20130046715; 20130063434; 20130063550; 20130080127; 20130120246; 20130127980; 20130185144; 20130189663; 20130204085; 20130211238; 20130226464; 20130242262; 20130245424; 20130281759; 20130289360; 20130293844; 20130308099; 20130318546; 20140058528; 20140155714; 20140171757; 20140200432; 20140214335; 20140221866; 20140243608; 20140243614; 20140243652; 20140276130; 20140276944; 20140288614; 20140296750; 20140300532; 20140303508; 20140304773; 20140313303; 20140315169; 20140316191; 20140316192; 20140316235; 20140316248; 20140323899; 20140335489; 20140343408; 20140347491; 20140350353; 20140350431; 20140364721; 20140378810; 20150002815; 20150003698; 20150003699; 20150005640; 20150005644; 20150006186; 20150012111; 20150038869; 20150045606; 20150051663; 20150099946; 20150112409; 20150120007; 20150124220; 20150126845; 20150126873; 20150133812; 20150141773; 20150145676; 20150154889; 20150174362; 20150196800; 20150213191; 20150223731; 20150234477; 20150235088; 20150235370; 20150235441; 20150235447; 20150241705; 20150241959; 20150242575; 20150242943; 20150243100; 20150243105; 20150243106; 20150247723; 20150247975; 20150247976; 20150248169; 20150248170; 20150248787; 20150248788; 20150248789; 20150248791; 20150248792; 20150248793; 20150290453; 20150290454; 20150305685; 201503040; 20150309563; 20150313496; 20150313539; 20150324692; 20150325151; 20150335288; 20150339363; 20150351690; 20150366497; 20150366504; 20150366656; 20150366659; 20150369864; 20150370320; 20160000354; 20160004298; 20160005320; 20160007915; 20160008620; 20160012749; 20160015289; 20160022167; 20160022206; 20160029946; 20160029965; 201600038069; 20160051187; 20160051793; 20160066838; 20160073886; 20160077547; 20160078780; 20160106950; 20160112684; 2016120436; 20160143582; 20160166219; 20160167672; 20160176053; 20160180054; 20160198950; 20160199577; 20160202755; 20160216760; 20160220439; 2016028640; 20160232625; 20160232811; 20160235323; 20160239084; 20160248994; 20160249826; 20160256108; 20160267809; 20160270656; 20160287157; 20160302711; 20160306942; 20160313798; 20160317060; 20160317383; 20160324478; 20160324580; 20160334866; 20160338644; 20160338825; 20160339300; 20163045901; 20160357256; 201606360970; 20168363483; 20170000324; 20170000325; 20170000326; 20170000329; 20170000330; 20170000331; 20170000332; 20170000333; 20170000334; 20170000335; 20170000337; 20170000340; 20170000341; 20170000342; 20170000343; 20170000345; 20170000454; 2017000683; 20170001032; 20170006931; 20170007111; 20170007115; 20170007116; 20170007122; 20170007123; 20170007165; 20170007182; 20170007450; 20170007799; 20170007843; 20170010469; 20170010470; 20170017083; 20170020447; 20170020454; 20170020627; 20170027467; 20170027651; 20170027812; 20170031440; 20170032098; 20170035344; 20170043160; 20170055900; 2017006098; 20170061034; 20170071523; 20170071537; 20170071546; 20170071551; 20170080320; 20170086729; 20170095157; 20170099479; 20170100540; 20170103440; 20170112427; 20170112671; 20170113046; 20170113056; 20170119994; 20170135597; 20170135633; 20170136264; 20170136265; 20170143249; 20170143442; 20170148340; 20170156662; 20170162072; 20170184876; 20170164878; 20170168568; 20170173262; 20170173326; 20170177023; 20170188947; 20170202633; 20170209043; 20170209094; and 20170209737.

REFERENCE LIST 3 en.wikipedia.org/wiki/Brainwave_entrainment;
U.S. Pat. and Pub. App. Nos. 5,070,399; 5,306,228; 5,409,445; 6,656,137; 7,749,155; 7,819,794; 7,988,613; 8,088,057; 8,167,784; 8,213,8670; 8,267,851; 8,298,078; 8,517,909; 8,517,912; 8,579,793; 8,579,795; 8,597,171; 8,636,640; 8,638,950; 8,668,496; 8,852,073; 8,932,218; 8,968,176; 9,330,523; 9,357,941; 9,459,597; 9,480,812; 9,563,273; 9,609,453; 9,640,187; 9,707,372; 20050153268; 20050182287; 20080106434; 20080206174; 20060281543; 20070066403; 20080039677; 20080304691; 20100010289; 20100010844; 20100028841; 20100056854; 20100076253; 20100130812; 20100222640; 20100286747; 20100298624; 20110298706; 20110319482; 20120003615; 20120053394; 20120150545; 20130030241; 20130072292; 20130131537; 20130172663; 20130184516; 20130203019; 20130234823; 20130338738; 20140088341; 20140107401; 20140114242; 20140154647; 20140174277; 20140275741; 20140309484; 20140371516; 20150142082; 20150283019; 20150296288; 20150313496; 20150313949; 2016008568; 20160019434; 20160055842; 20160205489; 20160235980; 20160239084; 20160345901; 20170034638; 20170061760; 20170087330; 20170094385; 20170095157; 20170099713; 20170135597; and 20170149945.

Buck R (1999) The biological affects: A typology. Psychological Review 106: 301-336; Izard C E (2007) Basic Emotions, Natural Kinds, Emotion Schemes, and a New Paradigm. Perspect Psychol Sci 2: 260-280;

Canolty R T, Edwards E, Dalai S S, et al. High gamma power is phase-locked to theta oscillations in human neocortex. Science. 2006; 313:1626-1628.

Carter, J., and H. Russell. "A pilot investigation of auditory and visual entrainment of brain wave activity in learning disabled boys." Texas Researcher 4.1 (1993): 65-75;

Casciaro, Francesco, et al. "Alpha-rhythm stimulation using brain entrainment enhances heart rate variability in subjects with reduced HRV." World J. Neuroscience 3.04 (2013): 213;

Helfrich, Randolph F., et al. "Entrainment of brain oscillations by transcranial alternating current stimulation." Current Biology 24.3 (2014): 333-339;

Hoogenboom N, Schoffelen J M, Oostenveld R, Parkes L M, Fries P. Localizing human visual gamma-band activity in frequency, time and space. Neuroimage. 2006; 29:784-773;

Huang, Tina L., and Christine Charyton. "A comprehensive review of the psychological effects of brainwave entrainment." Alternative therapies in health and medicine 14.5 (2008): 38;

James W (1884.) What is an emotion? Mind 9:188-205; Lacey J I, Bateman D E, Vanlehn R (1953) Autonomic response specificity; an experimental study. Psychosom Med 15: 8-21;

Joyce, Michael, and Dave Siever. "Audio-visual entrainment program as a treatment for behavior disorders in a school setting." J. Neurotherapy 4.2 (2000): 9-25;

Keitel, Christian, Cliodhne Duigley, and Philipp Ruhnau. "Stimulus-driven brain oscillations in the alpha range: entrainment of intrinsic rhythms or frequency-following response?" J. Neuroscience 34.31 (2014): 10137-10140;

Lachaux J P, Rodriguez E, Martinerie J, Varela F J. Measuring phase synchrony in brain signals. Hum Brain Mapp. 1999; 8:194-208, Lakatos, Peter, et al. "Entrainment of neuronal oscillations as a mechanism of attentional selection." Science 320.5872 (2008): 110-113;

Le Van Duyen M, Foucher J, Lachaux J, et al. Comparison of Hilbert transform and wavelet methods for the analysis of neuronal synchrony. J Neurosci Methods. 2001; 111: 83-98, Levenson R W, Heider K, Ekman P, Friesen W V (1992) Emotion and Autonomic Nervous-System Activity in the Minangkabau of West Sumatra. J Pers Soc Psychol 62: 972-988.

Mori, Toshio, and Shuichi Kai. "Noise-induced entrainment and stochastic resonance in human brainwaves." Physical review letters 88.21 (2002): 218101;

Padmanabhan, R., A. J. Hildreth, and D. Laws. "A prospective, randomised, controlled study examining binaural beat audio and pre-operative anxiety in patients undergoing general anaesthesia for day case surgery." Anaesthesia 60.9 (2005): 874-877;

Panksepp J (2007) Neurologizing the Psychology of Affects How Appraisal-Based Constructivism and Basic Emotion Theory Can Coexist. Perspect Psychol Sci 2: 281-296.

REFERENCE LIST 4

Rodriguez E, George N, Lachaux J P, Martinerie J, Renault B, Varela F J. Perception's shadow: long-distance synchronization of human brain activity. Nature. 1999; 397: 430-433, Schalles, Matt D., and Jaime A. Pineda. "Musical sequence learning and EEG correlates of audiomotor processing." Behavioural neurology 2015 (2015). www.hindawi.com/journals/bn/2015/638202/

Some studies have indicated that the physiological correlates of emotions are likely to be found in the central nervous system (CNS). See, for example:

Spencer K M, Nestor P R Perlmutter R, et al. Neural synchrony indexes disordered perception and cognition in schizophrenia. Proc Natl Acad Sci USA. 2004; 101: 17288-17293;

Thaut, Michael H., David A. Peterson, and Gerald C. McIntosh. "Temporal entrainment of cognitive functions." Annals of the New York Academy of Sciences 1060.1 (2005): 243-254.

Thut, Gregor, Philippe G. Schyns, and Joachim Gross. "Entrainment of perceptually relevant brain oscillations by non-invasive rhythmic stimulation of the human brain." Frontiers in Psychology 2 (2011);

Trost, W., Frühholz, S., Schön, D., Labbé, C., Pichon, S., Grandjean, D., & Vuilleumier, P. (2014). Getting the beat: entrainment of brain activity by musical rhythm and pleasantness. NeuroImage, 103, 55-64;

Will, Udo, and Eric Berg. "Brain wave synchronization and entrainment to periodic acoustic stimuli." Neuroscience letters 424.1 (2007): 55-60;

Zhuang, Tianbao, Hong Zhao, and Zheng Tang. "A study of brainwave entrainment based on EEG brain dynamics." Computer and information science 2.2 (2009): 80.

REFERENCE LIST 5

Abeln, Vera, et al. "Brainwave entrainment for better sleep and post-sleep state of young elite soccer players-A pilot study." European J. Sport science 14.5 (2014): 393-402;

Acton, George. "Methods for independent entrainment of visual field zones." U.S. Pat. No. 9,629,976. 25 Apr. 2017;

Albouy, Philippe, et al. "Selective entrainment of theta oscillations in the dorsal stream causally enhances auditory working memory performance." Neuron 94.1 (2017): 193-206.

Amengual, J., et al. "PO18 Local entrainment and distribution across cerebral networks of natural oscillations elicited in implanted epilepsy patients by intracranial stimulation: Paving the way to develop causal connectomics of the healthy human brain." Clin. Neurophysiology 128.3 (2017): e18;

Argento, Emanuele, et al. "Augmented Cognition via Brainwave Entrainment in Virtual Reality: An Open, Integrated Brain Augmentation in a Neuroscience System Approach." Augmented Human Research 2.1 (2017): 3;

Bello, Nicholas P. "Altering Cognitive and Brain States Through Cortical Entrainment." (2014); Costa-Faidella, Jordi, Elyse S. Sussman, and Carles Escera. "Selective entrainment of brain oscillations drives auditory perceptual organization." NeuroImage (2017);

Börgers, Christoph. "Entrainment by Excitatory Input Pulses." An Introduction to Modeling Neuronal Dynamics. Springer International Publishing, 2017. 183-192;

Calderone, Daniel J., et al. "Entrainment of neural oscillations as a modifiable substrate of attention." Trends in cognitive sciences 18.6 (2014): 300-309;

Chang, Daniel Wonchul. "Method and system for brain entertainment." U.S. Pat. No. 8,636,640. 28 Jan. 2014;

Colzato, Lorenza S., Amengual, Julià L., et al. "Local entrainment of oscillatory activity induced by direct brain stimulation in humans." Scientific Reports 7 (2017);

Conte, Elio, et al. "A Fast Fourier Transform analysis of time series data of heart rate variability during alfa-rhythm stimulation in brain entrainment." NeuroQuantology 11.3 (2013);

Dikker, Suzanne, et al. "Brain-to-brain synchrony tracks real-world dynamic group interactions in the classroom." Current Biology 27.9 (2017): 1375-1380;

Ding, Nai, and Jonathan Z. Simon. "Cortical entrainment to continuous speech: functional roles and interpretations." Frontiers in human neuroscience 8 (2014);

Doherty, Cormac. "A comparison of alpha brainwave entrainment, with and without musical accompaniment." (2014);

Falk, Simone, Cosima Lanzilotti, and Daniele Schön. "Tuning neural phase entrainment to speech." J. Cognitive Neuroscience (2017);

Gao, Junling, et al. "Entrainment of chaotic activities in brain and heart during MBSR mindfulness training." Neuroscience letters 616 (2016): 218-223;

Gooding-Williams, Gerard, Hongfang Wang, and Klaus Kessler. "THETA-Rhythm Makes the World Go Round: Dissociative Effects of TMS Theta Versus Alpha Entrainment of Right pTPJ on Embodied Perspective Transformations." Brain Topography (2017): 1-4;

Hanslmayr, Simon, Jonas Matuschek, and Marie-Christin Fellner. "Entrainment of prefrontal beta oscillations induces an endogenous echo and impairs memory formation." Current Biology 24.8 (2014): 904-909;

Heideman, Simone G., Erik S. te Woerd, and Peter Praamstra. "Rhythmic entrainment of slow brain activity preceding leg movements." Clin. Neurophysiology 126.2 (2015): 348-355;

Henry, Molly J., et al. "Aging affects the balance of neural entrainment and top-down neural modulation in the listening brain." Nature Communications 8 (2017): ncomms15801;

Horr, Ninja K., Maria Wimber, and Massimiliano Di Luca. "Perceived time and temporal structure: Neural entrainment to isochronous stimulation increases duration estimates." Neuroimage 132 (2016): 148-156;

Irwin, Rosie. "Entraining Brain Oscillations to Influence Facial Perception." (2015);

Kalyan, Ritu, and Bipan Kaushal. "Binaural Entrainment and Its Effects on Memory." (2016);

Keitel, Anne, et al. "Auditory cortical delta-entrainment interacts with oscillatory power in multiple fronto-parietal networks." Neuroimage 147 (2017): 32-42

Koelsch, Stefan. "Music-evoked emotions: principles, brain correlates, and implications for therapy." Annals of the New York Academy of Sciences 1337.1 (2015): 193-201;

Kösem, Anne, et al. "Neural entrainment reflects temporal predictions guiding speech comprehension." the Eighth Annual Meeting of the Society for the Neurobiology of Language (SNL 2016). 2016;

Lee, Daniel Keewoong, Dongyeup Daniel Synn, and Daniel Chesong Lee. "Intelligent earplug system." U.S. patent application Ser. No. 15/106,989;

Lefournour, Joseph, Ramaswamy Palaniappan, and Ian V. McLoughlin. "Inter-hemispheric and spectral power analyses of binaural beat effects on the brain." Matters 2.9 (2016): e201607000001;

Mai, Guangting, James W. Minett, and William S-Y. Wang. "Delta, theta, beta, and gamma brain oscillations index levels of auditory sentence processing." Neuroimage 133 (2016):516-528;

Marconi, Pier Luigi, et al. "The phase amplitude coupling to assess brain network system integration." Medical Measurements and Applications (MeMeA), 2016 IEEE International Symposium on. IEEE, 2016;

McLaren, Elgin-Skye, and Alissa N. Antle. "Exploring and Evaluating Sound for Helping Children Self-Regulate with a Brain-Computer Application." Proceedings of the 2017 Conference on Interaction Design and Children. ACM, 2017;

Moisa, Marius, et al. "Brain network mechanisms underlying motor enhancement by transcranial entrainment of gamma oscillations." J. Neuroscience 38.47 (2016): 12053-12065;

Molinaro, Nicola, et al. "Out-of-synchrony speech entrainment in developmental dyslexia." Human brain mapping 37.8 (2016): 2767-2783;

Moseley, Ralph. "Immersive brain entrainment in virtual worlds: actualizing meditative states." Emerging Trends and Advanced Technologies for Computational Intelligence. Springer International Publishing, 2016. 315-346;

Neuling, Toralf, et al. "Friends, not foes: magnetoencephalography as a tool to uncover brain dynamics during transcranial alternating current stimulation." Neuroimage 118 (2015): 406-413;

Notbohm, Annika, Jurgen Kurths, and Christoph S. Herrmann. "Modification of brain oscillations via rhythmic light stimulation provides evidence for entrainment but not for superposition of event-related responses." Frontiers in human neuroscience 10 (2016);

Nozaradan, S., et al. "P943: Neural entrainment to musical rhythms in the human auditory cortex, as revealed by intracerebral recordings." Clin. Neurophysiology 125 (2014): S299;

Palaniappan, Ramaswamy, et al. "Improving the feature stability and classification performance of bimodal brain and heart biometrics." Advances in Signal Processing and Intelligent Recognition Systems. Springer, Cham, 2016. 175-186;

Palaniappan, Ramaswamy, Somnuk Phon-Amnuaisuk, and Chikkannan Eswaran. "On the binaural brain entrainment indicating lower heart rate variability." Int. J. Cardiol 190 (2015): 262-263;

Papagiannakis, G., et al. A virtual reality brainwave entrainment method for human augmentation applications. Technical Report, FORTH-ICS/TR-458, 2015;

Park, Hyojin, et al. "Frontal top-down signals increase coupling of auditory low-frequency oscillations to continuous speech in human listeners." Current Biology 25.12 (2015): 1649-1653;

Pérez, Alejandro, Manuel Carreiras, and Jon Andoni Duñabeitia. "Brain-to-brain entrainment: EEG interbrain synchronization while speaking and listening." Scientific Reports 7 (2017);

Riecke, Lars, Alexander T. Sack, and Charles E. Schroeder. "Endogenous delta/theta sound-brain phase entrainment accelerates the buildup of auditory streaming." Current Biology 25.24 (2015): 3196-3201;

Spaak, Eelke, Floris P. de Lange, and Ole Jensen. "Local entrainment of alpha oscillations by visual stimuli causes cyclic modulation of perception." J. Neuroscience 34.10 (2014):3536-3544;

Thaut, Michael H. "The discovery of human auditory-motor entrainment and its role in the development of neurologic music therapy." Progress in brain research 217 (2015): 253-266;

Thaut, Michael H., Gerald C. McIntosh, and Volker Hoemberg. "Neurobiological foundations of neurologic music therapy: rhythmic entrainment and the motor system." Frontiers in psychology 5 (2014);

Thut, G. "T030 Guiding TMS by EEG/MEG to interact with oscillatory brain activity and associated functions." Clin. Neurophysiology 128.3 (2017): e9;

Treviño, Guadalupe Villarreal, et al. "The Effect of Audio Visual Entrainment on Pre-Attentive Dysfunctional Processing to Stressful Events in Anxious Individuals." Open J. Medical Psychology 3.05 (2014): 364;

Tsai, Shu-Hui, and Yue-Der Lin. "Autonomie feedback with brain entrainment." Awareness Science and Technology and Ubi-Media Computing (iCAST-UMEDIA), 2013 International Joint Conference on. IEEE, 2013;

Vossen, Alexandra, Joachim Gross, and Gregor Thut. "Alpha power increase after transcranial alternating current stimulation at alpha frequency (α-tACS) reflects plastic changes rather than entrainment." Brain Stimulation 8.3 (2015): 499-508;

Witkowski, Matthias, et al. "Mapping entrained brain oscillations during transcranial alternating current stimulation (tACS)." Neuroimage 140 (2016): 89-98;

Zlotnik, Anatoly, Raphael Nagao, and István Z. Kiss Jr-Shin Li. "Phase-selective entrainment of nonlinear oscillator ensembles." Nature Communications 7 (2016).

REFERENCE LIST 6 en.wikipedia.org/wiki/Beat_(acoustics)#Binaural_beats.

Atwater, F. H. (2001). Binaural beats and the regulation of arousal levels. Proceedings of the TANS, 11;

Brain Entrainment Frequency Following Response (or FFR). See, "Stimulating the Brain with Light and Sound," Transparent Corporation, Neuroprogrammer™ 3, www.transparentcorp.com/products/np/entrainment.php.

Colzato, L. S., Barone, H., Sellaro, R., & Hammel, B. (2017). More attentional focusing through binaural beats: evidence from the global-local task. Psychological research, 81(1), 271-277;

Conte, E., Conte, S., Santacroce, N., Federici, A., Todarello, O., Orsucci, F, . . . & Laterza, V. (2013). A Fast Fourier Transform analysis of time series data of heart rate variability during alfa-rhythm stimulation in brain entrainment. NeuroQuantology, 11(3);

Doherty, C. (2014). A comparison of alpha brainwave entrainment, with and without musical accompaniment;

Foster, D. S. (1990). EEG and subjective correlates of alpha frequency binaural beats stimulation combined with alpha biofeedback (Doctoral dissertation, Memphis State University);

Gao, X., Cm, H., Ming, D., Eli, H., Wang, X., Wang, X., & Zhou, P. (2014). Analysis of EEG activity in response to binaural beats with different frequencies. International Journal of Psychophysiology, 94(3), 399-406;

Hink, R. F., Kodera, K., Yamada, O., Kaga, K., & Suzuki, J. (1980). Binaural interaction of a beating frequency-following response. Audiology, 19(1), 36-43;

Huang, T. L., 9 Charyton, C. (2008). A comprehensive review of the psychological effects of brainwave entrainment. Alternative therapies in health and medicine, 14(5), 38;

Kasprzak, C. (2011). Influence of binaural beats on EEG signal. Acta Physica Polonica A, 119(6A), 986-990;

Lane, J. D., Kasian, S. J., Owens, J. E., & Marsh, G. R. (1998). Binaural auditory beats affect vigilance performance and mood. Physiology & behavior, 63(2), 249-252;

Mortazavi, S. M. J., Zahraei-Moghadam, S. M., Masoumi, S., Rafati, A., Haghani, M., Mortazavi, S. A. R., & Zehtabian, M. (2017). Short Term Exposure to Binaural Beats Adversely Affects Learning and Memory in Rats. Journal of Biomedical Physics and Engineering.

Moseley, R. (2015, July). Inducing targeted brain states utilizing merged reality systems. In Science and Information Conference (SAI), 2015 (pp. 657-663). IEEE.

Oster, G (October 1973). "Auditory beats in the brain". Scientific American. 229 (4): 94-102. See:

Oster, G. (1973). Auditory beats in the brain. Scientific American, 229(4), 94-102;

Padmanabhan, R., Hildreth, A. J., B Laws, D. (2005).A prospective, randomised, controlled study examining binaural beat audio and pre-operative anxiety in patients undergoing general anaesthesia for day case surgery. Anaesthesia, 60(9), 874-877;

Pratt, H., Starr, A., Michalewski, H. J., Dimitrijevic, A., Bleich, N., & Mittelman, N. (2009). Cortical evoked potentials to an auditory illusion: binaural beats. Clinical Neurophysiology, 120(8), 1514-1524;

Pratt, H., Starr, A., Michalewski, H. J., Dimitrijevic, A., Bleich, N., & Mittelman, N. (2010). A comparison of auditory evoked potentials to acoustic beats and to binaural beats. Hearing research, 262(1), 34-44;

Reedijk, S. A., Bolders, A., 9 Hammel, B. (2013). The impact of binaural beats on creativity. Frontiers in human neuroscience, 7;

REFERENCE LIST 7

Schulze, H. H. (1989). The perception of temporal deviations in isochronic patterns. Attention, Perception, & Psychophysics, 45(4), 291-296;

Sung, H. C., Lee, W. L., Li, H. M., Lin, C. Y., Wu, Y. Z., Wang, J. J., & Li, T. L. (2017). Familiar Music Listening with Binaural Beats for Older People with Depressive Symptoms in Retirement Homes. Neuropsychiatry, 7(4); www.livingflow.net/isochronic-tones-work/;

REFERENCE LIST 8

U.S. Pat. and Pub. App. Nos. 6,196,972; 6,338,713; 6,442,421; 6,507,754; 6,524,249; 6,547,738; 6,616,611; 6,816,744; 6,865,494; 6,915,241; 6,936,012; 6,996,261; 7,043,293; 7,054,454; 7,079,977; 7,128,713; 7,146,211; 7,149,572; 7,194,941; 7,209,788; 7,254,439; 7,280,867; 7,282,030; 7,321,837; 7,330,032; 7,333,619; 7,381,185; 7,537,568; 7,559,903; 7,565,193; 7,567,693; 7,604,603; 7,624,293; 7,640,055; 7,715,919; 7,725,174; 7,729,755; 7,751,878; 7,778,693; 7,794,406; 7,797,040; 7,801,592; 7,803,118; 7,803,119; 7,879,043; 7,896,807; 7,899,524; 7,917,206; 7,933,646; 7,937,138; 7,979,695; 8,014,847; 8,033,996; 8,073,534; 8,095,210; 8,137,269; 8,137,270; 8,175,696; 8,177,724; 8,177,726; 8,180,601; 8,187,181; 8,197,437; 8,233,965; 8,236,005; 8,244,341; 8,248,069; 8,249,698; 8,280,514; 8,295,914; 8,326,433; 8,335,664; 8,346,342; 8,355,768; 8,386,312; 8,386,313; 8,392,250; 8,392,253; 8,392,254; 8,392,255; 8,396,542; 8,406,841; 8,409,862 8,412,655; 8,428,703; 8,428,704; 8,463,374; 8,464,288; 8,475,387; 8,483,815; 8,494,610; 8,494,829; 8,494,905; 8,498,699; 8,509,881; 8,533,042; 8,548,786; 8,571,629; 8,579,786; 8,591,419; 8,606,360; 8,628,480; 8,655,428; 8,666,478; 8,682,422; 8,706,183; 8,706,205; 8,718,747; 8,725,238; 8,738,136; 8,747,382; 8,755,877; 8,761,869; 8,762,202; 8,768,449; 8,781,796; 8,790,255; 8,790,272; 8,821,408; 8,825,149; 8,831,731; 8,843,210; 8,849,392; 8,849,632; 8,855,773; 8,858,440; 8,862,210; 8,862,581; 8,903,479; 8,918,178; 8,934,965; 8,951,190; 8,954,139; 8,955,010; 8,958,868; 8,983,628; 8,983,629; 8,989,835; 9,020,789; 9,026,217; 9,031,644; 9,050,470; 9,060,671; 9,070,492; 9,072,832; 9,072,905; 9,078,584; 9,084,896; 9,095,295; 9,101,276; 9,107,595; 9,116,835; 9,125,574; 9,149,719; 9,155,487; 9,192,309; 9,198,621; 9,204,835; 9,211,417; 9,215,978; 9,232,910; 9,232,984; 9,238,142; 9,242,067; 9,247,911; 9,248,286; 9,254,383; 9,277,871; 9,277,873; 9,282,934; 9,289,603; 9,302,110; 9,307,944; 9,308,372; 9,320,450; 9,336,535; 9,357,941; 9,375,151; 9,375,171; 9,375,571; 9,403,038; 9,415,219; 9,427,581; 9,443,141; 9,451,886; 9,454,646; 9,462,956; 9,462,975; 9,468,541; 9,471,978; 9,480,402; 9,492,084; 9,504,410; 9,522,278; 9,533,113; 9,545,285; 9,560,984; 9,583,740; 9,615,749; 9,616,166; 9,622,672; 9,622,676; 9,622,702; 9,622,703; 9,623,240; 9,636,019; 9,649,036; 9,659,229; 9,668,694; 9,681,814; 9,681,820; 9,682,232; 9,713,428; 20020035338; 20020091319; 20020095099; 20020103428; 20020103429; 20020193670; 20030032889; 20030046018; 20030093129; 20030160622; 20030185408; 20030216654; 20040039268; 20040049484; 20040092809; 20040133119; 20040133120; 20040133390; 20040138536; 20040138580; 20040138711; 20040152958; 20040158119; 20050010091; 20050018858; 20050033174; 20050075568; 20050085744; 20050119547; 20050148893; 20050148894; 20050148895; 20050154290; 20050167588; 20050240087; 20050245796; 20050267343; 20050267344; 20050283053; 20050283090; 20060020184; 20060038152; 20080036153; 20060074290; 20060078183; 20060135879; 20060153396; 20060155495; 20060181384; 20060217816; 20070016095; 20070179395; 200702090669; 20070255135; 20070287896; 20080064934; 20080091118; 20080177196; 20080243014; 20080262367; 20090036791; 20090177144; 20090270758; 20090287272; 20090299169; 20090318794; 20100036211; 20100069739; 20100106041; 20100204748; 20100331976; 20110015539; 20110066042; 20110092834; 20110160543; 20110184305; 20110257519; 20110288431; 20110313268; 20120004561; 20120029378; 20120053473; 20120053479; 20120108997; 20120150545; 20120172682; 20120209139; 20120271151; 20120310105; 20130041235; 20130066395; 20130102897; 20130127708; 201301065804; 20130172772; 20130204122; 20130226261; 20130238050; 20130245485; 20130245712; 20130289364; 20130310909; 20130338803; 20140058218; 20140074180; 20140107521; 20140148716; 20140180160; 20140243647; 20140275807; 20140303454; 20140316217; 20140330334; 20140330404; 20140350864; 20080173364; 2006033390; 20070066915; 20070179734; 20070225932; 20070260151; 20080021345; 20080074307; 20080097197; 20080221401; 20080243017; 20090005667; 20090054801; 20090220425; 20090281448; 20090287273; 20090306534; 20090322331; 20100049276; 20100094152; 20100198090; 20100249638; 20110004115; 20110040713; 20110074396; 20110092839; 20110172725; 20110191350; 20110270074; 20110295143; 20110313487; 20120021394; 20120041279; 20120053476; 20120083708; 20120143038; 20120157804; 20120184826; 20120253261; 20120271376; 20120321759; 20130060125; 20130072775; 20130116520; 20130131438; 20130167360; 20130178733; 20130211238; 20130237874; 20130245416; 20130245486; 20130281490; 20130295016; 20130317380; 20140039279; 20140058528; 20140094710; 20140142654; 20140148726; 20140187901; 20140243714; 20140276130; 20140303508; 20140316248; 20140330335; 20140335489; 20150005646; 20060200013; 20060281980; 20070100278; 20070191704; 20070255122; 20070265508; 20080033508; 20080077015; 20080119716; 20080221441; 20080255949; 20090033333; 20090062676; 20090221930; 20090287271; 20090287467; 20090312646; 20100030073; 20100068751; 20100099975; 20100204604; 20100280372; 20110015515; 20110066041; 20110077538; 20110098583; 20110178441; 20110218950; 20110282230; 20110301441; 20120004518; 20120022343; 20120046535; 20120053478; 20120108918; 20120145152; 20120159656; 20120197153; 20120265267; 20120289869; 20130012804; 20130066392; 20130079621; 20130123607; 20130131461; 20130172716; 20130184597; 20130223709; 20130238049; 20130245424; 20130245711; 20130274562; 20130310422; 20130338518; 20140057232; 20140074179; 20140094720; 20140148657; 20140180153; 20140228702; 20140257128; 20140276187; 20140309614; 20140324118; 20140330336; 20140350634; 20150005660;

20150011907; 20150018665; 20150018699; 20150018702; 20150025422; 20150038869; 20150073294; 20150073306; 20150073505; 20150080671; 20150080695; 20150099962; 20150126821; 20150151142; 20150164431; 20150190070; 20150190636; 20150190637; 20150196213; 20150196249; 20150213191; 20150216439; 20150245800; 20150248470; 20150248615; 20150272652; 20150297106; 20150297893; 20150305686; 20150313498; 20150366482; 20150379370; 20160000348; 20160007899; 20160022167; 20160022168; 20160022207; 20160027423; 20160029985; 20160038042; 20160038043; 20160045128; 20160051812; 20160058304; 20160066838; 20160107309; 20160113587; 20160120428; 20160120432; 20160120437; 20160120457; 20160128596; 20160128597; 20160135754; 20160143594; 20160144175; 20160151628; 20160157742; 20160157828; 20160174863; 20160174907; 20160176053; 20160183881; 20160184029; 20160198973; 20160206380; 20160213261; 20160213317; 20160220850; 20160228028; 20160228702; 20160235324; 20160239966; 20160239968; 20160242645; 20160242665; 20160242669; 20160242690; 201060249841; 20160250355; 20160256083; 20160256105; 20160262664; 20160276853; 20160278713; 20160287117; 20160287162; 20160287169; 20160287869; 2016080303402; 20160331264; 201860331307; 20160345895; 20160345911; 20160346542; 20160361041; 20160361546; 20160367186; 20160367198; 20170031440; 20170031441; 20170039706; 20170042444; 20170045601; 20170071521; 20170079588; 20170079589; 20170091418; 20170113046; 20170120041; 20170128015; 20170135594; 20170135626; 20170136240; 20170165020; 20170172446; 20170173326; 20170188870; 20170188905; 201701889186; 20170188922 and 20170196519.

REFERENCE LIST 9

U.S. Pat. and Pub. App. Nos. 5,273,038; 5,503,149; 6,240,308; 6,272,370; 6,298,259; 6,370,414; 6,385,479; 6,490,472; 6,556,695; 6,697,660; 6,801,648; 6,907,280; 6,996,281; 7,092,748; 7,254,500; 7,338,455; 7,346,382; 7,490,085; 7,497,828; 7,539,528; 7,585,193; 7,567,693; 7,577,472; 7,597,665; 7,627,370; 7,680,526; 7,729,755; 7,809,434; 7,840,257; 7,860,548; 7,872,235; 7,899,524; 7,904,134; 7,904,139; 7,907,998; 7,983,740; 7,983,741; 8,000,773; 8,014,847; 8,069,125; 8,233,682; 8,233,965; 8,235,907; 8,248,069; 8,356,004; 8,379,952; 8,406,838; 8,423,125; 8,445,851; 8,553,956; 8,586,932; 8,606,349; 8,615,479; 8,644,910; 8,679,009; 8,696,722; 8,712,512; 8,718,747; 8,761,866; 8,781,557; 8,814,923; 8,821,376; 8,834,546; 8,852,103; 8,870,737; 8,936,630; 8,951,189; 8,951,192; 8,958,882; 8,983,155; 9,005,126; 9,020,586; 9,022,936; 9,028,412; 9,033,884; 9,042,958; 9,078,584; 9,101,279; 9,135,400; 9,144,392; 9,149,255; 9,155,521; 9,167,970; 9,179,854; 9,179,858; 9,198,637; 9,204,835; 9,208,558; 9,211,077; 9,213,076; 9,235,885; 9,242,067; 9,247,924; 9,268,014; 9,286,015; 9,271,651; 9,271,674; 9,275,191; 9,292,920; 9,307,925; 9,322,895; 9,326,742; 9,330,206; 9,368,265; 9,395,425; 9,402,558; 9,414,776; 9,438,989; 9,451,883; 9,451,899; 9,468,541; 9,471,978; 9,480,402; 9,480,425; 9,486,168; 9,592,389; 9,615,789; 9,626,756; 9,672,302; 9,672,617; 9,682,232; 20020033454; 20020035317; 20020037095; 20020042563; 20020058867; 20020103428; 20020103429; 20030018277; 20030093004; 20030128801; 20040082862; 20040092809; 20040096395; 20040116791; 20040116798; 20040122787; 20040122790; 20040166536; 20040215082; 20050007091; 20050020918; 20050033154; 20050079636; 20050119547; 20050154290; 20050222639; 20050240253; 20050283053; 20060036152; 20060036153; 20060052706; 20060058683; 20060074290; 20060078183; 20060084858; 20060149160; 20060161218; 2006041382; 2006041718; 20070191704; 20070239059; 20080001600; 20080009772; 20080033291; 20080039737; 20080042067; 20080097235; 20080097785; 20080128626; 20080154126; 20080221441; 20080228077; 20080228239; 20080230702; 20080230705; 20080249430; 20080262327; 20080275340; 20090012387; 20090018407; 20090022825; 20090024050; 20090062660; 20090078875; 20090118610; 20090156955; 20090156907; 20090157323; 20090157481; 20090157482; 20090157625; 20090157751; 20090157813; 20090183777; 20090164131; 20090164132; 20090171164; 20090172540; 20090179642; 20090209831; 20090221930; 20090246138; 20090299169; 20090304582; 20090306532; 20090306534; 20090312808; 20090312817; 20090318773; 20090318794; 20090322331; 20090326604; 20100021378; 20100036233; 20100041949; 20100042011; 20100049482; 20100069739; 20100069777; 20100082506; 20100113959; 20100249573; 20110015515; 20110015539; 20110028827; 20110077503; 20110118536; 20110125077; 20110125078; 20110129129; 20110160543; 20110161011; 20110172509; 20110172553; 20110178359; 20110190846; 20110218405; 20110224571; 20110230738; 20110257519; 20110263962; 20110263968; 20110270074; 20110288400; 20110301448; 20110306845; 20110306846; 20110313274; 20120021394; 20120022343; 20120035433; 20120053483; 20120163689; 20120165904; 20120215114; 20120219195; 20120219507; 20120245474; 20120253261; 20120253434; 20120289854; 20120310107; 20120316793; 20130012804; 20130080125; 20130063550; 20130085678; 20130096408; 20130110616; 20130116561; 20130123607; 20130131438; 20130131461; 20130178693; 20130178733; 20130184558; 20130211238; 20130221961; 20130245424; 20130274586; 20130289385; 20130289386; 20130303934; 20140058528; 20140066763; 20140119621; 20140151563; 20140155730; 20140163368; 20140171757; 20140180088; 20140180092; 20140180093; 20140180094; 20140180095; 20140180096; 20140180097; 20140180099; 20140180100; 20140180112; 20140180113; 20140180176; 20140180177; 20140184550; 20140193336; 20140200414; 20140243614; 20140257047; 20140275807; 20140303486; 20140315169; 20140316248; 20140323849; 20140335489; 20140343397; 20140343399; 20140343408;

20140364721; 20140378830; 20150011866; 20150038812; 20150051663; 20150099959; 20150112409; 20150119658; 20150119689; 20150148700; 20150150473; 20150196800; 20150200046; 20150219732; 20150223905; 20150227702; 20150247921; 20150248615; 20150253410; 20150289779; 20150290453; 20150290454; 20150313540; 20150317796; 20150324692; 20150366482; 20150375006; 20160005320; 20160027342; 20180029965; 20160051161; 20160051162; 20160055304; 20160058304; 20160058392; 20160066838; 20160103487; 20160120437; 20160120457; 20160143541; 20160157742; 20160184029; 20160196393; 20160228702; 2016031401; 2016039966; 20170039968; 20160206216; 20160267809; 20160270723; 20160302720; 20160303397; 20160317077; 20160345911; 20170027539; 20170039706; 20170045601; 20170061034; 20170085855; 20170091418; 20170112403; 20170113046; 20170120041; 201701060360; 20170164861; 20170169714; 20170172527; and 20170202475.

REFERENCE LIST 10

U.S. Pat. and Pub. App. Nos. 8,406,890; 8,509,879; 8,542,916; 8,852,103; 8,934,986; 9,022,936; 9,028,412; 9,031,653; 9,033,884; 9,037,530; 9,055,974; 9,149,255; 9,155,521; 9,198,637; 9,247,924; 9,268,014; 9,268,015; 9,367,131; 9,414,780; 9,420,970; 9,430,615; 9,442,525; 9,444,998; 9,445,763; 9,462,956; 9,474,481; 9,489,854; 9,504,420; 9,510,790; 9,519,981; 9,526,906; 9,538,948; 9,585,581; 9,622,672; 9,641,665; 9,652,626; 9,684,335; 9,687,187; 9,693,684; 9,693,724; 9,706,963; 9,712,736; 20090118622; 20100098289; 20110066041; 20110066042; 20110098583; 20110301441; 20120130204; 20120265271; 20120321759; 20130060158; 20130113816; 20130131438; 20130184786; 20140031889; 20140031903; 20140039975; 20140114889; 20140226131; 20140279341; 20140296733; 20140303424; 20140313303; 20140315169; 20140316235; 20140364721; 20140378810; 20150003698; 20150003699; 20150005640; 20150005644; 20150006186; 20150029087; 20150033245; 20150033258; 20150033259; 20150033262; 20150033266; 20150081226; 20150088093; 20150093729; 20150105701; 20150112899; 20150126845; 20150150122; 20150190062; 20150190070; 20150190077; 20150190094; 20150192776; 20150196213; 20150196800; 20150199010; 20150241916; 20150242608; 20150272496; 20150272510; 20150282705; 20150282749; 20150289217; 20150297109; 20150305689; 20150335295; 20150351855; 20150366482; 20160027342; 201029896; 20160058366; 20160058376; 20160058673; 20160060926; 20160065724; 20160065840; 20160077547; 20160081625; 20160103487; 20160104006; 20160109959; 20160113517; 20160120048; 20160120428; 20160120457; 20160125228; 20160157773; 20160157828; 20160183812; 20160191517; 20160193499; 20160196185; 20160196635; 20160206241; 20160213317; 20160228064; 20160235341; 20160235359; 20160249857; 20160249864; 20160256086; 20160282680; 20160262685; 20160270656; 20180278672; 20160282113; 20160287142; 20160306942; 20160310071; 20160317056; 20160324445; 20160324457; 20160342241; 20160360100; 20160361027; 20160366482; 20160367138; 20160367195; 20160374616; 20160378608; 20160378965; 20170000324; 20170000325; 20170000326; 20170000329; 20170000330; 20170000331; 20170000332; 20170000333; 20170000334; 20170000335; 20170000337; 20170000340; 20170000341; 20170000342; 20170000343; 20170000345; 20170000454; 20170000683; 20170001032; 20170007111; 20170007115; 20170007116; 20170007122; 20170007123; 20170007182; 20170007450; 20170007799; 20170007843; 20170010469; 20170010470; 20170013562; 20170017083; 20170020627; 20170027521; 20170028563; 20170031440; 20170032221; 20170035309; 20170035317; 20170041699; 20170042485; 20170046052; 20170065349; 20170086695; 20170086727; 20170090475; 20170103440; 20170112446; 20170113056; 20170128006; 20170143249; 20170143442; 20170156593; 20170156606; 20170164893; 20170171441; 20170172499; 20170173262; 20170185714; 20170188933; 20170196503; 20170205259; 20170206913; and 20170214786.

U.S. Pat. and Pub. App. Nos. 9,443,141; 20110218950; 20150248167; 20150248764; 20150248765; 20150310862; 20150331929; 20150338915; 20160026913; 20160062459; 20160085302; 20160125572; 20160247064; 20160274660; 20170053665; 20170069306; 20170173262; and 20170206691.

Amari, S., Natural gradient works efficiently in learning, Neural Computation 10:251-276, 1998.

Amari S., Cichocki, A. Yang, H. H., A new learning algorithm for blind signal separation. In: Advances in Neural Information Processing Systems 8, MIT Press, 1996.

Bandettini P A, Wong E C, Hinks R S, Tikofsky R S, Hyde J S, Time course EPI of human brain function during task activation. Magn Reson Med 25:390-7, 1992

Bell A. J. & Sejnowski T. J. An information-maximization approach to blind separation and blind deconvolution. Neural Comput 7:1129-59, 1995.

Bell, A. J. & Sejnowski, T. J., Learning the higher-order structure of a natural sound, Network: Computation in Neural Systems 7, 1996b.

Bench C J, Frith C D, Grasby P M, Friston K J, Paulesu E, Frackowiak R S, Dolan R I, Investigations of the functional anatomy of attention using the Stroup test. Neuropsychologia 31:907-22,1993.

Boynton G M, Engel S A, Glover G H, Heeger D J, Linear systems analysis of functional magnetic resonance imaging in human VI. J Neurosci 16:4207-21, 1996.

Bringer, Julien, Hervé Chabanne, and Bruno Kindarji. "Error-tolerant searchable encryption." In Communications, 2009. ICC'09. IEEE International Conference on, pp. 1-6. IEEE, 2009.

Buckner, R. L., Bandettini, P. A., O'Craven, KM, Savoy, R. L., Petersen, S. E., Raichle, M. E. 9 Rosen, B. R., Proc Natl Acad Sci USA 93, 14878-83, 1996.

Cardoso, J-F. & Laheld, B., Equivalent adaptive source separation, IEEE Trans. Signal Proc., in press.

Chapman, R. M. & McCrary, J. W., EP component identification and measurement by principal components analysis. Brain Lang. 27, 288-301, 1995.

Cichocki A., Unbehauen R., & Rummert E., Robust learning algorithm for blind separation of signals, Electronics Letters 30, 1386-1387, 1994.

Comon P, Independent component analysis, A new concept? Signal Processing 36:11-20, 1994.

Cover, T. M. & Thomas, J. A., Elements of Information Theory John Wiley, 1991.

Cox, R. W., AFNI: software for analysis and visualization of functional magnetic resonance neuroimages. Comput Biomed Res 29:162-73, 1996.

Cox, R. W. & Hyde J. S. Software tools for analysis and visualization of fMRI data, NMR in Biomedicine, in press.

Dale, A. M. & Sereno, M. I., Improved localization of cortical activity by combining EEG and MEG with MRI cortical surface reconstruction a linear approach. J. Cogn. Neurosci. 5:162-176, 1993.

Friston K. J., Modes or models: A critique on independent component analysis for fMRI. Trends in Cognitive Sciences, in press.

Friston K. J., Commentary and opinion: II. Statistical parametric mapping: ontology and current issues. J Earth Blood Flow Metab 15:361-70, 1995.

Friston K. J., Statistical Parametric Mapping and Other Analyses of Functional Imaging Data. In: A. W. Toga, J. C. Mazziotta eds., Brain Mapping, The Methods. San Diego: Academic Press, 1996:363-396, 1995.

Friston K J, Frith C D, Liddle P F, Frackowiak R S, Functional connectivity: the principal-component analysis of large (PET) data sets. J Cereb Blood Flow Metab 13:5-14, 1993.

Friston K J, Holmes A P, Worsley K J, Poline J P, Frith C D, and Frackowiak R. S. J., Statistical Parametric Maps in Functional Imaging: A General Linear Approach, Human Brain Mapping 2: 189-210, 1995.

Friston K J, Williams S, Howard R, Frackowiak R S and Turner R, Movement-related effects in fMRI time-series. Magn Reson Med 35:346-55,1996.

Galambos, R. and S. Makeig, "Dynamic changes in steady-state potentials," in: Dynamics of Sensory and Cognitive Processing of the Brain, ed. E. Basar Springer, pp. 178-199, 1987.

Galambos, R., S. Makeig, and P. Talmachoff, A 40 Hz auditory potential recorded from the human scalp, Proc Natl Aced Sci USA 78(4)2643-2647, 1981.

Galil, Zvi, Stuart Haber, and Moti Yung. "Cryptographic computation: Secure fault-tolerant protocols and the public-key model." In Conference on the Theory and Application of Cryptographic Techniques, pp. 135-155. Springer, Berlin, Heidelberg, 1987.

George J S, Aine C J, Mosher J C, Schmidt D M, Ranken D M, Schlitt H A, Wood C C, Lewine J D, Sanders J A, Belliveau J W. Mapping function in the human brain with magnetoencephalography, anatomical magnetic resonance imaging, and functional magnetic resonance imaging. J Clin Neurophysiol 12:406-31, 1995.

Ives, J. R., Warach S, Schmitt F, Edelman R. R. and Schomer D L. Monitoring the patient's EEG during echo planar MRI, Electroencephalogr Clin Neurophysiol, 87:417-420, 1993.

Jackson, J. E., A User's Guide to Principal Components. New York: John Wiley B Sons, Inc., 1991.

Jokeit, H. and Makeig, S., Different event-related patterns of gamma-band power in brainwaves of fast and slow-reacting subjects, Proc. Nat. Acad. Sci USA 91:6339-6343, 1994.

Juels, An, and Madhu Sudan. "A fuzzy vault scheme." Designs, Codes and Cryptography 38, no. 2 (2006): 237-257.

Jueptner, M., K. M. Stephan, C. D. Frith, D. J. Brooks, R. S J. Frackowiak B R. E. Passingham, Anatomy of Motor Learning. I. Frontal Cortex and Attention. J. Neurophysiology 77:1313-1324, 1977.

Jung, T-P., Humphries, C., Lee, T-W., Makeig, S., McKeown, M., Iragui, V. and Sejnowski, T. J., "Extended ICA removes artifacts from electroencephalographic recordings," In: Advances in Neural Information Processing Systems 10: MIT Press, Cambridge, Mass., in press.

Jung, T-P., Humphries, C., Lee, T.-W., McKeown, M. J., Iragui, V., Makeig, S. B Sejnowski, T. J., Removing electroencephalographic artifacts by blind source separation, submitted-a.

Jung, T-P., S. Makeig, M. Stensmo B T. Sejnowski, Estimating Alertness from the EEG Power Spectrum, IEEE Transactions on Biomedical Engineering, 44(1), 60-69, 1997.

Jung, T-R, Makeig, S., Westerfield, M., Townsend, J., Courchesne, E. and Sejnowski, T. J., Analysis and visualization of single-trial event-related potentials, submitted-b.

Jutten, C. & Herault, J., Blind separation of sources, part I: an adaptive algorithm based on neuromimetic architecture. Signal Processing 24, 1-10, 1991.

Karhumen, J., DO, E., Wang, L., Vigario, R. & Joutsenalo, J., A class of neural networks for independent component analysis, IEEE Trans. Neural Networks, in press.

Kwong K. K., Functional magnetic resonance imaging with echo planar imaging. Magn Reson Q 11:1-20, 1995.

Kwong K. K., Belliveau J W, Chesler D A, Goldberg I E, Weisskoff R M, Poncelet B R Kennedy D N, Hoppel B E, Cohen M S, Turner R, et al., Dynamic magnetic resonance imaging of human brain activity during primary sensory stimulation. Proc Natl Aced Sci USA 89:5675-9, 1992.

Lee, T.-W., Girolami, M., and Sejnowski, T. J., Independent component analysis using an extended infomax algorithm for mixed Sub-gaussian and Super-gaussian sources, Neural Computation, submitted for publication.

Lewicki, Michael S., and Sejnowski, Terence J., Learning nonlinear overcomplete representations for efficient coding, Eds. M. Kearns, M. Jordan, and S. Solla, Advances in Neural Information Processing Systems 10 in press.

Linsker, R., Local synaptic learning rules suffice to maximise mutual information in a linear network. Neural Computation 4, 691-702, 1992.

Liu A K, Belliveau J W, Dale A M. Spatiotemporal imaging of human brain activity using functional MRI-constrained magnetoencephalography data: Monte Carlo simulations. Proc Natl Aced Sci USA 95:8945-50, 1998

Manoach D S, Schlaug G, Siewert B, Darby D G, Bly B M, Benfield A, Edelman R. R., Warach S, Prefrontal cortex fMRI signal changes are correlated with working memory load. Neuroreport 8:545-9, 1997.

McCarthy, G., Luby, M., Gore, J. and Goldman-Rakic, P., Infrequent events transiently activate human prefrontal and parietal cortex as measured by functional MRI. J. Neurophysiology 77:1630-1634, 1997.

McKeown, M., Makeig, S., Brown, G., Jung, T-P., Kindermann, S., Bell, Iragui, V. and Sejnowski, T. J., Blind separation of functional magnetic resonance imaging (fMRI) data, Human Brain Mapping, 6:160, 18, 1998a.

McKeown, M I, Humphries, C., Achermann, P., Borbely, A. A. and Sejnowski, T. J., A new method for detecting state changes in the EEG: exploratory application to sleep data. J. Sleep Res. 7 suppl. 1:48-56, 1998b.

McKeown, M. J., Tzyy-Ping Jung, Scott Makeig, Greg Brown, Sandra S. Kindermann, Te-Won Lee and Terrence J. Sejnowski, Spatially independent activity patterns in functional magnetic resonance imaging data during the Stroup color-naming task, Proc. Natl. Acad. Sci USA, 95:803-810, 1998c.

McKeown, M. J. and Sejnowski, T. J., Independent component analysis of fMRI data: examining the assumptions. Human Brain Mapping 6:368-372, 1998d.

Makeig, S. Auditory event-related dynamics of the EEG spectrum and effects of exposure to tones, Electroencephalogr Clin Neurophysiol, 86:283-293, 1993.

Makeig, S. Toolbox for independent component analysis of psychophysiological data, www.cnl.salk.edu/~scott/ica.html, 1997.

Makeig, S. and Galambos, R., The CERP: Event-related perturbations in steady-state responses, in: Brain Dynamics Progress and Perspectives, (pp. 375-400), ed. E. Basar and T. H. Bullock, 1989.

Makeig, S. and Inlow, M., Lapses in alertness: coherence of fluctuations in performance and the EEG spectrum, Electroencephalogr clin Neurophysiol, 86:23-35, 1993.

Makeig, S. and Jung, T-P., Changes in alertness are a principal component of variance in the EEG spectrum, NeuroReport 7:213-216, 1995.

Makeig, S. and T-P. Jung, Tonic, phasic, and transient EEG correlates of auditory awareness during drowsiness, Cognitive Brain Research 4:15-25, 1996.

Makeig, S., Bell, A. J., Jung, T-P. and Sejnowski, T. J., "Independent component analysis of electroencephalographic data," In: D. Touretzky, M. Mazer and M. Hasselmo (Eds). Advances in Neural Information Processing Systems 8:145-151 MIT Press, Cambridge, Mass., 1996.

Makeig, S., Jung, T-P, and Sejnowski, T. J., "Using feedforward neural networks to monitor alertness from changes in EEG correlation and coherence," In: D. Touretzky, M. Mazer & M. Hasselmo (Eds). Advances in Neural Information Processing Systems 8:931-937 MIT Press, Cambridge, Mass., 1996.

Makeig, S., T-P. Jung, D. Ghahremani, A. J. Bell & T. J. Sejnowski, Blind separation of auditory event-related brain responses into independent components. Proc. Natl. Acad. Sci. USA, 94:10979-10984, 1997.

Makeig, S., Westerfield, M., Jung, T-P., Covington, J., Townsend, J., Sejnowski, T. J. and Courchesne, E., Independent components of the late positive event-related potential in a visual spatial attention task, submitted.

Mitra P P, Ogawa S, Hu X, Ugurbil K The nature of spatiotemporal changes in cerebral hemodynamics as manifested in functional magnetic resonance imaging. Magn Reson Med. 37:511-8, 1997.

Nobre A C, Sebestyen G N, Gitelman D R, Mesulam M M, Frackowiak R S, Frith C D, Functional localization of the system for visuospatial attention using positron emission tomography. Brain 120:515-33, 1997.

Nunez, P. L., Electric Fields of the Brain. New York: Oxford, 1981.

Ogawa S, Tank D W, Menon R, Ellermann J M, Kim S G, Merkle H, Ugurbil K, Intrinsic signal changes accompanying sensory stimulation: functional brain mapping with magnetic resonance imaging. Proc Natl Aced Sci USA 89:5951-5, 1992

Pearlmutter, B. and Parra, L. C. Maximum likelihood blind source separation: a context-sensitive generalization of ICA. In: M. C. Mazer, M. I. Jordan and T. Petsche (Eds.), Advances in Neural Information Processing Systems 9:613-619 MIT Press, Cambridge, Mass. 1996.

Sakai K, Hikosaka O, Miyauchi S, Takino R, Sasaki Y, Putz B. Transition of brain activation from frontal to parietal areas in visuomotor sequence learning. J Neurosci 18:1827-40, 1998.

Sahai, Amit, and Brent Waters. "Fuzzy identity-based encryption." In Annual International Conference on the Theory and Applications of Cryptographic Techniques, pp. 457-473. Springer, Berlin, Heidelberg, 2005.

Scherg, M. & Von Cramon, D., Evoked dipole source potentials of the human auditory cortex. Electroencephalogr. Clin. Neurophysiol. 65:344-601, 1986.

Tallon-Baudry, C., Bertrand, O., Delpuech, C., & Pernier, J., Stimulus Specificity of Phase-Locked and Non-Phase-Locked 40 Hz Visual Responses in Human. J. Neurosci. 16: 4240-4249, 1996.

Thaker, Darshan D., Diana Franklin, John Oliver, Susmit Biswas, Derek Lockhart, Tzvetan Metodi, and Frederic T. Chong. "Characterization of error-tolerant applications when protecting control data." In Workload Characterization, 2006 IEEE International Symposium on, pp. 142-149. IEEE, 2006.

Tulving E, Markowitsch H J, Craik F E, Habib R, Houle S, Novelty and familiarity activations in PET studies of memory encoding and retrieval. Cereb Cortex 6:71-6, 1996.

Warach, S., J. R. Ives, G. Schaug, M. R. Patel, D. G. Darby, V. Thangaraj, R. R. Edelman and D. L. Schomer, EEG-triggered echo-planar functional MRI in epilepsy, Neurology 47: 89-93, 1996.

REFERENCE LIST 11

U.S. Pat. Nos. 3,595,059; 3,735,753; 3,957,036; 4,375,219; 4,638,807; 4,967,038; 4,972,492; 5,273,037; 5,313,952; 5,479,934; 6,076,003; 6,154,699; 6,574,513; 6,640,122; 7,103,398; 7,773,767; 7,885,419; 8,055,722; 8,128,422; 8,155,736; 8,160,287; 8,170,637; 8,209,224; 8,270,814; 8,271,075; 8,284,233; 8,290,563; 8,301,218; 8,335,715; 8,335,716; 8,389,261; 8,386,312; 8,386,313; 8,391,966; 8,392,250; 8,392,251; 8,392,253; 8,392,254; 8,392,255; 8,396,529; 8,396,744; 8,417,185; 8,438,659; 8,442,626; 8,464,288; 8,473,345; 8,494,610; 8,494,905; 8,533,042; 8,548,555; 8,548,558; 8,634,892; 8,635,105; 8,655,428; 8,655,437; 8,659,397; 8,676,230; 8,679,013; 8,696,113; 8,706,518; 8,733,927; 8,733,928; 8,738,395; 8,755,879; 8,780,512; 8,781,570; 8,798,736; 8,812,075; 8,816,861; 8,821,397; 8,868,039; 8,868,218; 8,897,859; 8,898,344; 8,983,591; 8,988,350; 8,989,835; 9,014,661; 9,031,631; 9,032,110; 9,042,201; 9,058,200; 9,086,884; 9,104,467; 9,104,969; 9,129,478; 9,146,618; 9,171,131; 9,179,855; 9,186,105; 9,210,517; 9,213,403; 9,224,309; 9,239,615; 9,258,301; 9,259,180; 9,268,905; 9,292,858; 9,320,450; 9,330,497; 9,354,445; 9,357,240; 9,357,941; 9,367,131; 9,377,869; 9,392,956; 9,405,366; 9,408,575; 9,408,997; 9,412,233; 9,414,780; 9,426,582; 9,432,777; 9,436,279; 9,439,593; 9,439,595; 9,439,596; 9,439,736; 9,445,763; 9,445,768; 9,451,303; 9,451,406; 9,454,646; 9,454,777; 9,462,433; 9,477,290; 9,477,317; 9,477,701; 9,482,606; 9,497,530; 9,504,420; 9,507,974; 9,516,430; 9,521,976;

9,531,708; 9,532,748; 9,557,957; 9,560,984; 9,593,927; 9,569,986; 9,577,992; 9,579,060; 9,585,581; 9,590,986; 9,594,500; 9,599,492; 9,615,746; 9,619,613; 9,622,703; 9,636,063; 9,658,473; 9,692,756; 9,693,734; 9,700,261; 9,704,205; 9,706,237; 9,722,472; 9,723,422; 9,729,252; 9,736,603; 9,737,231; 9,740,285; 9,793,613; 9,775,545; 9,779,575; 9,781,521; 9,782,122; 9,794,672; 9,795,324; 9,800,717; 9,805,339; 9,805,381; 98018156; 9,811,154; 9,814,426; 9,818,150; 9,820,120; 9,830,576; 9,830,577; 9,832,353; 9,833,142; 9,833,185; 9,836,896; 9,836,931; 9,842,299; 9,844,344; 9,853,976; 9,857,590; 9,858,745; 9,865,093; 9,883,396; 9,886,981; 9,888,090; 9,898,793; 9,900,669; 9,904,891; 9,904,892; 9,905,239; 9,910,298; 9916010; 9,936,250; 9,949,640; 9,953,650; 9,955,902; 9,962,082; 9,962,083; 9,978,095; 9,983,670; 9,990,727; 9993190; 9993386; 9994228; D613267; D626949; D643013S1; D643400S1; D671523; D717956; D743039; D747495; D809474; 10009644; 10019060; 10026138; 10029067; 10031580; 10042038; 10042993; 10052023; 10052452; 10058285; 10068373; 10075896; 10079788; 10089074; 10095191; 10108783; 10110805; 10113913; 10123133; 10123134; 10126816; 10130278; 10130279; 10130766; 10136856; 10136862; 10137363; 10143415; 10149161; 10152957; 10154333; 10154815; 10162707; 10166091; 10168704; 10169712; 10173059; 10176894; 10180339; 10185147; 10186014; 10188307; 10191545; 10198505; 10206625; 10209779; 10212593; 10213156; 10219736; 10223710; 10226209; 10227063; 10231673; 10234942; 10244033; 10254785; 10257177; 10257555; 10258243; 10258291; 10261947; 10262356; 10264990; 10271087; 10279192; 10285634; 10290225; 10291977; 10293177; 10300240; 10303258; 10303988; 10307085; 10307104; 10307611; 20040073129; 20050215916; 20060094974; 20080177197; 20090112077; 20090156925; 20090214060; 20090281408; 20100068146; 20100090835; 20100094097; 20100163027; 20100163028; 20100163035; 20100168525; 20100168529; 20100168802; 20100201780; 20100234752; 20110004089; 20110040202; 20110162879; 20110224503; 20110313308; 20120029379; 20120046569; 20120108999; 20120136274; 20120150545; 20120176302; 20120190959; 20120197092; 20120220889; 20120245450; 20120250197; 20120295589; 20120296476; 20120330178; 20130012830; 20130035578; 20130039509; 20130041243; 20130044055; 20130046206; 20130066183; 20130066184; 20130096440; 20130096575; 20130127708; 20130130799; 20130177883; 20130179087; 20130197401; 20130208234; 20130211226; 20130211276; 20130237867; 20130242262; 20130260361; 20130278492; 20130338738; 20130343584; 20130343585; 20130345524; 20140012152; 20140020089; 20140058219; 20140073969; 20140096210; 20140098981; 20140099623; 20140106710; 20140107520; 20140108842; 20140114165; 20140114207; 20140121017; 20140146987; 20140148715; 20140160250; 20140164056; 20140179986; 20140195221; 20140210709; 20140211593; 20140221779; 20140221855; 20140223462; 20140228853; 20140257833; 20140277292; 20140278786; 20140282772; 20140304122; 20140307878; 20140313303; 20140316230; 20140316235; 20140321682; 20140330334; 20140336473; 20140342818; 20140368601; 20140369537; 20140378810; 20150003699; 20150006186; 20150033056; 20150045007; 20150091791; 20150112153; 20150126281; 20150142082; 20150162802; 20150190085; 20150227193; 20150242120; 20150250415; 20150257674; 20150272508; 20150289065; 20150297109; 20150323986; 20150347734; 20150351655; 20160005320; 20160022206; 20160042123; 20160054568; 20160062596; 20160070334; 20160081623; 20160117829; 20160132189; 20160144173; 20160156682; 20160166208; 20160170998; 20160192166; 20160213354; 20160232625; 20160259905; 20160267809; 20160299568; 20160306844; 20160316288; 20160324478; 20160342644; 20160358091; 20160361602; 20160374594; 20170000404; 20170010647; 20170020434; 20170048626; 20170065218; 20170068921; 20170071532; 20170071551; 20170086695; 20170093848; 20170103668; 20170127975; 20170142656; 20170160703; 20170164878; 20170171441; 20170177023; 20170189640; 20170215011; 20170221463; 20150000025; 20150005640; 20150012426; 20150038889; 20150073294; 20150094914; 20150121474; 20150131159; 20150150753; 20150185482; 20150199010; 20150227844; 20150248651; 20150256956; 20150264028; 20150277560; 20150293592; 20150302543; 20150338917; 20150350794; 20150366518; 20160015289; 20160029947; 20160044460; 20160054569; 20160063611; 20160071390; 20186103322; 20160119726; 20160133052; 20160150582; 20160157777; 20160167672; 20160171514; 20160196635; 20160219000; 20160235324; 20160262704; 20160269999; 2016030252; 20160310698; 20160317056; 20160331925; 20160344569; 20160358092; 20160364586; 20160378608; 20170007165; 20170010677; 20170039045; 20170049524; 20170065379; 20170071495; 20170071537; 20170078883; 20170087453; 20170095157; 20170112671; 20170133009; 20170143249; 20170162072; 20170169176; 20170172445; 20170180882; 20170193314; 20170215757; 20170243023; 20150003698; 20150005644; 20150016664; 20150040139; 20150073907; 20150105111; 20150123984; 20150135309; 20150157255; 20150185506; 20150213722; 20150235134; 20150250401; 20150257104; 20150268483; 20150278980; 20150297106; 20150305686; 20150343242; 20150350820; 20160005229; 20160022167; 20160029965; 20160045150; 20160055236; 20160065557; 20160078657; 20160109954; 20160128629; 20160142407; 20160156575; 20160164949; 20160170996; 20160191269; 20160196758; 20160224803; 20160235983; 20160265952; 20160296157; 20160302711; 20160310838; 20160320930; 20160339300; 20160349841; 20160360990; 20160387138; 20160381621; 20170007173; 20170011210; 20170042439; 20170064434; 20170068920; 20170071523; 20170071546; 20170080332; 20170091532; 20170095199; 20170119994; 20170139484; 20170157435; 20170164293; 20170169295; 20170175287; 20170185762; 20170213311; 20170221121; 20170244702;

20170245145; 20170249009; 20170251945; 20170258390; 20170259167; 20170262943; 20170265807; 20170272699; 20170272842; 20170281001; 20170293846; 20170300654; 20170309152; 20170311023; 20170311097; 20170311832; 20170323073; 20170331563; 20170332964; 20170337834; 20170347181; 20170352233; 20170367606; 20170367610; 20170367651; 20180000255; 20180005442; 20180011676; 20180011689; 20180014130; 20180025368; 20180027347; 20180042523; 20180047216; 20180070823; 20180075364; 20180081439; 20180098710; 20180103859; 20180110960; 20180113509; 20180115808; 20180116543; 20180125386; 20180133431; 20180133504; 20180133507; 20180139518; 20180150762; 20180154104; 20180157336; 20180158133; 20180160982; 20180165593; 20180173220; 20180182161; 20180184964; 20180189678; 20180193589; 20180196511; 20180214028; 20180217666; 20180220957; 20180221620; 20180234847; 20180236202; 20180246570; 20180250494; 20180263562; 20180275747; 20180276833; 20180278984; 20180279960; 20180289310; 20180296112; 20180301061; 20180317795; 20180321700; 20180321898; 20180324516; 20180333585; 20180338068; 20180344969; 20180348764; 20180364810; 20180368717; 20180368722; 20180369847; 20180373272; 20190001039; 20190008992; 20190012758; 20190013960; 201900208610; 20190029587; 20190029595; 20190033968; 20190034164; 20190043154; 20190053731; 20190053756; 20190053766; 20190070386; 20190083212; 20190086919; 20190097430; 20190108191; 20190110726; 20190113973; 20190117933; 20190133445; 20190142349; 20190167370; 20190174237; 20190174238; AU667199; AU729772; CN102458242A; CN104605844A; EP0483698; EP1090583; EP1778922; JP4582509; JP4699694; JP4801839; JP4829231; KR100895297; RU2586433; and WO2015143031.

What is claimed is:

1. A method of treating a Severe Acute Respiratory Syndrome Coronavirus 2 (SARS-CoV-2) related sleep disorder of a person, comprising:
defining a desired sleep cycle pattern for the person;
presenting, under control of an automated processor, a non-infrasonic auditory stimulation pattern comprising an acoustic emission lacking infrasonic acoustic waves to the person through at least one of binaural beats, and isochronic tones, the stimulation pattern representing a series of brainwave patterns comprising infrasonic brainwave frequencies, progressing dependent on a current awake or sleep stage of the person and the defined desired sleep cycle pattern;
wherein the stimulation pattern is presented acoustically, the stimulation pattern has a modulated pattern corresponding to a brainwave signal obtained from at least one other healthy sleeping donor, the brainwave signal comprises infrasonic frequencies, and the presented stimulation pattern lacks infrasonic frequencies; and
entraining brainwaves of the person with the presented modulated stimulation pattern representing the infrasonic brainwave frequencies, to thereby induce a sleep cycle in the person according to the sleep cycle pattern.

2. The method according to claim 1, further comprising administering a SARS-Cov-2 vaccine to the person, wherein the sleep cycle enhances immune response to the SARS-Cov-2 vaccine as compared to the SARS-Cov-2 related sleep disorder,
wherein the presenting, and entraining steps are continued in a postvaccination period.

3. The method according to claim 1, wherein the current awake or sleep stage of the person is determined based on a monitoring at least one of a respiratory pattern, a heartrate, a heart rate variability, a temperature, and a movement pattern of the person.

4. The method according to claim 1, wherein the stimulation pattern further includes at least one of an optical signal and a near-infrared signal presented to the person.

5. The method according to claim 1, wherein the stimulation pattern is presented based on signals defined by an app executing on a smartphone, the app being downloadable and upgradable from a remote server.

6. The method of claim 1, further comprising detecting an unexpected awakening of the person with respect to the desired sleep cycle pattern, and resetting the sleep cycle pattern presentation dependent on the detected awakening.

7. The method of claim 1, wherein the stimulation pattern comprises different audio signals presented in each ear by a spatialized audio transducer system.

8. A method of improving sleep of a person having a Severe Acute Respiratory Syndrome Coronavirus 2 (SARS-CoV-2) related sleep disorder, comprising:
generating, by an automated processor, an excitation pattern comprising a non-infrasonic auditory acoustic emission lacking infrasound acoustic waves and comprising a representation of infrasonic brainwave frequencies, the excitation pattern being configured and adapted to induce neural correlates of sleep stage 1 having frequencies in the alpha band, followed by neural correlates of sleep stage 2 having frequencies in the theta band, followed by neural correlates of sleep stage 3 or 4 having frequencies in the delta band below 4 Hz, corresponding to a desired sleep cycle pattern;
wherein the excitation pattern is presented acoustically, the excitation pattern has a modulated pattern corresponding to brainwave frequencies obtained from at least one other healthy sleeping donor, the brainwave frequencies comprises infrasonic frequencies, and the excitation pattern lacks infrasonic frequencies; and
entraining brainwaves of the person with the modulated excitation pattern comprising the representation of infrasonic brainwave frequencies according to the desired sleep cycle pattern, to enhance sleep of the person.

9. The method according to claim 7, further comprising administering SARS-Cov-2 vaccine to the person.

10. The method according to claim 8, wherein the excitation pattern is conveyed to the person in a spatialized audio soundfield, further comprising detecting at least one of sounds and scattered radio frequency waves from the person indicative of a sleep state, and synchronizing the sleep cycle pattern based on the detected sounds or scattered radio frequency waves.

11. A system for improving sleep in a person suffering from a Severe Acute Respiratory Syndrome Coronavirus 2 (SARS-CoV-2) anxiety related sleep disorder, comprising:
at least one sensor configured to determine a current brain state of the person, being one of a waking state and a sleeping state;

at least one microprocessor, configured to:
define a desired sleep cycle pattern, dependent on the determined current brain state of the person;
generate a non-infrasonic audio stimulation pattern modulated with a waveform comprising infrasonic brainwave frequencies derived from cortical signatures extracted from EEG recordings of at least one healthy sleeping donor corresponding to the desired sleep cycle pattern, the modulated audio stimulation pattern lacking infrasonic acoustic waves and being adapted and configured to entrain brainwaves in the brain of the person with the waveform comprising the infrasonic brainwave frequencies derived from the cortical signatures extracted from the EEG recordings of the at least one healthy sleeping donor corresponding to the desired sleep cycle pattern, to thereby induce a sleep cycle in the person according to the sleep cycle pattern; and
detect an unexpected awakening of the person with respect to the desired sleep cycle pattern, and to reset the desired sleep cycle pattern dependent on the detected awakening; and
a database configured to store a plurality of modulated stimulation pattern portions corresponding to different sleep stages and comprising brainwave patterns of humans.

12. The system according to claim 11, wherein the person has coronavirus pandemic-induced insomnia and the modulated stimulation pattern is configured and adapted to reduce the coronavirus pandemic-induced insomnia.

13. The system according to claim 11, wherein the sensor comprises at least one of:
a microphone configured to receive respiratory sounds of the person;
a radar sensor configured to detect at least one of respiratory and cardiac signals, and an electroencephalography sensor for receiving brainwaves of the person.

14. The system according to claim 11, further comprising stimulating the person with an optical stimulation pattern which comprises a modulated visual or near-infrared signal.

15. The system according to claim 11, wherein the at least one microprocessor is part of a smartphone, and the modulated stimulation pattern is generated based on signals defined by an app executing on the smartphone, the app being downloadable and upgradable from a remote server.

16. A method of treating a person suffering from a Severe Acute Respiratory Syndrome Coronavirus 2 (SARS-CoV-2) related sleep disorder, comprising:
selecting a waveform derived from cortical signatures extracted from EEG recordings of a healthy sleeping donor;
modulating the waveform on at least one non-infrasonic acoustic stimulus using a microprocessor, wherein the stimulus is an auditory stimulus including at least one of binaural beats, and isochronic tones;
wherein the waveform is modulated on said at least one acoustic stimulus by varying at least one of a frequency and an amplitude of said at least one acoustic stimulus corresponding to at least one of a frequency and an amplitude of the cortical signatures, wherein the cortical signatures comprise infrasonic frequencies and the acoustic stimulus achieves entrainment via the at least one of an isochronic tone stimulus, and the binaural beats stimulus;
stimulating the person with said at least one acoustic stimulus configured and adapted to achieve brain entrainment without emitting infrasound acoustic waves;
entraining brainwaves of the person with the cortical signatures extracted from EEG recordings of the healthy sleeping donor comprising infrasonic brainwave frequencies, to induce sleep in the person and thereby treat the SARS-Cov-2 related sleep disorder and improve immunity in the person;
monitoring at least one physiological parameter of the person to determine a brain state of the person; and
upon determining that the brain state of the person is the state of sleep, automatically modifying the stimulation.

17. The method according to claim 16, wherein the acoustic stimulus is modified by cessation when the brain state of the person indicates a sleep state.

18. The method according to claim 16, wherein the effectiveness of a SARS-Cov-2 related vaccine in the person is improved by treating the SARS-Cov-2 related sleep disorder.

19. The method according to claim 16, wherein the SARS-Cov-2 related sleep disorder is caused by at least one of a SARS-Cov-2 pandemic-related anxiety, a SARS-Cov-2 pandemic-related stress, a SARS-Cov-2 infection, and a persistent Coronavirus Disease 2019 (COVID-2019) disease.

20. The method according to claim 16, wherein said entraining brainwaves involves locking phase with the person's endogenous brainwaves and establishing an Arnold tongue condition.

21. The method according to claim 16, further comprising administering at least one dose of a SARS-Cov-2-related vaccine, after determining that the brain state of the person was in the state of sleep.

* * * * *